(12) United States Patent
Nave et al.

(10) Patent No.: US 9,968,092 B2
(45) Date of Patent: May 15, 2018

(54) COMBINATION OF NOVEL NITRIFICATION INHIBITORS AND BIOPESTICIDES AS WELL AS COMBINATION OF (THIO)PHOSPHORIC ACID TRIAMIDES AND BIOPESTICIDES

(71) Applicant: BASF SE, Ludwigshafen (DE)

(72) Inventors: Barbara Nave, Ruppertsberg (DE); Joachim Dickhaut, Heidelberg (DE); Mihiret Tekeste Sisay, Mannheim (DE); Alexander Wissemeier, Speyer (DE); Wolfram Zerulla, Maikammer (DE); Gregor Pasda, Neustadt (DE); Markus Schmid, Deidesheim (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/327,819

(22) PCT Filed: Apr. 16, 2015

(86) PCT No.: PCT/IB2015/052771
§ 371 (c)(1),
(2) Date: Jan. 20, 2017

(87) PCT Pub. No.: WO2015/104698
PCT Pub. Date: Jul. 16, 2015

(65) Prior Publication Data
US 2017/0181435 A1    Jun. 29, 2017

(30) Foreign Application Priority Data
Apr. 17, 2014 (EP) ..................... 14165222

(51) Int. Cl.
*A01N 57/28* (2006.01)
*A01N 31/14* (2006.01)

(52) U.S. Cl.
CPC ............. *A01N 57/28* (2013.01); *A01N 31/14* (2013.01)

(58) Field of Classification Search
None
See application file for complete search history.

(56) References Cited

U.S. PATENT DOCUMENTS

| | | | |
|---|---|---|---|
| 3,060,084 A | 10/1962 | Littler | |
| 3,299,566 A | 1/1967 | MacMullen | |
| 3,920,442 A | 11/1975 | Albert et al. | |
| 4,144,050 A | 3/1979 | French | |
| 4,172,714 A | 10/1979 | Albert | |
| 4,673,429 A | 6/1987 | Rieber et al. | |
| 5,180,587 A | 1/1993 | Moore | |
| 5,208,030 A | 5/1993 | Hoy et al. | |
| 5,232,701 A | 8/1993 | Ogawa | |
| 6,124,117 A | 9/2000 | Kilburn et al. | |
| 6,180,141 B1 | 1/2001 | Lemercier | |
| 6,406,690 B1 | 6/2002 | Peleg et al. | |
| 6,994,849 B2 | 2/2006 | Droby | |
| 8,206,972 B2 | 6/2012 | Hua | |
| 8,221,736 B2 | 7/2012 | Hick et al. | |
| 8,430,942 B2 * | 4/2013 | Urrutia ..................... C05G 3/08 504/127 |
| 2007/0280981 A1 | 12/2007 | Birthisel | |
| 2013/0035230 A1 | 2/2013 | Suchanek | |
| 2014/0047883 A1 | 2/2014 | Gabrielson et al. | |

FOREIGN PATENT DOCUMENTS

| | | |
|---|---|---|
| CA | 2471555 A1 | 12/2005 |
| CN | 1331064 A | 1/2002 |
| CN | 1989144 A | 6/2007 |
| EP | 0 917 526 A2 | 5/1999 |
| EP | 0 585 215 B1 | 9/1999 |
| EP | 1 124 414 A1 | 8/2001 |
| EP | 854213 B1 | 7/2002 |
| GB | 2095558 A | 10/1982 |
| WO | 91/007481 A1 | 5/1991 |
| WO | 91/013546 A1 | 9/1991 |
| WO | 93/007278 A1 | 4/1993 |
| WO | 1996/021358 A1 | 7/1996 |
| WO | 98/005607 A2 | 2/1998 |
| WO | 01/013722 A1 | 3/2001 |
| WO | 2001/040441 A2 | 6/2001 |
| WO | 03/018810 A2 | 3/2003 |
| WO | 03/031477 A1 | 4/2003 |
| WO | 03/052073 A2 | 6/2003 |
| WO | 2003/057861 A2 | 7/2003 |
| WO | 2006/112700 A1 | 4/2005 |
| WO | 2005/102045 A1 | 11/2005 |
| WO | 2005/120226 A1 | 12/2005 |
| WO | 07/067042 A1 | 6/2007 |
| WO | 07/067044 A1 | 6/2007 |
| WO | 2009/124707 A2 | 10/2009 |
| WO | 2009/126473 A1 | 10/2009 |
| WO | 2010/080169 A1 | 7/2010 |
| WO | 2010085795 A2 | 7/2010 |
| WO | 2011002809 A2 | 1/2011 |
| WO | 2012/064527 A1 | 5/2012 |
| WO | 2013/032693 A2 | 3/2013 |
| WO | 2013/138398 A1 | 9/2013 |

OTHER PUBLICATIONS

Subbarao et al., 2012 Advances in Agronomy, 114, 249-302.
D.W. Nelson et al. "Nitrification inhibitors for corn-production" (2001), National Corn Handbook, Iowa State University.
Colby, S. R., "Calculating synergistic and antagonistic responses of herbicide Combinations," Weeds, 15, pp. 20-22, 1967.

(Continued)

Primary Examiner — Brian J Davis
(74) Attorney, Agent, or Firm — Armstrong Teasdale LLC

(57) ABSTRACT

A composition including (a) at least one (thio)phosphoric acid triamide (T) according to the general formula (Ia)

$$R^{a1}R^{a2}N—P(X)(NH_2)_2 \qquad (Ia)$$

wherein X is oxygen or sulfur; $R^{a1}$ is a $C_1$ to $C_{20}$ alkyl, $C_3$ to $C_{20}$ cycloalkyl, $C_6$ to $C_{20}$ aryl, or dialkylaminocarbonyl group; $R^{a2}$ is H, or $R^{a1}$ and $R^{a2}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur; and (b) at least one biopesticide.

16 Claims, No Drawings

(56) References Cited

OTHER PUBLICATIONS

Nature vol. 280, Aug. 1979, pp. 697-699.
Perry's Chemical Engineer's Handbok, 4th Ed. McGraw-Hill, New York, 1963. S. 8-57.
F. Cassan et al."Azospirillum brasilense Az39 and Bradyrhizobium japonicum E109, inoculated singly or in combination, promote seed germination and early seedling growth in corn (*Zea mays* L.) and soybean (*Glycine max* L.)" Eur. J. Soil Biol 45(1), 28-35, 2009.
M. Hungria et al. "Inoculation with selected strains of Azospirillum brasilense and A. lipoferum improves yields of maize and wheat in Brazil" Plant Soil 331, 413-425, 2010.
Ryu et al. "A Two-Strain Mixture of Rhizobacteria Elicits Induction of Systemic Resistance Against Pseudomonas syringae and Cucumber Mosaic Virus Coupled to Promotion of Plant Growth on *Arabidopsis thaliana*" Biotechnol. 17(2), 280-286, 2007.
Environmental Protection Agency, Federal Register vol. 77, No. 7, 1633-1637.
A.G. Williams et al. Glutamate dehydrogenase activity in lactobacilli and the use of glutamate dehydrogenase-producing adjunct *Lactobacillus* spp. cultures in the manufacture of cheddar cheeseJ. App. Microbiol. 100(5), 1063-72, 2006.
S. Lurie et al. "Efficacy of Candida oleophila Strain 182 in Preventing Penicillium expansun Infection of Nectarine Fruits" Phytoparasitica 23(3), 231-234, 1995.
R. Lahlali et al. "Enhancement of the biocontrol agent Candida oleophila (strain O) survival and control efficiency under extreme conditions of water activity and relative humidity" Biological Control 51, 403-408, 2009.
M.R.Behrens Dicamba Resistance: Enlarging and Preserving Biotechnology-Based Weed Management Strategies Science 316, 2007, 1185.
Guang-Hai Ji et al "Biological control of rice bacterial blight by Lysobacter antibioticus strain 13-1" Biological Control, 45, 288-296, 2008.
Hyun-Sun Ko et al. "Biocontrol Ability of Lysobacter antibioticus HS124 Against Phytophthora Blight is Mediated by the Production of 4-Hydroxyphenylacetic Acid and Several Lytic Enzymes" Current Microbiol. 59(6), 608-615, 2009.
L. B. Folman et al. "Production of antifungal compounds by Lysobacter enzymogenes isolate 3.1T8 under different conditions in relation to its efficacy as a biocontrol agent of Pythium aphanidermatum in cucumber" Biological Control 31(2), 145-154, 2004.
O.Carisse"*Microsphaeropsis ochracea* sp. nov. associated with dead apple leaves" Mycologia 94(2), 297-301, 2002.
T.H.M.Smits et al. "Genome Sequence of the Biocontrol Agent Pantoea vagans Strain C9-1" J. Bacteriol. 192(24) 6486-6487, 2010.
R.J.Goos et al. Penicillium bilaji and phosphorus fertilization effects on the growth, development, yield and common root rot severity of spring wheatFertilizer Res. 39, 97-103, 1994.
D.P. Molloy "Pseudomonas fluorescens strain CL145A—A biopesticide for the control of zebra and quagga mussels (Bivalvia: Dreissenidae)" J. Invertebr. Pathol. 113(1): 104-14, 2013.
L. A. Materon et al. "Competitiveness of Rhizobium trifolii Strains Associated with Red Clover (*Trifolium pratense* L.) in Mississippi Soils" Micrbiol. 44(5), 1982 1096-1101.
Depret et al."Plant phenology and genetic variability in root and nodule development strongly influence genetic structuring of Rhizobium leguminosarum biovar viciae populations nodulating pea" New Phytologist 179(1) 224-235, 2008.
L. Grange et al. "New insights into the origins and evolution of rhizobia that nodulate common bean (Phaseolus vulgaris) in Brazil" Soil Biology & Biochemistry 39, 867-876, 2007.
E. Krol et al. "Global transcriptional analysis of the phosphate starvation response in Sinorhizobium meliloti strains 1021 and 2011" Mo. Gen. Genomics 272, 1-17, 2004.
Browning, "Agglomeration", Chemical Engineering, Dec. 4, 1967, 147-48.
M.G.Williams et al. "Differences in zoospore germination and host penetration in response to temperature among Western Australian isolates of Plasmopara viticola" Australian Journal of Agricultural Research, 2007, 58, 702-710.
Siyuan Tan, et al. "Imidazolinone-tolerant crops: history, current status and future" Pest Manag. Sci. 61, 2005, 246-257.
R.S.Arias et al. "Molecular evolution of herbicide resistance to phytoene desaturase inhibitors in Hydrilla verticillata and its potential use to generate herbicide-resistant crops" Pest Manag. Sci. 61, 2005, 258-268.
M. Matringe et al. "p-Hydroxyphenylpyruvate dioxygenase inhibitor-resistant plants" Pest Manag. Sci. 61, 2005, 269-276.
X. Li "Development of PPO inhibitor-resistant cultures and crops" Pest Manag. Sci. 61, 2005, 277-285.
H.Inui et al. "Herbicide resistance in transgenic plants with mammalian P450 monooxygenase genes" Pest Manag. Sci. 61, 2005, 286-291.
G.M.Dill et al. "Glyphosate-resistant crops: adoption, use and future considerations" Pest Manag. Sci. 61, 2008, 326-331.
J.M. Green "New multiple-herbicide crop resistance and formulation technology to augment the utility of glyphosate" Pest Manag. Sci. 61, 2008, 332-339.
J.M. Green "Evolution of Glyphosate-Resistant Crop Technology" Weed Science, 57, 2009, 108-117.
International Search Report for International Application No. PCT/IB2015/052771 dated Sep. 22, 2015.
L.B. Folman et al. Microbiol. Res. 158, 107-115, Oct. 25, 2002.

\* cited by examiner

COMBINATION OF NOVEL NITRIFICATION INHIBITORS AND BIOPESTICIDES AS WELL AS COMBINATION OF (THIO)PHOSPHORIC ACID TRIAMIDES AND BIOPESTICIDES

CROSS-REFERENCE TO RELATED APPLICATIONS

This application is a U.S. National Phase Application of PCT/IB2015/052771, filed Apr. 16, 2015, which claims the benefit of priority to EP 14165222.2, filed Apr. 17, 2014, the contents of which are hereby expressly incorporated by reference in their entirety.

DESCRIPTION

The present invention relates to the combination of novel nitrification inhibitors of formula I and biopesticides, as well as to the combination of (thio)phosphoric acid triamide(s) and biopesticides. Moreover, the invention relates to the use of this combination of novel nitrification inhibitors and biopesticides for increasing the health of a plant, and to the use of the combination of (thio)phosphoric acid triamide(s) and biopesticides for increasing the health of a plant, as well as compositions comprising the nitrification inhibitor or (T) and a biopesticide, and compositions comprising the (thio) phosphoric acid triamide(s) and a biopesticide. Further encompassed by the present invention are methods for increasing the health of a plant comprising the treatment of plants, soil and/or loci with said combination of the novel nitrification inhibitor or (T) and a biopesticide or with said combination of (thio)phosphoric acid triamide(s) and a biopesticide.

Nitrogen is an essential element for plant growth, plant health and reproduction. About 25% of the plant available nitrogen in soils (ammonium and nitrate) originate from decomposition processes (mineralization) of organic nitrogen compounds such as humus, plant and animal residues and organic fertilizers. Approximately 5% derive from rainfall. On a global basis, the biggest part (70%), however, are supplied to the plant by inorganic nitrogen fertilizers. The mainly used nitrogen fertilizers comprise ammonium compounds or derivatives thereof, i.e. nearly 90% of the nitrogen fertilizers applied worldwide is in the $NH_4^+$ form (Subbarao et al., 2012, Advances in Agronomy, 114, 249-302) or are based on neem-extract, including various compounds such as neemoil-coated fertilizers, neem-coated fertilizers, nimincoated fertilizers and fertilizers with neem cake from the Indian neem tree (*Azadirachta indica*). This is, inter alia, due to the fact that $NH_4^+$ assimilation is energetically more efficient than assimilation of other nitrogen sources such as $NO_3^-$.

Moreover, being a cation, $NH_4^+$ is held electrostatically by the negatively charged clay surfaces and functional groups of soil organic matter. This binding is strong enough to limit $NH_4^+$-loss by leaching to groundwater. By contrast, $NO_3^-$, being negatively charged, does not bind to the soil and is liable to be leached out of the plants' root zone. In addition, nitrate may be lost by denitrification which is the microbiological conversion of nitrate and nitrite ($NO_2^-$) to gaseous forms of nitrogen such as nitrous oxide ($N_2O$) and molecular nitrogen ($N_2$).

However, ammonium ($NH_4^+$) compounds are converted by soil microorganisms to nitrates ($NO_3^-$) in a relatively short time in a process known as nitrification. The nitrification is carried out primarily by two groups of chemolithotrophic bacteria, ammonia-oxidizing bacteria (AOB) of the genus *Nitrosomonas* and *Nitrobacter*, which are ubiquitous component of soil bacteria populations. The enzyme, which is essentially responsible for nitrification is ammonia monooxygenase (AMO), which was also found in ammoniaoxidizing archaea (Subbarao et al., 2012, Advances in Agronomy, 114, 249-302).

The nitrification process typically leads to nitrogen leakage and environmental pollution. As a result of the various losses, approximately 50% of the applied nitrogen fertilizers is lost during the year following fertilizer addition (see Nelson and Huber; Nitrification inhibitors for corn production (2001), National Corn Handbook, Iowa State University).

As countermeasures the use of nitrification inhibitors, mostly together with fertilizers, was suggested. Suitable nitrification inhibitors include biological nitrification inhibitors (BNIs) such as linoleic acid, alpha-linolenic acid, methyl p-coumarate, methyl ferulate, MHPP, Karanjin, brachialacton or the p-benzoquinone sorgoleone (Subbarao et al., 2012, Advances in Agronomy, 114, 249-302). Further suitable nitrification inhibitors are synthetic chemical inhibitors such as Nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), or 2-sulfanilamidothiazole (ST) (Slangen and Kerkhoff, 1984, Fertilizer research, 5(1), 1-76).

EP 0 917 526 further mentions the use of polyacids to treat mineral fertilizers containing a nitrification inhibitor in order to improve the fixation of the nitrification inhibitors in the inorganic fertilizer. Moreover, the volatility of the nitrification inhibitor can be reduced.

However, many of these inhibitors only work sub-optimal or have undesirable side effects.

In view of this situation there is hence a continuous need for compositions that increase the health of plants. Healthier plants are desirable since they result among other in better crop yields and/or a better quality of the plants or crops. Healthier plants also better resist to biotic and abiotic stress. A better resistance to stress in turn allows reducing the quantity of pesticides, which also helps avoiding the development of resistances against the respective pesticides.

One object of the present invention is to provide a composition containing a nitrification inhibitor which increases the health of plants, and/or provides better crop yields and/or a better quality of the plants or crops, and/or shows a better resistance to stress, and/or allows the reduction of the quantity of pesticides used, and/or helps avoiding the development of resistances against the respective pesticides Another object of the present invention is to provide a composition containing the (thio)phosphoric acid triamide(s) (T) which—each preferably through a synergistic action—

(i) enhances the stability of the (thio)phosphoric acid triamide(s), and/or (ii) enhances the urease inhibiting effect of the (thio)phosphoric acid triamide(s), and/or (iii) enhances the yield increase effect of the (thio)phosphoric acid triamide(s), and/or (iv) has a relatively long storage life, particularly before being applied to or coated on nitrogen-containing fertilizers, and/or (v) reduces the emission of nitrous oxide from soils, and/or (vi) reduces the ammonia emission from soils, particularly when applied with urea-containing fertilizer on the same locus, (vii) is toxicologically unobjectionable, and/or (viii) does not adversely affect the urease-inhibiting effect and/or activity of the (thio)phosphoric acid triamide, and/or (ix) can be easily and safely packaged, transported and shipped, even in large quantities, and/or (x) can be easily and safely handled and applied for soil treatment, even in large quantities, and/or (xi) improves the nutrient use efficiency, and/or (xii) improves the delivery of the biopesticide to the plant, and/or (xiii) improves the plant growth (e.g. biomass, yield, root branching and length; compact growth in case of ornamental plants), and/or (xiv) enables a better developed root system, a larger leaf area, greener leaves, stronger shoots and/or (xv) improves the plant defense of the plants, and/or (xvi) improves the plant health of the plants, and/or (xvii) improves the quality of the plants, and/or (xviii) improves the storage or survivability of the biopesticide and/or prolong the availability of biopesticides to the plants, and/or (xix) enhances the biopesticidal effect of the biopesticide, and/or (xx) allows the reduction of the quantity of biopesticides used, and/or (xxi) increase the survivability rate of seedlings, for example transplanted seedlings, and/or (xxii) reduce or avoid unfavorable environmental or toxicological effects whilst still allowing effective pest control, and/or (xxiii) enable earlier seed germination and/or blooming.

The objects (xiii), (xiv), (xv), (xvi), (xvii) and (xxi) particularly pertains to such plants or seedlings wherein such plants or seedlings were, or the soil in which the such plants or seedlings were placed was subject to the application of compositon of the present invention.

The preferred objects of the present invention are (i), (ii), (v), (vi), (vii), (xi), (xii), (xiii), (xiv), (xv), (xvi), (xvii), (xviii), (xix), (xx), the more preferred objects of the present invention are (ii), (vi), (xii), (xiii), (xv), (xvi), (xix), and/or (xx), the most preferred objects of the present invention are (ii), (vi), (xvi), and/or (xix), the particularly preferred objects of the present invention are (xvi) and/or (xix).

The term "in a synergistic way" means that the composition comprising the (thio)phosphoric acid triamide (T) and a further compound can fulfil the one or more of the objects (i) to (xxvii) significantly better than the individual compounds—i.e. the (thio)phosphoric acid triamide (T) or said further compound—alone can do, and preferably, this better fulfilment of the objects by said composition compared to the individual compounds is evidenced by calculations according to Colby's formula, see Colby, S. R. (Calculating synergistic and antagonistic responses of herbicide Combinations", Weeds, 15, pp. 20-22, 1967)

The present invention addresses this need and relates to a combination of a novel nitrification inhibitor of formula I

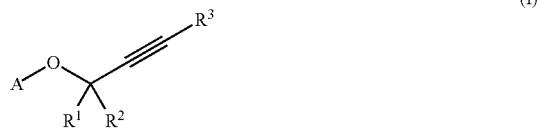
(I)

or a stereoisomer, salt, tautomer or N-oxide thereof, wherein

A is aryl or hetaryl, wherein the aromatic ring may in each case be unsubstituted or may be partially or fully substituted by substituents, which are independently of each other selected from $R^A$;

$R^1$ and $R^2$ are independently of each other selected from H and $C_1$-$C_2$-alkyl; and $R^3$ is H, $C_1$-$C_4$-haloalkyl, $C_1$-$C_4$-hydroxyalkyl, ethynylhydroxymethyl, phenylhydroxymethyl, or aryl, wherein the aromatic ring may be unsubstituted or may be partially or fully substituted by substituents, which are independently of each other selected from $R^B$;

and wherein $R^A$ is (i) halogen, CN, $NR^aR^b$, $OR^c$, $SR^c$, $C(=Y^1)R^c$, $C(=Y^1)OR^c$, $C(=Y^1)SR^c$, $C(=Y^1)NR^aR^b$, $Y^2C(=Y^1)R^c$, $Y^2C(=Y^1)OR^c$, $Y^2C(=Y^1)SR^c$, $Y^2C(=Y^1)NR^aR^b$, $Y^3Y^2C(=Y^1)R^c$, $NR^gN=C(R^d)(R^e)$, $C(=N-OR^c)R^g$, $C(=N-OR^c)R^g$, $C(=N-SR^c)R^g$, $C(=N-NR^aR^b)R^g$, $S(=O)_2R^f$, $NR^gS(=O)_2R^f$, $S(=O)_2Y^2C(=Y^1)R^c$, $S(=O)_2Y^2C(=Y^1)OR^c$, $S(=O)_2Y^2C(=Y^1)SR^c$, $S(=O)_2Y^2C(=Y^1)NR^aR^b$, $NO_2$, NON-CN, $C_1$-$C_6$-alkyl, $C_2$-$C_6$-alkenyl, $C_2$-$C_6$-alkynyl, $C_1$-$C_4$-haloalkyl, $C_1$-$C_4$-cyanoalkyl, $C_1$-$C_4$-hydroxyalkyl, $C_1$-$C_4$-alkoxy, $C_2$-$C_4$-alkynyl-$C_1$-$C_2$-hydroxyalkyl, $C_2$-$C_4$-alkynyloxy;

(ii) $C_1$-$C_4$-alkylene-$C(=Y^1)R^c$, $C_2$-$C_4$-alkenylene-$C(=Y^1)R^c$, $C_1$-$C_4$-alkylene-$C(=Y^1)OR^c$, $C_2$-$C_4$-alkenylene-$C(=Y^1)OR^c$, $C_1$-$C_4$-alkylene-$C(=Y^1)SR^c$, $C_2$-$C_4$-alkenylene-$C(=Y^1)SR^c$, $C_1$-$C_4$-alkylene-$C(=Y^1)NR^aR^b$, $C_2$-$C_4$-alkenylene-$C(=Y^1)NR^aR^b$, $C_1$-$C_4$-alkylene-$Y^2$-$C(=Y^1)R^c$, $C_2$-$C_4$-alkenylene-$Y^2$-$C(=Y^1)R^c$, $C_1$-$C_4$-alkylene-$NR^aR^b$, $C_2$-$C_4$-alkenylene-$NR^aR^b$, $C_1$-$C_4$-alkylene-$OR^c$, $C_2$-$C_4$-alkenylene-$OR^c$, $C_1$-$C_4$-alkylene-$SR^c$, $C_2$-$C_4$-alkenylene-$SR^c$, wherein the $C_1$-$C_4$-alkylene or $C_2$-$C_4$-alkenylene chain may in each case be unsubstituted or may be partially or fully substituted by $OR^g$, CN, halogen or phenyl;

(iii) aryl, aryl-$C_1$-$C_2$-alkyl, hetaryl or hetaryl-$C_1$-$C_2$-alkyl, wherein the aromatic ring of the aryl or hetaryl group may be unsubstituted or may be partially or fully substituted by substituents, which are independently of each other selected from $R^h$;

(iv) a 3- to 14-membered saturated or unsaturated carbocycle or heterocycle, which may contain 1, 2, or 3 heteroatoms which, independently of each other, are selected from $NR^{1b}$, O, and S, wherein S may be oxidized and/or wherein the carbocycle or heterocycle may be unsubstituted or may be partially or fully substituted by substituents which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$; or (v) L-B, wherein L is —$CH_2$—, —CH=CH—, —C≡C—, —C(=O)— or —CH=, and B is aryl or hetaryl, wherein the aromatic ring of the ary or hetaryl group may be unsubstituted or may be partially or fully substituted by substituents, which are independently of each other selected from $R^h$;

or a 3- to 14-membered saturated or unsaturated carbocycle or heterocycle, which may contain 1, 2, or 3 heteroatoms which, independently of each other, are selected from $NR^{1b}$, O, and S, wherein S may be oxidized and/or wherein the carbocycle or heterocycle may be unsubstituted or may be partially or fully substituted by substituents which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$; or (vi) two substituents $R^A$ together represent a carbocyclic or heterocyclic ring, which is fused to A and may contain 1, 2, or 3 heteroatoms which, independently of each other, are selected from $NR^{1c}$, O, and S, wherein S may be oxidized and/or wherein the carbocycle or heterocycle may be unsubstituted or may be partially or fully substituted by substituents which, independently of each other, are selected from $R^i$; and wherein $R^{1c}$ is H, $C_1$-$C_4$-alkyl, $C_2$-$C_4$-alkenyl, $C_3$-$C_6$-cycloalkyl, $C_3$-$C_6$-cycloalkylmethyl, $C_3$-$C_6$-heterocyclyl, $C_3$-$C_6$-heterocyclylmethyl or $OR^g$;

and wherein $R^B$ is NH—C(=O)—($C_1$-$C_4$-alkyl), NH—C(=O)—($C_2$-$C_4$-alkenyl), NH—C(=O)—($C_1$-$C_2$-alkoxy-$C_1$-$C_2$-alkyl), NH—C(=O)—($C_3$-$C_6$-cycloalkyl), NH—S(=O)$_2$—($C_1$-$C_4$-alkyl), or $NO_2$;

and wherein $Y^1$, $Y^2$ and $Y^3$ are independently of each other selected from O, S and $NR^{1a}$, wherein $R^{1a}$ is in each case independently H, $C_1$-$C_4$-alkyl, $C_2$-$C_4$-alkenyl, $C_3$-$C_6$-cycloalkyl, $C_3$-$C_6$-cycloalkylmethyl, $OR^g$, $SR^g$ or $NR^mR^n$;

$R^a$ and $R^b$ are independently of each other selected from
(i) H, $NR^jR^k$, $OR^l$, $SR^l$, $C_1$-$C_4$-alkyl, $C_2$-$C_4$-alkenyl, $C_2$-$C_4$-alkynyl, $C_1$-$C_4$-hydroxyalkyl, $C_1$-$C_4$-alkoxy, C(=$Y^1$)$R^l$, C(=$Y^1$)$OR^l$, C(=$Y^1$)$SR^l$, C(=$Y^1$)$NR^jR^k$, C(=$Y^1$)C(=$Y^2$)$R^l$, S(=O)$_2R^l$;
(ii) aryl or hetaryl, wherein the aromatic ring of the aryl or hetaryl group may be unsubstituted or may be partially or fully substituted by substituents, which are independently of each other selected from $R^h$; or $R^a$ and $R^b$ together with the nitrogen atom to which they are bound form
(iii) a hetaryl group which may be unsubstituted or may be partially or fully substituted by substituents, which are independently of each other selected from $R^h$; or
(iv) a 3- to 10-membered, saturated or unsaturated heterocycle, which may contain 1, 2, or 3 heteroatoms which, independently of each other, are selected from $NR^{1b}$, O, and S, wherein S may be oxidized and/or wherein the heterocycle may be unsubstituted or may be partially or fully substituted by substituents which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$;

$R^c$ is
(i) H, $C_1$-$C_4$-alkyl, $C_2$-$C_4$-alkenyl, $C_2$-$C_4$-alkynyl, C(=O)$OR^l$, C(=O)$SR^l$, C(=O)$NR^jR^k$;
(ii) $C_1$-$C_4$-alkylene-C(=O)$R^l$, $C_1$-$C_4$-alkylene-C(=O)$OR^l$, wherein the $C_1$-$C_4$-alkylene chain may in each case be unsubstituted or may be partially or fully substituted by $OR^g$, CN, halogen, or phenyl;
(iii) aryl, aryl-$C_1$-$C_2$-alkyl, hetaryl, or hetaryl-$C_1$-$C_2$-alkyl, wherein the aromatic ring of the aryl or hetaryl group may be unsubstituted or may be partially or fully substituted by substituents, which are independently of each other selected from $R^h$; or
(iv) a 3- to 10-membered saturated or unsaturated carbocycle or heterocycle, which may contain 1, 2, or 3 heteroatoms which, independently of each other, are selected from $NR^{1b}$, O, and S, wherein S may be oxidized and/or wherein the carbocycle or heterocycle may be unsubstituted or may be partially or fully substituted by substituents which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$;

$R^d$ and $R^e$ are independently selected from $C_1$-$C_4$-alkyl, $C_1$-$C_4$-haloalkyl, $NR^jR^k$, $OR^l$, $SR^l$, CN, C(=$Y^1$)$R^l$, C(=$Y^1$)$OR^l$, C(=$Y^1$)$SR^l$, or C(=$Y^1$)$NR^jR^k$;

$R^f$ is $C_1$-$C_4$-alkyl, $C_1$-$C_4$-haloalkyl, $NR^jR^k$, $OR^l$, $SR^l$, aryl or hetaryl, wherein the aromatic ring of the aryl or hetaryl group may be unsubstituted or may be partially or fully substituted by substituents, which are independently of each other selected from $R^h$;

$R^g$ is H or $C_1$-$C_4$-alkyl;

$R^h$ is halogen, CN, $NO_2$, $NR^jR^k$, $OR^l$, $SR^l$, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_2$-$C_4$-alkynyloxy, C(=$Y^1$)$R^l$, C(=$Y^1$)$OR^l$, C(=$Y^1$)$SR^l$, C(=$Y^1$)$NR^jR^k$, aryl, aryloxy, hetaryl and hetaryloxy;

$R^i$ is
(i) halogen, CN, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl;
(ii) =$NR^{1d}$, wherein $R^{1d}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$;
(iii) =O, =S, $NR^jR^k$, $OR^l$, $SR^l$, C(=$Y^1$)$R^l$, C(=$Y^1$)$OR^l$, C(=$Y^1$)$SR^l$, C(=$Y^1$)$NR^jR^k$;
(iv) aryl, aryl-$C_1$-$C_2$-alkyl, hetaryl, or hetaryl-$C_1$-$C_2$-alkyl, wherein the aromatic ring of the aryl or hetaryl group may be unsubstituted or may be partially or fully substituted by substituents, which are independently of each other selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$; or
(v) $C_3$-$C_6$-cycloalkyl, or 3- to 6-membered heterocyclyl, wherein the cycloalkyl ring or the heterocyclyl ring may be unsubstituted or may be partially or fully substituted by substituents, which are independently of each other selected from halogen, CN, $C_1$-$C_4$-alkyl, $OR^g$, and $SR^g$;

$R^j$ and $R^k$ are independently selected from H, $OR^g$, $SR^g$, C(=$Y^1$)$R^g$, C(=$Y^1$)$OR^g$, C(=$Y^1$)$SR^g$, C(=$Y^1$)$NR^mR^n$, $C_1$-$C_4$-alkyl, $C_2$-$C_4$-alkenyl, $C_2$-$C_4$-alkynyl, $C_1$-$C_4$-haloalkyl, aryl or hetaryl, wherein the aromatic ring of the aryl or hetaryl group may be unsubstituted or may be partially or fully substituted by substituents, which are independently selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$;

$R^l$ is H, $C_1$-$C_4$-alkyl, $C_2$-$C_4$-alkenyl, $C_2$-$C_4$-alkynyl, $C_1$-$C_4$-haloalkyl, C(=$Y^1$)$R^g$, C(=$Y^1$)$OR^g$, C(=$Y^1$)$SR^g$, C(=$Y^1$)$NR^mR^n$, aryl or hetaryl, wherein the aromatic ring of the aryl or hetaryl group may be unsubstituted or may be partially or fully substituted by substituents, which are independently selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$; and $R^m$ and $R^n$ are independently selected from H and $C_1$-$C_4$-alkyl; and a biopesticide.

The inventors surprisingly found that by applying the compound of formula I as defined herein above and of a biopesticide the nitrification of ammonium to nitrate could significantly be reduced, biotic stress could be reduced and in consequence the health of a plant could be increased.

The inventors surprisingly found that by applying the (thio)phosphoric acid triamide (T) as defined herein above and of a biopesticide the urease inhibiting effect of the (thio)phosphoric acid triamide(s) could be enhanced, biotic stress could be reduced and in consequence the health of a plant could be increased, also the biopesticidal activity of the biopesticide could be enhanced, and other objects as mentioned above under the list (i) to (xxviii) could be fulfilled preferably in a synergistic way.

The present invention relates in another aspect to the composition (Q) comprising a biopesticide and a (thio) phosphoric acid triamide according to the general formula (Ia)

$R^{a1}R^{a2}N\text{---}P(X)(NH_2)_2$ (Ia)

wherein
X is oxygen or sulfur;
$R^{a1}$ is a $C_1$ to $C_{20}$ alkyl, $C_3$ to $C_{20}$ cycloalkyl, $C_6$ to $C_{20}$ aryl, or dialkylaminocarbonyl group;
$R^{a2}$ is H, or
$R^{a1}$ and $R^{a2}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur,
and the present invention preferably relates to a composition (Q) comprising a biopesticide and a (thio)phosphoric acid triamide according to the general formula (Ia) and not comprising any nitrification inhibitor of the compound of formula I.

The "(thio)phosphoric acid triamide according to the general formula (Ia)" is also referred to as "(thio)phosphoric acid triamide (T)" or "(T)" in the present patent application. "wt. %" refers to "percent by weight".

The composition (Q) also includes kit-of-parts comprising a biopesticide and (T). Here, the term "kit-of-parts" is to be understood to denote a kit comprising at least two separate parts wherein each of the parts can be independently removed from the kit. A kit includes a box, a tool, a vessel, a container, a bag or any kit-like equipment. Also a kit whose separate parts are only together in this one kit for a extremely short period of time are regarded as kit-of-parts. Kit-of-parts are useful for the combined application (of the contents) of the separate parts of the kit.

The present invention relates in another aspect to the use of a composition (Q) comprising a biopesticide and a (thio)phosphoric acid triamide (T) for increasing the health of a plant, and the present invention preferably relates to the use of a composition (Q) comprising a biopesticide and a (thio)phosphoric acid triamide (T) and not comprising any nitrification inhibitor of the compound of formula I for increasing the health of a plant.

X in the general formula (Ia) is preferably sulfur.

$R^{a1}$ in the general formula (Ia) is preferably $C_1$-$C_{20}$-alkyl, more preferably $C_1$-$C_{10}$-alkyl, most preferably $C_2$-$C_7$ alkyl, for example $C_3$-$C_4$ alkyl. Examples of alkyl groups are methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isooctyl, nonyl, isononyl, decyl and isodecyl. Examples of cycloalkyl groups are cyclopropyl, cyclobutyl, cyclopentyl, cyclohexyl and cyclooctyl, examples of aryl groups are phenyl or naphthyl. Examples of heterocyclic radicals $R^{a1}R^{a2}N\text{---}$ are piperazinyl, morpholinyl, pyrrolyl, pyrazolyl, triazolyl, oxazolyl, thiazolyl or imidazolyl groups.

According to one embodiment, the (thio)phosphoric acid triamide (T) is preferably N-n-butylthiophosphoric acid triamide (NBPT) and/or N-n-propylthiophosphoric acid triamide (NPPT), more preferably NBPT. According to another embodiment, (T) is preferably NPPT. According to another embodiment, (T) is preferably LIMUS, i.e. a mixture of NBPT and NPPT with about NBPT at 63% and NPPT at 22%, secondary compounds at 10%, further secondary compounds such as amines below 4% and dimerease derivatives below 1%.

According to another embodiment, the composition (Q) comprises a biopesticide and at least two different (thio) phosphoric acid triamides (T) having structures of the general formula (Ia) and wherein said at least two different (thio)phosphoric acid triamides differ in a of radicals $R^{a1}$ or $R^{a2}$, and preferably, one of said at least two different (thio)phosphoric acid triamides is N-nbutylthiophosphoric acid triamide (NBPT), and more preferably, the other of said at least two different (thio)phosphoric acid triamides is selected from the group consisting of N-cyclohexyl-, N-pentyl-, N-isobutyl- and N-n-propylphosphoric acid triamide and -thiophosphoric acid triamide. More preferably, (Q) comprises a biopesticide, NBPT and NPPT. Particularly preferably, (Q) comprises a biopesticide, NBPT and NPPT, wherein NBPT is present in amounts of from 1 to 99.99 wt. %, more preferably from 10 to 99.9 wt. %, most preferably from 20 to 99 wt. %, particularly preferably from 30 to 98 wt. %, more particularly preferably from 40 to 95 wt. %, most particularly preferably from 50 to 90 wt. %, especially from 60 to 85 wt. %, especially preferably from 72 to 80 wt. %, for example from 74 to 77 wt. %, in each case based on the total weight of the (thio)phosphoric acid triamides (T) contained in the composition (Q).

Generally, the (thio)phosphoric acid triamides (T) can be contained in varying amounts in the composition (Q). Preferably, the amount of (T) is not more than 95 wt. % (wt. % stands for "percent by weight"), more preferably not more than 90 wt. %, most preferably not more than 85 wt. %, more particularly preferably not more than 75 wt. %, most particularly preferably not more than 65 wt. %, particularly not more than 55 wt. %, especially not more than 45 wt. % for example not more than 35 wt. %, based on the total weight of the composition (Q). Preferably, the amount of (T) is at least 1 wt. %, more preferably at least 4 wt. %, most preferably at least 14 wt. %, more particularly preferably at least 24 wt. %, most particularly preferably at least 34 wt. %, particularly at least 44 wt. %, especially at least 54 wt. %, for example at least 64 wt. %, based on the total weight of the composition (Q).

According to another embodiment, the composition (Q) preferably does not comprise any nitrification inhibitor of the compound of formula I.

Thus, in one aspect the present invention relates to the use of combination of a biopesticide and a nitrification inhibitor for increasing the health of a plant, wherein said nitrification inhibitor is a compound of formula I as defined herein above.

Thus, in one aspect the present invention relates to the use of combination of a biopesticide and (T) for increasing the health of a plant.

In a preferred embodiment of said use, in said compound of formula I, A is phenyl or a 5- or 6-membered hetaryl, wherein the aromatic ring may in each case be unsubstituted or may be partially or fully substituted by substituents, which are independently of each other selected from $R^4$.

In another preferred embodiment of said use, in said compound of formula I, $R^1$ and $R^2$ both represent hydrogen.

In yet another preferred embodiment of said use, in said compound of formula I, $R^3$ is hydrogen, $C_1$-$C_4$-haloalkyl or ethinylhydroxymethyl, and preferably $R^3$ is hydrogen.

In still another preferred embodiment of said use, in said compound of formula I, $R^4$, if present, is
(i) halogen, CN, $NR^aR^b$, $OR^c$, $C(=Y^1)R^c$, $C(=Y^1)OR^c$, $C(=Y^1)SR^c$, $C(=Y^1)NR^aR^b$, $Y^2C(=Y^1)R^c$, $Y^2C(=Y^1)NR^aR^b$, $NR^gN=C(R^d)(R^e)$, $S(=O)_2R^f$, $NO_2$,

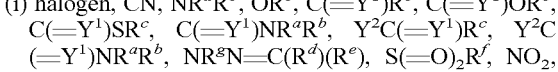

$C_1$-$C_6$-alkyl, $C_2$-$C_6$-$C_1$-$C_4$-haloalkyl, $C_1$-$C_4$-alkoxy, $C_2$-$C_4$-alkynyl-$C_1$-$C_2$-hydroxyalkyl, $C_2$-$C_4$-alkynyloxy;

(ii) $C_2$-$C_4$-alkenylene-C(=Y$^1$)R$^c$, $C_2$-$C_4$-alkenylene-Y$^2$—C(=Y$^1$)R$^c$, wherein the $C_1$-$C_4$-alkylene or $C_2$-$C_4$-alkenylene chain may in each case be unsubstituted or may be partially or fully substituted by CN or halogen;

(iii) aryl, wherein the aromatic ring of the aryl group may be unsubstituted or may be partially or fully substituted by substituents, which are independently of each other selected from R$^h$; or (iv) a 3- to 14-membered saturated or unsaturated heterocycle, which may contain 1, 2, or 3 heteroatoms which, independently of each other, are selected from NR$^{1b}$, O, and S, wherein S may be oxidized and/or wherein the heterocycle may be unsubstituted or may be partially or fully substituted by substituents which, independently of each other, are selected from R$^i$; and wherein R$^{1b}$ is H, $C_1$-$C_4$-alkyl, $C_2$-$C_4$-alkenyl, $C_3$-$C_6$-cycloalkyl, $C_3$-$C_6$-cycloalkylmethyl, or OR$^g$.

In a further preferred embodiment of said use, the biopesticide is at least one biopesticide selected form the group of biopesticides comprising:

aluminium silicate,
an *Agrobacterium* species such as *Agrobacterium radiobacter* K1026, or *A. radiobacter* K84,
an *Ampelomyces* species such as *Ampelomyces quisqualis* M-10,
an *Ascophyllum nodosum* (Norwegian kelp, Brown kelp) extract or filtrate,
an *Aspergillus* species such as *Aspergillus flavus* NRRL 21882,
mixtures of *Aureobasidium pullulans* DSM 14940 and DSM 14941,
an *Azospirillum* species such as *Azospirillum amazonense* BR 11140 (SpY2T), *A. brasilense* AZ39, *A. brasilense* XOH (B.1), *A. brasilense* BR 11002 (B.2), *A. brasilense* BR 11005 (B.3), *A. brasilense* strains Ab-V5 and Ab-V6 (B.4), or *A. lipoferum* BR 11646,
a *Bacillus amyloliquefaciens* microorganism such as *Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MB1600 (B.9),
a *Bacillus cereus* microorganism such as *B. cereus* CNCM I-1562 (B.10),
a *Bacillus firmus* microorganism such as *B. firmus* CNCM I-1582 (B.11),
a *Bacillus pumilus* microorganism such as *B. pumilus* GB34, *B. pumilus* KFP9F (B.12), *B. pumilus* QST 2808 (B.13),
a *Bacillus subtilis* microorganism such as *B. subtilis* CX-9060, *B. subtilis* GB03, *B. subtilis* GB07, *B. subtilis* QST-713, *B. subtilis* var. *amyloliquefaciens* FZB24, *B. subtilis* var. *amyloliquefaciens* D747,
a *Bacillus thuringiensis* microorganism such as *B. thuringiensis* ssp. *aizawai* ABTS-1857, *B. t.* ssp. *aizawai* SAN 401 I, ABG-6305 and ABG-6346, *Bacillus t.* ssp. *israelensis* AM65-52, *Bacillus thuringiensis* ssp. *kurstaki* SB4, *B. t.* ssp. *kurstaki* ABTS-351 identical to HD-1, *B. t.* ssp. *kurstaki* EG 2348, *B. t.* ssp. *tenebrionis* DSM 2803, *B. t.* ssp. *tenebrionis* NB-125, *B. t.* ssp. *tenebrionis* NB-176,
a *Beauveria* species such as *Beauveria bassiana* ATCC 74040, *B. bassiana* DSM 12256, *B. bassiana* GHA, or *B. bassiana* PPRI 5339, *B. brongniartii*,
a *Bradyrhizobium* species such as *Bradyrhizobium japonicum* (B.14),
a *Burkholderia* species such as *Burkholderia* sp. A396,
a *Candida* species such as *Candida oleophila* 1-182, *C. oleophila* strain O, *Candida saitoana*,
chitosan,
a *Clonostachys* species such as *Clonostachys rosea f. catenulata*,
a *Chromobacterium* species such as *Chromobacterium subtsugae* PRAA4-1,
a *Coniothyrium* species such as *Coniothyrium minitans* CON/M/91-08 (B.15),
a *Cryphonectria* species such as *Cryphonectria parasitica*,
a *Cryptococcus* species such as *Cryptococcus albidus*,
*Cryptophlebia leucotreta* granulovirus (CrleGV),
*Cydia pomonella* granulovirus (CpGV) V03, CpGV V22,
a *Delftia* species such as *Delftia acidovorans* RAY$^{209}$,
a *Dilophosphora* species such as *Dilophosphora alopecuri*,
*Ecklonia maxima* (kelp) extract,
a *Flavobacterium* species such as *Flavobacterium* sp. H492,
formononetin,
a *Fusarium* species such as *Fusarium oxysporum*,
a *Glomus* species such as *Glomus intraradices* RTI-801,
grapefruit seeds and pulp extract,
harpin (alpha-beta) protein,
*Helicoverpa armigera* nucleopolyhedrovirus (HearNPV),
a *Heterorhabditis* species such as *Heterorhabditis bacteriophaga*,
an *Isaria* species such as *Isaria fumosorosea* Apopka-97,
cis-jasmone,
laminarin,
a *Lecanicillium* species such as *Lecanicillium longisporum* KV42 and KV71, or *L. muscarium* KV01 (formerly *Verticillium lecanii*),
a *Lysobacter* species such as *Lysobacter antibioticus* 13-1, *L. antibioticus* HS124, or *L. enzymogenes* 3.1T8,
a *Metarhizium* species such as *Metarhizium anisopliae* var. *acridum* IMI 330189, *M. a.* var. *acridum* FI-985, *M. anisopliae* FI-1045, *M. anisopliae* F52, or *M. anisopliae* ICIPE 69,
a *Metschnikowia* species such as *Metschnikowia fructicola*,
a *Microdochium* species such as *Microdochium dimerum*,
a *Microsphaeropsis* species such as *Microsphaeropsis ochracea* P130A,
a *Muscodor* species such as *Muscodor albus* QST 20799, or *M. albus* SA-13;
Neem oil,
a *Nomuraea* species such as *Nomuraea rileyi* strains SA86101, GU87401, SR86151, CG128 and VA9101,
a *Paecilomyces* species such as *Paecilomyces fumosoroseus* FE 9901, *P. lilacinus* 251, *P. lilacinus* DSM 15169, or *P. lilacinus* BCP2,
a mixture of *Paenibacillus alvei* NAS6G6 and *Bacillus pumilus*,
a *Pantoea* species such as *Pantoea vagans* (formerly *agglomerans*) C9-1,
a *Pasteuria* species such as *Pasteuria* sp. ATCC PTA-9643, *P. nishizawae* Pn1 (B.16), *Pasteuria* sp. ATCC SD-5832, *P. nishizawae*, *P. penetrans*, *P. ramose*, *P. thornea*, *P. usgae*,
a *Penicillium* species such as *Penicillium bilaiae* (B.17),
a *Phlebiopsis* species such as *Phlebiopsis gigantea*, a *Pichia* species such as *Pichia anomala* WRL-076, potassium bicarbonate, potassium silicate, a *Pseudozyma* species such as *Pseudozyma flocculosa* PF-A22 UL, a *Pseudomonas* species such as *Pseudomonas* sp. DSM 13134, *P. chloraphis* MA 342, or *P. fluorescens* CL 145A (B.18), a *Pythium* species such as *Pythium oligandrum* DV 74, *Reynoutria sachlinensis* extract, a *Rhizobium* species such as *Rhizobium leguminosarum* bv. *Phaseoli* (B.19), *R. l.* bv. *trifolii* RP113-7 (B.20), *R. l.* bv. *viciae* P1NP3Cst (B.21), *R. l.* bv. *viciae* SU303 (B.22), *R. l.* bv. *viciae* WSM1455 (B.23), or *R. tropici* SEMIA 4080 (B.24), a *Sinorhizobium* species such as *Sinorhizobium meliloti* MSDJ0848 (B.25), a *Sphaerodes* species such as *Sphaerodes mycoparasitica* IDAC 301008-01,

*Spodoptera littoralis* nucleopolyhedrovirus, a *Steinernema* species such as *Steinernema carpocapsae, S. feltiae, S. kraussei* L137, a *Streptomyces* species such as *Streptomyces griseoviridis* K61, *S. lydicus* WYEC 108, or *S. violaceusniger* YCED-9, a *Talaromyces* species such as *Talaromyces flavus* V117b, a *Trichoderma* species such as *Trichoderma asperellum* SKT-1, *T. asperellum* ICC 012, *T. atroviride* LC52, *T. atroviride* CNCM 1-1237, *T. fertile* JM41R (B.26), *T. gamsii* ICC 080, *T. harzianum* T-22, *T. harzianum* TH 35, *T. harzianum* T-39, mixture of *T. harzianum* and *T. viride, T. harzianum* ICC012 and *T. viride* ICC080, *T. polysporum* and *T. harzianum, T. stromaticum, T. virens* G1-3, *T. virens* GL-21, *T. virens* G-41, *T. viride*, or *T. viride* TV1; and

*Ulocladium oudemansii* HRU3.

In a particularly preferred embodiment, said biopesticide is A *Azospirillum brasilense* XOH (B.1), *A. brasilense* BR 11002 (B.2), *A. brasilense* BR 11005 (B.3), *A. brasilense* strains Ab-V5 and Ab-V6 (B.4), *Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MBI600 (B.9), *B. cereus* CNCM 1-1562 (B.10), *B. firmus* CNCM 1-1582 (B.11), *Bacillus pumilus* KFP9F (B.12), *B. pumilus* QST 2808 (B.13), *Bradyrhizobium japonicum* (B.14), *Coniothyrium minitans* CON/M/91-08 (B.15), *Pasteuria nishizawae* Pn1 (B.16), *Penicillium bilaiae* (B.17), *P. fluorescens* CL 145A (B.18), *Rhizobium leguminosarum* bv. *Phaseoli* (B.19), *R. l.* bv. *trifolii* RP113-7 (B.20), *R. l.* bv. *viciae* P1NP3Cst (B.21), *R. l.* bv. *viciae* SU303 (B.22), *R. l.* bv. *viciae* WSM1455 (B.23), *R. tropici* SEMIA 4080 (B.24), *Sinorhizobium meliloti* MSDJ0848 (B.25), *Trichoderma fertile* JM41R (B.26), cis-jasmone (B.27), methyl jasmonate (B.28), or Neem oil (B.29).

In a further preferred embodiment, said combination of a nitrification inhibitor or (T) and a biopesticide further comprises a fertilizer.

In a further aspect the present invention relates to a composition for increasing the health of a plant comprising at least one nitrification inhibitor as defined herein above and at least one biopesticide as defined herein above.

In a further aspect the present invention relates to a composition for increasing the health of a plant comprising at least one (thio)phosphoric acid triamide (T) and at least one biopesticide as defined herein above.

In a preferred embodiment said agricultural compositon additionally comprises at least one carrier.

In another aspect the present invention relates to a method for increasing the health of a plant, comprising treating a plant growing on soil or soil substituents and/or the locus or soil or soil substituents where the plant is growing or is intended to grow with a combination of (T) or at least one nitrification inhibitor and at least one biopesticide as defined herein above, or a composition as defined herein above.

In a preferred embodiment of the method the plant and/or the locus or soil or soil substituents where the plant is growing or is intended to grow is additionally provided with a fertilizer.

In a further preferred embodiment of the method, the application of said nitrification inhibitor (A) and of said biopesticide (B), and optionally of said fertilizer (C) is carried out simultaneously or with a time lag.

In a further preferred embodiment of the method, the application of (T) and of said biopesticide (B), and optionally of said fertilizer (C) is carried out simultaneously or with a time lag.

In a particularly preferred embodiment, said time lag is an interval of 1 day, 2 days, 3 days, 1 week, 2 weeks or 3 weeks.

In a further preferred embodiment of a use, composition or method of the invention as mentioned herein above, said increase of the health of a plant is reflected by an increase in growth of root and shoot, an overall increase in productivity and/or a faster and more efficient development of the plant.

In a further preferred embodiment of the use, composition or method of the invention as mentioned herein above, said plant is an agricultural plant such as wheat, barley, oat, rye, soybean, corn, oilseed rape, canola, sunflower, cotton, sugar cane, sugar beet, rice or a vegetable such as spinach, lettuce, asparagus, or cabbages; or sorghum; a silvicultural plant; an ornamental plant; or a horticultural plant, each in its natural or in a genetically modified form.

In addition, a process for treating the soil comprising applying the compositions of the invention into the soil in-furrow and/or as side dress and/or as broadcast was found.

The present invention relates in one aspect to the use of a biopesticide and (T) or a nitrification inhibitor for increasing the health of a plant, wherein said nitrification inhibitor is a compound of formula I as defined herein.

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "nitrification inhibitor" is to be understood in this context as a chemical substance which slows down or stops the nitrification process. Nitrification inhibitors accordingly retard the natural transformation of ammonium into nitrate, by inhibiting the activity of bacteria such as *Nitrosomonas* spp. The term "nitrification" as used herein is to be understood as the biological oxidation of ammonia ($NH_3$) or ammonium ($NH_4^+$) with oxygen into nitrite ($NO_2^-$) followed by the oxidation of these nitrites into nitrates ($NO_3^-$) by microorganisms. Besides nitrate ($NO_3^-$) nitrous oxide is also produced though nitrification. Nitrification is an important step in the nitrogen cycle in soil. The inhibition of nitrification may thus also reduce $NO_2$ losses.

The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

Salts of the compounds of the formula I are preferably agriculturally acceptable salts. They can be formed in a customary manner, e.g. by reacting the compound with an acid of the anion in question if the compound of formula I has a basic functionality. Agriculturally useful salts of the compounds of formula I encompass especially the acid addition salts of those acids whose cations and anions, respectively, have no adverse effect on the mode of action of the compounds of formula I. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formula I with an acid of the corresponding anion, preferably of hydrochloric acid, hydrobromic acid, sulfuric acid, phosphoric acid or nitric acid.

The term "N-oxide" includes any compound of formula I which has at least one tertiary nitrogen atom that is oxidized to an N-oxide moiety.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "cyanoalkyl" as used herein denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with cyano groups. Preferred cyanoalkyl moieties are selected from $C_1$-$C_4$-cyanoalkyl, more preferably from $C_1$-$C_3$-cyanooalkyl or $C_1$-$C_2$-cyanoalkyl.

The term "hydroxyalkyl" as used herein denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with hydroxy groups. Preferred hydroxyalkyl moieties are selected from $C_1$-$C_4$-hydroxyalkyl, more preferably from $C_1$-C-hydroxyalkyl or $C_1$-$C_2$-hydroxyalkyl. Preferred hydroxyalkyl moieties are selected from hydroxymethyl, dihydroxymethyl, trihydroxymethyl, 1-hydroxyethyl and 2-hydroxyethyl.

The term "ethynylhydroxymethyl" as used herein refers to the following substituent.

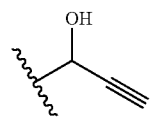 [SMILES: *C(O)C#C]

The term "phenylhydroxymethyl" as used herein refers to the following substituent.

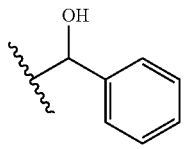

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert-butyloxy, and the like.

The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "alkylene" as used herein and in the moieties of e.g. $C_1$-$C_4$-alkylene-C(=$Y^1$)$R^c$, $C_1$-$C_4$-alkylene-C(=$Y^1$)O$R^c$, $C_1$-$C_4$-alkylene-C(=$Y^1$)S$R^c$, $C_1$-$C_4$-alkylene-C(=$Y^1$)N$R^a$N$R^b$, $C_1$-$C_4$-alkylene-$Y^2$—C(=$Y^1$)$R^c$, $C_1$-$C_4$-alkylene-N$R^a$$R^b$, $C_1$-$C_4$-alkylene-O$R^c$, and $C_1$-$C_4$-alkylene-S$R^c$ refers to a straight-chain or branched alkylene group having usually from 1 to 10 carbon atoms, frequently from 1 to 6 carbon atoms, preferably 1 to 4 carbon atoms, more preferably from 1 to 3 carbon atoms. Preferably, said alkenylene group connects a substituent, such as C(=$Y^1$)$R^c$, C(=$Y^1$)O$R^c$ C(=$Y^1$)S$R^c$, C(=$Y^1$)N$R^a$N$R^b$, $Y^2$—C(=$Y^1$)$R^c$, N$R^a$$R^b$, O$R^c$, S$R^c$, with the remainder of the molecule.

The term "alkenyl" as used herein denotes in each case an at least singly unsaturated hydrocarbon radical, i.e. a hydrocarbon radical having at least one carbon-carbon double bond, having usually 2 to 10, frequently 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkenylene" as used herein and in the moieties of e.g. $C_2$-$C_4$-alkenylene-C(=$Y^1$)$R^c$, $C_2$-$C_4$-alkenylene-C(=$Y^1$)O$R^c$, $C_2$-$C_4$-alkenylene-C(=$Y^1$)S$R^c$, $C_2$-$C_4$-alkenylene-C(=$Y^1$)N$R^a$N$R^b$, $C_2$-$C_4$-alkenylene-$Y^2$—C(=$Y^1$)$R^c$, $C_2$-$C_4$-alkenylene-N$R^a$$R^b$, $C_2$-$C_4$-alkenylene-O$R^c$, and $C_2$-$C_4$-alkenylene-S$R^c$ refers to a straight-chain or branched alkenylene group, which is at least singly unsaturated, and has usually from 2 to 10 carbon atoms, frequently from 2 to 6 carbon atoms, preferably 2 to 4 carbon atoms, more preferably from 2 to 3 carbon atoms. Preferably, said alkenylene group connects a substituent, such as C(=$Y^1$)$R^c$, C(=$Y^1$)O$R^c$, C(=$Y^1$)S$R^c$, C(=$Y^1$)N$R^a$N$R^b$, $Y^2$—C(=$Y^1$)$R^c$, N$R^a$$R^b$, O$R^c$, S$R^c$, with the remainder of the molecule.

The term "alkynyl" as used herein denotes in each case a hydrocarbon radical having at least one carbon-carbon triple bond and having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "alkynylalkyl" as used herein refers to alkyl usually comprising 1 to 10, frequently 1 to 4, preferably 1 to 2 carbon atoms, wherein 1 carbon atom carries an alkynyl radical usually comprising 2 to 4, preferably 2 or 3 carbon atoms as defined above.

The term "alkynylhydroxyalkyl" as used herein refers to an hydroxyalkyl as defined above usually comprising 1 to 10, frequently 1 to 4, preferably 1 to 2 carbon atoms, wherein 1 carbon atom carries an alkynyl radical usually comprising 2 to 4, preferably 2 or 3 carbon atoms as defined above. An exemplary alkynylhydroxyalkyl is ethynyl hydroxymethyl.

The term "alkynyloxy" as used herein denotes in each case an alkynyl group which is bound to the remainder of the molecule via an oxygen atom and has usually from 2 to 6 carbon atoms, frequently from 2 to 4 carbon atoms, preferably 2 to 3 carbon atoms.

The term "cycloalkyl" as used herein and in the cycloalkyl moieties of cycloalkoxy and cycloalkylmethyl denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "cycloalkylalkyl" refers to a cycloalkyl group as defined above which is bound via an alkyl group, such as a $C_1$-$C_5$-alkyl group or a $C_1$-$C_4$-alkyl group, in particular a methyl group (=cycloalkylmethyl), to the remainder of the molecule.

The term "cycloalkenyl" as used herein denotes in each case a monocyclic singly unsaturated non-aromatic radical having usually from 5 to 10 or from 3 to 8 carbon atoms, including e.g. cycloheptenyl or cyclooctenyl.

The term "heterocyclyl" or "heterocycle" includes in general 3- to 14-membered, preferably 3- to 10-membered, more preferably 5-, or 6-membered non-aromatic radicals with at least one heteroatom. The term "heterocyclyl" or "heterocycle" refers to monocyclic, bicyclic or tricyclic heterocyclic non-aromatic radicals. The term "heterocyclyl" or "heterocycle" also includes bicyclic or tricyclic radicals, which comprise a non-aromatic ring and a fused aryl or hetaryl ring. Particularly preferred are 5- and 6-membered monocyclic heterocyclic non-aromatic radicals. The heterocyclic radicals usually comprise 1, 2, 3, 4 or 5, preferably 1, 2 or 3 heteroatoms selected from N, O and S as ring members, where S-atoms as ring members may be present as S, SO or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxid (Soxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahyd roth iopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic rings also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like. Particularly preferred are also bicyclic 8- to 10-membered heterocyclic radicals comprising as ring members 1, 2, 3, 4 or 5, preferably 1, 2 or 3 heteroatoms selected from N, O and S members, where S-atoms as ring members may be present as S, SO or $SO_2$. Preferably, said bicyclic 8- to 10-membered heterocyclic radicals comprise a 5- or 6-membered non-aromatic ring as defined above, which is fused to an aryl or hetaryl ring or to another heterocyclic ring. These fused heterocyclyl radicals may be bound to the remainder of the molecule via any ring atom of the 5- or 6-membered ring or the fused ring.

The term "heterocyclylalkyl" refers to heterocyclyl as defined above, which is bound via a $C_1$-$C_5$-alkyl group or a $C_1$-$C_4$-alkyl group, in particular a methyl group (=heterocyclylmethyl), to the remainder of the molecule.

The term "carbocyclyl" or "carbocycle" includes in general 3- to 14-membered, preferably 3- to 10-membered, more preferably 5- or 6-membered non-aromatic radicals. The term "carbocyclyl" or "carbocycle" may refer to monocyclic, bicyclic or tricyclic carbocyclic non-aromatic radicals.

Preferred carbocycles are cycloalkyl and cycloalkenyl groups having from 3 to 10, preferably 5 or 6 carbon atoms.

Particularly preferred are also bicyclic 8- to 10-membered carbocyclic radicals, wherein a 5- or 6-membered non-aromatic ring is fused to an aryl ring or another carbocyclic ring. These fused carbocyclyl radicals may be bonded to the remainder of the molecule via any ring atom of the 5- or 6-membered ring or the fused ring.

The term "carbocyclylalkyl" refers to carbocyclyl as defined above which is bound via a $C_1$-$C_5$-alkyl group or a $C_1$-$C_4$-alkyl group, in particular a methyl group (=carbocyclylmethyl), to the remainder of the molecule.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 13-membered, preferably 8- to 10 membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The term "hetarylalkyl" refers to hetaryl as defined above which is bound via a $C_1$-$C_5$-alkyl group or a $C_1$-$C_4$-alkyl group, in particular a methyl group (=hetarylmethyl),to the remainder of the molecule.

The term "hetaryloxy" refers to hetaryl as defined above, which is bound via an oxygen atom to the remainder of the molecule.

The term "aryl" includes monocyclic, bicyclic or tricyclic aromatic radicals comprising 6 to 14 carbon atoms, preferably 6 or 10 carbon atoms, more preferably 6 carbon atoms. Exemplary aryl radicals include anthracenyl, naphthalenyl and phenyl. A preferred aryl radical is phenyl.

The term "arylalkyl" refers to aryl as defined above which is bound via a $C_1$-$C_5$-alkyl group or a $C_1$-$C_4$-alkyl group, in particular a methyl group (=arylmethyl), to the remainder of the molecule. A preferred arylalkyl group is phenylmethyl, i.e. benzyl.

The term "aryloxy" refers to aryl as defined above, which is bound via an oxygen atom to the remainder of the molecule. A preferred aryloxy group is e.g. benzyloxy.

As has been set out above, the present invention concerns in one aspect the use of a nitrification inhibitor for reducing nitrification, wherein said nitrification inhibitor is a compound of formula I

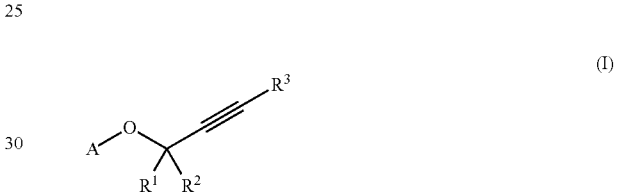

(I)

or a stereoisomer, salt, tautomer or N-oxide thereof, wherein

A is aryl or hetaryl, wherein the aromatic ring may in each case be unsubstituted or may be partially or fully substituted by substituents, which are independently of each other selected from $R^A$;

$R^1$ and $R^2$ are independently of each other selected from H and $C_1$-$C_2$-alkyl; and $R^3$ is H, $C_1$-$C_4$-haloalkyl, $C_1$-$C_4$-hydroxyalkyl, ethynylhydroxymethyl, phenylhydroxymethyl, or aryl, wherein the aromatic ring may be unsubstituted or may be partially or fully substituted by substituents, which are independently of each other selected from $R^B$;

and wherein $R^A$ is (i) halogen, CN, $NR^aR^b$, $OR^c$, $SR^c$, $C(=Y^1)R^c$, $C(=Y^1)OR^c$, $C(=Y^1)SR^c$, $C(=Y^1)NR^aR^b$, $Y^2C(=Y^1)R^c$, $Y^2C(=Y^1)OR^c$, $Y^2C(=Y^1)SR^c$, $Y^2C(=Y^1)NR^aR^b$, $Y^3Y^2C(=Y^1)R^c$, $NR^gN=C(R^d)(R^e)$, $C(=N-OR^c)R^g$, $C(=N-OR^c)R^g$, $C(=N-SR^c)R^g$, $C(=N-NR^aR^b)R^g$, $S(=O)_2R^f$, $NR^gS(=O)_2R^f$, $S(=O)_2Y^2C(=Y^1)R^c$, $S(=O)_2Y^2C(=Y^1)OR^c$, $S(=O)_2Y^2C(=Y^1)SR^c$, $S(=O)_2Y^2C(=Y^1)NR^aR^b$, $NO_2$, $NON-CN$, $C_1$-$C_6$-alkyl, $C_2$-$C_6$-alkenyl, $C_2$-$C_6$-alkynyl, $C_1$-$C_4$-haloalkyl, $C_1$-$C_4$-cyanoalkyl, $C_1$-$C_4$-hydroxyalkyl, $C_1$-$C_4$-alkoxy, $C_2$-$C_4$-alkynyl-$C_1$-$C_2$-hydroxyalkyl, $C_2$-$C_4$-alkynyloxy;

(ii) $C_1$-$C_4$-alkylene-$C(=Y^1)R^c$, $C_2$-$C_4$-alkenylene-$C(=Y^1)R^c$, $C_1$-$C_4$-alkylene-$C(=Y^1)OR^c$, $C_2$-$C_4$-alkenylene-$C(=Y^1)OR^c$, $C_1$-$C_4$-alkylene-$C(=Y^1)SR^c$, $C_2$-$C_4$-alkenylene-$C(=Y^1)SR^c$, $C_1$-$C_4$-alkylene-$C(=Y^1)NR^aNR^b$, $C_2$-$C_4$-alkenylene-$C(=Y^1)NR^aNR^b$, $C_1$-$C_4$-alkylene-$Y^2-C(=Y^1)R^c$, $C_2$-$C_4$-alkenylene-$Y^2-C(=Y^1)R^c$, $C_1$-$C_4$-alkylene-$NR^aR^b$, $C_2$-$C_4$-alkenylene-NR$^a$R$^b$, C$_1$-C$_4$-alkylene-OR$^c$, C$_2$-C$_4$-alkenylene-OR$^c$, C$_1$-C$_4$-alkylene-SR$^c$, C$_2$-C$_4$-alkenylene-SR$^c$, wherein the C$_1$-C$_4$-alkylene or C$_2$-C$_4$-alkenylene chain may in each case be unsubstituted or may be partially or fully substituted by OR$^g$, CN, halogen or phenyl;

(iii) aryl, aryl-C$_1$-C$_2$-alkyl, hetaryl or hetaryl-C$_1$-C$_2$-alkyl, wherein the aromatic ring of the aryl or hetaryl group may be unsubstituted or may be partially or fully substituted by substituents, which are independently of each other selected from R$^h$;

(iv) a 3- to 14-membered saturated or unsaturated carbocycle or heterocycle, which may contain 1, 2, or 3 heteroatoms which, independently of each other, are selected from NR$^{1b}$, O, and S, wherein S may be oxidized and/or wherein the carbocycle or heterocycle may be unsubstituted or may be partially or fully substituted by substituents which, independently of each other, are selected from R$^i$; and wherein R$^{1b}$ is H, C$_1$-C$_4$-alkyl, C$_2$-C$_4$-alkenyl, C$_3$-C$_6$-cycloalkyl, C$_3$-C$_6$-cycloalkylmethyl, or OR$^g$; or (v) L-B, wherein
L is —CH$_2$—, —CH=CH—, —C≡C—, —C(=O)— or —CH=, and
B is aryl or hetaryl, wherein the aromatic ring of the ary or hetaryl group may be unsubstituted or may be partially or fully substituted by substituents, which are independently of each other selected from R$^h$; or
a 3- to 14-membered saturated or unsaturated carbocycle or heterocycle, which may contain 1, 2, or 3 heteroatoms which, independently of each other, are selected from NR$^{1b}$, O, and S, wherein S may be oxidized and/or wherein the carbocycle or heterocycle may be unsubstituted or may be partially or fully substituted by substituents which, independently of each other, are selected from R$^1$; and wherein R$^{1b}$ is H, C$_1$-C$_4$-alkyl, C$_2$-C$_4$-alkenyl, C$_3$-C$_6$-cycloalkyl, C$_3$-C$_6$-cycloalkylmethyl, or OR$^g$; or (vi) two substituents R$^A$ together represent a carbocyclic or heterocyclic ring, which is fused to A and may contain 1, 2, or 3 heteroatoms which, independently of each other, are selected from NR$^{1c}$, O, and S, wherein S may be oxidized and/or wherein the carbocycle or heterocycle may be unsubstituted or may be partially or fully substituted by substituents which, independently of each other, are selected from R$^i$; and wherein R$^{1c}$ is H, C$_1$-C$_4$-alkyl, C$_2$-C$_4$-alkenyl, C$_3$-C$_6$-cycloalkyl, C$_3$-C$_6$-cycloalkylmethyl, C$_3$-C$_6$-heterocyclyl, C$_3$-C$_6$-heterocyclylmethyl or OR$^g$;

and wherein
R$^B$ is NH—C(=O)—(C$_1$-C$_4$-alkyl), NH—C(=O)—(C$_2$-C$_4$-alkenyl), NH—C(=O)—(C$_1$-C$_2$-alkoxy-C$_1$-C$_2$-alkyl), NH—C(=O)—(C$_3$-C$_6$-cycloalkyl), NH—S(=O)$_2$—(C$_1$-C$_4$-alkyl), or NO$_2$;

and wherein
Y$^1$, Y$^2$ and Y$^3$ are independently of each other selected from O, S and NR$^{1a}$, wherein R$^{1a}$ is in each case independently H, C$_1$-C$_4$-alkyl, C$_2$-C$_4$-alkenyl, C$_3$-C$_6$-cycloalkyl, C$_3$-C$_6$-cycloalkylmethyl, OR$^g$, SR$^g$ or NR$^m$R$^n$;
R$^a$ and R$^b$ are independently of each other selected from
(i) H, NR$^j$R$^k$, OR$^l$, SR$^l$, C$_1$-C$_4$-alkyl, C$_2$-C$_4$-alkenyl, C$_2$-C$_4$-alkynyl, C$_1$-C$_4$-hydroxyalkyl, C$_1$-C$_4$-alkoxy, C(=Y$^1$)R$^l$, C(=Y$^1$)OR$^l$, C(=Y$^1$)SR$^l$, C(=Y$^1$)NR$^j$R$^k$, C(=Y$^1$)C(=Y$^2$)R$^l$, S(=O)$_2$R$^l$;

(ii) aryl or hetaryl, wherein the aromatic ring of the aryl or hetaryl group may be unsubstituted or may be partially or fully substituted by substituents, which are independently of each other selected from R$^h$; or R$^a$ and R$^b$ together with the nitrogen atom to which they are bound form
(iii) a hetaryl group which may be unsubstituted or may be partially or fully substituted by substituents, which are independently of each other selected from R$^h$; or
(iv) a 3- to 10-membered, saturated or unsaturated heterocycle, which may contain 1, 2, or 3 heteroatoms which, independently of each other, are selected from NR$^{1b}$, O, and S, wherein S may be oxidized and/or wherein the heterocycle may be unsubstituted or may be partially or fully substituted by substituents which, independently of each other, are selected from R$^i$; and wherein R$^{1b}$ is H, C$_1$-C$_4$-alkyl, C$_2$-C$_4$-alkenyl, C$_3$-C$_6$-cycloalkyl, C$_3$-C$_6$-cycloalkylmethyl, or OR$^g$;

R$^c$ is
(i) H, C$_1$-C$_4$-alkyl, C$_2$-C$_4$-alkenyl, C$_2$-C$_4$-alkynyl, C(=O)OR$^l$, C(=O)SR$^l$, C(=O)NR$^j$R$^k$;
(ii) C$_1$-C$_4$-alkylene-C(=O)R$^l$, C$_1$-C$_4$-alkylene-C(=O)OR$^l$, wherein the C$_1$-C$_4$-alkylene chain may in each case be unsubstituted or may be partially or fully substituted by OR$^g$, CN, halogen, or phenyl;
(iii) aryl, aryl-C$_1$-C$_2$-alkyl, hetaryl, or hetaryl-C$_1$-C$_2$-alkyl, wherein the aromatic ring of the aryl or hetaryl group may be unsubstituted or may be partially or fully substituted by substituents, which are independently of each other selected from R$^h$; or
(iv) a 3- to 10-membered saturated or unsaturated carbocycle or heterocycle, which may contain 1, 2, or 3 heteroatoms which, independently of each other, are selected from NR$^{1b}$, O, and S, wherein S may be oxidized and/or wherein the carbocycle or heterocycle may be unsubstituted or may be partially or fully substituted by substituents which, independently of each other, are selected from R$^i$; and wherein R$^{1b}$ is H, C$_1$-C$_4$-alkyl, C$_2$-C$_4$-alkenyl, C$_3$-C$_6$-cycloalkyl, C$_3$-C$_6$-cycloalkylmethyl, or OR$^g$;

R$^d$ and R$^e$ are independently selected from C$_1$-C$_4$-alkyl, C$_1$-C$_4$-haloalkyl, NR$^j$R$^k$, OR$^l$, SR$^l$, CN, C(=Y$^1$)R$^l$, C(=Y$^1$)OR$^l$, C(=Y$^1$)SR$^l$, or C(=Y$^1$)NR$^j$R$^k$;

R$^f$ is C$_1$-C$_4$-alkyl, C$_1$-C$_4$-haloalkyl, NR$^j$R$^k$, OR$^l$, SR$^l$, aryl or hetaryl, wherein the aromatic ring of the aryl or hetaryl group may be unsubstituted or may be partially or fully substituted by substituents, which are independently of each other selected from R$^h$;

R$^g$ is H or C$_1$-C$_4$-alkyl;
R$^h$ is halogen, CN, NO$_2$, NR$^j$R$^k$, OR$^l$, SR$^l$, C$_1$-C$_4$-alkyl, C$_2$-C$_4$-alkenyl, C$_2$-C$_4$-alkynyl, C$_1$-C$_4$-haloalkyl, C$_1$-C$_4$-alkoxy, C$_2$-C$_4$-alkynyloxy, C(=Y$^1$)R$^l$, C(=Y$^1$)OR$^l$, C(=Y$^1$)SR$^l$, C(=Y$^1$)NR$^j$R$^k$, aryl, aryloxy, hetaryl and hetaryloxy;

R$^i$ is
(i) halogen, CN, C$_1$-C$_4$-alkyl, C$_2$-C$_4$-alkenyl, C$_2$-C$_4$-alkynyl, C$_1$-C$_4$-haloalkyl, C$_2$-C$_4$-haloalkenyl;
(ii) =NR$^{1d}$, wherein R$^{1d}$ is H, C$_1$-C$_4$-alkyl, C$_2$-C$_4$-alkenyl, C$_3$-C$_6$-cycloalkyl, C$_3$-C$_6$-cycloalkylmethyl, or OR$^g$;
(iii) =O, =S, NR$^j$R$^k$, OR$^l$, SR$^l$, C(=Y$^1$)R$^l$, C(=Y$^1$)OR$^l$, C(=Y$^1$)SR$^l$, C(=Y$^1$)NR$^j$R$^k$;
(iv) aryl, aryl-C$_1$-C$_2$-alkyl, hetaryl, or hetaryl-C$_1$-C$_2$-alkyl, wherein the aromatic ring of the aryl or hetaryl group may be unsubstituted or may be partially or fully substituted by substituents, which are independently of each other selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$; or (v) $C_3$-$C_6$-cycloalkyl, or 3- to 6-membered heterocyclyl, wherein the cycloalkyl ring or the heterocyclyl ring may be unsubstituted or may be partially or fully substituted by substituents, which are independently of each other selected from halogen, CN, $C_1$-$C_4$-alkyl, $OR^g$, and $SR^g$;

$R^j$ and $R^k$ are independently selected from H, $OR^g$, $SR^g$, $C(=Y^1)R^g$, $C(=Y^1)OR^g$, $C(=Y^1)SR^g$, $C(=Y^1)NR'''R''$, $C_1$-$C_4$-alkyl, $C_2$-$C_4$-alkenyl, $C_2$-$C_4$-alkynyl, $C_1$-$C_4$-haloalkyl, aryl or hetaryl, wherein the aromatic ring of the aryl or hetaryl group may be unsubstituted or may be partially or fully substituted by substituents, which are independently selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$;

$R^l$ is H, $C_1$-$C_4$-alkyl, $C_2$-$C_4$-alkenyl, $C_2$-$C_4$-alkynyl, $C_1$-$C_4$-haloalkyl, $C(=Y^1)R^g$, $C(=Y^1)OR^g$, $C(=Y^1)SR^g$, $C(=Y^1)NR'''R''$, aryl or hetaryl, wherein the aromatic ring of the aryl or hetaryl group may be unsubstituted or may be partially or fully substituted by substituents, which are independently selected from halogen, CN, $C_1$-$C_4$-alkyl, $C_1$-$C_4$-haloalkyl, $C_1$-$C_4$-alkoxy, $C_2$-$C_4$-alkynyloxy, $OR^g$, and $SR^g$; and $R'''$ and $R''$ are independently selected from H and $C_1$-$C_4$-alkyl.

In a preferred embodiment of said compound of formula I, A is phenyl or a 5- or 6-membered hetaryl, wherein the aromatic ring may in each case be unsubstituted or may be partially or fully substituted by substituents, which are independently of each other selected from $R^A$. These compounds correspond to compounds of formula I.1, wherein A' represents phenyl or a 5- or 6-membered hetaryl, wherein the aromatic ring may in each case be unsubstituted or may be partially or fully substituted by substituents, which are independently of each other selected from $R^A$.

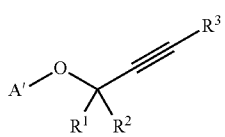

I.1

In a further preferred embodiment of said compound of formula I, $R^1$ and $R^2$ both represent hydrogen. These compounds correspond to compounds of formula I.A.

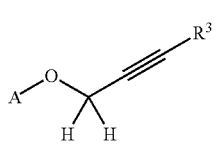

I.A

In another preferred embodiment of said compound of formula I, $R^3$ is hydrogen, $C_1$-$C_4$-haloalkyl or ethynylhydroxymethyl. It is even more preferred that $R^3$ is hydrogen. These compounds correspond to compounds of formula I.X.

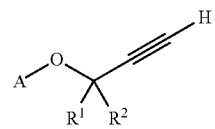

I.X

In a particularly preferred embodiment of said compound of formula I, A is A', i.e. phenyl or a 5- or 6-membered hetaryl, wherein the aromatic ring may in each case be unsubstituted or may be partially or fully substituted by substituents, which are independently of each other selected from $R^A$, and $R^1$ and $R^2$ are both hydrogen. These compounds correspond to compounds of formula I.1.A.

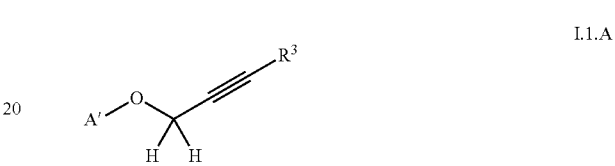

I.1.A

In another more preferred embodiment of said compound of formula I, A is A', i.e. phenyl or a 5- or 6-membered hetaryl, wherein the aromatic ring may in each case be unsubstituted or may be partially or fully substituted by substituents, which are independently of each other selected from $R^A$, and $R^3$ is hydrogen. These compounds corespond to compounds of formula I.1.X.

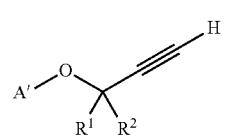

I.1.X

In another more preferred embodiment of said compound of formula I, $R^1$ and $R^2$ are both hydrogen, and $R^3$ is hydrogen. These compounds correspond to compounds of formula I.A.X.

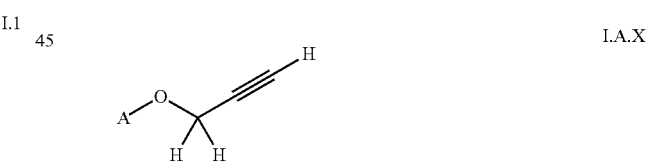

I.A.X

In the most preferred embodiment of said compound of formula I, A is A', i.e. phenyl or a 5- or 6-membered hetaryl, wherein the aromatic ring may in each case be unsubstituted or may be partially or fully substituted by substituents, which are independently of each other selected from $R^A$, $R^1$ and $R^2$ are both hydrogen, and $R^3$ is hydrogen.

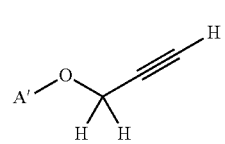

I.1.A.X

Further preferred embodiments of said compound of formula I relate to the substituents $R^A$, with which A may be partially or fully substituted.

In a preferred embodiment of the compound of formula I, $R^A$, if present, is
- (i) halogen, CN, $NR^aR^b$, $OR^c$, $C(=Y^1)R^c$, $C(=Y^1)OR^c$, $C(=Y^1)SR^c$, $C(=Y^1)NR^aR^b$, $Y^2C(=Y^1)R^c$, $Y^2C(=Y^1)NR^aR^b$, $NR^gN=C(R^d)(R^e)$, $S(=O)_2R^f$, $NO_2$, $C_1$-$C_6$-alkyl, $C_2$-$C_6$-$C_1$-$C_4$-haloalkyl, $C_1$-$C_4$-alkoxy, $C_2$-$C_4$-alkynyl-$C_1$-$C_2$-hydroxyalkyl, $C_2$-$C_4$-alkynyloxy;
- (ii) $C_2$-$C_4$-alkenylene-$C(=Y^1)R^c$, $C_2$-$C_4$-alkenylene-$Y^2$—$C(=Y^1)R^c$, wherein the $C_1$-$C_4$-alkylene or $C_2$-$C_4$-alkenylene chain may in each case be unsubstituted or may be partially or fully substituted by CN or halogen;
- (iii) aryl, wherein the aromatic ring of the aryl group may be unsubstituted or may be partially or fully substituted by substituents, which are independently of each other selected from $R^h$; or
- (iv) a 3- to 14-membered saturated or unsaturated heterocycle, which may contain 1, 2, or 3 heteroatoms which, independently of each other, are selected from $NR^{1b}$, O, and S, wherein S may be oxidized and/or wherein the heterocycle may be unsubstituted or may be partially or fully substituted by substituents, which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$.

In a particularly preferred embodiment of the present invention, the compound of formula I, is a compound of formula I.1, I.A, I.X, I.1.A, I.1.X, I.A.X or I.1.A.X, wherein $R^A$, if present, is
- (i) halogen, CN, $NR^aR^b$, $OR^c$, $C(=Y^1)R^c$, $C(=Y^1)OR^c$, $C(=Y^1)SR^c$, $C(=Y^1)NR^aR^b$, $Y^2C(=Y^1)R^c$, $Y^2C(=Y^1)NR^aR^b$, $NR^gN=C(R^d)(R^e)$, $S(=O)_2R^f$, $NO_2$, $C_1$-$C_6$-alkyl, $C_2$-$C_6$—$C_1$-$C_4$-haloalkyl, $C_1$-$C_4$-alkoxy, $C_2$-$C_4$-alkynyl-$C_1$-$C_2$-hydroxyalkyl, $C_2$-$C_4$-alkynyloxy;
- (ii) $C_2$-$C_4$-alkenylene-$C(=Y^1)R^c$, $C_2$-$C_4$-alkenylene-$Y^2$—$C(=Y^1)R^c$, wherein the $C_1$-$C_4$-alkylene or $C_2$-$C_4$-alkenylene chain may in each case be unsubstituted or may be partially or fully substituted by CN or halogen;
- (iii) aryl, wherein the aromatic ring of the aryl group may be unsubstituted or may be partially or fully substituted by substituents, which are independently of each other selected from $R^h$; or
- (iv) a 3- to 14-membered saturated or unsaturated heterocycle, which may contain 1, 2, or 3 heteroatoms which, independently of each other, are selected from $NR^{1b}$, O, and S, wherein S may be oxidized and/or wherein the heterocycle may be unsubstituted or may be partially or fully substituted by substituents, which, independently of each other, are selected from $R^i$; and wherein $R^{1b}$ is H, $C_1$-$C_4$-alkyl, $C_2$-$C_4$-alkenyl, $C_3$-$C_6$-cycloalkyl, $C_3$-$C_6$-cycloalkylmethyl, or $OR^g$.

If $R^A$ is present in the compounds of formula I or a compound of any one of formulae I.1, I.A, I.X, I.1.A, I.1.X, I.A.X or I.1.A.X, and preferably if $R^A$ is selected as indicated above, the following substituent definitions are particularly preferred according to the present invention.

Preferably, $Y^1$, $Y^2$ and $Y^3$ are independently of each other selected from O, S and $NR^{1a}$, wherein preferably $R^{1a}$ is in each case independently H, $C_1$-$C_4$-alkyl, $OR^g$, or $NR^mR^n$.

Preferably, $R^a$ and $R^b$ are independently of each other selected from
- (i) H, $NR^jR^k$, $C_1$-$C_4$-alkyl, $C_1$-$C_4$-hydroxyalkyl, $C(=Y^1)R^i$; or $R^a$ and $R^b$ together with the nitrogen atom to which they are bound form
- (iv) a 3- to 10-membered, saturated or unsaturated heterocycle, which may contain 1, 2, or 3 heteroatoms which, independently of each other, are selected from $NR^{1b}$, O, and S, wherein S may be oxidized and/or wherein the heterocycle may be unsubstituted or may be partially or fully substituted by substituents which, independently of each other, are selected from $R^i$; and wherein $R^{1b}$ is preferably H, $C_1$-$C_4$-alkyl, or $OR^g$.

Preferably, $R^c$ is
- (i) H, $C_1$-$C_4$-alkyl; or
- (iv) a 3- to 10-membered saturated or unsaturated carbocycle or heterocycle, which may contain 1, 2, or 3 heteroatoms which, independently of each other, are selected from $NR^{1b}$, O, and S, wherein S may be oxidized and/or wherein the carbocycle or heterocycle may be unsubstituted or may be partially or fully substituted by substituents which, independently of each other, are selected from $R^i$; and wherein $R^{1b}$ is preferably H, $C_1$-$C_4$-alkyl, or $OR^g$.

Preferably, $R^d$ and $R^e$ are independently selected from $NR^jR^k$ and $C(=Y^1)OR^l$;

Preferably, $R^f$ is $C_1$-$C_4$-alkyl.

Preferably, $R^g$ is H.

Preferably, $R^h$ is halogen or $C_1$-$C_4$-alkoxy.

Preferably, $R^i$ is
- (i) $C_1$-$C_4$-alkyl, $C_1$-$C_4$-haloalkyl, $C_2$-$C_4$-haloalkenyl; or
- (iii) =O.

Preferably, $R^j$ and $R^k$ are both H.

Preferably, $R^l$ is H.

Preferably, $R^m$ and $R^n$ are both H.

Preferred compounds of the present invention are listed in the following Table 1:

| Entry (No. comp. A) | Compound structure |
|---|---|
| 1 | 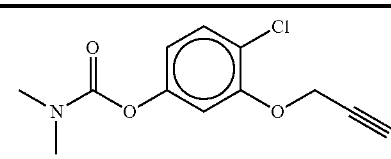 |
| 2 | 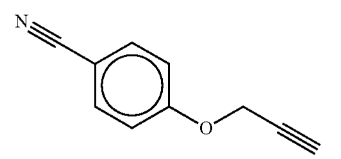 |
| 3 | 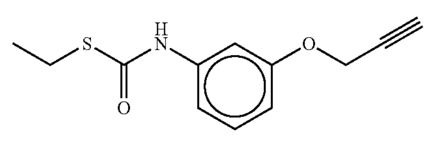 |
| 4 | 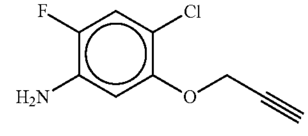 |
| 5 | 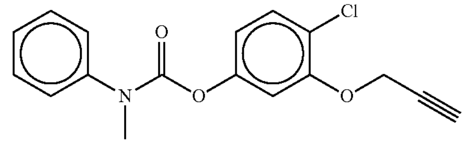 |

| Entry (No. comp. A) | Compound structure |
|---|---|
| 6 | 3-(prop-2-yn-1-yloxy)pyrazine-2-carbonitrile |
| 7 | N-(4-chloro-2-fluoro-5-(prop-2-yn-1-yloxy)phenyl)formamide |
| 8 | 3-(prop-2-yn-1-yloxy)aniline |
| 9 | 1-methoxy-4-(prop-2-yn-1-yloxy)benzene |
| 10 | 2-(4-(but-3-yn-2-yloxy)phenoxy)pyrimidine |
| 11 | 3,5-dichloro-4-(prop-2-yn-1-yloxy)benzaldehyde oxime |
| 12 | 4-chloro-2-fluoro-5-(prop-2-yn-1-yloxy)aniline |
| 13 | 1-methoxy-2-nitro-4-(prop-2-yn-1-yloxy)benzene |
| 4 | (Z)-3-methyl-5-(4-(prop-2-yn-1-yloxy)benzylidene)-2-thioxoimidazolidin-4-one |
| 15 | 4-(prop-2-yn-1-yloxy)benzonitrile |
| 16 | 2-((1-methyl-3-(trifluoromethyl)-1H-pyrazol-5-yl)oxy)-6-(prop-2-yn-1-yloxy)pyridine |
| 17 | 3-chloro-2-(prop-2-yn-1-yloxy)-5-(trifluoromethyl)pyridin-6-amine |
| 18 | 2-methoxy-4-nitro-1-(prop-2-yn-1-yloxy)benzene (N-oxide diazonium) |
| 19 | (4-chloro-2-fluoro-5-(prop-2-yn-1-yloxy)phenyl)hydrazine |
| 20 | methyl 3-(prop-2-yn-1-yloxy)benzoate |
| 21 | (4-bromo-2-methoxy-5-(prop-2-yn-1-yloxy)phenyl)methanol |
| 22 | 2-(4-(prop-2-yn-1-yloxy)phenyl)acetic acid |
| 23 | (E)-4-(4-(prop-2-yn-1-yloxy)phenyl)but-3-en-2-one |
| 24 | 2-(prop-2-yn-1-yloxy)benzo[d]thiazole |

| Entry (No. comp. A) | Compound structure |
|---|---|
| 25 | 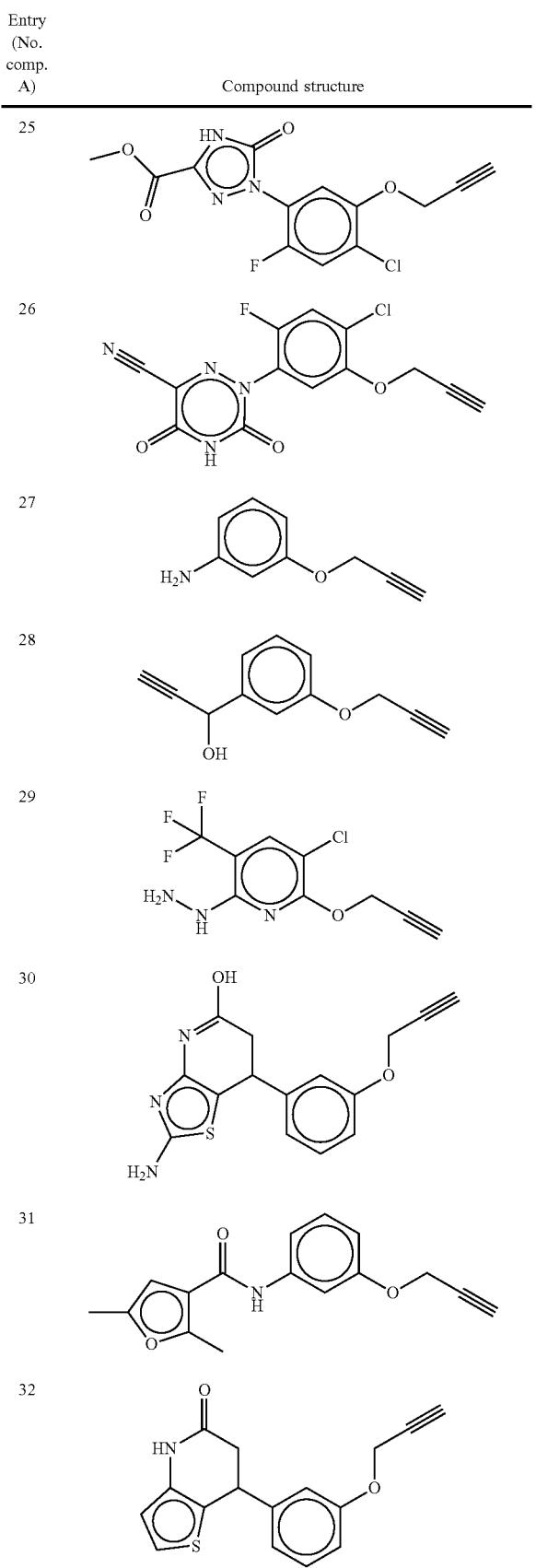 |
| 26 | |
| 27 | |
| 28 | |
| 29 | |
| 30 | |
| 31 | |
| 32 | |
| Entry (No. comp. A) | Compound structure |
|---|---|
| 33 | 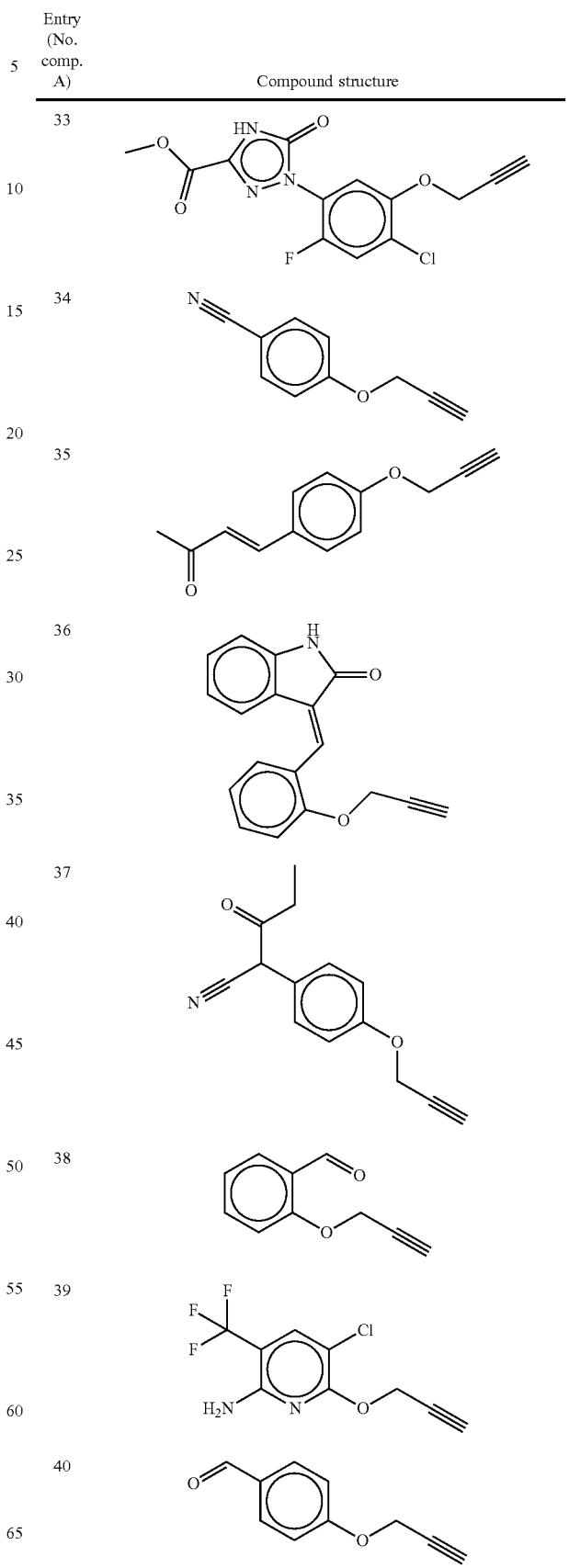 |
| 34 | |
| 35 | |
| 36 | |
| 37 | |
| 38 | |
| 39 | |
| 40 | |

-continued

| Entry (No. comp. A) | Compound structure |
|---|---|
| 41 | 1-(but-2-yn-1-yloxy)naphthalene with OH |
| 42 | 1,5-dimethyl-4-[4-chloro-2-fluoro-5-(prop-2-yn-1-yloxy)phenyl]-1,2,4-triazine-3,6-dione |
| 43 | 4-amino-5-fluoro-2-(prop-2-yn-1-yloxy)benzonitrile |
| 44 | [5-bromo-2-(prop-2-yn-1-yloxy)phenyl]methanol |
| 45 | 6-nitro-3-(prop-2-yn-1-yloxy)-1,2-benzothiazole |
| 46 | 3-{[3-(prop-2-yn-1-yloxy)benzyl]}-6,7-dihydroimidazo[1,2-c]pyrimidin-5(3H)-one |
| 47 | N-(2,4-dichlorophenyl)-3-(prop-2-yn-1-yloxy)benzamide |
| 48 | 2-(prop-2-yn-1-yloxy)benzenesulfonamide |

| Entry (No. comp. A) | Compound structure |
|---|---|
| 49 | pyrrolidine-1-carboxylic acid 3-chloro-4-(prop-2-yn-1-yloxy)phenyl ester |
| 50 | 2-[3-methoxy-4-(prop-2-yn-1-yloxy)phenyl]acetonitrile |
| 51 | 5-{[4-(prop-2-yn-1-yloxy)phenyl]methylidene}imidazolidine-2,4-dione |
| 52 | 1-nitro-4-(prop-2-yn-1-yloxy)benzene |
| 53 | 2-[5-(prop-2-yn-1-yloxy)pyridin-2-yl]-5-methyl-5-(propan-2-yl)-4,5-dihydro-1H-imidazol-4-one |
| 54 | 1-ethyl-5-{[4-(prop-2-yn-1-yloxy)phenyl]methylidene}-2-thioxoimidazolidin-4-one |
| 55 | methyl 3-methoxy-4-(prop-2-yn-1-yloxy)benzoate |
| 56 | 5-chloro-6-ethyl-N-{2-[4-(prop-2-yn-1-yloxy)phenyl]ethyl}pyrimidin-4-amine |

US 9,968,092 B2
31
-continued
| Entry (No. comp. A) | Compound structure |
|---|---|
| 57 | 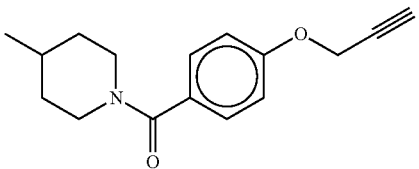 |
| 58 | 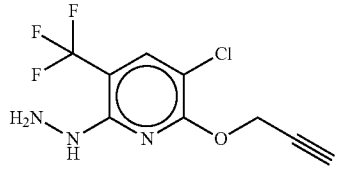 |
| 59 | 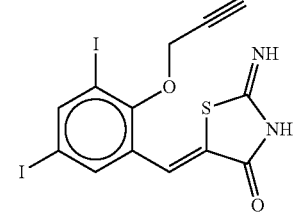 |
| 60 | 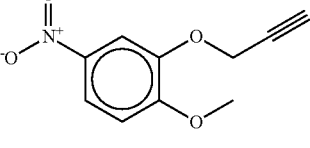 |
| 61 | 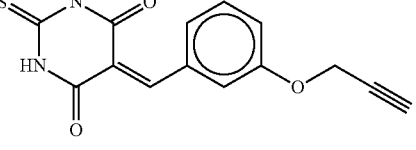 |
| 62 | 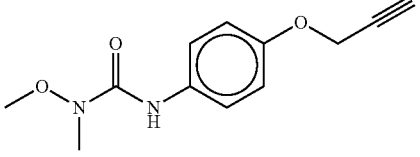 |
| 63 | 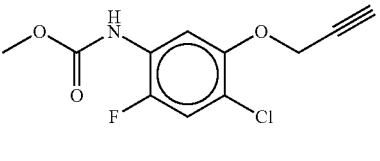 |
| 64 | 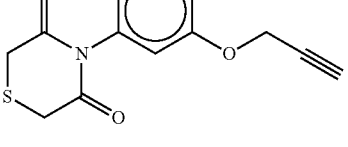 |
32
-continued
| Entry (No. comp. A) | Compound structure |
|---|---|
| 65 | 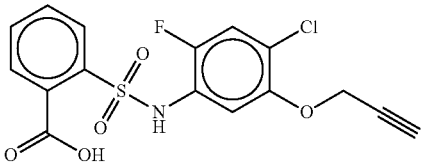 |
| 66 | 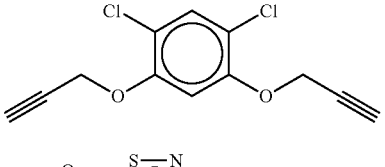 |
| 67 | 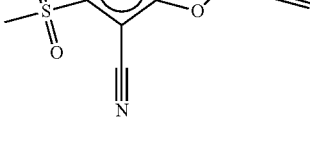 |
| 68 | 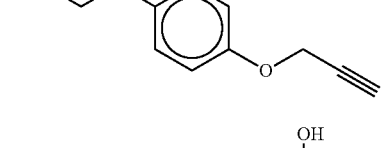 |
| 69 | 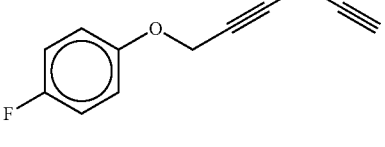 |
| 70 | 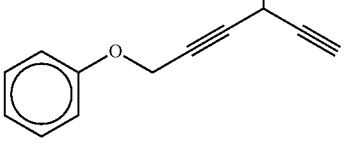 |
| 71 | 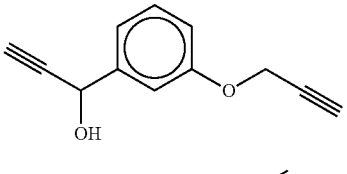 |
| 72 | 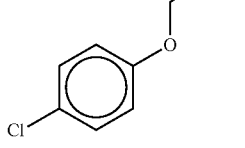 |
| 73 | 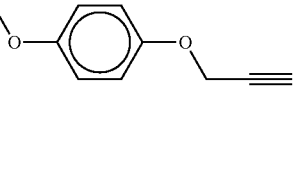 |

| Entry (No. comp. A) | Compound structure |
|---|---|
| 74 | 4-(morpholine-4-carbonyl)phenyl propargyl ether |
| 75 | 4-chloro-6-(prop-2-yn-1-yloxy)pyrimidine |
| 76 | 1-(4-fluorophenoxy)pent-1-en-4-yn-3-ol (propargyl ether with terminal alkyne and OH) |
| 77 | 5-chloro-4-fluoro-2-(prop-2-yn-1-yloxy)aniline |
| 78 | 1-phenoxypent-1-yn... with OH and terminal alkyne |
| 79 | N-(2-hydroxyethyl)-N'-[4-chloro-2-fluoro-5-(prop-2-yn-1-yloxy)phenyl]hydrazinecarbothioamide |
| 80 | complex chrysanthemate-like ester with propargyloxyphenyl group |
| 81 | 1,1-dimethyl-3-[3-chloro-4-(prop-2-yn-1-yloxy)phenyl]urea |
| 82 | 6-chloro-2-(prop-2-yn-1-yloxy)quinoxaline |

| Entry (No. comp. A) | Compound structure |
|---|---|
| 83 | 4-phenoxy-1-phenylbut-2-yn-1-ol |
| 84 | [2-bromo-5-methoxy-4-(prop-2-yn-1-yloxy)phenyl]methanol |
| 85 | S-ethyl [3-(prop-2-yn-1-yloxy)phenyl]carbamothioate |
| 86 | methyl 2-[5-(prop-2-yn-1-yloxy)-1,2-benzoxazol-3-yl]acetate |
| 87 | 1-chloro-4-(prop-2-yn-1-yloxy)benzene |
| 88 | 1-methoxy-4-nitro-2-(prop-2-yn-1-yloxy)benzene |
| 89 | 4-(prop-2-yn-1-yloxy)benzoic acid |
| 90 | 2-hydroxy-2-[4-(prop-2-yn-1-yloxy)phenyl]acrylonitrile |

| Entry (No. comp. A) | Compound structure |
|---|---|
| 91 | 2-amino-3-chloro-6-(prop-2-yn-1-yloxy)-5-(trifluoromethyl)pyridine |
| 92 | 1-phenoxy-4-(prop-2-yn-1-yloxy)benzene |
| 93 | 2-amino-7-(3-(prop-2-yn-1-yloxy)phenyl)-6,7-dihydrothiazolo[4,5-b]pyridin-5-ol |
| 94 | N-(3-(prop-2-yn-1-yloxy)phenyl)acetamide |
| 95 | 4-(prop-2-yn-1-yloxy)benzofuro[3,2-d]pyrimidine |
| 96 | (Z)-3-hydroxy-2-(4-(prop-2-yn-1-yloxy)phenyl)acrylonitrile |
| 97 | 1-methoxy-4-(prop-2-yn-1-yloxy)benzene |
| 98 | (E)-2-(prop-2-yn-1-yloxy)benzaldehyde oxime |

| Entry (No. comp. A) | Compound structure |
|---|---|
| 99 | 2-(prop-2-yn-1-yloxy)benzenesulfonamide |
| 100 | 1-(4-chloro-2-fluoro-5-(prop-2-yn-1-yloxy)phenyl)-3-methylurea |
| 101 | 2-amino-7-(3-(prop-2-yn-1-yloxy)phenyl)-6,7-dihydrothiazolo[5,4-b]pyridin-5-ol |
| 102 | 1-methyl-2,3-bis(prop-2-yn-1-yloxy)benzene |
| 103 | 2-(prop-2-yn-1-yloxy)benzo[d]thiazole |
| 104 | N-(4-chloro-2-fluoro-5-(prop-2-yn-1-yloxy)phenyl)formamide |
| 105 | 1-(but-3-yn-2-yloxy)-3-methoxybenzene |
| 106 | 1-(4-chloro-2-fluoro-5-(prop-2-yn-1-yloxy)phenyl)-4,4-dimethylsemicarbazide |
| 107 | (E)-2-(prop-2-yn-1-yloxy)benzaldehyde oxime |

-continued

| Entry (No. comp. A) | Compound structure |
|---|---|
| 108 | ethyl 2-(4-chloro-5-fluoro-2-(prop-2-yn-1-yloxy)phenyl)-4,5,6,7-tetrahydro-2H-indazole-3-carboxylate |
| 109 | 5-amino-1-(4-(prop-2-yn-1-yloxy)benzoyl)-1H-1,2,4-triazole |
| 110 | 2-amino-7-(3-(prop-2-yn-1-yloxy)phenyl)-6,7-dihydrothiazolo[5,4-b]pyridin-5-ol |
| 111 | 4-chloro-5-fluoro-2-(prop-2-yn-1-yloxy)aniline |
| 112 | 2-methyl-1-(prop-2-yn-1-yloxy)naphthalene |
| 113 | 4-(prop-2-yn-1-yloxy)benzonitrile |
| 114 | 1-phenyl-5-(prop-2-yn-1-yloxy)-1H-tetrazole |

-continued

| Entry (No. comp. A) | Compound structure |
|---|---|
| 115 | 5,5-dimethyl-2-(4-chloro-5-fluoro-2-(prop-2-yn-1-yloxy)phenyl)-1,2,4-triazolidin-3-one |
| 116 | 3-nitro-2-(prop-2-yn-1-yloxy)pyridine |
| 117 | 4-chloro-5-fluoro-2-(prop-2-yn-1-yloxy)aniline |
| 118 | N-(4-chloro-5-fluoro-2-(prop-2-yn-1-yloxy)phenyl)formamide |
| 119 | 1-(3-chloro-4-(prop-2-yn-1-yloxy)phenyl)-3,3-dimethylurea |
| 120 | 3-(prop-2-yn-1-yloxy)pyrazine-2-carbonitrile |
| 121 | N'-(4-chloro-5-fluoro-2-(prop-2-yn-1-yloxy)phenyl)pivalohydrazide |
| 122 | methyl (Z)-2-amino-2-(2-(4-chloro-5-fluoro-2-(prop-2-yn-1-yloxy)phenyl)hydrazono)acetate |
| 123 | (E)-4-(4-(prop-2-yn-1-yloxy)phenyl)but-3-en-2-one |

| Entry (No. comp. A) | Compound structure |
|---|---|
| 124 | 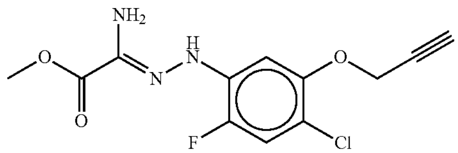 |
| 125 | 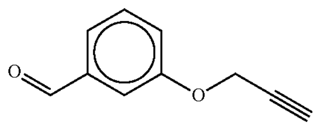 |
| 126 | 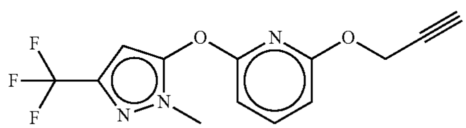 |
| 127 | 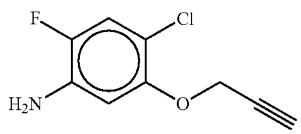 |
| 128 | 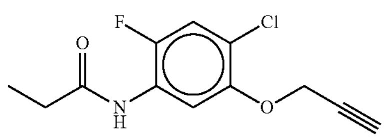 |
| 129 | 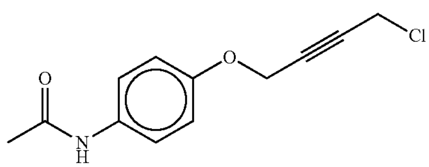 |
| 130 | 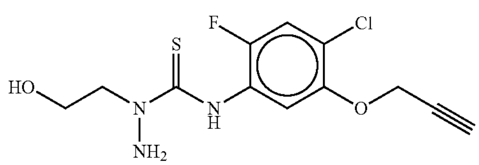 |
| 131 | 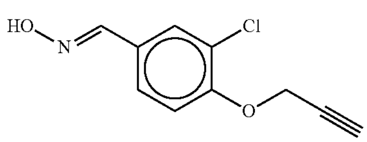 |
| 132 | 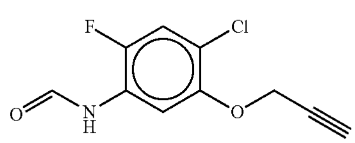 |
| 133 | 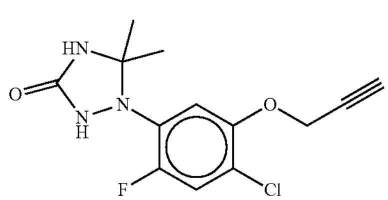 |
| 134 | |
| 135 | |
| 136 | |
| 137 | |
| 138 | |
| 139 | |
| 140 | |
| 141 | |
| 142 | |

| Entry (No. comp. A) | Compound structure |
|---|---|
| 143 | 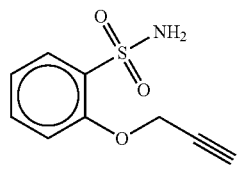 |
| 144 | 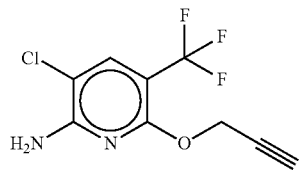 |
| 145 | 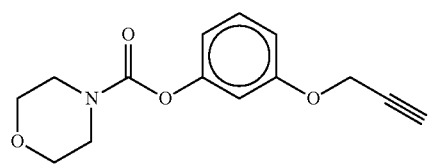 |
| 146 | 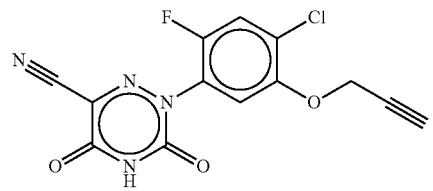 |
| 147 | 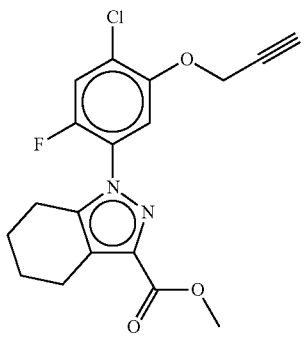 |
| 148 | 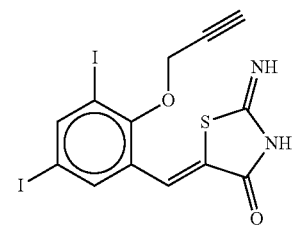 |
| 149 | 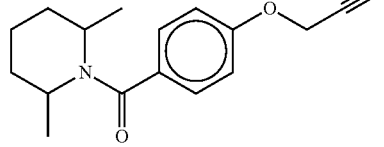 |
| Entry (No. comp. A) | Compound structure |
|---|---|
| 150 | 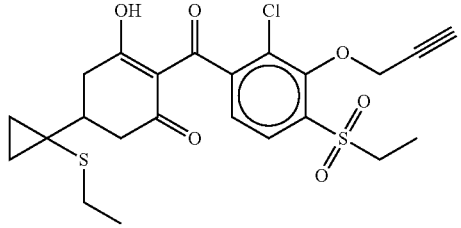 |
| 151 |  |
| 152 | 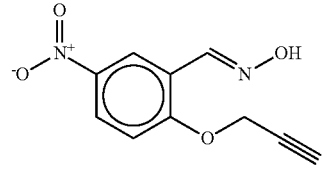 |
| 153 | 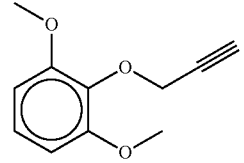 |
| 154 | 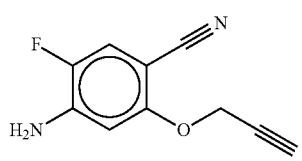 |
| 155 | 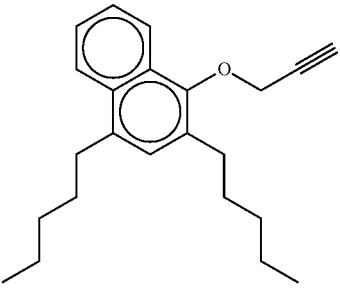 |
| 156 | 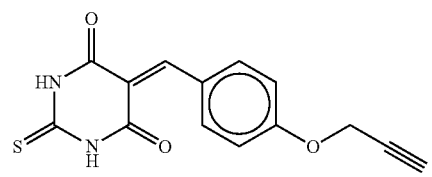 |

-continued
| Entry (No. comp. A) | Compound structure |
|---|---|
| 157 | 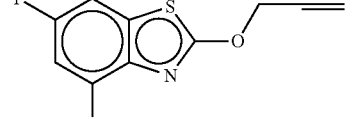 |
| 158 | 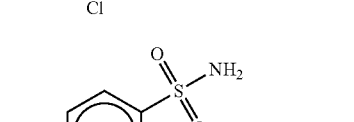 |
| 159 | 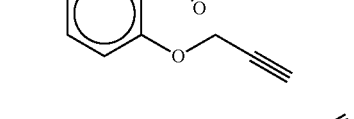 |
| 160 | 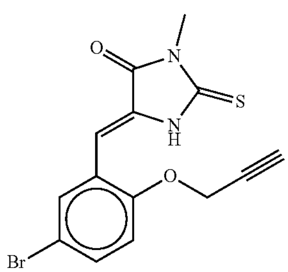 |
| 161 | 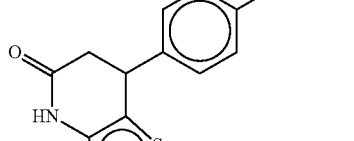 |
| 162 | 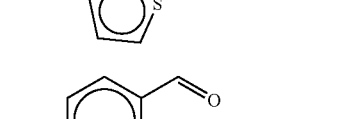 |
| 163 | 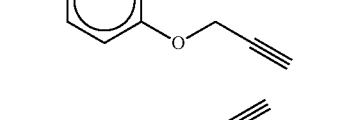 |
-continued
| Entry (No. comp. A) | Compound structure |
|---|---|
| 164 | 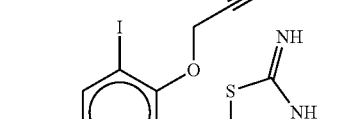 |
| 165 | 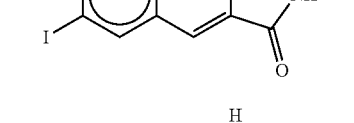 |
| 166 | 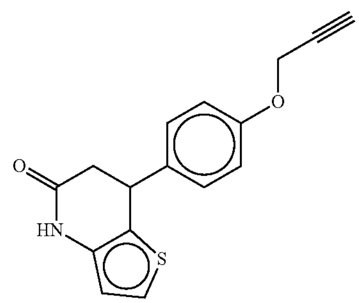 |
| 167 | 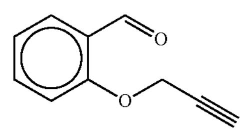 |
| 168 | 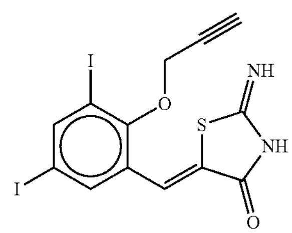 |
| 169 | 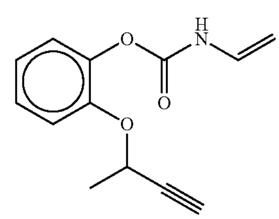 |
| 170 | 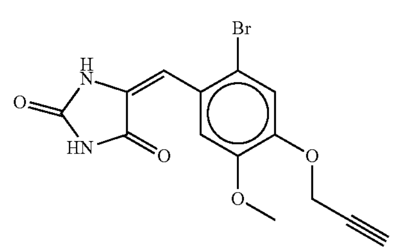 |

-continued
| Entry (No. comp. A) | Compound structure |
|---|---|
| 171 | 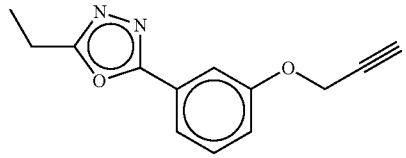 |
| 172 | 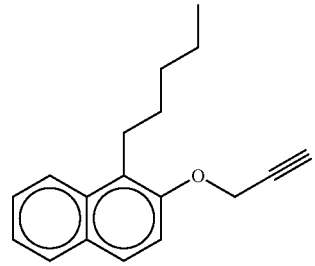 |
| 173 | 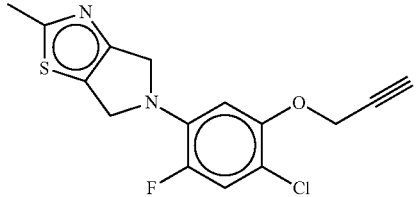 |
| 174 | 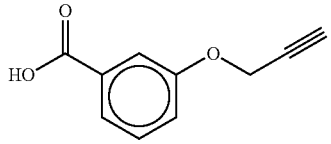 |
| 175 | 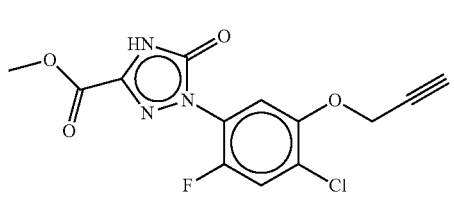 |
| 176 | 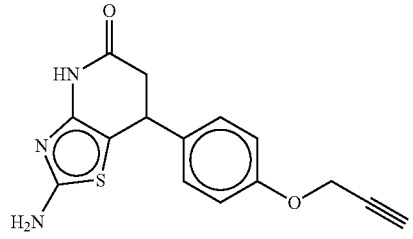 |
| 177 | 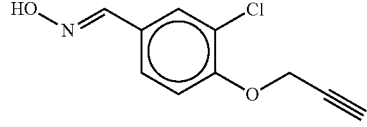 |
| 178 | 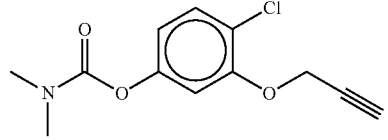 |
-continued
| Entry (No. comp. A) | Compound structure |
|---|---|
| 179 | 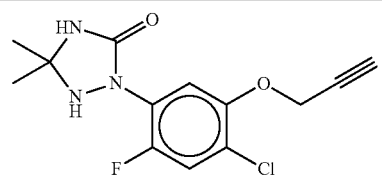 |
| 180 | 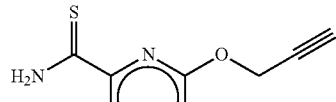 |
| 181 | 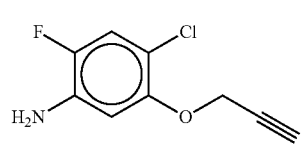 |
| 182 | 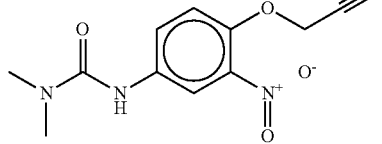 |
| 183 | 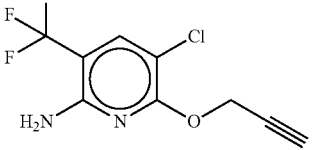 |
| 184 | 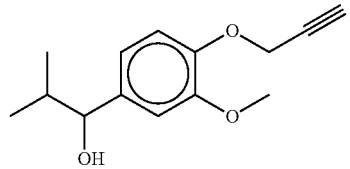 |
| 185 | 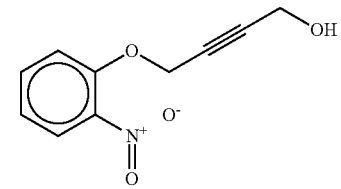 |
| 186 | 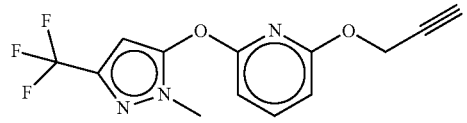 |
| 187 | 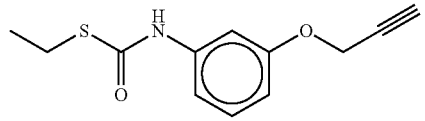 |

| Entry (No. comp. A) | Compound structure |
|---|---|
| 188 | 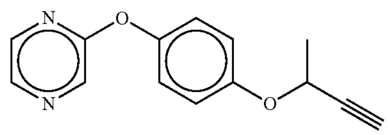 |
| 189 | 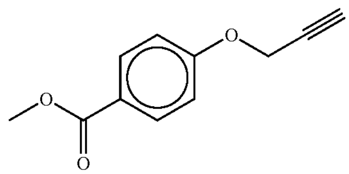 |
| 190 | 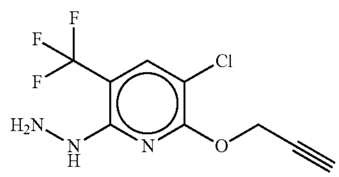 |
| 191 | 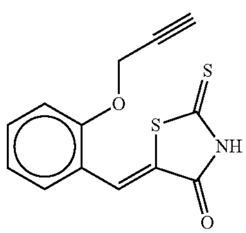 |
| 192 | 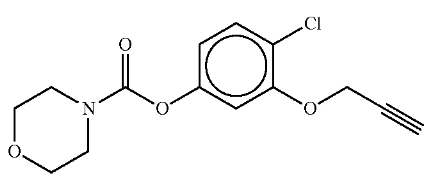 |
| 193 | 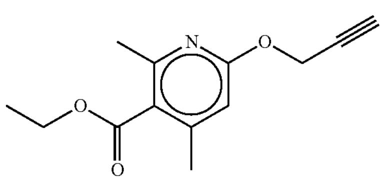 |
| 194 | 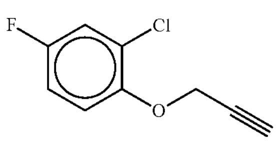 |
| 195 | 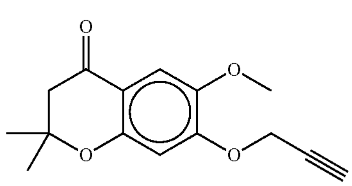 |
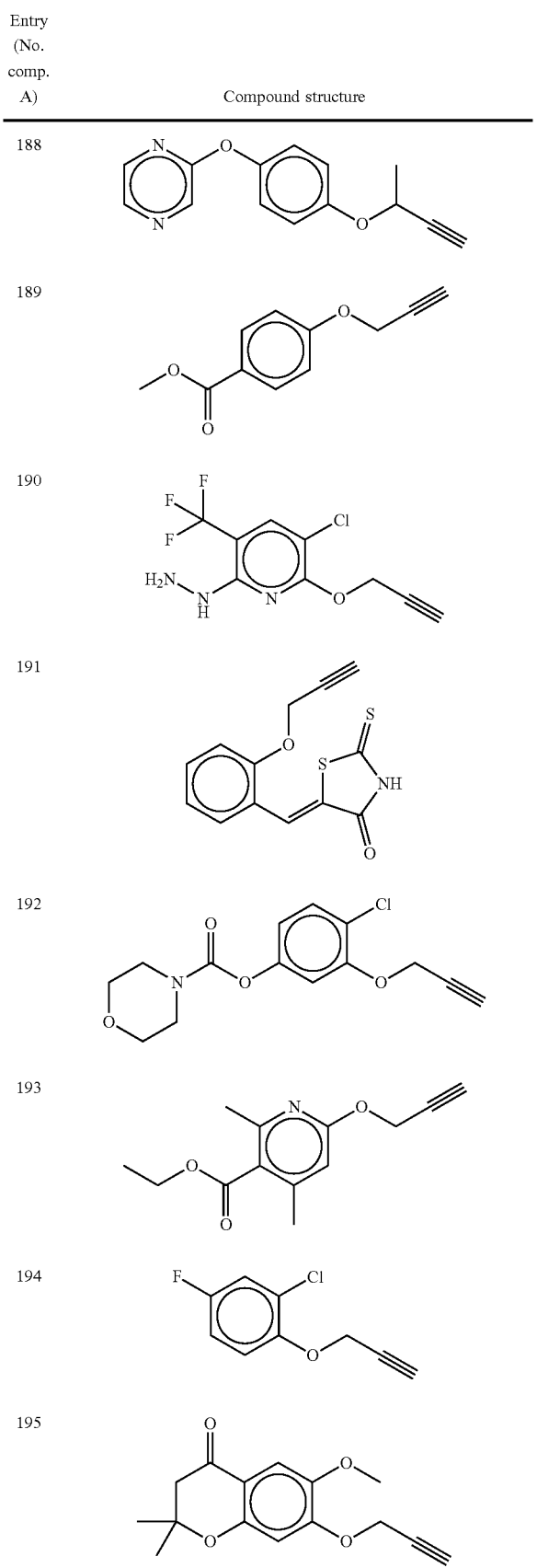
| Entry (No. comp. A) | Compound structure |
|---|---|
| 196 | 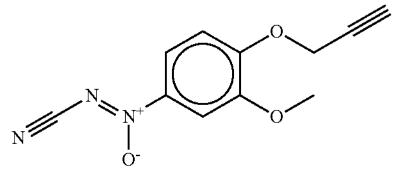 |
| 197 | 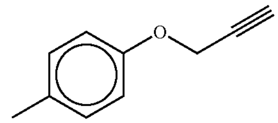 |
| 198 | 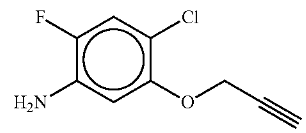 |
| 199 | 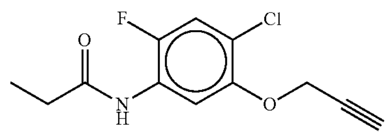 |
| 200 | 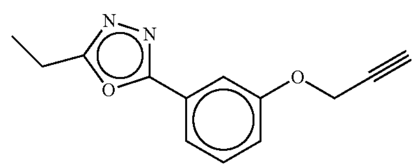 |
| 201 | 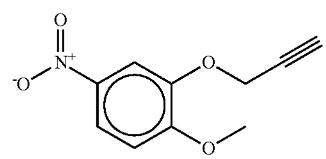 |
| 202 | 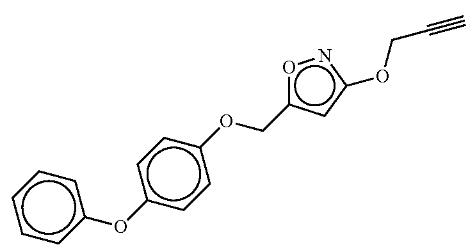 |
| 203 | 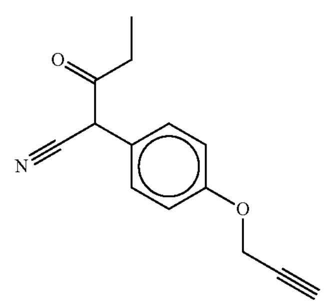 |
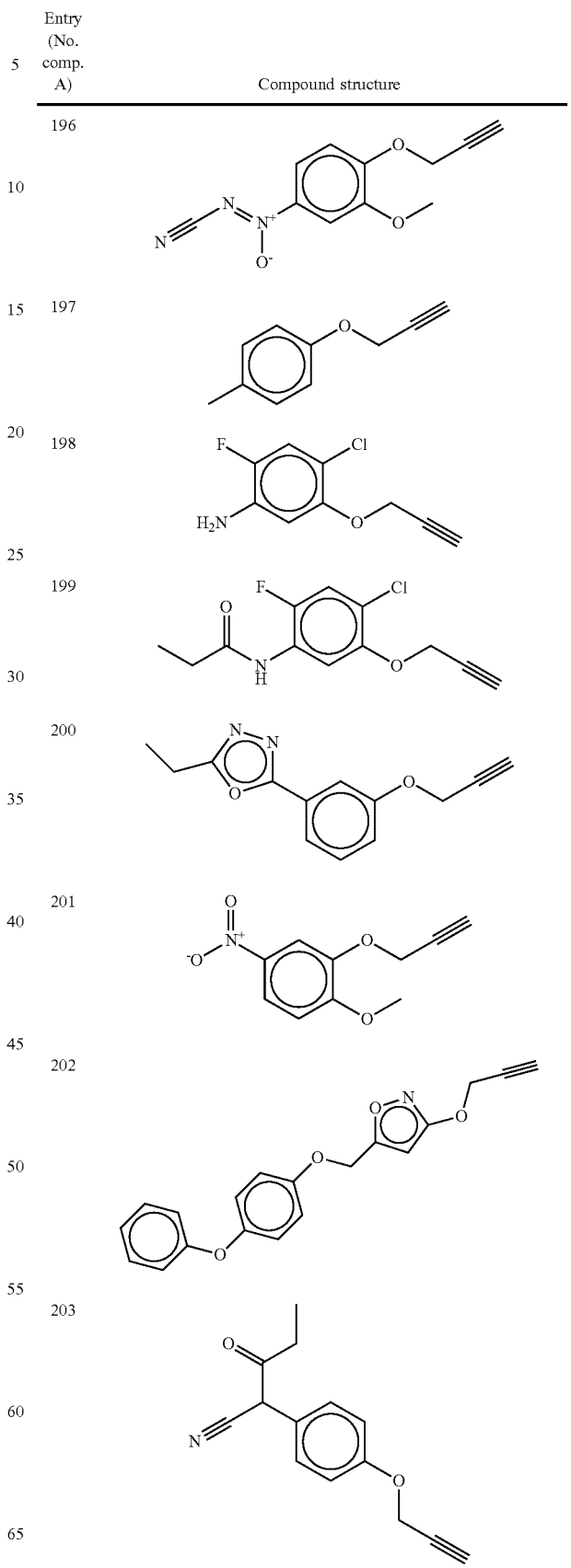

| Entry (No. comp. A) | Compound structure |
|---|---|
| 204 | 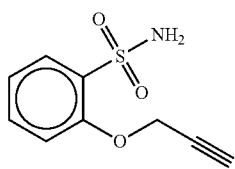 |
| 205 | 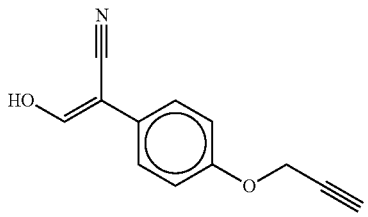 |
| 206 | 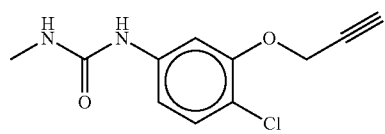 |
| 207 | 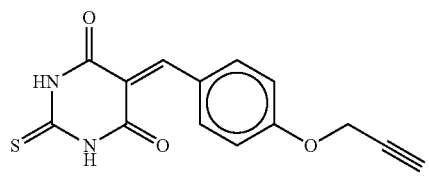 |
| 208 | 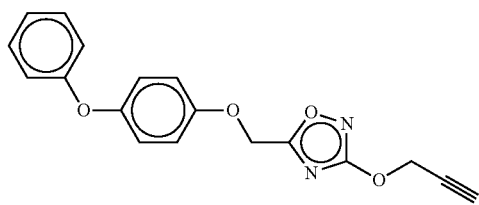 |
| 209 | 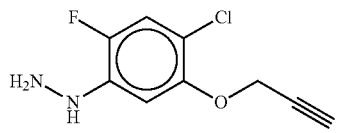 |
| 210 | 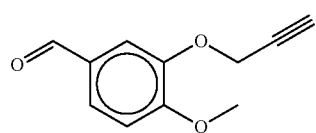 |
| 211 | 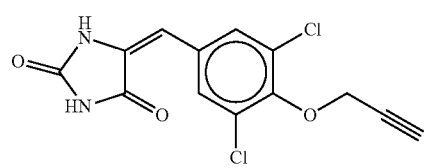 |

| Entry (No. comp. A) | Compound structure |
|---|---|
| 212 | 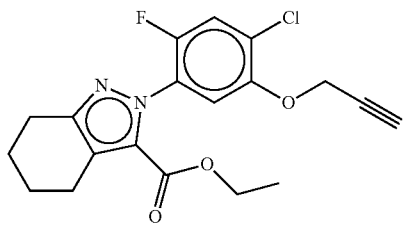 |
| 213 | 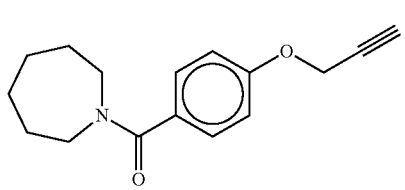 |
| 214 | 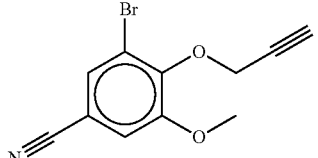 |
| 215 | 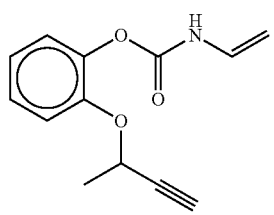 |

In a central aspect the present invention thus relates to the use of a combination of a nitrification inhibitor or (T) and a biopesticide as defined herein above, or of a composition comprising said combination of a nitrification inhibitor or (T) and a biopesticide as defined herein for increasing the health of a plant. The nitrification inhibitor or derivatives or salts thereof as defined herein above in combination with a biopesticide, in particular compounds of formula I and/or salts or suitable derivatives thereof in combination with a biopesticide, as well as compositions comprising said nitrification inhibitor or (T) and a biopesticide as defined herein may be used for increasing the health of a plant.

The use may be based on an application of the combination of the nitrification inhibitor or (T) and a biopesticide, the or the composition as defined herein to a plant growing on soil and/or the locus where the plant is growing or is intended to grow, or the application of the combination of the nitrification inhibitor or (T) and a biopesticide, or the composition as defined herein to soil where a plant is growing or is intended to grow or to soil substituents. In specific embodiments, the combination of the nitrification inhibitor or (T) and a biopesticide may be used in the absence of plants, e.g. as preparatory activity for subsequent agricultural activity.

The use may further include the application of a combination of a biopesticide and (T) or the nitrification inhibitor or derivatives or salts thereof as defined herein above, in particular compounds of formula I and/or salts or suitable derivatives thereof, as well as compositions comprising said combination of a biopesticide and (T) or the nitrification inhibitor, as defined herein above to environments, areas or zones, where nitrification takes place or is assumed or expected to take place. Such environments, areas or zones may, in specific embodiments, not comprise plants or soil, but be planned for subsequent growth of plants. Examples of such environments are laboratory envirnonments or green houses or similar indoor facilities.

The term "plant health" as used herein is intended to mean a condition of the plant which is determined by several aspects alone or in combination with each other. One indicator (indicator 1) for the condition of the plant is the crop yield. "Crop" and "fruit" are to be understood as any plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant. Another indicator (indicator 2) for the condition of the plant is the plant vigor. The plant vigor becomes manifest in several aspects, too, some of which are visual appearance, e.g. leaf color, fruit color and aspect, amount of dead basal leaves and/or extent of leaf blades, plant weight, plant height, extent of plant verse (lodging), number, strong ness and productivity of tillers, panicles' length, extent of root system, strongness of roots, extent of nodulation, in particular of rhizobial nodulation, point of time of germination, emergence, flowering, grain maturity and/or senescence, protein content, sugar content and the like. Another indicator (indicator 3) for an increase of a plant's health is the reduction of biotic or abiotic stress factors.

The three above mentioned indicators for the health condition of a plant may be interdependent and may result from each other. For example, a reduction of biotic stress may lead to a better plant vigor, e.g. to better and bigger crops, and thus to an increased yield.

Biotic stress, especially over longer terms, can have harmful effects on plants. The term "biotic stress" as used in the context of the present invention refers in particular to stress caused by living organisms, such as fungi, bacteria, or viruses. As a result, the quantity and the quality of the stressed plants, their crops and fruits decrease. As far as quality is concerned, reproductive development is usually severely affected with consequences on the crops which are important for fruits or seeds. Growth may be slowed by the stresses; polysaccharide synthesis, both structural and storage, may be reduced or modified: these effects may lead to a decrease in biomass and to changes in the nutritional value of the product. A reduction of biotic stress factors may, for example, be due to a fungicidal, bactericidal, viricidal, nematicidal and/or plant defense activator activity of a biopesticide as defined herein.

Abiotic stress includes drought, cold, increased UV, increased heat, or other changes in the environment of the plant, that leads to sub-optimal growth conditions. A reduction of abiotic stress factors may, for example, be due to a reduction of nitrification and a corresponding improvement of uptake of nitrogen nutrients.

The term "increased yield" of a plant as used herein means that the yield of a product of the respective plant is increased by a measurable amount over the yield of the same product of the plant produced under the same conditions, but without the application of the composition of the invention. According to the present invention, it is preferred that the yield be increased by at least 0.5%, more preferred at least 1%, even more preferred at least 2%, still more preferred at least 4%. An increased yield may, for example, be due to a reduction of nitrification and a corresponding improvement of uptake of nitrogen nutrients, as well as a fungicidal, bactericidal, viricidal, nematicidal and/or plant defense activator activity of a biopesticide as defined herein.

The term "improved plant vigor" as used herein means that certain crop characteristics are increased or improved by a measurable or noticeable amount over the same factor of the plant produced under the same conditions, but without the application of the composition of the present invention. Improved plant vigor can be characterized, among others, by following improved properties of a plant:

(a) improved vitality of the plant,
(b) improved quality of the plant and/or of the plant products, e.g.
(b) enhanced protein content,
(c) improved visual appearance,
(d) delay of senescence,
(e) enhanced root growth and/or more developed root system (e.g. determined by the dry mass of the root),
(f) enhanced nodulation, in particular rhizobial nodulation,
(g) longer panicles,
(h) bigger leaf blade,
(i) less dead basal leaves,
(j) increased chlorophyll content
(k) prolonged photosynthetically active period The improvement of the plant vigor according to the present invention particularly means that the improvement of anyone or several or all of the above mentioned plant characteristics are improved. It further means that if not all of the above characteristics are improved, those which are not improved are not worsened as compared to plants which were not treated according to the invention or are at least not worsened to such an extent that the negative effect exceeds the positive effect of the improved characteristic (i.e. there is always an overall positive effect which preferably results in an improved crop yield). An improved plant vigor may, for example, be due to a reduction of nitrification and a corresponding improvement of uptake of nitrogen nutrients, as well as a fungicidal, bactericidal, viricidal, nematicidal and/or plant defense activator activity of a biopesticide as defined herein.

It is particularly preferred that said increase of the health of a plant is reflected by an increase in growth of root and shoot and/or an overall increase in productivity and/or a faster and more efficient development of the plant.

The term "reducing nitrification" or "reduction of nitrification" as used herein refers to a slowing down or stopping of nitrification processes, e.g. by retarding or eliminating the natural transformation of ammonium into nitrate. Such reduction may be a complete or partial elimination of nitrification at the plant or locus where the inhibitor or composition comprising said inhibitor is applied. For example, a partial elimination may result in a residual nitrification on or in the plant, or in or on the soil or soil substituents where a plant grows or is intended to grow of about 90% to 1%, e.g. 90%, 85%, 80%, 70%, 60%, 50%, 40%, 30%, 20%, 10% or less than 10%, e.g. 5% or less than 5% in comparison to a control situation where the nitrification inhibitor is not used. In certain embodiments, a partial elimination may result in a residual nitrification on or in the plant or in or on the soil or soil substituents where a plant grows or is intended to grow of below 1%, e.g. at 0.5%, 0.1% or less in comparison to a control situation where the nitrification inhibitor is not used.

A "biopesticide" as mentioned herein above may be any biopesticide known to the skilled person. Biopesticides are typically defined as a form of pesticides based on microorganisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). In the context of the present invention the term also relates to biostimulants. A "biostimulant" as used herein means any material of biological origin that enhances plant growth or development when applied. In certain embodiments, the biostimulant may further be of non biological origin or be a mixture of material of biological and non-biological origin.

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes, and have received much practical attention as substitutes to synthetic chemical plant protection products (PPPs).

Biopesticides may be understood as comprising at least the major classes of microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (such as growth or developmental regulation, attractents, repellents or defence activators (e.g. induced resistance) and are relatively non-toxic to mammals.

Examples for biochemical pesticides include, but are not limited to semiochemicals (insect pheromones and kairomones), natural plant and insect regulators, naturally-occurring repellents and attractants, and proteins (e.g. enzymes).

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

Biopesticides are, for example, useful is in the area of seed treatments and soil amendments. Biopesticidal seed treatments may e.g. be used to control, i.e. reduce or eliminate soil borne fungal pathogens that cause seed rots, damping-off, root rot and seedling blights, thereby reducing biotic stresses to plants. They can also be used to control or reduce internal seed borne fungal pathogens as well as fungal pathogens that are on the surface of the seed. Biopesticides further show capacities which lead to a reduced biotic stress of treated plants, e.g. by stimulating plant host defences or physiological processes, thus leading to enhanced plant growth or health.

Biopesticides may, for example, be microbial pesticides with fungicidal, bactericidal, viricidal and/or plant defense activator activity, e.g. *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea f. catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. microflavus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum*; *T. stromaticum, T. virens* (also named *Gliocladium virens*), *T. viride, Typhula phacorrhiza, Ulocladium oudemansii, Verticillium dahlia*, zucchini yellow mosaic virus (avirulent strain).

Biopesticides may, for example, further be biochemical pesticides with fungicidal, bactericidal, viricidal and/or plant defense activator activity e.g. chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil.

In further embodiments, the biopesticides may be microbial pesticides with insecticidal, acaricidal, molluscidal and/or nematicidal activity, e.g. *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* sp., *Chromobacterium subtsugae, Cydia pomonella* granulosis virus, *Cryptophlebia leucotreta* granulovirus (CrleGV), *Flavobacterium* sp., *Helicoverpa armigera* nucleopolyhedrovirus (HearNPV), *Isaria fumosorosea, Heterorhabditis bacteriophora, Lecanicillium longisporum, L. muscarium* (formerly *Verticillium lecanii*), *Metarhizium anisopliae, M. anisopliae* var. *acridum, Nomuraea rileyi, Paecilomyces fumosoroseus, P. lilacinus, Paenibacillus popilliae, Pasteuria* sp., *P. nishizawae, P. penetrans, P. ramose, P. reneformis, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces microflavus*.

Also envisaged are biochemical pesticides with insecticidal, acaricidal, molluscidal, pheromone and/or nematicidal activity, for example, L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone (B.27), 2-methyl 1-butanol, methyl eugenol, methyl jasmonate (B.28), (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodes*, Catnip oil, Neem oil (B.29), Quillay extract (B.30), Tagetes oil.

Also envisaged are microbial pesticides with plant stress reducing, plant growth regulator, plant growth promoting and/or yield enhancing activity, for example, *Azospirillum amazonense, A. brasilense, A. lipoferum, A. irakense, A. halopraeferens, Bradyrhizobium* sp., *B. elkanii, B. japonicum, B. liaoningense, B. lupini, Delftia acidovorans, Glo-*

*mus intraradices, Mesorhizobium* sp., *Paenibacillus alvei, Penicillium bilaiae, Rhizobium leguminosarum* bv. *phaseoli, R. l.* bv. *trifolii, R. l.* bv. *viciae, R. tropici, Sinorhizobium meliloti.*

Biopesticides may also be biochemical pesticides with plant stress reducing, plant growth regulator and/or plant yield enhancing activity, e.g. abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract or *Ecklonia maxima* (kelp) extract.

In a specific embodiment, the biopesticide may be at least one element selected from aluminium silicate (Screen™ Duo from Certis LLC, USA), *Agrobacterium radio¬bacter* K1026 (e. g. NoGall® from BASF Agricultural Specialties Pty Ltd, Australia), *A. radiobacter* K84 (Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialities (Pty) Ltd., South Africa; or Goemar® from Laboratoires Goemar, France), *Aspergillus flavus* NRRL 21882 isolated from a peanut in Georgia in 1991 by USDA, National Peanut Research Labora¬tory (e. g. in Afla-Guard® from Syngenta, CH), mixtures of *Aureobasidium pullulans* DSM 14940 and DSM 14941 (e. g. blastospores in BlossomProtect® from bio-ferm GmbH, Germany), *Azospirillum amazonense* BR 11140 (SpY2T) (Proc. 9th Int. and 1st Latin American PGPR meeting, Quimara, Medellin, Colombia 2012, p. 60, ISBN 978-958-46-0908-3), *A. brasilense* AZ39 (Eur. J. Soil Biol 45(1), 28-35, 2009), *A. brasilense* XOH (e. g. AZOS from Xtreme Garde¬ning, USA or RTI Reforestation Technologies International; USA) (B.1), *A. brasilense* BR 11002 (Proc. 9th Int. and 1st Latin American PGPR meeting, Quimara, Medellin, Colombia 2012, p. 60, ISBN 978-958-46-0908-3) (B.2), *A. brasilense* BR 11005 (SP245; e. g. in GELFIX Gramineas from BASF Agricultural Specialties Ltd., Brazil) (B.3), *A. brasilense* strains Ab-V5 and Ab-V6 (e. g. in AzoMax from Novozymes BioAg Produtos papra Agricultura Ltda., Quattro Barras, Brazil or SimbioseMaiz® from Simbiose-Agro, Cruz Alta, RS, Brazil; Plant Soil 331, 413-425, 2010) (B.4), *A. lipoferum* BR 11646 (Sp31) (Proc. 9th Int. and 1st Latin American PGPR meeting, Quimara, Medellin, Colombia 2012, p. 60), *Bacillus amyloliquefaciens* FZB42 (e. g. in RhizoVital® 42 from AbiTEP GmbH, Berlin, Germany) (B.5), *B. amyloliquefaciens* IN937a (J. Microbiol. Biotechnol. 17(2), 280-286, 2007; e. g. in BioYield® from Gustafson LLC, TX, USA) (B.6), *B. amyloliquefaciens* IT-45 (CNCM I 3800) (e. g. Rhizocell C from ITHEC, France) (B.7), *B. amyloliquefaciens* TJ 1000 (also called 1 BE; ATCC BAA-390; e.g. QuickRoots™ from TJ Technologies, Watertown, S. Dak., USA; CA 2471555 A1) (B.8), *B. amylolique¬faciens* ssp. *plantarum* MBI600 (NRRL B-50595, deposited at USDA) (e. g. Integral®, Subtilex® NG from BASF Corp., USA) (B.9), *B. cereus* CNCM 1-1562 (U.S. Pat. No. 6,406,690) (B.10), *B. firmus* CNCM 1-1582 (WO 2009/126473, WO 2009/124707, U.S. Pat. No. 6,406,690; Votivo® from Bayer Crop Science LP, USA) (B.11), *B. pumilus* GB34 (ATCC 700814; e. g. in YieldShield® from Gustafson LLC, TX, USA), and *Bacillus pumilus* KFP9F (NRRL B-50754) (e. g. in BAC-UP or FUSION-P from BASF Agricultural Specialities (Pty) Ltd., South Africa) (B.12), *B. pumilus* QST 2808 (NRRL B 30087) (e. g. Sonata® and Ballad® Plus from AgraQuest Inc., USA) (B.13), *B. subtilis* CX-9060 (Federeal Register 77(7), 1633-1637; Certis U.S.A., L.L.C.), *B. subtilis* GB03 (e. g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B 21661 in Rhapsody®, Serenade® MAX and Serenade® ASO from AgraQuest Inc., USA), *B. subtilis* var. *amylolique¬faciens* FZB24 (e. g. Taegro® from Novozyme Biologicals, Inc., USA), *B. subtilis* var. *amyloliquefaciens* D747 (FERM BP-8234; KR 100903253; e. g. Double Nickel™ 55 WDG or Double Nickel™ LC from Certis LLC, USA), *B. thuringiensis* ssp. *aizawai* ABTS-1857 (e. g. in XenTari® from BioFa AG, Münsingen, Germany), *B. t.* ssp. *aizawai* SAN 401 I, ABG-6305 and ABG-6346, *Bacillus t.* ssp. *israelensis* AM65-52 (e. g. in VectoBac® from Valent BioSciences, IL, USA), *Bacillus thuringiensis* ssp. *kurstaki* SB4 (NRRL B-50753; e. g. Beta Pro® from BASF Agricultural Specialities (Pty) Ltd., South Africa), *B. t.* ssp. *kurstaki* ABTS-351 identical to HD-1 (ATCC SD-1275; e. g. in Dipel® DF from Valent BioSciences, IL, USA), *B. t.* ssp. *kurstaki* EG 2348 (e. g. in Lepinox® or Rapax® from CBC (Europe) S.r.l., Italy), *B. t.* ssp. *tenebrionis* DSM 2803 (EP 0 585 215 B1; identical to NRRL B-15939; Mycogen Corp.), *B. t.* ssp. *tenebrionis* NB-125 (DSM 5526; EP 0 585 215 B1; also referred to as SAN 418 I or ABG-6479; former production strain of Novo-Nordisk), *B. t.* ssp. *tenebrionis* NB-176 (or NB-176-1; a gamma-irridated, induced high-yielding mutant of strain NB125; DSM 5480; EP 585 215 B1; Novodor® from Valent BioSciences, Switzerland), *Beauveria bassiana* ATCC 74040 (e. g. in Naturalis® from CBC (Europe) S.r.l., Italy), *B. bassiana* DSM 12256 (US 200020031495; e. g. BioExpert® SC from Live Sytems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e. g. BroadBand® from BASF Agricultural Specialities (Pty) Ltd., South Africa), *B. brongniartii* (e. g. in Melocont® from Agrifutur, Agrianello, Italy, for control of cockchafer; J. Appl. Microbiol. 100(5), 1063-72, 2006), *Bradyrhizobium* sp. (e. g. Vault® from BASF Corp., USA), *B. japonicum* (e. g. VAULT® from BASF Corp., USA) (B.14), *Burkholderia* sp. A396 (NRRL B-50319; WO 2013/032693; Marrone Bio Innovations, Inc., USA), *Candida oleophila* I182 (NRRL Y-18846; e. g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e. g. Biocure® (in mixture with lysozyme) and BioCoat® from Micro Flo Company, USA (BASF SE) and Arysta), chitosan (e. g. Armour-Zen® from BotriZen Ltd., NZ), *Clonostachys rosea* f. *catenulata*, also named *Gliocladium catenulatum* (e. g. isolate J 1446: Prestop® from Verdera Oy, Finland), *Chromobacterium subtsugae* PRAA4-1 isolated from soil under an eastern hemlock (*Tsuga canadensis*) in the Catoctin Mountain region of central Maryland (e. g. in GRANDEVO from Marrone Bio Innovations, USA), *Coniothyrium minitans* CON/M/91-08 (DSM 9660; e. g. Contans® WG, Intercept® WG from Prophyta Biologischer Pflanzenschutz GmbH, Germany; WO 1996/021358) (B.15), *Cryphonectria parasitica* (e. g. product *Endothia parasitica* from CNICM, France), *Cryptococcus albidus* (e. g. YIELD PLUS® from Anchor BioTechnologies, South Africa), *Cryptophlebia leucotreta* granulovirus (CrleGV) (e. g. in CRYPTEX from Adermatt Biocontrol, Switzerland), *Cydia pomonella* granulovirus (CpGV) V03 (DSM GV0006; e. g. in MADEX Max from Andermatt Biocontrol, Switzerland), CpGV V22 (DSM GV-0014; e. g. in MADEX Twin from Adermatt Biocontrol, Switzerland), *Delftia acidovorans* RAY[209] (ATCC PTA-4249; WO 2003/57861; e. g. in BIOBOOST from Brett Young, Winnipeg, Canada), *Dilophosphora alopecuri* (Twist Fungus from BASF Agricultural Specialties Pty Ltd, Australia), *Ecklonia maxima* (kelp) extract (e. g. KELPAK SL from Kelp Products Ltd, South Africa), *Flavobacterium* sp. H492 (ATCC B-505584, WO 2013/138398), formononetin (e. g. in MYCONATE from Plant Health Care plc, U.K.), *Fusarium oxysporum* (e. g. BIOFOX® from S.I.A.P.A., Italy, FUSACLEAN® from Natural Plant Protection, France), *Glomus intraradices* (e. g. MYC 4000 from ITHEC, France), *Glomus intraradices* RTI-801 (e. g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e. g. MESSENGER or HARP-N Tek from Plant Health Care plc, U.K.; Science 257, 1-132, 1992), *Helicoverpa armigera* nucleopolyhedrovirus (HearNPV) (e.g. in HELICOVEX from Adermatt Biocontrol, Switzerland), *Heterorhabditis bacteriophaga* (e. g. Nemasys® G from BASF Agricultural Specialities Limited, UK), *Isaria fumosorosea* Apopka-97 (ATCC 20874) (PFR-97™ from Certis LLC, USA), cis-jas¬mone (U.S. Pat. No. 8,221,736), laminarin (e. g. in VACCIPLANT from Laboratoires Goemar, St. Malo, France or Stähler S A, Switzerland), *Lecanicillium longisporum* KV42 and KV71 (e. g. VERTA¬LEC® from Koppert B V, Netherlands), *L. muscarium* KV01 (formerly *Verticillium lecanii*) (e. g. MYCOTAL from Koppert B V, Netherlands), *Lysobacter antibioticus* 13-1 (Biological Con¬trol 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium an¬iso¬pliae* var. *acridum* IMI 330189 (isolated from *Ornithacris cavroisi* in Niger; NRRL 50758) (e.g. GREEN MUSCLE® from BASF Agricultural Specialities (Pty) Ltd., South Africa), *M. a.* var. *acridum* FI-985 (e. g. GREEN GUARD® SC from BASF Agricultural Specialties Pty Ltd, Australia), *M. anisopliae* FI-1045 (e. g. BIOCANE® from BASF Agricultural Specialties Pty Ltd, Australia), *M. anisopliae F*52 (DSM 3884, ATCC 90448; e. g. MET52® Novozymes Biologicals BioAg Group, Canada), *M. anisopliae* ICIPE 69 (e. g. METATHRIPOL from ICIPE, Nairobe, Kenya), *Metschnikowia fructicola* (NRRL Y-30752; e. g. SHEMER® from Agrogreen, Israel, now distributed by Bayer CropSciences, Germany; U.S. Pat. No. 6,994,849), *Microdochium dimerum* (e. g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e. g. in development products Muscudor™ or QRD300 from AgraQuest, USA), *Muscodor. albus* SA-13 (MBI-601 EP Nematicide Marrone Biosciences), Neem oil (e. g. TRILOGY®, TRIACT® 70 EC from Certis LLC, USA), *Nomu¬raea rileyi* strains SA86101, GU87401, SR86151, CG128 and VA9101, *Paecilomyces fumoso¬roseus* FE 9901 (e. g. NO FLY™ from Natural Industries, Inc., USA), *P. lilacinus* 251 (e. g. in BioAct®/MeloCon® from Prophyta, Germany; Crop Protection 27, 352-361, 2008; originally isolated from infected nematode eggs in the Philippines), *P. lilacinus* DSM 15169 (e. g. NEMATA® SC from Live Systems Technology S.A., Colombia), *P. lilacinus* BCP2 (NRRL 50756; e. g. PL GOLD from BASF Agricultural Specialities (Pty) Ltd., South Africa), mixture of *Paenibacillus alvei* NAS6G6 (NRRL B-50755) and *Bacillus pumilus* (e.g. BAC-UP from BASF Agricultural Specialities (Pty) Ltd., South Africa), *Pantoea vagans* (formerly *agglomerans*) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* sp. ATCC PTA-9643 (WO 2010/085795), *P. nishizawae* Pn1 (e.g. CLARIVA PN from Syngenta Crop Protection, LLC, Greenborom;C, USA) (B.16), *Pasteuria* sp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e. g. Jump Start® from Novozymes Biologicals BioAg Group, Canada, originally isolated from soil in southern Alberta; Fertilizer Res. 39, 97-103, 1994) (B.17), *Phlebiopsis gigantea* (e. g. RotStop® from Verdera Oy, Finland), *Pichia anomala* WRL-076 (NRRL Y-30842; U.S. Pat. No. 8,206,972), potassium bicarbonate (e. g. Amicarb® from Stähler S A, Switzerland), potassium silicate (e. g. Sil-MATRIX™ from Certis LLC, USA), *Pseudozyma flocculosa* PF-A22 UL (e. g. Sporodex® from Plant Products Co. Ltd., Canada), *Pseudomonas* sp. DSM 13134 (WO 2001/40441, e. g. in PRORADIX from Sourcon Padena GmbH & Co. KG, Hechinger Str. 262, 72072 Tübingen, Germany), *P. chloraphis* MA 342 (e. g. in CERALL or CEDEMON from BioAgri AB, Uppsala, Sweden), *P. fluorescens* CL 145A (e. g. in ZEQUANOX from Marrone BioInnovations, Davis, Calif., USA; J. Invertebr. Pathol. 113(1):104-14, 2013) (B.18), *Pythium oligandrum* DV 74 (ATCC 38472; e. g. POLYVERSUM® from Remeslo SSRO, Biopreparaty, Czech Rep. and GOWAN, USA; US 2013/0035230), *Reynoutria sachlinensis* extract (e. g. REGALIA® SC from Marrone BioInno¬vations, Davis, Calif., USA), *Rhizobium leguminosarum* bv. *phaseoli* (e. g. RHIZO-STICK from BASF Corp., USA) (B.19), *R. l.* bv. *trifolii* RP113-7 (e. g. DORMAL from BASF Corp., USA; Appl. Environ. Microbiol. 44(5), 1096-1101) (B.20), *R. l.* bv. *viciae* P1NP3Cst (also referred to as 1435; New Phytol. 179(1), 224-235, 2008; e. g. in NODULATOR PL Peat Granule from BASF Corp., USA; or in NODULATOR XL PL from BASF Agricultural Specialties Ltd., Canada) (B.21), *R. l.* bv. *viciae* SU303 (e. g. NODULAID Group E from BASF Agricultural Specialties Pty Ltd, Australia) (B.22), *R. l.* bv. *viciae* WSM1455 (e. g. NODULAID Group F from BASF Agricultural Specialties Pty Ltd, Australia) (B.23), *R. tropici* SEMIA 4080 (identical to PRF 81; Soil Biology & Biochemistry 39, 867-876, 2007) (B.24), *Sinorhizobium meliloti* MSDJ0848 (INRA, France) also referred to as strain 2011 or RCR2011 (Mol. Gen. Genomics 272, 1-17, 2004; e. g. DORMAL ALFALFA from BASF Corp., USA; NITRAGIN® Gold from Novozymes Biologicals BioAg Group, Canada) (B.25), *Sphaerodes mycoparasitica* IDAC 301008-01 (WO 2011/022809), *Spodoptera littoralis* nucleopolyhedrovirus (SpliNPV) (e.g. in LITTOVIR from Adermatt Biocontrol, Switzerland), *Steinernema carpocapsae* (e. g. MILLE¬NIUM® from BASF Agricultural Specialities Limited, UK), *S. feltiae* (NEMASHIELD® from BioWorks, Inc., USA; NEMASYS® from BASF Agricultural Specialities Limited, UK), *S. kraussei* L137 (NEMASYS® L from BASF Agricultural Specialities Limited, UK), *Streptomyces griseoviridis* K61 (e. g. MYCOSTOP® from Verdera Oy, Espoo, Finland; Crop Protection 25, 468-475, 2006), *S. lydicus* WYEC 108 (e. g. Actinovate® from Natural Industries, Inc., USA, U.S. Pat. No. 5,403, 584), *S. violaceusniger* YCED-9 (e. g. DT-9® from Natural Industries, Inc., USA, U.S. Pat. No. 5,968,503), *Talaromyces flavus* V117b (e. g. PROTUS® from Prophyta, Germany), *Tricho¬derma asperellum* SKT-1 (e. g. ECO-HOPE® from Kumiai Chemical Industry Co., Ltd., Japan), *T. asperellum* ICC 012 (e. g. in TENET WP, REMDIER WP, BIOTEN WP from Isagro NC, USA, BIO-TAM from Agra-Quest, USA), *T. atroviride* LC52 (e. g. SENTINEL® from Agrimm Technolo¬gies Ltd, NZ), *T. atroviride* CNCM I-1237 (e. g. in Esquive WG from Agrauxine S.A., France, e. g. against pruning wound diseases on vine and plant root pathogens), *T. fertile* JM41R (NRRL 50759; e. g. TRICHOPLUS™ from BASF Agricultural Specialities (Pty) Ltd., South Africa) (B.26), *T. gamsii* ICC 080 (e. g. in TENET WP, REMDIER WP, BIOTEN WP from Isagro NC, USA, BIO-TAM from AgraQuest, USA), *T. harzianum* T-22 (also called KRL-AG2; ATCC 20847; e. g. PLANTSHIELD® from BioWorks Inc., USA or SabrEx™ from Advanced Biological Marketing Inc., Van Wert, Ohio, USA; BioControl 57, 687-696, 2012), *T. harzianum* TH 35 (e. g. ROOT PRO® from Mycontrol Ltd., Israel), *T. harzianum* T-39 (e. g. TRICHODEX® and TRICHODERMA 2000® from Mycontrol Ltd., Israel and Makhteshim Ltd., Israel), mixture of *T. harzianum* and *T. viride* (e. g. TRICHOPEL from Agrimm Technologies Ltd, NZ), *T. harzianum* ICC012 and *T. viride* ICC080 (e. g. REMEDIER® WP from Isagro Ricerca, Italy), *T. polysporum* and *T. harzianum* (e. g. BINAB® from BINAB Bio-Innovation AB, Sweden), *T. stromaticum* (e. g. TRICOVAB® from C.E.P.L.A.C., Brazil), *T. virens* G1-3 (also called GI-3; ATCC 58678; e.g. QuickRoots™ from TJ Technologies, Watertown, S. Dak., USA; CA 2471555 A1), *T. virens* GL-21 (also called G1-21; U.S. Pat. No. 7,429,477 B2; e. g. SOILGARD® 12G from Certis LLC, USA, EPA Registration Number: 70051-3 and EPA Establishment Number: 067250-IL-001), *T. virens* G-41 (also called 041, #41X or ABM 127; isolated from soil samples taken from Aphanomyces-suppressive bean fields in Livingston County, New York; U.S. Pat. No. 4,996,157; e. g. ROOTSHIELD® PLUS from BioWorks, Inc., USA), *T. viride* (e. g. TRIECO® from Ecosense Labs. (India) Pvt. Ltd., Indien, BIO-CURE® F from T. Stanes & Co. Ltd., Indien), *T. viride* TV1 (e. g. *T. viride* TV1 from Agribiotec srl, Italy) or *Ulocladium oudemansii* HRU3 (e. g. in BOTRY-ZEN® from Botry-Zen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-Institut DSMZ-Deutsche Sammlung von Mikroorganismen und Zellkulturen GmbH, Inhoffenstraβe 7 B, 38124 Braunschweig, Germany (strains with prefix DSM); International Depositary Authority of Canada Collection, Canada (strains with prefix IDAC); International Collection of Micro-organisms from Plants, Landcare Research, Private Bag 92170, Auckland Mail Centre, Auckland 1142, New Zealand (strains with prefix ICMP); IITA, PMB 5320, Ibadan, Nigeria (strains with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundagao Estadual de Pesquisa Agropecuaria, Rua Gongalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Beltsville, Md. 20705, USA (strains with prefix USDA: Beltsville Rhizob. Culture Coll. Catalog March 1987 USDA-ARS ARS-30: http://pdf.usaid.gov/pdf_docs/PNAAW891.pdf); and Murdoch University, Perth, Western Australia (strains with prefix WSM). Further strains may be found at the Global catalogue of Microorganisms: http://gcm.wfcc.info/ and http://www.landcareresearch.co.nz/resources/collections/icmp and further references to strain collections and their prefixes at http://refs.wdcm.org/collections.htm.

In preferred embodiments, the biopesticide may be at least one biopesticidee selected from the following group of biopesticides:

*Azospirillum* amazonense BR 11140 (SpY2T), *A. brasilense* AZ39, *A. brasilense* XOH (B.1), *A. brasilense* BR 11002 (B.2), *A. brasilense* BR 11005 (B.3), *A. brasilense* strains Ab-V5 and Ab-V6 (B.4), *A. lipoferum* BR 11646,

*Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MBI600 (B.9),

*Bacillus cereus* CNCM 1-1562 (B.10),

*Bacillus firmus* CNCM 1-1582 (B.11),

*Bacillus pumilus* GB34, *B. pumilus* KFP9F (B.12), *B. pumilus* QST 2808 (B.13),

*Bacillus subtilis* CX-9060, *B. subtilis* GB03, *B. subtilis* GB07, *B. subtilis* QST-713, *B. subtilis* var. *amyloliquefaciens* FZB24, *B. subtilis* var. *amyloliquefaciens* D747,

*Bradyrhizobium* sp., *Bradyrhizobium japonicum* (B.14),

*Burkholderia* sp. A396,

*Candida oleophila* 1-182,

*Coniothyrium minitans* CON/M/91-08 (B.15),

*Muscodor. albus* SA-13,

*Paecilomyces fumosoroseus* FE 9901, *P. lilacinus* 251, *P. lilacinus* DSM 15169, or *P. lilacinus* BCP2, mixtures of *Paenibacillus alvei* NAS6G6 and *Bacillus pumilus*,

*Pasteuria* sp. ATCC PTA-9643, *P. nishizawae* Pn1 (B.16), *Pasteuria* sp. ATCC SD-5832, *P. nishizawae, P. penetrans, P. ramose, P. thornea, P. usgae,*

*Penicillium bilaiae* (B.17),

*Pseudomonas* sp. DSM 13134, *P. chloraphis* MA 342, or *P. fluorescens* CL 145A (B.18),

*Rhizobium leguminosarum* bv. *Phaseoli* (B.19), *R. l.* bv. *trifolii* RP113-7 (B.20), *R. l.* bv. *viciae* P1NP3Cst (B.21), *R. l.* bv. *viciae* SU303 (B.22), *R. l.* bv. *viciae* WSM1455 (B.23), *R. tropici* SEMIA 4080 (B.24),

*Sinorhizobium meliloti* MSDJ0848 (B.25),

*Trichoderma asperellum* SKT-1, *T. asperellum* ICC 012, *T. atroviride* LC52, *T. atroviride* CNCM 1-1237, *T. fertile* JM41R (B.26), *T. gamsii* ICC 080, *T. harzianum*

T-22, *T. harzianum* TH 35, *T. harzianum* T-39, mixture of *T. harzianum* and *T. viride*, *T. harzianum* ICC012 and *T. viride* ICC080, *T. polysporum* and *T. harzianum*, *T. stromaticum*, *T. virens* G1-3, *T. virens* GL-21, *T. virens* G-41, *T. viride*, and *T. viride* TV1.

In a particularly preferred embodiment, the biopesticide is *Azospirillum* brasilense XOH (B.1), *A. brasilense* BR 11002 (B.2), *A. brasilense* BR 11005 (B.3), *A. brasilense* strains Ab-V5 and Ab-V6 (B.4), *Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MBI600 (B.9), *B. cereus* CNCM I-1562 (B.10), *B. firmus* CNCM I-1582 (B.11), *Bacillus pumilus* KFP9F (B.12), *B. pumilus* QST 2808 (B.13), *Bradyrhizobium japonicum* (B.14), *Coniothyrium minitans* CON/M/91-08 (B.15), *Pasteuria nishizawae* Pn1 (B.16), *Penicillium bilaiae* (B.17), *P. fluorescens* CL 145A (B.18), *Rhizobium leguminosarum* bv. *Phaseoli* (B.19), *R. l.* bv. *trifolii* RP113-7 (B.20), *R. l.* bv. *viciae* P1NP3Cst (B.21), *R. l.* bv. *viciae* SU303 (B.22), *R. l.* bv. *viciae* WSM1455 (B.23), *R. tropici* SEMIA 4080 (B.24), *Sinorhizobium meliloti* MSDJ0848 (B.25), *Trichoderma* fertile JM41R (B.26), cis-jasmone (B.27), methyl jasmonate (B.28), or Neem oil (B.29).

Accordingly, the present invention furthermore relates to compositions comprising as compound I (component A) a nitrification inhibitor as defined herein above and as compound II (component B) a biopesticide as defined herein, i.e. a combination of component A and B. In preferred embodiments, such compositions may be selected from the component A of Table 2 in column 2 (Com. A) and from component B of Table 2 in column 3 (Com. B). The number of component A of Table 2 corresponds to the number of component A as shown in Table 1, supra ("Entry").

Preferred embodiments thus include the specified combinations or compositions comprising component A and B as defined in Cb-1 to Cb-6235 of the following Table 2:

| Comb. | Com. A | Com. B |
|---|---|---|
| Cb-1 | 1 | B.1 |
| Cb-2 | 2 | B.1 |
| Cb-3 | 3 | B.1 |
| Cb-4 | 4 | B.1 |
| Cb-5 | 5 | B.1 |
| Cb-6 | 6 | B.1 |
| Cb-7 | 7 | B.1 |
| Cb-8 | 8 | B.1 |
| Cb-9 | 9 | B.1 |
| Cb-10 | 10 | B.1 |
| Cb-11 | 11 | B.1 |
| Cb-12 | 12 | B.1 |
| Cb-13 | 13 | B.1 |
| Cb-14 | 14 | B.1 |
| Cb-15 | 15 | B.1 |
| Cb-16 | 16 | B.1 |
| Cb-17 | 17 | B.1 |
| Cb-18 | 18 | B.1 |
| Cb-19 | 19 | B.1 |
| Cb-20 | 20 | B.1 |
| Cb-21 | 21 | B.1 |
| Cb-22 | 22 | B.1 |
| Cb-23 | 23 | B.1 |
| Cb-24 | 24 | B.1 |
| Cb-25 | 25 | B.1 |
| Cb-26 | 26 | B.1 |
| Cb-27 | 27 | B.1 |
| Cb-28 | 28 | B.1 |
| Cb-29 | 29 | B.1 |
| Cb-30 | 30 | B.1 |
| Cb-31 | 31 | B.1 |
| Cb-32 | 32 | B.1 |
| Cb-33 | 33 | B.1 |
| Cb-34 | 34 | B.1 |
| Cb-35 | 35 | B.1 |
| Cb-36 | 36 | B.1 |
| Cb-37 | 37 | B.1 |
| Cb-38 | 38 | B.1 |
| Cb-39 | 39 | B.1 |
| Cb-40 | 40 | B.1 |
| Cb-41 | 41 | B.1 |
| Cb-42 | 42 | B.1 |
| Cb-43 | 43 | B.1 |
| Cb-44 | 44 | B.1 |
| Cb-45 | 45 | B.1 |
| Cb-46 | 46 | B.1 |
| Cb-47 | 47 | B.1 |
| Cb-48 | 48 | B.1 |
| Cb-49 | 49 | B.1 |
| Cb-50 | 50 | B.1 |
| Cb-51 | 51 | B.1 |
| Cb-52 | 52 | B.1 |
| Cb-53 | 53 | B.1 |
| Cb-54 | 54 | B.1 |
| Cb-55 | 55 | B.1 |
| Cb-56 | 56 | B.1 |
| Cb-57 | 57 | B.1 |
| Cb-58 | 58 | B.1 |
| Cb-59 | 59 | B.1 |
| Cb-60 | 60 | B.1 |
| Cb-61 | 61 | B.1 |
| Cb-62 | 62 | B.1 |
| Cb-63 | 63 | B.1 |
| Cb-64 | 64 | B.1 |
| Cb-65 | 65 | B.1 |
| Cb-66 | 66 | B.1 |
| Cb-67 | 67 | B.1 |
| Cb-68 | 68 | B.1 |
| Cb-69 | 69 | B.1 |
| Cb-70 | 70 | B.1 |
| Cb-71 | 71 | B.1 |
| Cb-72 | 72 | B.1 |
| Cb-73 | 73 | B.1 |
| Cb-74 | 74 | B.1 |
| Cb-75 | 75 | B.1 |
| Cb-76 | 76 | B.1 |
| Cb-77 | 77 | B.1 |
| Cb-78 | 78 | B.1 |
| Cb-79 | 79 | B.1 |
| Cb-80 | 80 | B.1 |
| Cb-81 | 81 | B.1 |
| Cb-82 | 82 | B.1 |
| Cb-83 | 83 | B.1 |
| Cb-84 | 84 | B.1 |
| Cb-85 | 85 | B.1 |
| Cb-86 | 86 | B.1 |
| Cb-87 | 87 | B.1 |
| Cb-88 | 88 | B.1 |
| Cb-89 | 89 | B.1 |
| Cb-90 | 90 | B.1 |
| Cb-91 | 91 | B.1 |
| Cb-92 | 92 | B.1 |
| Cb-93 | 93 | B.1 |
| Cb-94 | 94 | B.1 |
| Cb-95 | 95 | B.1 |
| Cb-96 | 96 | B.1 |
| Cb-97 | 97 | B.1 |
| Cb-98 | 98 | B.1 |
| Cb-99 | 99 | B.1 |
| Cb-100 | 100 | B.1 |
| Cb-101 | 101 | B.1 |
| Cb-102 | 102 | B.1 |
| Cb-103 | 103 | B.1 |
| Cb-104 | 104 | B.1 |
| Cb-105 | 105 | B.1 |
| Cb-106 | 106 | B.1 |
| Cb-107 | 107 | B.1 |
| Cb-108 | 108 | B.1 |

-continued

| Comb. | Com. A | Com. B |
|---|---|---|
| Cb-109 | 109 | B.1 |
| Cb-110 | 110 | B.1 |
| Cb-111 | 111 | B.1 |
| Cb-112 | 112 | B.1 |
| Cb-113 | 113 | B.1 |
| Cb-114 | 114 | B.1 |
| Cb-115 | 115 | B.1 |
| Cb-116 | 116 | B.1 |
| Cb-117 | 117 | B.1 |
| Cb-118 | 118 | B.1 |
| Cb-119 | 119 | B.1 |
| Cb-120 | 120 | B.1 |
| Cb-121 | 121 | B.1 |
| Cb-122 | 122 | B.1 |
| Cb-123 | 123 | B.1 |
| Cb-124 | 124 | B.1 |
| Cb-125 | 125 | B.1 |
| Cb-126 | 126 | B.1 |
| Cb-127 | 127 | B.1 |
| Cb-128 | 128 | B.1 |
| Cb-129 | 129 | B.1 |
| Cb-130 | 130 | B.1 |
| Cb-131 | 131 | B.1 |
| Cb-132 | 132 | B.1 |
| Cb-133 | 133 | B.1 |
| Cb-134 | 134 | B.1 |
| Cb-135 | 135 | B.1 |
| Cb-136 | 136 | B.1 |
| Cb-137 | 137 | B.1 |
| Cb-138 | 138 | B.1 |
| Cb-139 | 139 | B.1 |
| Cb-140 | 140 | B.1 |
| Cb-141 | 141 | B.1 |
| Cb-142 | 142 | B.1 |
| Cb-143 | 143 | B.1 |
| Cb-144 | 144 | B.1 |
| Cb-145 | 145 | B.1 |
| Cb-146 | 146 | B.1 |
| Cb-147 | 147 | B.1 |
| Cb-148 | 148 | B.1 |
| Cb-149 | 149 | B.1 |
| Cb-150 | 150 | B.1 |
| Cb-151 | 151 | B.1 |
| Cb-152 | 152 | B.1 |
| Cb-153 | 153 | B.1 |
| Cb-154 | 154 | B.1 |
| Cb-155 | 155 | B.1 |
| Cb-156 | 156 | B.1 |
| Cb-157 | 157 | B.1 |
| Cb-158 | 158 | B.1 |
| Cb-159 | 159 | B.1 |
| Cb-160 | 160 | B.1 |
| Cb-161 | 161 | B.1 |
| Cb-162 | 162 | B.1 |
| Cb-163 | 163 | B.1 |
| Cb-164 | 164 | B.1 |
| Cb-165 | 165 | B.1 |
| Cb-166 | 166 | B.1 |
| Cb-167 | 167 | B.1 |
| Cb-168 | 168 | B.1 |
| Cb-169 | 169 | B.1 |
| Cb-170 | 170 | B.1 |
| Cb-171 | 171 | B.1 |
| Cb-172 | 172 | B.1 |
| Cb-173 | 173 | B.1 |
| Cb-174 | 174 | B.1 |
| Cb-175 | 175 | B.1 |
| Cb-176 | 176 | B.1 |
| Cb-177 | 177 | B.1 |
| Cb-178 | 178 | B.1 |
| Cb-179 | 179 | B.1 |
| Cb-180 | 180 | B.1 |
| Cb-181 | 181 | B.1 |
| Cb-182 | 182 | B.1 |
| Cb-183 | 183 | B.1 |
| Cb-184 | 184 | B.1 |
| Cb-185 | 185 | B.1 |

-continued

| Comb. | Com. A | Com. B |
|---|---|---|
| Cb-186 | 186 | B.1 |
| Cb-187 | 187 | B.1 |
| Cb-188 | 188 | B.1 |
| Cb-189 | 189 | B.1 |
| Cb-190 | 190 | B.1 |
| Cb-191 | 191 | B.1 |
| Cb-192 | 192 | B.1 |
| Cb-193 | 193 | B.1 |
| Cb-194 | 194 | B.1 |
| Cb-195 | 195 | B.1 |
| Cb-196 | 196 | B.1 |
| Cb-197 | 197 | B.1 |
| Cb-198 | 198 | B.1 |
| Cb-199 | 199 | B.1 |
| Cb-200 | 200 | B.1 |
| Cb-201 | 201 | B.1 |
| Cb-202 | 202 | B.1 |
| Cb-203 | 203 | B.1 |
| Cb-204 | 204 | B.1 |
| Cb-205 | 205 | B.1 |
| Cb-206 | 206 | B.1 |
| Cb-207 | 207 | B.1 |
| Cb-208 | 208 | B.1 |
| Cb-209 | 209 | B.1 |
| Cb-210 | 210 | B.1 |
| Cb-211 | 211 | B.1 |
| Cb-212 | 212 | B.1 |
| Cb-213 | 213 | B.1 |
| Cb-214 | 214 | B.1 |
| Cb-215 | 215 | B.1 |
| Cb-216 | 1 | B.2 |
| Cb-217 | 2 | B.2 |
| Cb-218 | 3 | B.2 |
| Cb-219 | 4 | B.2 |
| Cb-220 | 5 | B.2 |
| Cb-221 | 6 | B.2 |
| Cb-222 | 7 | B.2 |
| Cb-223 | 8 | B.2 |
| Cb-224 | 9 | B.2 |
| Cb-225 | 10 | B.2 |
| Cb-226 | 11 | B.2 |
| Cb-227 | 12 | B.2 |
| Cb-228 | 13 | B.2 |
| Cb-229 | 14 | B.2 |
| Cb-230 | 15 | B.2 |
| Cb-231 | 16 | B.2 |
| Cb-232 | 17 | B.2 |
| Cb-233 | 18 | B.2 |
| Cb-234 | 19 | B.2 |
| Cb-235 | 20 | B.2 |
| Cb-236 | 21 | B.2 |
| Cb-237 | 22 | B.2 |
| Cb-238 | 23 | B.2 |
| Cb-239 | 24 | B.2 |
| Cb-240 | 25 | B.2 |
| Cb-241 | 26 | B.2 |
| Cb-242 | 27 | B.2 |
| Cb-243 | 28 | B.2 |
| Cb-244 | 29 | B.2 |
| Cb-245 | 30 | B.2 |
| Cb-246 | 31 | B.2 |
| Cb-247 | 32 | B.2 |
| Cb-248 | 33 | B.2 |
| Cb-249 | 34 | B.2 |
| Cb-250 | 35 | B.2 |
| Cb-251 | 36 | B.2 |
| Cb-252 | 37 | B.2 |
| Cb-253 | 38 | B.2 |
| Cb-254 | 39 | B.2 |
| Cb-255 | 40 | B.2 |
| Cb-256 | 41 | B.2 |
| Cb-257 | 42 | B.2 |
| Cb-258 | 43 | B.2 |
| Cb-259 | 44 | B.2 |
| Cb-260 | 45 | B.2 |
| Cb-261 | 46 | B.2 |
| Cb-262 | 47 | B.2 |

| Comb. | Com. A | Com. B |
|---|---|---|
| Cb-263 | 48 | B.2 |
| Cb-264 | 49 | B.2 |
| Cb-265 | 50 | B.2 |
| Cb-266 | 51 | B.2 |
| Cb-267 | 52 | B.2 |
| Cb-268 | 53 | B.2 |
| Cb-269 | 54 | B.2 |
| Cb-270 | 55 | B.2 |
| Cb-271 | 56 | B.2 |
| Cb-272 | 57 | B.2 |
| Cb-273 | 58 | B.2 |
| Cb-274 | 59 | B.2 |
| Cb-275 | 60 | B.2 |
| Cb-276 | 61 | B.2 |
| Cb-277 | 62 | B.2 |
| Cb-278 | 63 | B.2 |
| Cb-279 | 64 | B.2 |
| Cb-280 | 65 | B.2 |
| Cb-281 | 66 | B.2 |
| Cb-282 | 67 | B.2 |
| Cb-283 | 68 | B.2 |
| Cb-284 | 69 | B.2 |
| Cb-285 | 70 | B.2 |
| Cb-286 | 71 | B.2 |
| Cb-287 | 72 | B.2 |
| Cb-288 | 73 | B.2 |
| Cb-289 | 74 | B.2 |
| Cb-290 | 75 | B.2 |
| Cb-291 | 76 | B.2 |
| Cb-292 | 77 | B.2 |
| Cb-293 | 78 | B.2 |
| Cb-294 | 79 | B.2 |
| Cb-295 | 80 | B.2 |
| Cb-296 | 81 | B.2 |
| Cb-297 | 82 | B.2 |
| Cb-298 | 83 | B.2 |
| Cb-299 | 84 | B.2 |
| Cb-300 | 85 | B.2 |
| Cb-301 | 86 | B.2 |
| Cb-302 | 87 | B.2 |
| Cb-303 | 88 | B.2 |
| Cb-304 | 89 | B.2 |
| Cb-305 | 90 | B.2 |
| Cb-306 | 91 | B.2 |
| Cb-307 | 92 | B.2 |
| Cb-308 | 93 | B.2 |
| Cb-309 | 94 | B.2 |
| Cb-310 | 95 | B.2 |
| Cb-311 | 96 | B.2 |
| Cb-312 | 97 | B.2 |
| Cb-313 | 98 | B.2 |
| Cb-314 | 99 | B.2 |
| Cb-315 | 100 | B.2 |
| Cb-316 | 101 | B.2 |
| Cb-317 | 102 | B.2 |
| Cb-318 | 103 | B.2 |
| Cb-319 | 104 | B.2 |
| Cb-320 | 105 | B.2 |
| Cb-321 | 106 | B.2 |
| Cb-322 | 107 | B.2 |
| Cb-323 | 108 | B.2 |
| Cb-324 | 109 | B.2 |
| Cb-325 | 110 | B.2 |
| Cb-326 | 111 | B.2 |
| Cb-327 | 112 | B.2 |
| Cb-328 | 113 | B.2 |
| Cb-329 | 114 | B.2 |
| Cb-330 | 115 | B.2 |
| Cb-331 | 116 | B.2 |
| Cb-332 | 117 | B.2 |
| Cb-333 | 118 | B.2 |
| Cb-334 | 119 | B.2 |
| Cb-335 | 120 | B.2 |
| Cb-336 | 121 | B.2 |
| Cb-337 | 122 | B.2 |
| Cb-338 | 123 | B.2 |
| Cb-339 | 124 | B.2 |
| Cb-340 | 125 | B.2 |
| Cb-341 | 126 | B.2 |
| Cb-342 | 127 | B.2 |
| Cb-343 | 128 | B.2 |
| Cb-344 | 129 | B.2 |
| Cb-345 | 130 | B.2 |
| Cb-346 | 131 | B.2 |
| Cb-347 | 132 | B.2 |
| Cb-348 | 133 | B.2 |
| Cb-349 | 134 | B.2 |
| Cb-350 | 135 | B.2 |
| Cb-351 | 136 | B.2 |
| Cb-352 | 137 | B.2 |
| Cb-353 | 138 | B.2 |
| Cb-354 | 139 | B.2 |
| Cb-355 | 140 | B.2 |
| Cb-356 | 141 | B.2 |
| Cb-357 | 142 | B.2 |
| Cb-358 | 143 | B.2 |
| Cb-359 | 144 | B.2 |
| Cb-360 | 145 | B.2 |
| Cb-361 | 146 | B.2 |
| Cb-362 | 147 | B.2 |
| Cb-363 | 148 | B.2 |
| Cb-364 | 149 | B.2 |
| Cb-365 | 150 | B.2 |
| Cb-366 | 151 | B.2 |
| Cb-367 | 152 | B.2 |
| Cb-368 | 153 | B.2 |
| Cb-369 | 154 | B.2 |
| Cb-370 | 155 | B.2 |
| Cb-371 | 156 | B.2 |
| Cb-372 | 157 | B.2 |
| Cb-373 | 158 | B.2 |
| Cb-374 | 159 | B.2 |
| Cb-375 | 160 | B.2 |
| Cb-376 | 161 | B.2 |
| Cb-377 | 162 | B.2 |
| Cb-378 | 163 | B.2 |
| Cb-379 | 164 | B.2 |
| Cb-380 | 165 | B.2 |
| Cb-381 | 166 | B.2 |
| Cb-382 | 167 | B.2 |
| Cb-383 | 168 | B.2 |
| Cb-384 | 169 | B.2 |
| Cb-385 | 170 | B.2 |
| Cb-386 | 171 | B.2 |
| Cb-387 | 172 | B.2 |
| Cb-388 | 173 | B.2 |
| Cb-389 | 174 | B.2 |
| Cb-390 | 175 | B.2 |
| Cb-391 | 176 | B.2 |
| Cb-392 | 177 | B.2 |
| Cb-393 | 178 | B.2 |
| Cb-394 | 179 | B.2 |
| Cb-395 | 180 | B.2 |
| Cb-396 | 181 | B.2 |
| Cb-397 | 182 | B.2 |
| Cb-398 | 183 | B.2 |
| Cb-399 | 184 | B.2 |
| Cb-400 | 185 | B.2 |
| Cb-401 | 186 | B.2 |
| Cb-402 | 187 | B.2 |
| Cb-403 | 188 | B.2 |
| Cb-404 | 189 | B.2 |
| Cb-405 | 190 | B.2 |
| Cb-406 | 191 | B.2 |
| Cb-407 | 192 | B.2 |
| Cb-408 | 193 | B.2 |
| Cb-409 | 194 | B.2 |
| Cb-410 | 195 | B.2 |
| Cb-411 | 196 | B.2 |
| Cb-412 | 197 | B.2 |
| Cb-413 | 198 | B.2 |
| Cb-414 | 199 | B.2 |
| Cb-415 | 200 | B.2 |
| Cb-416 | 201 | B.2 |

| Comb. | Com. A | Com. B |
|---|---|---|
| Cb-417 | 202 | B.2 |
| Cb-418 | 203 | B.2 |
| Cb-419 | 204 | B.2 |
| Cb-420 | 205 | B.2 |
| Cb-421 | 206 | B.2 |
| Cb-422 | 207 | B.2 |
| Cb-423 | 208 | B.2 |
| Cb-424 | 209 | B.2 |
| Cb-425 | 210 | B.2 |
| Cb-426 | 211 | B.2 |
| Cb-427 | 212 | B.2 |
| Cb-428 | 213 | B.2 |
| Cb-429 | 214 | B.2 |
| Cb-430 | 215 | B.2 |
| Cb-431 | 1 | B.3 |
| Cb-432 | 2 | B.3 |
| Cb-433 | 3 | B.3 |
| Cb-434 | 4 | B.3 |
| Cb-435 | 5 | B.3 |
| Cb-436 | 6 | B.3 |
| Cb-437 | 7 | B.3 |
| Cb-438 | 8 | B.3 |
| Cb-439 | 9 | B.3 |
| Cb-440 | 10 | B.3 |
| Cb-441 | 11 | B.3 |
| Cb-442 | 12 | B.3 |
| Cb-443 | 13 | B.3 |
| Cb-444 | 14 | B.3 |
| Cb-445 | 15 | B.3 |
| Cb-446 | 16 | B.3 |
| Cb-447 | 17 | B.3 |
| Cb-448 | 18 | B.3 |
| Cb-449 | 19 | B.3 |
| Cb-450 | 20 | B.3 |
| Cb-451 | 21 | B.3 |
| Cb-452 | 22 | B.3 |
| Cb-453 | 23 | B.3 |
| Cb-454 | 24 | B.3 |
| Cb-455 | 25 | B.3 |
| Cb-456 | 26 | B.3 |
| Cb-457 | 27 | B.3 |
| Cb-458 | 28 | B.3 |
| Cb-459 | 29 | B.3 |
| Cb-460 | 30 | B.3 |
| Cb-461 | 31 | B.3 |
| Cb-462 | 32 | B.3 |
| Cb-463 | 33 | B.3 |
| Cb-464 | 34 | B.3 |
| Cb-465 | 35 | B.3 |
| Cb-466 | 36 | B.3 |
| Cb-467 | 37 | B.3 |
| Cb-468 | 38 | B.3 |
| Cb-469 | 39 | B.3 |
| Cb-470 | 40 | B.3 |
| Cb-471 | 41 | B.3 |
| Cb-472 | 42 | B.3 |
| Cb-473 | 43 | B.3 |
| Cb-474 | 44 | B.3 |
| Cb-475 | 45 | B.3 |
| Cb-476 | 46 | B.3 |
| Cb-477 | 47 | B.3 |
| Cb-478 | 48 | B.3 |
| Cb-479 | 49 | B.3 |
| Cb-480 | 50 | B.3 |
| Cb-481 | 51 | B.3 |
| Cb-482 | 52 | B.3 |
| Cb-483 | 53 | B.3 |
| Cb-484 | 54 | B.3 |
| Cb-485 | 55 | B.3 |
| Cb-486 | 56 | B.3 |
| Cb-487 | 57 | B.3 |
| Cb-488 | 58 | B.3 |
| Cb-489 | 59 | B.3 |
| Cb-490 | 60 | B.3 |
| Cb-491 | 61 | B.3 |
| Cb-492 | 62 | B.3 |
| Cb-493 | 63 | B.3 |
| Cb-494 | 64 | B.3 |
| Cb-495 | 65 | B.3 |
| Cb-496 | 66 | B.3 |
| Cb-497 | 67 | B.3 |
| Cb-498 | 68 | B.3 |
| Cb-499 | 69 | B.3 |
| Cb-500 | 70 | B.3 |
| Cb-501 | 71 | B.3 |
| Cb-502 | 72 | B.3 |
| Cb-503 | 73 | B.3 |
| Cb-504 | 74 | B.3 |
| Cb-505 | 75 | B.3 |
| Cb-506 | 76 | B.3 |
| Cb-507 | 77 | B.3 |
| Cb-508 | 78 | B.3 |
| Cb-509 | 79 | B.3 |
| Cb-510 | 80 | B.3 |
| Cb-511 | 81 | B.3 |
| Cb-512 | 82 | B.3 |
| Cb-513 | 83 | B.3 |
| Cb-514 | 84 | B.3 |
| Cb-515 | 85 | B.3 |
| Cb-516 | 86 | B.3 |
| Cb-517 | 87 | B.3 |
| Cb-518 | 88 | B.3 |
| Cb-519 | 89 | B.3 |
| Cb-520 | 90 | B.3 |
| Cb-521 | 91 | B.3 |
| Cb-522 | 92 | B.3 |
| Cb-523 | 93 | B.3 |
| Cb-524 | 94 | B.3 |
| Cb-525 | 95 | B.3 |
| Cb-526 | 96 | B.3 |
| Cb-527 | 97 | B.3 |
| Cb-528 | 98 | B.3 |
| Cb-529 | 99 | B.3 |
| Cb-530 | 100 | B.3 |
| Cb-531 | 101 | B.3 |
| Cb-532 | 102 | B.3 |
| Cb-533 | 103 | B.3 |
| Cb-534 | 104 | B.3 |
| Cb-535 | 105 | B.3 |
| Cb-536 | 106 | B.3 |
| Cb-537 | 107 | B.3 |
| Cb-538 | 108 | B.3 |
| Cb-539 | 109 | B.3 |
| Cb-540 | 110 | B.3 |
| Cb-541 | 111 | B.3 |
| Cb-542 | 112 | B.3 |
| Cb-543 | 113 | B.3 |
| Cb-544 | 114 | B.3 |
| Cb-545 | 115 | B.3 |
| Cb-546 | 116 | B.3 |
| Cb-547 | 117 | B.3 |
| Cb-548 | 118 | B.3 |
| Cb-549 | 119 | B.3 |
| Cb-550 | 120 | B.3 |
| Cb-551 | 121 | B.3 |
| Cb-552 | 122 | B.3 |
| Cb-553 | 123 | B.3 |
| Cb-554 | 124 | B.3 |
| Cb-555 | 125 | B.3 |
| Cb-556 | 126 | B.3 |
| Cb-557 | 127 | B.3 |
| Cb-558 | 128 | B.3 |
| Cb-559 | 129 | B.3 |
| Cb-560 | 130 | B.3 |
| Cb-561 | 131 | B.3 |
| Cb-562 | 132 | B.3 |
| Cb-563 | 133 | B.3 |
| Cb-564 | 134 | B.3 |
| Cb-565 | 135 | B.3 |
| Cb-566 | 136 | B.3 |
| Cb-567 | 137 | B.3 |
| Cb-568 | 138 | B.3 |
| Cb-569 | 139 | B.3 |
| Cb-570 | 140 | B.3 |

| Comb. | Com. A | Com. B |
|---|---|---|
| Cb-571 | 141 | B.3 |
| Cb-572 | 142 | B.3 |
| Cb-573 | 143 | B.3 |
| Cb-574 | 144 | B.3 |
| Cb-575 | 145 | B.3 |
| Cb-576 | 146 | B.3 |
| Cb-577 | 147 | B.3 |
| Cb-578 | 148 | B.3 |
| Cb-579 | 149 | B.3 |
| Cb-580 | 150 | B.3 |
| Cb-581 | 151 | B.3 |
| Cb-582 | 152 | B.3 |
| Cb-583 | 153 | B.3 |
| Cb-584 | 154 | B.3 |
| Cb-585 | 155 | B.3 |
| Cb-586 | 156 | B.3 |
| Cb-587 | 157 | B.3 |
| Cb-588 | 158 | B.3 |
| Cb-589 | 159 | B.3 |
| Cb-590 | 160 | B.3 |
| Cb-591 | 161 | B.3 |
| Cb-592 | 162 | B.3 |
| Cb-593 | 163 | B.3 |
| Cb-594 | 164 | B.3 |
| Cb-595 | 165 | B.3 |
| Cb-596 | 166 | B.3 |
| Cb-597 | 167 | B.3 |
| Cb-598 | 168 | B.3 |
| Cb-599 | 169 | B.3 |
| Cb-600 | 170 | B.3 |
| Cb-601 | 171 | B.3 |
| Cb-602 | 172 | B.3 |
| Cb-603 | 173 | B.3 |
| Cb-604 | 174 | B.3 |
| Cb-605 | 175 | B.3 |
| Cb-606 | 176 | B.3 |
| Cb-607 | 177 | B.3 |
| Cb-608 | 178 | B.3 |
| Cb-609 | 179 | B.3 |
| Cb-610 | 180 | B.3 |
| Cb-611 | 181 | B.3 |
| Cb-612 | 182 | B.3 |
| Cb-613 | 183 | B.3 |
| Cb-614 | 184 | B.3 |
| Cb-615 | 185 | B.3 |
| Cb-616 | 186 | B.3 |
| Cb-617 | 187 | B.3 |
| Cb-618 | 188 | B.3 |
| Cb-619 | 189 | B.3 |
| Cb-620 | 190 | B.3 |
| Cb-621 | 191 | B.3 |
| Cb-622 | 192 | B.3 |
| Cb-623 | 193 | B.3 |
| Cb-624 | 194 | B.3 |
| Cb-625 | 195 | B.3 |
| Cb-626 | 196 | B.3 |
| Cb-627 | 197 | B.3 |
| Cb-628 | 198 | B.3 |
| Cb-629 | 199 | B.3 |
| Cb-630 | 200 | B.3 |
| Cb-631 | 201 | B.3 |
| Cb-632 | 202 | B.3 |
| Cb-633 | 203 | B.3 |
| Cb-634 | 204 | B.3 |
| Cb-635 | 205 | B.3 |
| Cb-636 | 206 | B.3 |
| Cb-637 | 207 | B.3 |
| Cb-638 | 208 | B.3 |
| Cb-639 | 209 | B.3 |
| Cb-640 | 210 | B.3 |
| Cb-641 | 211 | B.3 |
| Cb-642 | 212 | B.3 |
| Cb-643 | 213 | B.3 |
| Cb-644 | 214 | B.3 |
| Cb-645 | 215 | B.3 |
| Cb-646 | 1 | B.4 |
| Cb-647 | 2 | B.4 |
| Cb-648 | 3 | B.4 |
| Cb-649 | 4 | B.4 |
| Cb-650 | 5 | B.4 |
| Cb-651 | 6 | B.4 |
| Cb-652 | 7 | B.4 |
| Cb-653 | 8 | B.4 |
| Cb-654 | 9 | B.4 |
| Cb-655 | 10 | B.4 |
| Cb-656 | 11 | B.4 |
| Cb-657 | 12 | B.4 |
| Cb-658 | 13 | B.4 |
| Cb-659 | 14 | B.4 |
| Cb-660 | 15 | B.4 |
| Cb-661 | 16 | B.4 |
| Cb-662 | 17 | B.4 |
| Cb-663 | 18 | B.4 |
| Cb-664 | 19 | B.4 |
| Cb-665 | 20 | B.4 |
| Cb-666 | 21 | B.4 |
| Cb-667 | 22 | B.4 |
| Cb-668 | 23 | B.4 |
| Cb-669 | 24 | B.4 |
| Cb-670 | 25 | B.4 |
| Cb-671 | 26 | B.4 |
| Cb-672 | 27 | B.4 |
| Cb-673 | 28 | B.4 |
| Cb-674 | 29 | B.4 |
| Cb-675 | 30 | B.4 |
| Cb-676 | 31 | B.4 |
| Cb-677 | 32 | B.4 |
| Cb-678 | 33 | B.4 |
| Cb-679 | 34 | B.4 |
| Cb-680 | 35 | B.4 |
| Cb-681 | 36 | B.4 |
| Cb-682 | 37 | B.4 |
| Cb-683 | 38 | B.4 |
| Cb-684 | 39 | B.4 |
| Cb-685 | 40 | B.4 |
| Cb-686 | 41 | B.4 |
| Cb-687 | 42 | B.4 |
| Cb-688 | 43 | B.4 |
| Cb-689 | 44 | B.4 |
| Cb-690 | 45 | B.4 |
| Cb-691 | 46 | B.4 |
| Cb-692 | 47 | B.4 |
| Cb-693 | 48 | B.4 |
| Cb-694 | 49 | B.4 |
| Cb-695 | 50 | B.4 |
| Cb-696 | 51 | B.4 |
| Cb-697 | 52 | B.4 |
| Cb-698 | 53 | B.4 |
| Cb-699 | 54 | B.4 |
| Cb-700 | 55 | B.4 |
| Cb-701 | 56 | B.4 |
| Cb-702 | 57 | B.4 |
| Cb-703 | 58 | B.4 |
| Cb-704 | 59 | B.4 |
| Cb-705 | 60 | B.4 |
| Cb-706 | 61 | B.4 |
| Cb-707 | 62 | B.4 |
| Cb-708 | 63 | B.4 |
| Cb-709 | 64 | B.4 |
| Cb-710 | 65 | B.4 |
| Cb-711 | 66 | B.4 |
| Cb-712 | 67 | B.4 |
| Cb-713 | 68 | B.4 |
| Cb-714 | 69 | B.4 |
| Cb-715 | 70 | B.4 |
| Cb-716 | 71 | B.4 |
| Cb-717 | 72 | B.4 |
| Cb-718 | 73 | B.4 |
| Cb-719 | 74 | B.4 |
| Cb-720 | 75 | B.4 |
| Cb-721 | 76 | B.4 |
| Cb-722 | 77 | B.4 |
| Cb-723 | 78 | B.4 |
| Cb-724 | 79 | B.4 |

| Comb. | Com. A | Com. B |
|---|---|---|
| Cb-725 | 80 | B.4 |
| Cb-726 | 81 | B.4 |
| Cb-727 | 82 | B.4 |
| Cb-728 | 83 | B.4 |
| Cb-729 | 84 | B.4 |
| Cb-730 | 85 | B.4 |
| Cb-731 | 86 | B.4 |
| Cb-732 | 87 | B.4 |
| Cb-733 | 88 | B.4 |
| Cb-734 | 89 | B.4 |
| Cb-735 | 90 | B.4 |
| Cb-736 | 91 | B.4 |
| Cb-737 | 92 | B.4 |
| Cb-738 | 93 | B.4 |
| Cb-739 | 94 | B.4 |
| Cb-740 | 95 | B.4 |
| Cb-741 | 96 | B.4 |
| Cb-742 | 97 | B.4 |
| Cb-743 | 98 | B.4 |
| Cb-744 | 99 | B.4 |
| Cb-745 | 100 | B.4 |
| Cb-746 | 101 | B.4 |
| Cb-747 | 102 | B.4 |
| Cb-748 | 103 | B.4 |
| Cb-749 | 104 | B.4 |
| Cb-750 | 105 | B.4 |
| Cb-751 | 106 | B.4 |
| Cb-752 | 107 | B.4 |
| Cb-753 | 108 | B.4 |
| Cb-754 | 109 | B.4 |
| Cb-755 | 110 | B.4 |
| Cb-756 | 111 | B.4 |
| Cb-757 | 112 | B.4 |
| Cb-758 | 113 | B.4 |
| Cb-759 | 114 | B.4 |
| Cb-760 | 115 | B.4 |
| Cb-761 | 116 | B.4 |
| Cb-762 | 117 | B.4 |
| Cb-763 | 118 | B.4 |
| Cb-764 | 119 | B.4 |
| Cb-765 | 120 | B.4 |
| Cb-766 | 121 | B.4 |
| Cb-767 | 122 | B.4 |
| Cb-768 | 123 | B.4 |
| Cb-769 | 124 | B.4 |
| Cb-770 | 125 | B.4 |
| Cb-771 | 126 | B.4 |
| Cb-772 | 127 | B.4 |
| Cb-773 | 128 | B.4 |
| Cb-774 | 129 | B.4 |
| Cb-775 | 130 | B.4 |
| Cb-776 | 131 | B.4 |
| Cb-777 | 132 | B.4 |
| Cb-778 | 133 | B.4 |
| Cb-779 | 134 | B.4 |
| Cb-780 | 135 | B.4 |
| Cb-781 | 136 | B.4 |
| Cb-782 | 137 | B.4 |
| Cb-783 | 138 | B.4 |
| Cb-784 | 139 | B.4 |
| Cb-785 | 140 | B.4 |
| Cb-786 | 141 | B.4 |
| Cb-787 | 142 | B.4 |
| Cb-788 | 143 | B.4 |
| Cb-789 | 144 | B.4 |
| Cb-790 | 145 | B.4 |
| Cb-791 | 146 | B.4 |
| Cb-792 | 147 | B.4 |
| Cb-793 | 148 | B.4 |
| Cb-794 | 149 | B.4 |
| Cb-795 | 150 | B.4 |
| Cb-796 | 151 | B.4 |
| Cb-797 | 152 | B.4 |
| Cb-798 | 153 | B.4 |
| Cb-799 | 154 | B.4 |
| Cb-800 | 155 | B.4 |
| Cb-801 | 156 | B.4 |
| Cb-802 | 157 | B.4 |
| Cb-803 | 158 | B.4 |
| Cb-804 | 159 | B.4 |
| Cb-805 | 160 | B.4 |
| Cb-806 | 161 | B.4 |
| Cb-807 | 162 | B.4 |
| Cb-808 | 163 | B.4 |
| Cb-809 | 164 | B.4 |
| Cb-810 | 165 | B.4 |
| Cb-811 | 166 | B.4 |
| Cb-812 | 167 | B.4 |
| Cb-813 | 168 | B.4 |
| Cb-814 | 169 | B.4 |
| Cb-815 | 170 | B.4 |
| Cb-816 | 171 | B.4 |
| Cb-817 | 172 | B.4 |
| Cb-818 | 173 | B.4 |
| Cb-819 | 174 | B.4 |
| Cb-820 | 175 | B.4 |
| Cb-821 | 176 | B.4 |
| Cb-822 | 177 | B.4 |
| Cb-823 | 178 | B.4 |
| Cb-824 | 179 | B.4 |
| Cb-825 | 180 | B.4 |
| Cb-826 | 181 | B.4 |
| Cb-827 | 182 | B.4 |
| Cb-828 | 183 | B.4 |
| Cb-829 | 184 | B.4 |
| Cb-830 | 185 | B.4 |
| Cb-831 | 186 | B.4 |
| Cb-832 | 187 | B.4 |
| Cb-833 | 188 | B.4 |
| Cb-834 | 189 | B.4 |
| Cb-835 | 190 | B.4 |
| Cb-836 | 191 | B.4 |
| Cb-837 | 192 | B.4 |
| Cb-838 | 193 | B.4 |
| Cb-839 | 194 | B.4 |
| Cb-840 | 195 | B.4 |
| Cb-841 | 196 | B.4 |
| Cb-842 | 197 | B.4 |
| Cb-843 | 198 | B.4 |
| Cb-844 | 199 | B.4 |
| Cb-845 | 200 | B.4 |
| Cb-846 | 201 | B.4 |
| Cb-847 | 202 | B.4 |
| Cb-848 | 203 | B.4 |
| Cb-849 | 204 | B.4 |
| Cb-850 | 205 | B.4 |
| Cb-851 | 206 | B.4 |
| Cb-852 | 207 | B.4 |
| Cb-853 | 208 | B.4 |
| Cb-854 | 209 | B.4 |
| Cb-855 | 210 | B.4 |
| Cb-856 | 211 | B.4 |
| Cb-857 | 212 | B.4 |
| Cb-858 | 213 | B.4 |
| Cb-859 | 214 | B.4 |
| Cb-860 | 215 | B.4 |
| Cb-861 | 1 | B.5 |
| Cb-862 | 2 | B.5 |
| Cb-863 | 3 | B.5 |
| Cb-864 | 4 | B.5 |
| Cb-865 | 5 | B.5 |
| Cb-866 | 6 | B.5 |
| Cb-867 | 7 | B.5 |
| Cb-868 | 8 | B.5 |
| Cb-869 | 9 | B.5 |
| Cb-870 | 10 | B.5 |
| Cb-871 | 11 | B.5 |
| Cb-872 | 12 | B.5 |
| Cb-873 | 13 | B.5 |
| Cb-874 | 14 | B.5 |
| Cb-875 | 15 | B.5 |
| Cb-876 | 16 | B.5 |
| Cb-877 | 17 | B.5 |
| Cb-878 | 18 | B.5 |

| Comb. | Com. A | Com. B |
|---|---|---|
| Cb-879 | 19 | B.5 |
| Cb-880 | 20 | B.5 |
| Cb-881 | 21 | B.5 |
| Cb-882 | 22 | B.5 |
| Cb-883 | 23 | B.5 |
| Cb-884 | 24 | B.5 |
| Cb-885 | 25 | B.5 |
| Cb-886 | 26 | B.5 |
| Cb-887 | 27 | B.5 |
| Cb-888 | 28 | B.5 |
| Cb-889 | 29 | B.5 |
| Cb-890 | 30 | B.5 |
| Cb-891 | 31 | B.5 |
| Cb-892 | 32 | B.5 |
| Cb-893 | 33 | B.5 |
| Cb-894 | 34 | B.5 |
| Cb-895 | 35 | B.5 |
| Cb-896 | 36 | B.5 |
| Cb-897 | 37 | B.5 |
| Cb-898 | 38 | B.5 |
| Cb-899 | 39 | B.5 |
| Cb-900 | 40 | B.5 |
| Cb-901 | 41 | B.5 |
| Cb-902 | 42 | B.5 |
| Cb-903 | 43 | B.5 |
| Cb-904 | 44 | B.5 |
| Cb-905 | 45 | B.5 |
| Cb-906 | 46 | B.5 |
| Cb-907 | 47 | B.5 |
| Cb-908 | 48 | B.5 |
| Cb-909 | 49 | B.5 |
| Cb-910 | 50 | B.5 |
| Cb-911 | 51 | B.5 |
| Cb-912 | 52 | B.5 |
| Cb-913 | 53 | B.5 |
| Cb-914 | 54 | B.5 |
| Cb-915 | 55 | B.5 |
| Cb-916 | 56 | B.5 |
| Cb-917 | 57 | B.5 |
| Cb-918 | 58 | B.5 |
| Cb-919 | 59 | B.5 |
| Cb-920 | 60 | B.5 |
| Cb-921 | 61 | B.5 |
| Cb-922 | 62 | B.5 |
| Cb-923 | 63 | B.5 |
| Cb-924 | 64 | B.5 |
| Cb-925 | 65 | B.5 |
| Cb-926 | 66 | B.5 |
| Cb-927 | 67 | B.5 |
| Cb-928 | 68 | B.5 |
| Cb-929 | 69 | B.5 |
| Cb-930 | 70 | B.5 |
| Cb-931 | 71 | B.5 |
| Cb-932 | 72 | B.5 |
| Cb-933 | 73 | B.5 |
| Cb-934 | 74 | B.5 |
| Cb-935 | 75 | B.5 |
| Cb-936 | 76 | B.5 |
| Cb-937 | 77 | B.5 |
| Cb-938 | 78 | B.5 |
| Cb-939 | 79 | B.5 |
| Cb-940 | 80 | B.5 |
| Cb-941 | 81 | B.5 |
| Cb-942 | 82 | B.5 |
| Cb-943 | 83 | B.5 |
| Cb-944 | 84 | B.5 |
| Cb-945 | 85 | B.5 |
| Cb-946 | 86 | B.5 |
| Cb-947 | 87 | B.5 |
| Cb-948 | 88 | B.5 |
| Cb-949 | 89 | B.5 |
| Cb-950 | 90 | B.5 |
| Cb-951 | 91 | B.5 |
| Cb-952 | 92 | B.5 |
| Cb-953 | 93 | B.5 |
| Cb-954 | 94 | B.5 |
| Cb-955 | 95 | B.5 |
| Cb-956 | 96 | B.5 |
| Cb-957 | 97 | B.5 |
| Cb-958 | 98 | B.5 |
| Cb-959 | 99 | B.5 |
| Cb-960 | 100 | B.5 |
| Cb-961 | 101 | B.5 |
| Cb-962 | 102 | B.5 |
| Cb-963 | 103 | B.5 |
| Cb-964 | 104 | B.5 |
| Cb-965 | 105 | B.5 |
| Cb-966 | 106 | B.5 |
| Cb-967 | 107 | B.5 |
| Cb-968 | 108 | B.5 |
| Cb-969 | 109 | B.5 |
| Cb-970 | 110 | B.5 |
| Cb-971 | 111 | B.5 |
| Cb-972 | 112 | B.5 |
| Cb-973 | 113 | B.5 |
| Cb-974 | 114 | B.5 |
| Cb-975 | 115 | B.5 |
| Cb-976 | 116 | B.5 |
| Cb-977 | 117 | B.5 |
| Cb-978 | 118 | B.5 |
| Cb-979 | 119 | B.5 |
| Cb-980 | 120 | B.5 |
| Cb-981 | 121 | B.5 |
| Cb-982 | 122 | B.5 |
| Cb-983 | 123 | B.5 |
| Cb-984 | 124 | B.5 |
| Cb-985 | 125 | B.5 |
| Cb-986 | 126 | B.5 |
| Cb-987 | 127 | B.5 |
| Cb-988 | 128 | B.5 |
| Cb-989 | 129 | B.5 |
| Cb-990 | 130 | B.5 |
| Cb-991 | 131 | B.5 |
| Cb-992 | 132 | B.5 |
| Cb-993 | 133 | B.5 |
| Cb-994 | 134 | B.5 |
| Cb-995 | 135 | B.5 |
| Cb-996 | 136 | B.5 |
| Cb-997 | 137 | B.5 |
| Cb-998 | 138 | B.5 |
| Cb-999 | 139 | B.5 |
| Cb-1000 | 140 | B.5 |
| Cb-1001 | 141 | B.5 |
| Cb-1002 | 142 | B.5 |
| Cb-1003 | 143 | B.5 |
| Cb-1004 | 144 | B.5 |
| Cb-1005 | 145 | B.5 |
| Cb-1006 | 146 | B.5 |
| Cb-1007 | 147 | B.5 |
| Cb-1008 | 148 | B.5 |
| Cb-1009 | 149 | B.5 |
| Cb-1010 | 150 | B.5 |
| Cb-1011 | 151 | B.5 |
| Cb-1012 | 152 | B.5 |
| Cb-1013 | 153 | B.5 |
| Cb-1014 | 154 | B.5 |
| Cb-1015 | 155 | B.5 |
| Cb-1016 | 156 | B.5 |
| Cb-1017 | 157 | B.5 |
| Cb-1018 | 158 | B.5 |
| Cb-1019 | 159 | B.5 |
| Cb-1020 | 160 | B.5 |
| Cb-1021 | 161 | B.5 |
| Cb-1022 | 162 | B.5 |
| Cb-1023 | 163 | B.5 |
| Cb-1024 | 164 | B.5 |
| Cb-1025 | 165 | B.5 |
| Cb-1026 | 166 | B.5 |
| Cb-1027 | 167 | B.5 |
| Cb-1028 | 168 | B.5 |
| Cb-1029 | 169 | B.5 |
| Cb-1030 | 170 | B.5 |
| Cb-1031 | 171 | B.5 |
| Cb-1032 | 172 | B.5 |

| Comb. | Com. A | Com. B |
|---|---|---|
| Cb-1033 | 173 | B.5 |
| Cb-1034 | 174 | B.5 |
| Cb-1035 | 175 | B.5 |
| Cb-1036 | 176 | B.5 |
| Cb-1037 | 177 | B.5 |
| Cb-1038 | 178 | B.5 |
| Cb-1039 | 179 | B.5 |
| Cb-1040 | 180 | B.5 |
| Cb-1041 | 181 | B.5 |
| Cb-1042 | 182 | B.5 |
| Cb-1043 | 183 | B.5 |
| Cb-1044 | 184 | B.5 |
| Cb-1045 | 185 | B.5 |
| Cb-1046 | 186 | B.5 |
| Cb-1047 | 187 | B.5 |
| Cb-1048 | 188 | B.5 |
| Cb-1049 | 189 | B.5 |
| Cb-1050 | 190 | B.5 |
| Cb-1051 | 191 | B.5 |
| Cb-1052 | 192 | B.5 |
| Cb-1053 | 193 | B.5 |
| Cb-1054 | 194 | B.5 |
| Cb-1055 | 195 | B.5 |
| Cb-1056 | 196 | B.5 |
| Cb-1057 | 197 | B.5 |
| Cb-1058 | 198 | B.5 |
| Cb-1059 | 199 | B.5 |
| Cb-1060 | 200 | B.5 |
| Cb-1061 | 201 | B.5 |
| Cb-1062 | 202 | B.5 |
| Cb-1063 | 203 | B.5 |
| Cb-1064 | 204 | B.5 |
| Cb-1065 | 205 | B.5 |
| Cb-1066 | 206 | B.5 |
| Cb-1067 | 207 | B.5 |
| Cb-1068 | 208 | B.5 |
| Cb-1069 | 209 | B.5 |
| Cb-1070 | 210 | B.5 |
| Cb-1071 | 211 | B.5 |
| Cb-1072 | 212 | B.5 |
| Cb-1073 | 213 | B.5 |
| Cb-1074 | 214 | B.5 |
| Cb-1075 | 215 | B.5 |
| Cb-1076 | 1 | B.6 |
| Cb-1077 | 2 | B.6 |
| Cb-1078 | 3 | B.6 |
| Cb-1079 | 4 | B.6 |
| Cb-1080 | 5 | B.6 |
| Cb-1081 | 6 | B.6 |
| Cb-1082 | 7 | B.6 |
| Cb-1083 | 8 | B.6 |
| Cb-1084 | 9 | B.6 |
| Cb-1085 | 10 | B.6 |
| Cb-1086 | 11 | B.6 |
| Cb-1087 | 12 | B.6 |
| Cb-1088 | 13 | B.6 |
| Cb-1089 | 14 | B.6 |
| Cb-1090 | 15 | B.6 |
| Cb-1091 | 16 | B.6 |
| Cb-1092 | 17 | B.6 |
| Cb-1093 | 18 | B.6 |
| Cb-1094 | 19 | B.6 |
| Cb-1095 | 20 | B.6 |
| Cb-1096 | 21 | B.6 |
| Cb-1097 | 22 | B.6 |
| Cb-1098 | 23 | B.6 |
| Cb-1099 | 24 | B.6 |
| Cb-1100 | 25 | B.6 |
| Cb-1101 | 26 | B.6 |
| Cb-1102 | 27 | B.6 |
| Cb-1103 | 28 | B.6 |
| Cb-1104 | 29 | B.6 |
| Cb-1105 | 30 | B.6 |
| Cb-1106 | 31 | B.6 |
| Cb-1107 | 32 | B.6 |
| Cb-1108 | 33 | B.6 |
| Cb-1109 | 34 | B.6 |
| Cb-1110 | 35 | B.6 |
| Cb-1111 | 36 | B.6 |
| Cb-1112 | 37 | B.6 |
| Cb-1113 | 38 | B.6 |
| Cb-1114 | 39 | B.6 |
| Cb-1115 | 40 | B.6 |
| Cb-1116 | 41 | B.6 |
| Cb-1117 | 42 | B.6 |
| Cb-1118 | 43 | B.6 |
| Cb-1119 | 44 | B.6 |
| Cb-1120 | 45 | B.6 |
| Cb-1121 | 46 | B.6 |
| Cb-1122 | 47 | B.6 |
| Cb-1123 | 48 | B.6 |
| Cb-1124 | 49 | B.6 |
| Cb-1125 | 50 | B.6 |
| Cb-1126 | 51 | B.6 |
| Cb-1127 | 52 | B.6 |
| Cb-1128 | 53 | B.6 |
| Cb-1129 | 54 | B.6 |
| Cb-1130 | 55 | B.6 |
| Cb-1131 | 56 | B.6 |
| Cb-1132 | 57 | B.6 |
| Cb-1133 | 58 | B.6 |
| Cb-1134 | 59 | B.6 |
| Cb-1135 | 60 | B.6 |
| Cb-1136 | 61 | B.6 |
| Cb-1137 | 62 | B.6 |
| Cb-1138 | 63 | B.6 |
| Cb-1139 | 64 | B.6 |
| Cb-1140 | 65 | B.6 |
| Cb-1141 | 66 | B.6 |
| Cb-1142 | 67 | B.6 |
| Cb-1143 | 68 | B.6 |
| Cb-1144 | 69 | B.6 |
| Cb-1145 | 70 | B.6 |
| Cb-1146 | 71 | B.6 |
| Cb-1147 | 72 | B.6 |
| Cb-1148 | 73 | B.6 |
| Cb-1149 | 74 | B.6 |
| Cb-1150 | 75 | B.6 |
| Cb-1151 | 76 | B.6 |
| Cb-1152 | 77 | B.6 |
| Cb-1153 | 78 | B.6 |
| Cb-1154 | 79 | B.6 |
| Cb-1155 | 80 | B.6 |
| Cb-1156 | 81 | B.6 |
| Cb-1157 | 82 | B.6 |
| Cb-1158 | 83 | B.6 |
| Cb-1159 | 84 | B.6 |
| Cb-1160 | 85 | B.6 |
| Cb-1161 | 86 | B.6 |
| Cb-1162 | 87 | B.6 |
| Cb-1163 | 88 | B.6 |
| Cb-1164 | 89 | B.6 |
| Cb-1165 | 90 | B.6 |
| Cb-1166 | 91 | B.6 |
| Cb-1167 | 92 | B.6 |
| Cb-1168 | 93 | B.6 |
| Cb-1169 | 94 | B.6 |
| Cb-1170 | 95 | B.6 |
| Cb-1171 | 96 | B.6 |
| Cb-1172 | 97 | B.6 |
| Cb-1173 | 98 | B.6 |
| Cb-1174 | 99 | B.6 |
| Cb-1175 | 100 | B.6 |
| Cb-1176 | 101 | B.6 |
| Cb-1177 | 102 | B.6 |
| Cb-1178 | 103 | B.6 |
| Cb-1179 | 104 | B.6 |
| Cb-1180 | 105 | B.6 |
| Cb-1181 | 106 | B.6 |
| Cb-1182 | 107 | B.6 |
| Cb-1183 | 108 | B.6 |
| Cb-1184 | 109 | B.6 |
| Cb-1185 | 110 | B.6 |
| Cb-1186 | 111 | B.6 |

-continued

| Comb. | Com. A | Com. B |
|---|---|---|
| Cb-1187 | 112 | B.6 |
| Cb-1188 | 113 | B.6 |
| Cb-1189 | 114 | B.6 |
| Cb-1190 | 115 | B.6 |
| Cb-1191 | 116 | B.6 |
| Cb-1192 | 117 | B.6 |
| Cb-1193 | 118 | B.6 |
| Cb-1194 | 119 | B.6 |
| Cb-1195 | 120 | B.6 |
| Cb-1196 | 121 | B.6 |
| Cb-1197 | 122 | B.6 |
| Cb-1198 | 123 | B.6 |
| Cb-1199 | 124 | B.6 |
| Cb-1200 | 125 | B.6 |
| Cb-1201 | 126 | B.6 |
| Cb-1202 | 127 | B.6 |
| Cb-1203 | 128 | B.6 |
| Cb-1204 | 129 | B.6 |
| Cb-1205 | 130 | B.6 |
| Cb-1206 | 131 | B.6 |
| Cb-1207 | 132 | B.6 |
| Cb-1208 | 133 | B.6 |
| Cb-1209 | 134 | B.6 |
| Cb-1210 | 135 | B.6 |
| Cb-1211 | 136 | B.6 |
| Cb-1212 | 137 | B.6 |
| Cb-1213 | 138 | B.6 |
| Cb-1214 | 139 | B.6 |
| Cb-1215 | 140 | B.6 |
| Cb-1216 | 141 | B.6 |
| Cb-1217 | 142 | B.6 |
| Cb-1218 | 143 | B.6 |
| Cb-1219 | 144 | B.6 |
| Cb-1220 | 145 | B.6 |
| Cb-1221 | 146 | B.6 |
| Cb-1222 | 147 | B.6 |
| Cb-1223 | 148 | B.6 |
| Cb-1224 | 149 | B.6 |
| Cb-1225 | 150 | B.6 |
| Cb-1226 | 151 | B.6 |
| Cb-1227 | 152 | B.6 |
| Cb-1228 | 153 | B.6 |
| Cb-1229 | 154 | B.6 |
| Cb-1230 | 155 | B.6 |
| Cb-1231 | 156 | B.6 |
| Cb-1232 | 157 | B.6 |
| Cb-1233 | 158 | B.6 |
| Cb-1234 | 159 | B.6 |
| Cb-1235 | 160 | B.6 |
| Cb-1236 | 161 | B.6 |
| Cb-1237 | 162 | B.6 |
| Cb-1238 | 163 | B.6 |
| Cb-1239 | 164 | B.6 |
| Cb-1240 | 165 | B.6 |
| Cb-1241 | 166 | B.6 |
| Cb-1242 | 167 | B.6 |
| Cb-1243 | 168 | B.6 |
| Cb-1244 | 169 | B.6 |
| Cb-1245 | 170 | B.6 |
| Cb-1246 | 171 | B.6 |
| Cb-1247 | 172 | B.6 |
| Cb-1248 | 173 | B.6 |
| Cb-1249 | 174 | B.6 |
| Cb-1250 | 175 | B.6 |
| Cb-1251 | 176 | B.6 |
| Cb-1252 | 177 | B.6 |
| Cb-1253 | 178 | B.6 |
| Cb-1254 | 179 | B.6 |
| Cb-1255 | 180 | B.6 |
| Cb-1256 | 181 | B.6 |
| Cb-1257 | 182 | B.6 |
| Cb-1258 | 183 | B.6 |
| Cb-1259 | 184 | B.6 |
| Cb-1260 | 185 | B.6 |
| Cb-1261 | 186 | B.6 |
| Cb-1262 | 187 | B.6 |
| Cb-1263 | 188 | B.6 |

-continued

| Comb. | Com. A | Com. B |
|---|---|---|
| Cb-1264 | 189 | B.6 |
| Cb-1265 | 190 | B.6 |
| Cb-1266 | 191 | B.6 |
| Cb-1267 | 192 | B.6 |
| Cb-1268 | 193 | B.6 |
| Cb-1269 | 194 | B.6 |
| Cb-1270 | 195 | B.6 |
| Cb-1271 | 196 | B.6 |
| Cb-1272 | 197 | B.6 |
| Cb-1273 | 198 | B.6 |
| Cb-1274 | 199 | B.6 |
| Cb-1275 | 200 | B.6 |
| Cb-1276 | 201 | B.6 |
| Cb-1277 | 202 | B.6 |
| Cb-1278 | 203 | B.6 |
| Cb-1279 | 204 | B.6 |
| Cb-1280 | 205 | B.6 |
| Cb-1281 | 206 | B.6 |
| Cb-1282 | 207 | B.6 |
| Cb-1283 | 208 | B.6 |
| Cb-1284 | 209 | B.6 |
| Cb-1285 | 210 | B.6 |
| Cb-1286 | 211 | B.6 |
| Cb-1287 | 212 | B.6 |
| Cb-1288 | 213 | B.6 |
| Cb-1289 | 214 | B.6 |
| Cb-1290 | 215 | B.6 |
| Cb-1291 | 1 | B.7 |
| Cb-1292 | 2 | B.7 |
| Cb-1293 | 3 | B.7 |
| Cb-1294 | 4 | B.7 |
| Cb-1295 | 5 | B.7 |
| Cb-1296 | 6 | B.7 |
| Cb-1297 | 7 | B.7 |
| Cb-1298 | 8 | B.7 |
| Cb-1299 | 9 | B.7 |
| Cb-1300 | 10 | B.7 |
| Cb-1301 | 11 | B.7 |
| Cb-1302 | 12 | B.7 |
| Cb-1303 | 13 | B.7 |
| Cb-1304 | 14 | B.7 |
| Cb-1305 | 15 | B.7 |
| Cb-1306 | 16 | B.7 |
| Cb-1307 | 17 | B.7 |
| Cb-1308 | 18 | B.7 |
| Cb-1309 | 19 | B.7 |
| Cb-1310 | 20 | B.7 |
| Cb-1311 | 21 | B.7 |
| Cb-1312 | 22 | B.7 |
| Cb-1313 | 23 | B.7 |
| Cb-1314 | 24 | B.7 |
| Cb-1315 | 25 | B.7 |
| Cb-1316 | 26 | B.7 |
| Cb-1317 | 27 | B.7 |
| Cb-1318 | 28 | B.7 |
| Cb-1319 | 29 | B.7 |
| Cb-1320 | 30 | B.7 |
| Cb-1321 | 31 | B.7 |
| Cb-1322 | 32 | B.7 |
| Cb-1323 | 33 | B.7 |
| Cb-1324 | 34 | B.7 |
| Cb-1325 | 35 | B.7 |
| Cb-1326 | 36 | B.7 |
| Cb-1327 | 37 | B.7 |
| Cb-1328 | 38 | B.7 |
| Cb-1329 | 39 | B.7 |
| Cb-1330 | 40 | B.7 |
| Cb-1331 | 41 | B.7 |
| Cb-1332 | 42 | B.7 |
| Cb-1333 | 43 | B.7 |
| Cb-1334 | 44 | B.7 |
| Cb-1335 | 45 | B.7 |
| Cb-1336 | 46 | B.7 |
| Cb-1337 | 47 | B.7 |
| Cb-1338 | 48 | B.7 |
| Cb-1339 | 49 | B.7 |
| Cb-1340 | 50 | B.7 |

| Comb. | Com. A | Com. B |
|---|---|---|
| Cb-1341 | 51 | B.7 |
| Cb-1342 | 52 | B.7 |
| Cb-1343 | 53 | B.7 |
| Cb-1344 | 54 | B.7 |
| Cb-1345 | 55 | B.7 |
| Cb-1346 | 56 | B.7 |
| Cb-1347 | 57 | B.7 |
| Cb-1348 | 58 | B.7 |
| Cb-1349 | 59 | B.7 |
| Cb-1350 | 60 | B.7 |
| Cb-1351 | 61 | B.7 |
| Cb-1352 | 62 | B.7 |
| Cb-1353 | 63 | B.7 |
| Cb-1354 | 64 | B.7 |
| Cb-1355 | 65 | B.7 |
| Cb-1356 | 66 | B.7 |
| Cb-1357 | 67 | B.7 |
| Cb-1358 | 68 | B.7 |
| Cb-1359 | 69 | B.7 |
| Cb-1360 | 70 | B.7 |
| Cb-1361 | 71 | B.7 |
| Cb-1362 | 72 | B.7 |
| Cb-1363 | 73 | B.7 |
| Cb-1364 | 74 | B.7 |
| Cb-1365 | 75 | B.7 |
| Cb-1366 | 76 | B.7 |
| Cb-1367 | 77 | B.7 |
| Cb-1368 | 78 | B.7 |
| Cb-1369 | 79 | B.7 |
| Cb-1370 | 80 | B.7 |
| Cb-1371 | 81 | B.7 |
| Cb-1372 | 82 | B.7 |
| Cb-1373 | 83 | B.7 |
| Cb-1374 | 84 | B.7 |
| Cb-1375 | 85 | B.7 |
| Cb-1376 | 86 | B.7 |
| Cb-1377 | 87 | B.7 |
| Cb-1378 | 88 | B.7 |
| Cb-1379 | 89 | B.7 |
| Cb-1380 | 90 | B.7 |
| Cb-1381 | 91 | B.7 |
| Cb-1382 | 92 | B.7 |
| Cb-1383 | 93 | B.7 |
| Cb-1384 | 94 | B.7 |
| Cb-1385 | 95 | B.7 |
| Cb-1386 | 96 | B.7 |
| Cb-1387 | 97 | B.7 |
| Cb-1388 | 98 | B.7 |
| Cb-1389 | 99 | B.7 |
| Cb-1390 | 100 | B.7 |
| Cb-1391 | 101 | B.7 |
| Cb-1392 | 102 | B.7 |
| Cb-1393 | 103 | B.7 |
| Cb-1394 | 104 | B.7 |
| Cb-1395 | 105 | B.7 |
| Cb-1396 | 106 | B.7 |
| Cb-1397 | 107 | B.7 |
| Cb-1398 | 108 | B.7 |
| Cb-1399 | 109 | B.7 |
| Cb-1400 | 110 | B.7 |
| Cb-1401 | 111 | B.7 |
| Cb-1402 | 112 | B.7 |
| Cb-1403 | 113 | B.7 |
| Cb-1404 | 114 | B.7 |
| Cb-1405 | 115 | B.7 |
| Cb-1406 | 116 | B.7 |
| Cb-1407 | 117 | B.7 |
| Cb-1408 | 118 | B.7 |
| Cb-1409 | 119 | B.7 |
| Cb-1410 | 120 | B.7 |
| Cb-1411 | 121 | B.7 |
| Cb-1412 | 122 | B.7 |
| Cb-1413 | 123 | B.7 |
| Cb-1414 | 124 | B.7 |
| Cb-1415 | 125 | B.7 |
| Cb-1416 | 126 | B.7 |
| Cb-1417 | 127 | B.7 |
| Cb-1418 | 128 | B.7 |
| Cb-1419 | 129 | B.7 |
| Cb-1420 | 130 | B.7 |
| Cb-1421 | 131 | B.7 |
| Cb-1422 | 132 | B.7 |
| Cb-1423 | 133 | B.7 |
| Cb-1424 | 134 | B.7 |
| Cb-1425 | 135 | B.7 |
| Cb-1426 | 136 | B.7 |
| Cb-1427 | 137 | B.7 |
| Cb-1428 | 138 | B.7 |
| Cb-1429 | 139 | B.7 |
| Cb-1430 | 140 | B.7 |
| Cb-1431 | 141 | B.7 |
| Cb-1432 | 142 | B.7 |
| Cb-1433 | 143 | B.7 |
| Cb-1434 | 144 | B.7 |
| Cb-1435 | 145 | B.7 |
| Cb-1436 | 146 | B.7 |
| Cb-1437 | 147 | B.7 |
| Cb-1438 | 148 | B.7 |
| Cb-1439 | 149 | B.7 |
| Cb-1440 | 150 | B.7 |
| Cb-1441 | 151 | B.7 |
| Cb-1442 | 152 | B.7 |
| Cb-1443 | 153 | B.7 |
| Cb-1444 | 154 | B.7 |
| Cb-1445 | 155 | B.7 |
| Cb-1446 | 156 | B.7 |
| Cb-1447 | 157 | B.7 |
| Cb-1448 | 158 | B.7 |
| Cb-1449 | 159 | B.7 |
| Cb-1450 | 160 | B.7 |
| Cb-1451 | 161 | B.7 |
| Cb-1452 | 162 | B.7 |
| Cb-1453 | 163 | B.7 |
| Cb-1454 | 164 | B.7 |
| Cb-1455 | 165 | B.7 |
| Cb-1456 | 166 | B.7 |
| Cb-1457 | 167 | B.7 |
| Cb-1458 | 168 | B.7 |
| Cb-1459 | 169 | B.7 |
| Cb-1460 | 170 | B.7 |
| Cb-1461 | 171 | B.7 |
| Cb-1462 | 172 | B.7 |
| Cb-1463 | 173 | B.7 |
| Cb-1464 | 174 | B.7 |
| Cb-1465 | 175 | B.7 |
| Cb-1466 | 176 | B.7 |
| Cb-1467 | 177 | B.7 |
| Cb-1468 | 178 | B.7 |
| Cb-1469 | 179 | B.7 |
| Cb-1470 | 180 | B.7 |
| Cb-1471 | 181 | B.7 |
| Cb-1472 | 182 | B.7 |
| Cb-1473 | 183 | B.7 |
| Cb-1474 | 184 | B.7 |
| Cb-1475 | 185 | B.7 |
| Cb-1476 | 186 | B.7 |
| Cb-1477 | 187 | B.7 |
| Cb-1478 | 188 | B.7 |
| Cb-1479 | 189 | B.7 |
| Cb-1480 | 190 | B.7 |
| Cb-1481 | 191 | B.7 |
| Cb-1482 | 192 | B.7 |
| Cb-1483 | 193 | B.7 |
| Cb-1484 | 194 | B.7 |
| Cb-1485 | 195 | B.7 |
| Cb-1486 | 196 | B.7 |
| Cb-1487 | 197 | B.7 |
| Cb-1488 | 198 | B.7 |
| Cb-1489 | 199 | B.7 |
| Cb-1490 | 200 | B.7 |
| Cb-1491 | 201 | B.7 |
| Cb-1492 | 202 | B.7 |
| Cb-1493 | 203 | B.7 |
| Cb-1494 | 204 | B.7 |

| Comb. | Com. A | Com. B |
|---|---|---|
| Cb-1495 | 205 | B.7 |
| Cb-1496 | 206 | B.7 |
| Cb-1497 | 207 | B.7 |
| Cb-1498 | 208 | B.7 |
| Cb-1499 | 209 | B.7 |
| Cb-1500 | 210 | B.7 |
| Cb-1501 | 211 | B.7 |
| Cb-1502 | 212 | B.7 |
| Cb-1503 | 213 | B.7 |
| Cb-1504 | 214 | B.7 |
| Cb-1505 | 215 | B.7 |
| Cb-1506 | 1 | B.8 |
| Cb-1507 | 2 | B.8 |
| Cb-1508 | 3 | B.8 |
| Cb-1509 | 4 | B.8 |
| Cb-1510 | 5 | B.8 |
| Cb-1511 | 6 | B.8 |
| Cb-1512 | 7 | B.8 |
| Cb-1513 | 8 | B.8 |
| Cb-1514 | 9 | B.8 |
| Cb-1515 | 10 | B.8 |
| Cb-1516 | 11 | B.8 |
| Cb-1517 | 12 | B.8 |
| Cb-1518 | 13 | B.8 |
| Cb-1519 | 14 | B.8 |
| Cb-1520 | 15 | B.8 |
| Cb-1521 | 16 | B.8 |
| Cb-1522 | 17 | B.8 |
| Cb-1523 | 18 | B.8 |
| Cb-1524 | 19 | B.8 |
| Cb-1525 | 20 | B.8 |
| Cb-1526 | 21 | B.8 |
| Cb-1527 | 22 | B.8 |
| Cb-1528 | 23 | B.8 |
| Cb-1529 | 24 | B.8 |
| Cb-1530 | 25 | B.8 |
| Cb-1531 | 26 | B.8 |
| Cb-1532 | 27 | B.8 |
| Cb-1533 | 28 | B.8 |
| Cb-1534 | 29 | B.8 |
| Cb-1535 | 30 | B.8 |
| Cb-1536 | 31 | B.8 |
| Cb-1537 | 32 | B.8 |
| Cb-1538 | 33 | B.8 |
| Cb-1539 | 34 | B.8 |
| Cb-1540 | 35 | B.8 |
| Cb-1541 | 36 | B.8 |
| Cb-1542 | 37 | B.8 |
| Cb-1543 | 38 | B.8 |
| Cb-1544 | 39 | B.8 |
| Cb-1545 | 40 | B.8 |
| Cb-1546 | 41 | B.8 |
| Cb-1547 | 42 | B.8 |
| Cb-1548 | 43 | B.8 |
| Cb-1549 | 44 | B.8 |
| Cb-1550 | 45 | B.8 |
| Cb-1551 | 46 | B.8 |
| Cb-1552 | 47 | B.8 |
| Cb-1553 | 48 | B.8 |
| Cb-1554 | 49 | B.8 |
| Cb-1555 | 50 | B.8 |
| Cb-1556 | 51 | B.8 |
| Cb-1557 | 52 | B.8 |
| Cb-1558 | 53 | B.8 |
| Cb-1559 | 54 | B.8 |
| Cb-1560 | 55 | B.8 |
| Cb-1561 | 56 | B.8 |
| Cb-1562 | 57 | B.8 |
| Cb-1563 | 58 | B.8 |
| Cb-1564 | 59 | B.8 |
| Cb-1565 | 60 | B.8 |
| Cb-1566 | 61 | B.8 |
| Cb-1567 | 62 | B.8 |
| Cb-1568 | 63 | B.8 |
| Cb-1569 | 64 | B.8 |
| Cb-1570 | 65 | B.8 |
| Cb-1571 | 66 | B.8 |
| Cb-1572 | 67 | B.8 |
| Cb-1573 | 68 | B.8 |
| Cb-1574 | 69 | B.8 |
| Cb-1575 | 70 | B.8 |
| Cb-1576 | 71 | B.8 |
| Cb-1577 | 72 | B.8 |
| Cb-1578 | 73 | B.8 |
| Cb-1579 | 74 | B.8 |
| Cb-1580 | 75 | B.8 |
| Cb-1581 | 76 | B.8 |
| Cb-1582 | 77 | B.8 |
| Cb-1583 | 78 | B.8 |
| Cb-1584 | 79 | B.8 |
| Cb-1585 | 80 | B.8 |
| Cb-1586 | 81 | B.8 |
| Cb-1587 | 82 | B.8 |
| Cb-1588 | 83 | B.8 |
| Cb-1589 | 84 | B.8 |
| Cb-1590 | 85 | B.8 |
| Cb-1591 | 86 | B.8 |
| Cb-1592 | 87 | B.8 |
| Cb-1593 | 88 | B.8 |
| Cb-1594 | 89 | B.8 |
| Cb-1595 | 90 | B.8 |
| Cb-1596 | 91 | B.8 |
| Cb-1597 | 92 | B.8 |
| Cb-1598 | 93 | B.8 |
| Cb-1599 | 94 | B.8 |
| Cb-1600 | 95 | B.8 |
| Cb-1601 | 96 | B.8 |
| Cb-1602 | 97 | B.8 |
| Cb-1603 | 98 | B.8 |
| Cb-1604 | 99 | B.8 |
| Cb-1605 | 100 | B.8 |
| Cb-1606 | 101 | B.8 |
| Cb-1607 | 102 | B.8 |
| Cb-1608 | 103 | B.8 |
| Cb-1609 | 104 | B.8 |
| Cb-1610 | 105 | B.8 |
| Cb-1611 | 106 | B.8 |
| Cb-1612 | 107 | B.8 |
| Cb-1613 | 108 | B.8 |
| Cb-1614 | 109 | B.8 |
| Cb-1615 | 110 | B.8 |
| Cb-1616 | 111 | B.8 |
| Cb-1617 | 112 | B.8 |
| Cb-1618 | 113 | B.8 |
| Cb-1619 | 114 | B.8 |
| Cb-1620 | 115 | B.8 |
| Cb-1621 | 116 | B.8 |
| Cb-1622 | 117 | B.8 |
| Cb-1623 | 118 | B.8 |
| Cb-1624 | 119 | B.8 |
| Cb-1625 | 120 | B.8 |
| Cb-1626 | 121 | B.8 |
| Cb-1627 | 122 | B.8 |
| Cb-1628 | 123 | B.8 |
| Cb-1629 | 124 | B.8 |
| Cb-1630 | 125 | B.8 |
| Cb-1631 | 126 | B.8 |
| Cb-1632 | 127 | B.8 |
| Cb-1633 | 128 | B.8 |
| Cb-1634 | 129 | B.8 |
| Cb-1635 | 130 | B.8 |
| Cb-1636 | 131 | B.8 |
| Cb-1637 | 132 | B.8 |
| Cb-1638 | 133 | B.8 |
| Cb-1639 | 134 | B.8 |
| Cb-1640 | 135 | B.8 |
| Cb-1641 | 136 | B.8 |
| Cb-1642 | 137 | B.8 |
| Cb-1643 | 138 | B.8 |
| Cb-1644 | 139 | B.8 |
| Cb-1645 | 140 | B.8 |
| Cb-1646 | 141 | B.8 |
| Cb-1647 | 142 | B.8 |
| Cb-1648 | 143 | B.8 |

| Comb. | Com. A | Com. B |
|---|---|---|
| Cb-1649 | 144 | B.8 |
| Cb-1650 | 145 | B.8 |
| Cb-1651 | 146 | B.8 |
| Cb-1652 | 147 | B.8 |
| Cb-1653 | 148 | B.8 |
| Cb-1654 | 149 | B.8 |
| Cb-1655 | 150 | B.8 |
| Cb-1656 | 151 | B.8 |
| Cb-1657 | 152 | B.8 |
| Cb-1658 | 153 | B.8 |
| Cb-1659 | 154 | B.8 |
| Cb-1660 | 155 | B.8 |
| Cb-1661 | 156 | B.8 |
| Cb-1662 | 157 | B.8 |
| Cb-1663 | 158 | B.8 |
| Cb-1664 | 159 | B.8 |
| Cb-1665 | 160 | B.8 |
| Cb-1666 | 161 | B.8 |
| Cb-1667 | 162 | B.8 |
| Cb-1668 | 163 | B.8 |
| Cb-1669 | 164 | B.8 |
| Cb-1670 | 165 | B.8 |
| Cb-1671 | 166 | B.8 |
| Cb-1672 | 167 | B.8 |
| Cb-1673 | 168 | B.8 |
| Cb-1674 | 169 | B.8 |
| Cb-1675 | 170 | B.8 |
| Cb-1676 | 171 | B.8 |
| Cb-1677 | 172 | B.8 |
| Cb-1678 | 173 | B.8 |
| Cb-1679 | 174 | B.8 |
| Cb-1680 | 175 | B.8 |
| Cb-1681 | 176 | B.8 |
| Cb-1682 | 177 | B.8 |
| Cb-1683 | 178 | B.8 |
| Cb-1684 | 179 | B.8 |
| Cb-1685 | 180 | B.8 |
| Cb-1686 | 181 | B.8 |
| Cb-1687 | 182 | B.8 |
| Cb-1688 | 183 | B.8 |
| Cb-1689 | 184 | B.8 |
| Cb-1690 | 185 | B.8 |
| Cb-1691 | 186 | B.8 |
| Cb-1692 | 187 | B.8 |
| Cb-1693 | 188 | B.8 |
| Cb-1694 | 189 | B.8 |
| Cb-1695 | 190 | B.8 |
| Cb-1696 | 191 | B.8 |
| Cb-1697 | 192 | B.8 |
| Cb-1698 | 193 | B.8 |
| Cb-1699 | 194 | B.8 |
| Cb-1700 | 195 | B.8 |
| Cb-1701 | 196 | B.8 |
| Cb-1702 | 197 | B.8 |
| Cb-1703 | 198 | B.8 |
| Cb-1704 | 199 | B.8 |
| Cb-1705 | 200 | B.8 |
| Cb-1706 | 201 | B.8 |
| Cb-1707 | 202 | B.8 |
| Cb-1708 | 203 | B.8 |
| Cb-1709 | 204 | B.8 |
| Cb-1710 | 205 | B.8 |
| Cb-1711 | 206 | B.8 |
| Cb-1712 | 207 | B.8 |
| Cb-1713 | 208 | B.8 |
| Cb-1714 | 209 | B.8 |
| Cb-1715 | 210 | B.8 |
| Cb-1716 | 211 | B.8 |
| Cb-1717 | 212 | B.8 |
| Cb-1718 | 213 | B.8 |
| Cb-1719 | 214 | B.8 |
| Cb-1720 | 215 | B.8 |
| Cb-1721 | 1 | B.9 |
| Cb-1722 | 2 | B.9 |
| Cb-1723 | 3 | B.9 |
| Cb-1724 | 4 | B.9 |
| Cb-1725 | 5 | B.9 |
| Cb-1726 | 6 | B.9 |
| Cb-1727 | 7 | B.9 |
| Cb-1728 | 8 | B.9 |
| Cb-1729 | 9 | B.9 |
| Cb-1730 | 10 | B.9 |
| Cb-1731 | 11 | B.9 |
| Cb-1732 | 12 | B.9 |
| Cb-1733 | 13 | B.9 |
| Cb-1734 | 14 | B.9 |
| Cb-1735 | 15 | B.9 |
| Cb-1736 | 16 | B.9 |
| Cb-1737 | 17 | B.9 |
| Cb-1738 | 18 | B.9 |
| Cb-1739 | 19 | B.9 |
| Cb-1740 | 20 | B.9 |
| Cb-1741 | 21 | B.9 |
| Cb-1742 | 22 | B.9 |
| Cb-1743 | 23 | B.9 |
| Cb-1744 | 24 | B.9 |
| Cb-1745 | 25 | B.9 |
| Cb-1746 | 26 | B.9 |
| Cb-1747 | 27 | B.9 |
| Cb-1748 | 28 | B.9 |
| Cb-1749 | 29 | B.9 |
| Cb-1750 | 30 | B.9 |
| Cb-1751 | 31 | B.9 |
| Cb-1752 | 32 | B.9 |
| Cb-1753 | 33 | B.9 |
| Cb-1754 | 34 | B.9 |
| Cb-1755 | 35 | B.9 |
| Cb-1756 | 36 | B.9 |
| Cb-1757 | 37 | B.9 |
| Cb-1758 | 38 | B.9 |
| Cb-1759 | 39 | B.9 |
| Cb-1760 | 40 | B.9 |
| Cb-1761 | 41 | B.9 |
| Cb-1762 | 42 | B.9 |
| Cb-1763 | 43 | B.9 |
| Cb-1764 | 44 | B.9 |
| Cb-1765 | 45 | B.9 |
| Cb-1766 | 46 | B.9 |
| Cb-1767 | 47 | B.9 |
| Cb-1768 | 48 | B.9 |
| Cb-1769 | 49 | B.9 |
| Cb-1770 | 50 | B.9 |
| Cb-1771 | 51 | B.9 |
| Cb-1772 | 52 | B.9 |
| Cb-1773 | 53 | B.9 |
| Cb-1774 | 54 | B.9 |
| Cb-1775 | 55 | B.9 |
| Cb-1776 | 56 | B.9 |
| Cb-1777 | 57 | B.9 |
| Cb-1778 | 58 | B.9 |
| Cb-1779 | 59 | B.9 |
| Cb-1780 | 60 | B.9 |
| Cb-1781 | 61 | B.9 |
| Cb-1782 | 62 | B.9 |
| Cb-1783 | 63 | B.9 |
| Cb-1784 | 64 | B.9 |
| Cb-1785 | 65 | B.9 |
| Cb-1786 | 66 | B.9 |
| Cb-1787 | 67 | B.9 |
| Cb-1788 | 68 | B.9 |
| Cb-1789 | 69 | B.9 |
| Cb-1790 | 70 | B.9 |
| Cb-1791 | 71 | B.9 |
| Cb-1792 | 72 | B.9 |
| Cb-1793 | 73 | B.9 |
| Cb-1794 | 74 | B.9 |
| Cb-1795 | 75 | B.9 |
| Cb-1796 | 76 | B.9 |
| Cb-1797 | 77 | B.9 |
| Cb-1798 | 78 | B.9 |
| Cb-1799 | 79 | B.9 |
| Cb-1800 | 80 | B.9 |
| Cb-1801 | 81 | B.9 |
| Cb-1802 | 82 | B.9 |

-continued

| Comb. | Com. A | Com. B |
|---|---|---|
| Cb-1803 | 83 | B.9 |
| Cb-1804 | 84 | B.9 |
| Cb-1805 | 85 | B.9 |
| Cb-1806 | 86 | B.9 |
| Cb-1807 | 87 | B.9 |
| Cb-1808 | 88 | B.9 |
| Cb-1809 | 89 | B.9 |
| Cb-1810 | 90 | B.9 |
| Cb-1811 | 91 | B.9 |
| Cb-1812 | 92 | B.9 |
| Cb-1813 | 93 | B.9 |
| Cb-1814 | 94 | B.9 |
| Cb-1815 | 95 | B.9 |
| Cb-1816 | 96 | B.9 |
| Cb-1817 | 97 | B.9 |
| Cb-1818 | 98 | B.9 |
| Cb-1819 | 99 | B.9 |
| Cb-1820 | 100 | B.9 |
| Cb-1821 | 101 | B.9 |
| Cb-1822 | 102 | B.9 |
| Cb-1823 | 103 | B.9 |
| Cb-1824 | 104 | B.9 |
| Cb-1825 | 105 | B.9 |
| Cb-1826 | 106 | B.9 |
| Cb-1827 | 107 | B.9 |
| Cb-1828 | 108 | B.9 |
| Cb-1829 | 109 | B.9 |
| Cb-1830 | 110 | B.9 |
| Cb-1831 | 111 | B.9 |
| Cb-1832 | 112 | B.9 |
| Cb-1833 | 113 | B.9 |
| Cb-1834 | 114 | B.9 |
| Cb-1835 | 115 | B.9 |
| Cb-1836 | 116 | B.9 |
| Cb-1837 | 117 | B.9 |
| Cb-1838 | 118 | B.9 |
| Cb-1839 | 119 | B.9 |
| Cb-1840 | 120 | B.9 |
| Cb-1841 | 121 | B.9 |
| Cb-1842 | 122 | B.9 |
| Cb-1843 | 123 | B.9 |
| Cb-1844 | 124 | B.9 |
| Cb-1845 | 125 | B.9 |
| Cb-1846 | 126 | B.9 |
| Cb-1847 | 127 | B.9 |
| Cb-1848 | 128 | B.9 |
| Cb-1849 | 129 | B.9 |
| Cb-1850 | 130 | B.9 |
| Cb-1851 | 131 | B.9 |
| Cb-1852 | 132 | B.9 |
| Cb-1853 | 133 | B.9 |
| Cb-1854 | 134 | B.9 |
| Cb-1855 | 135 | B.9 |
| Cb-1856 | 136 | B.9 |
| Cb-1857 | 137 | B.9 |
| Cb-1858 | 138 | B.9 |
| Cb-1859 | 139 | B.9 |
| Cb-1860 | 140 | B.9 |
| Cb-1861 | 141 | B.9 |
| Cb-1862 | 142 | B.9 |
| Cb-1863 | 143 | B.9 |
| Cb-1864 | 144 | B.9 |
| Cb-1865 | 145 | B.9 |
| Cb-1866 | 146 | B.9 |
| Cb-1867 | 147 | B.9 |
| Cb-1868 | 148 | B.9 |
| Cb-1869 | 149 | B.9 |
| Cb-1870 | 150 | B.9 |
| Cb-1871 | 151 | B.9 |
| Cb-1872 | 152 | B.9 |
| Cb-1873 | 153 | B.9 |
| Cb-1874 | 154 | B.9 |
| Cb-1875 | 155 | B.9 |
| Cb-1876 | 156 | B.9 |
| Cb-1877 | 157 | B.9 |
| Cb-1878 | 158 | B.9 |
| Cb-1879 | 159 | B.9 |
| Cb-1880 | 160 | B.9 |
| Cb-1881 | 161 | B.9 |
| Cb-1882 | 162 | B.9 |
| Cb-1883 | 163 | B.9 |
| Cb-1884 | 164 | B.9 |
| Cb-1885 | 165 | B.9 |
| Cb-1886 | 166 | B.9 |
| Cb-1887 | 167 | B.9 |
| Cb-1888 | 168 | B.9 |
| Cb-1889 | 169 | B.9 |
| Cb-1890 | 170 | B.9 |
| Cb-1891 | 171 | B.9 |
| Cb-1892 | 172 | B.9 |
| Cb-1893 | 173 | B.9 |
| Cb-1894 | 174 | B.9 |
| Cb-1895 | 175 | B.9 |
| Cb-1896 | 176 | B.9 |
| Cb-1897 | 177 | B.9 |
| Cb-1898 | 178 | B.9 |
| Cb-1899 | 179 | B.9 |
| Cb-1900 | 180 | B.9 |
| Cb-1901 | 181 | B.9 |
| Cb-1902 | 182 | B.9 |
| Cb-1903 | 183 | B.9 |
| Cb-1904 | 184 | B.9 |
| Cb-1905 | 185 | B.9 |
| Cb-1906 | 186 | B.9 |
| Cb-1907 | 187 | B.9 |
| Cb-1908 | 188 | B.9 |
| Cb-1909 | 189 | B.9 |
| Cb-1910 | 190 | B.9 |
| Cb-1911 | 191 | B.9 |
| Cb-1912 | 192 | B.9 |
| Cb-1913 | 193 | B.9 |
| Cb-1914 | 194 | B.9 |
| Cb-1915 | 195 | B.9 |
| Cb-1916 | 196 | B.9 |
| Cb-1917 | 197 | B.9 |
| Cb-1918 | 198 | B.9 |
| Cb-1919 | 199 | B.9 |
| Cb-1920 | 200 | B.9 |
| Cb-1921 | 201 | B.9 |
| Cb-1922 | 202 | B.9 |
| Cb-1923 | 203 | B.9 |
| Cb-1924 | 204 | B.9 |
| Cb-1925 | 205 | B.9 |
| Cb-1926 | 206 | B.9 |
| Cb-1927 | 207 | B.9 |
| Cb-1928 | 208 | B.9 |
| Cb-1929 | 209 | B.9 |
| Cb-1930 | 210 | B.9 |
| Cb-1931 | 211 | B.9 |
| Cb-1932 | 212 | B.9 |
| Cb-1933 | 213 | B.9 |
| Cb-1934 | 214 | B.9 |
| Cb-1935 | 215 | B.9 |
| Cb-1936 | 1 | B.10 |
| Cb-1937 | 2 | B.10 |
| Cb-1938 | 3 | B.10 |
| Cb-1939 | 4 | B.10 |
| Cb-1940 | 5 | B.10 |
| Cb-1941 | 6 | B.10 |
| Cb-1942 | 7 | B.10 |
| Cb-1943 | 8 | B.10 |
| Cb-1944 | 9 | B.10 |
| Cb-1945 | 10 | B.10 |
| Cb-1946 | 11 | B.10 |
| Cb-1947 | 12 | B.10 |
| Cb-1948 | 13 | B.10 |
| Cb-1949 | 14 | B.10 |
| Cb-1950 | 15 | B.10 |
| Cb-1951 | 16 | B.10 |
| Cb-1952 | 17 | B.10 |
| Cb-1953 | 18 | B.10 |
| Cb-1954 | 19 | B.10 |
| Cb-1955 | 20 | B.10 |
| Cb-1956 | 21 | B.10 |

| Comb. | Com. A | Com. B |
|---|---|---|
| Cb-1957 | 22 | B.10 |
| Cb-1958 | 23 | B.10 |
| Cb-1959 | 24 | B.10 |
| Cb-1960 | 25 | B.10 |
| Cb-1961 | 26 | B.10 |
| Cb-1962 | 27 | B.10 |
| Cb-1963 | 28 | B.10 |
| Cb-1964 | 29 | B.10 |
| Cb-1965 | 30 | B.10 |
| Cb-1966 | 31 | B.10 |
| Cb-1967 | 32 | B.10 |
| Cb-1968 | 33 | B.10 |
| Cb-1969 | 34 | B.10 |
| Cb-1970 | 35 | B.10 |
| Cb-1971 | 36 | B.10 |
| Cb-1972 | 37 | B.10 |
| Cb-1973 | 38 | B.10 |
| Cb-1974 | 39 | B.10 |
| Cb-1975 | 40 | B.10 |
| Cb-1976 | 41 | B.10 |
| Cb-1977 | 42 | B.10 |
| Cb-1978 | 43 | B.10 |
| Cb-1979 | 44 | B.10 |
| Cb-1980 | 45 | B.10 |
| Cb-1981 | 46 | B.10 |
| Cb-1982 | 47 | B.10 |
| Cb-1983 | 48 | B.10 |
| Cb-1984 | 49 | B.10 |
| Cb-1985 | 50 | B.10 |
| Cb-1986 | 51 | B.10 |
| Cb-1987 | 52 | B.10 |
| Cb-1988 | 53 | B.10 |
| Cb-1989 | 54 | B.10 |
| Cb-1990 | 55 | B.10 |
| Cb-1991 | 56 | B.10 |
| Cb-1992 | 57 | B.10 |
| Cb-1993 | 58 | B.10 |
| Cb-1994 | 59 | B.10 |
| Cb-1995 | 60 | B.10 |
| Cb-1996 | 61 | B.10 |
| Cb-1997 | 62 | B.10 |
| Cb-1998 | 63 | B.10 |
| Cb-1999 | 64 | B.10 |
| Cb-2000 | 65 | B.10 |
| Cb-2001 | 66 | B.10 |
| Cb-2002 | 67 | B.10 |
| Cb-2003 | 68 | B.10 |
| Cb-2004 | 69 | B.10 |
| Cb-2005 | 70 | B.10 |
| Cb-2006 | 71 | B.10 |
| Cb-2007 | 72 | B.10 |
| Cb-2008 | 73 | B.10 |
| Cb-2009 | 74 | B.10 |
| Cb-2010 | 75 | B.10 |
| Cb-2011 | 76 | B.10 |
| Cb-2012 | 77 | B.10 |
| Cb-2013 | 78 | B.10 |
| Cb-2014 | 79 | B.10 |
| Cb-2015 | 80 | B.10 |
| Cb-2016 | 81 | B.10 |
| Cb-2017 | 82 | B.10 |
| Cb-2018 | 83 | B.10 |
| Cb-2019 | 84 | B.10 |
| Cb-2020 | 85 | B.10 |
| Cb-2021 | 86 | B.10 |
| Cb-2022 | 87 | B.10 |
| Cb-2023 | 88 | B.10 |
| Cb-2024 | 89 | B.10 |
| Cb-2025 | 90 | B.10 |
| Cb-2026 | 91 | B.10 |
| Cb-2027 | 92 | B.10 |
| Cb-2028 | 93 | B.10 |
| Cb-2029 | 94 | B.10 |
| Cb-2030 | 95 | B.10 |
| Cb-2031 | 96 | B.10 |
| Cb-2032 | 97 | B.10 |
| Cb-2033 | 98 | B.10 |
| Cb-2034 | 99 | B.10 |
| Cb-2035 | 100 | B.10 |
| Cb-2036 | 101 | B.10 |
| Cb-2037 | 102 | B.10 |
| Cb-2038 | 103 | B.10 |
| Cb-2039 | 104 | B.10 |
| Cb-2040 | 105 | B.10 |
| Cb-2041 | 106 | B.10 |
| Cb-2042 | 107 | B.10 |
| Cb-2043 | 108 | B.10 |
| Cb-2044 | 109 | B.10 |
| Cb-2045 | 110 | B.10 |
| Cb-2046 | 111 | B.10 |
| Cb-2047 | 112 | B.10 |
| Cb-2048 | 113 | B.10 |
| Cb-2049 | 114 | B.10 |
| Cb-2050 | 115 | B.10 |
| Cb-2051 | 116 | B.10 |
| Cb-2052 | 117 | B.10 |
| Cb-2053 | 118 | B.10 |
| Cb-2054 | 119 | B.10 |
| Cb-2055 | 120 | B.10 |
| Cb-2056 | 121 | B.10 |
| Cb-2057 | 122 | B.10 |
| Cb-2058 | 123 | B.10 |
| Cb-2059 | 124 | B.10 |
| Cb-2060 | 125 | B.10 |
| Cb-2061 | 126 | B.10 |
| Cb-2062 | 127 | B.10 |
| Cb-2063 | 128 | B.10 |
| Cb-2064 | 129 | B.10 |
| Cb-2065 | 130 | B.10 |
| Cb-2066 | 131 | B.10 |
| Cb-2067 | 132 | B.10 |
| Cb-2068 | 133 | B.10 |
| Cb-2069 | 134 | B.10 |
| Cb-2070 | 135 | B.10 |
| Cb-2071 | 136 | B.10 |
| Cb-2072 | 137 | B.10 |
| Cb-2073 | 138 | B.10 |
| Cb-2074 | 139 | B.10 |
| Cb-2075 | 140 | B.10 |
| Cb-2076 | 141 | B.10 |
| Cb-2077 | 142 | B.10 |
| Cb-2078 | 143 | B.10 |
| Cb-2079 | 144 | B.10 |
| Cb-2080 | 145 | B.10 |
| Cb-2081 | 146 | B.10 |
| Cb-2082 | 147 | B.10 |
| Cb-2083 | 148 | B.10 |
| Cb-2084 | 149 | B.10 |
| Cb-2085 | 150 | B.10 |
| Cb-2086 | 151 | B.10 |
| Cb-2087 | 152 | B.10 |
| Cb-2088 | 153 | B.10 |
| Cb-2089 | 154 | B.10 |
| Cb-2090 | 155 | B.10 |
| Cb-2091 | 156 | B.10 |
| Cb-2092 | 157 | B.10 |
| Cb-2093 | 158 | B.10 |
| Cb-2094 | 159 | B.10 |
| Cb-2095 | 160 | B.10 |
| Cb-2096 | 161 | B.10 |
| Cb-2097 | 162 | B.10 |
| Cb-2098 | 163 | B.10 |
| Cb-2099 | 164 | B.10 |
| Cb-2100 | 165 | B.10 |
| Cb-2101 | 166 | B.10 |
| Cb-2102 | 167 | B.10 |
| Cb-2103 | 168 | B.10 |
| Cb-2104 | 169 | B.10 |
| Cb-2105 | 170 | B.10 |
| Cb-2106 | 171 | B.10 |
| Cb-2107 | 172 | B.10 |
| Cb-2108 | 173 | B.10 |
| Cb-2109 | 174 | B.10 |
| Cb-2110 | 175 | B.10 |

| Comb. | Com. A | Com. B |
|---|---|---|
| Cb-2111 | 176 | B.10 |
| Cb-2112 | 177 | B.10 |
| Cb-2113 | 178 | B.10 |
| Cb-2114 | 179 | B.10 |
| Cb-2115 | 180 | B.10 |
| Cb-2116 | 181 | B.10 |
| Cb-2117 | 182 | B.10 |
| Cb-2118 | 183 | B.10 |
| Cb-2119 | 184 | B.10 |
| Cb-2120 | 185 | B.10 |
| Cb-2121 | 186 | B.10 |
| Cb-2122 | 187 | B.10 |
| Cb-2123 | 188 | B.10 |
| Cb-2124 | 189 | B.10 |
| Cb-2125 | 190 | B.10 |
| Cb-2126 | 191 | B.10 |
| Cb-2127 | 192 | B.10 |
| Cb-2128 | 193 | B.10 |
| Cb-2129 | 194 | B.10 |
| Cb-2130 | 195 | B.10 |
| Cb-2131 | 196 | B.10 |
| Cb-2132 | 197 | B.10 |
| Cb-2133 | 198 | B.10 |
| Cb-2134 | 199 | B.10 |
| Cb-2135 | 200 | B.10 |
| Cb-2136 | 201 | B.10 |
| Cb-2137 | 202 | B.10 |
| Cb-2138 | 203 | B.10 |
| Cb-2139 | 204 | B.10 |
| Cb-2140 | 205 | B.10 |
| Cb-2141 | 206 | B.10 |
| Cb-2142 | 207 | B.10 |
| Cb-2143 | 208 | B.10 |
| Cb-2144 | 209 | B.10 |
| Cb-2145 | 210 | B.10 |
| Cb-2146 | 211 | B.10 |
| Cb-2147 | 212 | B.10 |
| Cb-2148 | 213 | B.10 |
| Cb-2149 | 214 | B.10 |
| Cb-2150 | 215 | B.10 |
| Cb-2151 | 1 | B.11 |
| Cb-2152 | 2 | B.11 |
| Cb-2153 | 3 | B.11 |
| Cb-2154 | 4 | B.11 |
| Cb-2155 | 5 | B.11 |
| Cb-2156 | 6 | B.11 |
| Cb-2157 | 7 | B.11 |
| Cb-2158 | 8 | B.11 |
| Cb-2159 | 9 | B.11 |
| Cb-2160 | 10 | B.11 |
| Cb-2161 | 11 | B.11 |
| Cb-2162 | 12 | B.11 |
| Cb-2163 | 13 | B.11 |
| Cb-2164 | 14 | B.11 |
| Cb-2165 | 15 | B.11 |
| Cb-2166 | 16 | B.11 |
| Cb-2167 | 17 | B.11 |
| Cb-2168 | 18 | B.11 |
| Cb-2169 | 19 | B.11 |
| Cb-2170 | 20 | B.11 |
| Cb-2171 | 21 | B.11 |
| Cb-2172 | 22 | B.11 |
| Cb-2173 | 23 | B.11 |
| Cb-2174 | 24 | B.11 |
| Cb-2175 | 25 | B.11 |
| Cb-2176 | 26 | B.11 |
| Cb-2177 | 27 | B.11 |
| Cb-2178 | 28 | B.11 |
| Cb-2179 | 29 | B.11 |
| Cb-2180 | 30 | B.11 |
| Cb-2181 | 31 | B.11 |
| Cb-2182 | 32 | B.11 |
| Cb-2183 | 33 | B.11 |
| Cb-2184 | 34 | B.11 |
| Cb-2185 | 35 | B.11 |
| Cb-2186 | 36 | B.11 |
| Cb-2187 | 37 | B.11 |
| Cb-2188 | 38 | B.11 |
| Cb-2189 | 39 | B.11 |
| Cb-2190 | 40 | B.11 |
| Cb-2191 | 41 | B.11 |
| Cb-2192 | 42 | B.11 |
| Cb-2193 | 43 | B.11 |
| Cb-2194 | 44 | B.11 |
| Cb-2195 | 45 | B.11 |
| Cb-2196 | 46 | B.11 |
| Cb-2197 | 47 | B.11 |
| Cb-2198 | 48 | B.11 |
| Cb-2199 | 49 | B.11 |
| Cb-2200 | 50 | B.11 |
| Cb-2201 | 51 | B.11 |
| Cb-2202 | 52 | B.11 |
| Cb-2203 | 53 | B.11 |
| Cb-2204 | 54 | B.11 |
| Cb-2205 | 55 | B.11 |
| Cb-2206 | 56 | B.11 |
| Cb-2207 | 57 | B.11 |
| Cb-2208 | 58 | B.11 |
| Cb-2209 | 59 | B.11 |
| Cb-2210 | 60 | B.11 |
| Cb-2211 | 61 | B.11 |
| Cb-2212 | 62 | B.11 |
| Cb-2213 | 63 | B.11 |
| Cb-2214 | 64 | B.11 |
| Cb-2215 | 65 | B.11 |
| Cb-2216 | 66 | B.11 |
| Cb-2217 | 67 | B.11 |
| Cb-2218 | 68 | B.11 |
| Cb-2219 | 69 | B.11 |
| Cb-2220 | 70 | B.11 |
| Cb-2221 | 71 | B.11 |
| Cb-2222 | 72 | B.11 |
| Cb-2223 | 73 | B.11 |
| Cb-2224 | 74 | B.11 |
| Cb-2225 | 75 | B.11 |
| Cb-2226 | 76 | B.11 |
| Cb-2227 | 77 | B.11 |
| Cb-2228 | 78 | B.11 |
| Cb-2229 | 79 | B.11 |
| Cb-2230 | 80 | B.11 |
| Cb-2231 | 81 | B.11 |
| Cb-2232 | 82 | B.11 |
| Cb-2233 | 83 | B.11 |
| Cb-2234 | 84 | B.11 |
| Cb-2235 | 85 | B.11 |
| Cb-2236 | 86 | B.11 |
| Cb-2237 | 87 | B.11 |
| Cb-2238 | 88 | B.11 |
| Cb-2239 | 89 | B.11 |
| Cb-2240 | 90 | B.11 |
| Cb-2241 | 91 | B.11 |
| Cb-2242 | 92 | B.11 |
| Cb-2243 | 93 | B.11 |
| Cb-2244 | 94 | B.11 |
| Cb-2245 | 95 | B.11 |
| Cb-2246 | 96 | B.11 |
| Cb-2247 | 97 | B.11 |
| Cb-2248 | 98 | B.11 |
| Cb-2249 | 99 | B.11 |
| Cb-2250 | 100 | B.11 |
| Cb-2251 | 101 | B.11 |
| Cb-2252 | 102 | B.11 |
| Cb-2253 | 103 | B.11 |
| Cb-2254 | 104 | B.11 |
| Cb-2255 | 105 | B.11 |
| Cb-2256 | 106 | B.11 |
| Cb-2257 | 107 | B.11 |
| Cb-2258 | 108 | B.11 |
| Cb-2259 | 109 | B.11 |
| Cb-2260 | 110 | B.11 |
| Cb-2261 | 111 | B.11 |
| Cb-2262 | 112 | B.11 |
| Cb-2263 | 113 | B.11 |
| Cb-2264 | 114 | B.11 |

| Comb. | Com. A | Com. B |
|---|---|---|
| Cb-2265 | 115 | B.11 |
| Cb-2266 | 116 | B.11 |
| Cb-2267 | 117 | B.11 |
| Cb-2268 | 118 | B.11 |
| Cb-2269 | 119 | B.11 |
| Cb-2270 | 120 | B.11 |
| Cb-2271 | 121 | B.11 |
| Cb-2272 | 122 | B.11 |
| Cb-2273 | 123 | B.11 |
| Cb-2274 | 124 | B.11 |
| Cb-2275 | 125 | B.11 |
| Cb-2276 | 126 | B.11 |
| Cb-2277 | 127 | B.11 |
| Cb-2278 | 128 | B.11 |
| Cb-2279 | 129 | B.11 |
| Cb-2280 | 130 | B.11 |
| Cb-2281 | 131 | B.11 |
| Cb-2282 | 132 | B.11 |
| Cb-2283 | 133 | B.11 |
| Cb-2284 | 134 | B.11 |
| Cb-2285 | 135 | B.11 |
| Cb-2286 | 136 | B.11 |
| Cb-2287 | 137 | B.11 |
| Cb-2288 | 138 | B.11 |
| Cb-2289 | 139 | B.11 |
| Cb-2290 | 140 | B.11 |
| Cb-2291 | 141 | B.11 |
| Cb-2292 | 142 | B.11 |
| Cb-2293 | 143 | B.11 |
| Cb-2294 | 144 | B.11 |
| Cb-2295 | 145 | B.11 |
| Cb-2296 | 146 | B.11 |
| Cb-2297 | 147 | B.11 |
| Cb-2298 | 148 | B.11 |
| Cb-2299 | 149 | B.11 |
| Cb-2300 | 150 | B.11 |
| Cb-2301 | 151 | B.11 |
| Cb-2302 | 152 | B.11 |
| Cb-2303 | 153 | B.11 |
| Cb-2304 | 154 | B.11 |
| Cb-2305 | 155 | B.11 |
| Cb-2306 | 156 | B.11 |
| Cb-2307 | 157 | B.11 |
| Cb-2308 | 158 | B.11 |
| Cb-2309 | 159 | B.11 |
| Cb-2310 | 160 | B.11 |
| Cb-2311 | 161 | B.11 |
| Cb-2312 | 162 | B.11 |
| Cb-2313 | 163 | B.11 |
| Cb-2314 | 164 | B.11 |
| Cb-2315 | 165 | B.11 |
| Cb-2316 | 166 | B.11 |
| Cb-2317 | 167 | B.11 |
| Cb-2318 | 168 | B.11 |
| Cb-2319 | 169 | B.11 |
| Cb-2320 | 170 | B.11 |
| Cb-2321 | 171 | B.11 |
| Cb-2322 | 172 | B.11 |
| Cb-2323 | 173 | B.11 |
| Cb-2324 | 174 | B.11 |
| Cb-2325 | 175 | B.11 |
| Cb-2326 | 176 | B.11 |
| Cb-2327 | 177 | B.11 |
| Cb-2328 | 178 | B.11 |
| Cb-2329 | 179 | B.11 |
| Cb-2330 | 180 | B.11 |
| Cb-2331 | 181 | B.11 |
| Cb-2332 | 182 | B.11 |
| Cb-2333 | 183 | B.11 |
| Cb-2334 | 184 | B.11 |
| Cb-2335 | 185 | B.11 |
| Cb-2336 | 186 | B.11 |
| Cb-2337 | 187 | B.11 |
| Cb-2338 | 188 | B.11 |
| Cb-2339 | 189 | B.11 |
| Cb-2340 | 190 | B.11 |
| Cb-2341 | 191 | B.11 |
| Cb-2342 | 192 | B.11 |
| Cb-2343 | 193 | B.11 |
| Cb-2344 | 194 | B.11 |
| Cb-2345 | 195 | B.11 |
| Cb-2346 | 196 | B.11 |
| Cb-2347 | 197 | B.11 |
| Cb-2348 | 198 | B.11 |
| Cb-2349 | 199 | B.11 |
| Cb-2350 | 200 | B.11 |
| Cb-2351 | 201 | B.11 |
| Cb-2352 | 202 | B.11 |
| Cb-2353 | 203 | B.11 |
| Cb-2354 | 204 | B.11 |
| Cb-2355 | 205 | B.11 |
| Cb-2356 | 206 | B.11 |
| Cb-2357 | 207 | B.11 |
| Cb-2358 | 208 | B.11 |
| Cb-2359 | 209 | B.11 |
| Cb-2360 | 210 | B.11 |
| Cb-2361 | 211 | B.11 |
| Cb-2362 | 212 | B.11 |
| Cb-2363 | 213 | B.11 |
| Cb-2364 | 214 | B.11 |
| Cb-2365 | 215 | B.11 |
| Cb-2366 | 1 | B.12 |
| Cb-2367 | 2 | B.12 |
| Cb-2368 | 3 | B.12 |
| Cb-2369 | 4 | B.12 |
| Cb-2370 | 5 | B.12 |
| Cb-2371 | 6 | B.12 |
| Cb-2372 | 7 | B.12 |
| Cb-2373 | 8 | B.12 |
| Cb-2374 | 9 | B.12 |
| Cb-2375 | 10 | B.12 |
| Cb-2376 | 11 | B.12 |
| Cb-2377 | 12 | B.12 |
| Cb-2378 | 13 | B.12 |
| Cb-2379 | 14 | B.12 |
| Cb-2380 | 15 | B.12 |
| Cb-2381 | 16 | B.12 |
| Cb-2382 | 17 | B.12 |
| Cb-2383 | 18 | B.12 |
| Cb-2384 | 19 | B.12 |
| Cb-2385 | 20 | B.12 |
| Cb-2386 | 21 | B.12 |
| Cb-2387 | 22 | B.12 |
| Cb-2388 | 23 | B.12 |
| Cb-2389 | 24 | B.12 |
| Cb-2390 | 25 | B.12 |
| Cb-2391 | 26 | B.12 |
| Cb-2392 | 27 | B.12 |
| Cb-2393 | 28 | B.12 |
| Cb-2394 | 29 | B.12 |
| Cb-2395 | 30 | B.12 |
| Cb-2396 | 31 | B.12 |
| Cb-2397 | 32 | B.12 |
| Cb-2398 | 33 | B.12 |
| Cb-2399 | 34 | B.12 |
| Cb-2400 | 35 | B.12 |
| Cb-2401 | 36 | B.12 |
| Cb-2402 | 37 | B.12 |
| Cb-2403 | 38 | B.12 |
| Cb-2404 | 39 | B.12 |
| Cb-2405 | 40 | B.12 |
| Cb-2406 | 41 | B.12 |
| Cb-2407 | 42 | B.12 |
| Cb-2408 | 43 | B.12 |
| Cb-2409 | 44 | B.12 |
| Cb-2410 | 45 | B.12 |
| Cb-2411 | 46 | B.12 |
| Cb-2412 | 47 | B.12 |
| Cb-2413 | 48 | B.12 |
| Cb-2414 | 49 | B.12 |
| Cb-2415 | 50 | B.12 |
| Cb-2416 | 51 | B.12 |
| Cb-2417 | 52 | B.12 |
| Cb-2418 | 53 | B.12 |

| Comb. | Com. A | Com. B |
|---|---|---|
| Cb-2419 | 54 | B.12 |
| Cb-2420 | 55 | B.12 |
| Cb-2421 | 56 | B.12 |
| Cb-2422 | 57 | B.12 |
| Cb-2423 | 58 | B.12 |
| Cb-2424 | 59 | B.12 |
| Cb-2425 | 60 | B.12 |
| Cb-2426 | 61 | B.12 |
| Cb-2427 | 62 | B.12 |
| Cb-2428 | 63 | B.12 |
| Cb-2429 | 64 | B.12 |
| Cb-2430 | 65 | B.12 |
| Cb-2431 | 66 | B.12 |
| Cb-2432 | 67 | B.12 |
| Cb-2433 | 68 | B.12 |
| Cb-2434 | 69 | B.12 |
| Cb-2435 | 70 | B.12 |
| Cb-2436 | 71 | B.12 |
| Cb-2437 | 72 | B.12 |
| Cb-2438 | 73 | B.12 |
| Cb-2439 | 74 | B.12 |
| Cb-2440 | 75 | B.12 |
| Cb-2441 | 76 | B.12 |
| Cb-2442 | 77 | B.12 |
| Cb-2443 | 78 | B.12 |
| Cb-2444 | 79 | B.12 |
| Cb-2445 | 80 | B.12 |
| Cb-2446 | 81 | B.12 |
| Cb-2447 | 82 | B.12 |
| Cb-2448 | 83 | B.12 |
| Cb-2449 | 84 | B.12 |
| Cb-2450 | 85 | B.12 |
| Cb-2451 | 86 | B.12 |
| Cb-2452 | 87 | B.12 |
| Cb-2453 | 88 | B.12 |
| Cb-2454 | 89 | B.12 |
| Cb-2455 | 90 | B.12 |
| Cb-2456 | 91 | B.12 |
| Cb-2457 | 92 | B.12 |
| Cb-2458 | 93 | B.12 |
| Cb-2459 | 94 | B.12 |
| Cb-2460 | 95 | B.12 |
| Cb-2461 | 96 | B.12 |
| Cb-2462 | 97 | B.12 |
| Cb-2463 | 98 | B.12 |
| Cb-2464 | 99 | B.12 |
| Cb-2465 | 100 | B.12 |
| Cb-2466 | 101 | B.12 |
| Cb-2467 | 102 | B.12 |
| Cb-2468 | 103 | B.12 |
| Cb-2469 | 104 | B.12 |
| Cb-2470 | 105 | B.12 |
| Cb-2471 | 106 | B.12 |
| Cb-2472 | 107 | B.12 |
| Cb-2473 | 108 | B.12 |
| Cb-2474 | 109 | B.12 |
| Cb-2475 | 110 | B.12 |
| Cb-2476 | 111 | B.12 |
| Cb-2477 | 112 | B.12 |
| Cb-2478 | 113 | B.12 |
| Cb-2479 | 114 | B.12 |
| Cb-2480 | 115 | B.12 |
| Cb-2481 | 116 | B.12 |
| Cb-2482 | 117 | B.12 |
| Cb-2483 | 118 | B.12 |
| Cb-2484 | 119 | B.12 |
| Cb-2485 | 120 | B.12 |
| Cb-2486 | 121 | B.12 |
| Cb-2487 | 122 | B.12 |
| Cb-2488 | 123 | B.12 |
| Cb-2489 | 124 | B.12 |
| Cb-2490 | 125 | B.12 |
| Cb-2491 | 126 | B.12 |
| Cb-2492 | 127 | B.12 |
| Cb-2493 | 128 | B.12 |
| Cb-2494 | 129 | B.12 |
| Cb-2495 | 130 | B.12 |
| Cb-2496 | 131 | B.12 |
| Cb-2497 | 132 | B.12 |
| Cb-2498 | 133 | B.12 |
| Cb-2499 | 134 | B.12 |
| Cb-2500 | 135 | B.12 |
| Cb-2501 | 136 | B.12 |
| Cb-2502 | 137 | B.12 |
| Cb-2503 | 138 | B.12 |
| Cb-2504 | 139 | B.12 |
| Cb-2505 | 140 | B.12 |
| Cb-2506 | 141 | B.12 |
| Cb-2507 | 142 | B.12 |
| Cb-2508 | 143 | B.12 |
| Cb-2509 | 144 | B.12 |
| Cb-2510 | 145 | B.12 |
| Cb-2511 | 146 | B.12 |
| Cb-2512 | 147 | B.12 |
| Cb-2513 | 148 | B.12 |
| Cb-2514 | 149 | B.12 |
| Cb-2515 | 150 | B.12 |
| Cb-2516 | 151 | B.12 |
| Cb-2517 | 152 | B.12 |
| Cb-2518 | 153 | B.12 |
| Cb-2519 | 154 | B.12 |
| Cb-2520 | 155 | B.12 |
| Cb-2521 | 156 | B.12 |
| Cb-2522 | 157 | B.12 |
| Cb-2523 | 158 | B.12 |
| Cb-2524 | 159 | B.12 |
| Cb-2525 | 160 | B.12 |
| Cb-2526 | 161 | B.12 |
| Cb-2527 | 162 | B.12 |
| Cb-2528 | 163 | B.12 |
| Cb-2529 | 164 | B.12 |
| Cb-2530 | 165 | B.12 |
| Cb-2531 | 166 | B.12 |
| Cb-2532 | 167 | B.12 |
| Cb-2533 | 168 | B.12 |
| Cb-2534 | 169 | B.12 |
| Cb-2535 | 170 | B.12 |
| Cb-2536 | 171 | B.12 |
| Cb-2537 | 172 | B.12 |
| Cb-2538 | 173 | B.12 |
| Cb-2539 | 174 | B.12 |
| Cb-2540 | 175 | B.12 |
| Cb-2541 | 176 | B.12 |
| Cb-2542 | 177 | B.12 |
| Cb-2543 | 178 | B.12 |
| Cb-2544 | 179 | B.12 |
| Cb-2545 | 180 | B.12 |
| Cb-2546 | 181 | B.12 |
| Cb-2547 | 182 | B.12 |
| Cb-2548 | 183 | B.12 |
| Cb-2549 | 184 | B.12 |
| Cb-2550 | 185 | B.12 |
| Cb-2551 | 186 | B.12 |
| Cb-2552 | 187 | B.12 |
| Cb-2553 | 188 | B.12 |
| Cb-2554 | 189 | B.12 |
| Cb-2555 | 190 | B.12 |
| Cb-2556 | 191 | B.12 |
| Cb-2557 | 192 | B.12 |
| Cb-2558 | 193 | B.12 |
| Cb-2559 | 194 | B.12 |
| Cb-2560 | 195 | B.12 |
| Cb-2561 | 196 | B.12 |
| Cb-2562 | 197 | B.12 |
| Cb-2563 | 198 | B.12 |
| Cb-2564 | 199 | B.12 |
| Cb-2565 | 200 | B.12 |
| Cb-2566 | 201 | B.12 |
| Cb-2567 | 202 | B.12 |
| Cb-2568 | 203 | B.12 |
| Cb-2569 | 204 | B.12 |
| Cb-2570 | 205 | B.12 |
| Cb-2571 | 206 | B.12 |
| Cb-2572 | 207 | B.12 |

| Comb. | Com. A | Com. B |
|---|---|---|
| Cb-2573 | 208 | B.12 |
| Cb-2574 | 209 | B.12 |
| Cb-2575 | 210 | B.12 |
| Cb-2576 | 211 | B.12 |
| Cb-2577 | 212 | B.12 |
| Cb-2578 | 213 | B.12 |
| Cb-2579 | 214 | B.12 |
| Cb-2580 | 215 | B.12 |
| Cb-2581 | 1 | B.13 |
| Cb-2582 | 2 | B.13 |
| Cb-2583 | 3 | B.13 |
| Cb-2584 | 4 | B.13 |
| Cb-2585 | 5 | B.13 |
| Cb-2586 | 6 | B.13 |
| Cb-2587 | 7 | B.13 |
| Cb-2588 | 8 | B.13 |
| Cb-2589 | 9 | B.13 |
| Cb-2590 | 10 | B.13 |
| Cb-2591 | 11 | B.13 |
| Cb-2592 | 12 | B.13 |
| Cb-2593 | 13 | B.13 |
| Cb-2594 | 14 | B.13 |
| Cb-2595 | 15 | B.13 |
| Cb-2596 | 16 | B.13 |
| Cb-2597 | 17 | B.13 |
| Cb-2598 | 18 | B.13 |
| Cb-2599 | 19 | B.13 |
| Cb-2600 | 20 | B.13 |
| Cb-2601 | 21 | B.13 |
| Cb-2602 | 22 | B.13 |
| Cb-2603 | 23 | B.13 |
| Cb-2604 | 24 | B.13 |
| Cb-2605 | 25 | B.13 |
| Cb-2606 | 26 | B.13 |
| Cb-2607 | 27 | B.13 |
| Cb-2608 | 28 | B.13 |
| Cb-2609 | 29 | B.13 |
| Cb-2610 | 30 | B.13 |
| Cb-2611 | 31 | B.13 |
| Cb-2612 | 32 | B.13 |
| Cb-2613 | 33 | B.13 |
| Cb-2614 | 34 | B.13 |
| Cb-2615 | 35 | B.13 |
| Cb-2616 | 36 | B.13 |
| Cb-2617 | 37 | B.13 |
| Cb-2618 | 38 | B.13 |
| Cb-2619 | 39 | B.13 |
| Cb-2620 | 40 | B.13 |
| Cb-2621 | 41 | B.13 |
| Cb-2622 | 42 | B.13 |
| Cb-2623 | 43 | B.13 |
| Cb-2624 | 44 | B.13 |
| Cb-2625 | 45 | B.13 |
| Cb-2626 | 46 | B.13 |
| Cb-2627 | 47 | B.13 |
| Cb-2628 | 48 | B.13 |
| Cb-2629 | 49 | B.13 |
| Cb-2630 | 50 | B.13 |
| Cb-2631 | 51 | B.13 |
| Cb-2632 | 52 | B.13 |
| Cb-2633 | 53 | B.13 |
| Cb-2634 | 54 | B.13 |
| Cb-2635 | 55 | B.13 |
| Cb-2636 | 56 | B.13 |
| Cb-2637 | 57 | B.13 |
| Cb-2638 | 58 | B.13 |
| Cb-2639 | 59 | B.13 |
| Cb-2640 | 60 | B.13 |
| Cb-2641 | 61 | B.13 |
| Cb-2642 | 62 | B.13 |
| Cb-2643 | 63 | B.13 |
| Cb-2644 | 64 | B.13 |
| Cb-2645 | 65 | B.13 |
| Cb-2646 | 66 | B.13 |
| Cb-2647 | 67 | B.13 |
| Cb-2648 | 68 | B.13 |
| Cb-2649 | 69 | B.13 |
| Cb-2650 | 70 | B.13 |
| Cb-2651 | 71 | B.13 |
| Cb-2652 | 72 | B.13 |
| Cb-2653 | 73 | B.13 |
| Cb-2654 | 74 | B.13 |
| Cb-2655 | 75 | B.13 |
| Cb-2656 | 76 | B.13 |
| Cb-2657 | 77 | B.13 |
| Cb-2658 | 78 | B.13 |
| Cb-2659 | 79 | B.13 |
| Cb-2660 | 80 | B.13 |
| Cb-2661 | 81 | B.13 |
| Cb-2662 | 82 | B.13 |
| Cb-2663 | 83 | B.13 |
| Cb-2664 | 84 | B.13 |
| Cb-2665 | 85 | B.13 |
| Cb-2666 | 86 | B.13 |
| Cb-2667 | 87 | B.13 |
| Cb-2668 | 88 | B.13 |
| Cb-2669 | 89 | B.13 |
| Cb-2670 | 90 | B.13 |
| Cb-2671 | 91 | B.13 |
| Cb-2672 | 92 | B.13 |
| Cb-2673 | 93 | B.13 |
| Cb-2674 | 94 | B.13 |
| Cb-2675 | 95 | B.13 |
| Cb-2676 | 96 | B.13 |
| Cb-2677 | 97 | B.13 |
| Cb-2678 | 98 | B.13 |
| Cb-2679 | 99 | B.13 |
| Cb-2680 | 100 | B.13 |
| Cb-2681 | 101 | B.13 |
| Cb-2682 | 102 | B.13 |
| Cb-2683 | 103 | B.13 |
| Cb-2684 | 104 | B.13 |
| Cb-2685 | 105 | B.13 |
| Cb-2686 | 106 | B.13 |
| Cb-2687 | 107 | B.13 |
| Cb-2688 | 108 | B.13 |
| Cb-2689 | 109 | B.13 |
| Cb-2690 | 110 | B.13 |
| Cb-2691 | 111 | B.13 |
| Cb-2692 | 112 | B.13 |
| Cb-2693 | 113 | B.13 |
| Cb-2694 | 114 | B.13 |
| Cb-2695 | 115 | B.13 |
| Cb-2696 | 116 | B.13 |
| Cb-2697 | 117 | B.13 |
| Cb-2698 | 118 | B.13 |
| Cb-2699 | 119 | B.13 |
| Cb-2700 | 120 | B.13 |
| Cb-2701 | 121 | B.13 |
| Cb-2702 | 122 | B.13 |
| Cb-2703 | 123 | B.13 |
| Cb-2704 | 124 | B.13 |
| Cb-2705 | 125 | B.13 |
| Cb-2706 | 126 | B.13 |
| Cb-2707 | 127 | B.13 |
| Cb-2708 | 128 | B.13 |
| Cb-2709 | 129 | B.13 |
| Cb-2710 | 130 | B.13 |
| Cb-2711 | 131 | B.13 |
| Cb-2712 | 132 | B.13 |
| Cb-2713 | 133 | B.13 |
| Cb-2714 | 134 | B.13 |
| Cb-2715 | 135 | B.13 |
| Cb-2716 | 136 | B.13 |
| Cb-2717 | 137 | B.13 |
| Cb-2718 | 138 | B.13 |
| Cb-2719 | 139 | B.13 |
| Cb-2720 | 140 | B.13 |
| Cb-2721 | 141 | B.13 |
| Cb-2722 | 142 | B.13 |
| Cb-2723 | 143 | B.13 |
| Cb-2724 | 144 | B.13 |
| Cb-2725 | 145 | B.13 |
| Cb-2726 | 146 | B.13 |

| Comb. | Com. A | Com. B |
|---|---|---|
| Cb-2727 | 147 | B.13 |
| Cb-2728 | 148 | B.13 |
| Cb-2729 | 149 | B.13 |
| Cb-2730 | 150 | B.13 |
| Cb-2731 | 151 | B.13 |
| Cb-2732 | 152 | B.13 |
| Cb-2733 | 153 | B.13 |
| Cb-2734 | 154 | B.13 |
| Cb-2735 | 155 | B.13 |
| Cb-2736 | 156 | B.13 |
| Cb-2737 | 157 | B.13 |
| Cb-2738 | 158 | B.13 |
| Cb-2739 | 159 | B.13 |
| Cb-2740 | 160 | B.13 |
| Cb-2741 | 161 | B.13 |
| Cb-2742 | 162 | B.13 |
| Cb-2743 | 163 | B.13 |
| Cb-2744 | 164 | B.13 |
| Cb-2745 | 165 | B.13 |
| Cb-2746 | 166 | B.13 |
| Cb-2747 | 167 | B.13 |
| Cb-2748 | 168 | B.13 |
| Cb-2749 | 169 | B.13 |
| Cb-2750 | 170 | B.13 |
| Cb-2751 | 171 | B.13 |
| Cb-2752 | 172 | B.13 |
| Cb-2753 | 173 | B.13 |
| Cb-2754 | 174 | B.13 |
| Cb-2755 | 175 | B.13 |
| Cb-2756 | 176 | B.13 |
| Cb-2757 | 177 | B.13 |
| Cb-2758 | 178 | B.13 |
| Cb-2759 | 179 | B.13 |
| Cb-2760 | 180 | B.13 |
| Cb-2761 | 181 | B.13 |
| Cb-2762 | 182 | B.13 |
| Cb-2763 | 183 | B.13 |
| Cb-2764 | 184 | B.13 |
| Cb-2765 | 185 | B.13 |
| Cb-2766 | 186 | B.13 |
| Cb-2767 | 187 | B.13 |
| Cb-2768 | 188 | B.13 |
| Cb-2769 | 189 | B.13 |
| Cb-2770 | 190 | B.13 |
| Cb-2771 | 191 | B.13 |
| Cb-2772 | 192 | B.13 |
| Cb-2773 | 193 | B.13 |
| Cb-2774 | 194 | B.13 |
| Cb-2775 | 195 | B.13 |
| Cb-2776 | 196 | B.13 |
| Cb-2777 | 197 | B.13 |
| Cb-2778 | 198 | B.13 |
| Cb-2779 | 199 | B.13 |
| Cb-2780 | 200 | B.13 |
| Cb-2781 | 201 | B.13 |
| Cb-2782 | 202 | B.13 |
| Cb-2783 | 203 | B.13 |
| Cb-2784 | 204 | B.13 |
| Cb-2785 | 205 | B.13 |
| Cb-2786 | 206 | B.13 |
| Cb-2787 | 207 | B.13 |
| Cb-2788 | 208 | B.13 |
| Cb-2789 | 209 | B.13 |
| Cb-2790 | 210 | B.13 |
| Cb-2791 | 211 | B.13 |
| Cb-2792 | 212 | B.13 |
| Cb-2793 | 213 | B.13 |
| Cb-2794 | 214 | B.13 |
| Cb-2795 | 215 | B.13 |
| Cb-2796 | 1 | B.14 |
| Cb-2797 | 2 | B.14 |
| Cb-2798 | 3 | B.14 |
| Cb-2799 | 4 | B.14 |
| Cb-2800 | 5 | B.14 |
| Cb-2801 | 6 | B.14 |
| Cb-2802 | 7 | B.14 |
| Cb-2803 | 8 | B.14 |
| Cb-2804 | 9 | B.14 |
| Cb-2805 | 10 | B.14 |
| Cb-2806 | 11 | B.14 |
| Cb-2807 | 12 | B.14 |
| Cb-2808 | 13 | B.14 |
| Cb-2809 | 14 | B.14 |
| Cb-2810 | 15 | B.14 |
| Cb-2811 | 16 | B.14 |
| Cb-2812 | 17 | B.14 |
| Cb-2813 | 18 | B.14 |
| Cb-2814 | 19 | B.14 |
| Cb-2815 | 20 | B.14 |
| Cb-2816 | 21 | B.14 |
| Cb-2817 | 22 | B.14 |
| Cb-2818 | 23 | B.14 |
| Cb-2819 | 24 | B.14 |
| Cb-2820 | 25 | B.14 |
| Cb-2821 | 26 | B.14 |
| Cb-2822 | 27 | B.14 |
| Cb-2823 | 28 | B.14 |
| Cb-2824 | 29 | B.14 |
| Cb-2825 | 30 | B.14 |
| Cb-2826 | 31 | B.14 |
| Cb-2827 | 32 | B.14 |
| Cb-2828 | 33 | B.14 |
| Cb-2829 | 34 | B.14 |
| Cb-2830 | 35 | B.14 |
| Cb-2831 | 36 | B.14 |
| Cb-2832 | 37 | B.14 |
| Cb-2833 | 38 | B.14 |
| Cb-2834 | 39 | B.14 |
| Cb-2835 | 40 | B.14 |
| Cb-2836 | 41 | B.14 |
| Cb-2837 | 42 | B.14 |
| Cb-2838 | 43 | B.14 |
| Cb-2839 | 44 | B.14 |
| Cb-2840 | 45 | B.14 |
| Cb-2841 | 46 | B.14 |
| Cb-2842 | 47 | B.14 |
| Cb-2843 | 48 | B.14 |
| Cb-2844 | 49 | B.14 |
| Cb-2845 | 50 | B.14 |
| Cb-2846 | 51 | B.14 |
| Cb-2847 | 52 | B.14 |
| Cb-2848 | 53 | B.14 |
| Cb-2849 | 54 | B.14 |
| Cb-2850 | 55 | B.14 |
| Cb-2851 | 56 | B.14 |
| Cb-2852 | 57 | B.14 |
| Cb-2853 | 58 | B.14 |
| Cb-2854 | 59 | B.14 |
| Cb-2855 | 60 | B.14 |
| Cb-2856 | 61 | B.14 |
| Cb-2857 | 62 | B.14 |
| Cb-2858 | 63 | B.14 |
| Cb-2859 | 64 | B.14 |
| Cb-2860 | 65 | B.14 |
| Cb-2861 | 66 | B.14 |
| Cb-2862 | 67 | B.14 |
| Cb-2863 | 68 | B.14 |
| Cb-2864 | 69 | B.14 |
| Cb-2865 | 70 | B.14 |
| Cb-2866 | 71 | B.14 |
| Cb-2867 | 72 | B.14 |
| Cb-2868 | 73 | B.14 |
| Cb-2869 | 74 | B.14 |
| Cb-2870 | 75 | B.14 |
| Cb-2871 | 76 | B.14 |
| Cb-2872 | 77 | B.14 |
| Cb-2873 | 78 | B.14 |
| Cb-2874 | 79 | B.14 |
| Cb-2875 | 80 | B.14 |
| Cb-2876 | 81 | B.14 |
| Cb-2877 | 82 | B.14 |
| Cb-2878 | 83 | B.14 |
| Cb-2879 | 84 | B.14 |
| Cb-2880 | 85 | B.14 |

| Comb. | Com. A | Com. B |
|---|---|---|
| Cb-2881 | 86 | B.14 |
| Cb-2882 | 87 | B.14 |
| Cb-2883 | 88 | B.14 |
| Cb-2884 | 89 | B.14 |
| Cb-2885 | 90 | B.14 |
| Cb-2886 | 91 | B.14 |
| Cb-2887 | 92 | B.14 |
| Cb-2888 | 93 | B.14 |
| Cb-2889 | 94 | B.14 |
| Cb-2890 | 95 | B.14 |
| Cb-2891 | 96 | B.14 |
| Cb-2892 | 97 | B.14 |
| Cb-2893 | 98 | B.14 |
| Cb-2894 | 99 | B.14 |
| Cb-2895 | 100 | B.14 |
| Cb-2896 | 101 | B.14 |
| Cb-2897 | 102 | B.14 |
| Cb-2898 | 103 | B.14 |
| Cb-2899 | 104 | B.14 |
| Cb-2900 | 105 | B.14 |
| Cb-2901 | 106 | B.14 |
| Cb-2902 | 107 | B.14 |
| Cb-2903 | 108 | B.14 |
| Cb-2904 | 109 | B.14 |
| Cb-2905 | 110 | B.14 |
| Cb-2906 | 111 | B.14 |
| Cb-2907 | 112 | B.14 |
| Cb-2908 | 113 | B.14 |
| Cb-2909 | 114 | B.14 |
| Cb-2910 | 115 | B.14 |
| Cb-2911 | 116 | B.14 |
| Cb-2912 | 117 | B.14 |
| Cb-2913 | 118 | B.14 |
| Cb-2914 | 119 | B.14 |
| Cb-2915 | 120 | B.14 |
| Cb-2916 | 121 | B.14 |
| Cb-2917 | 122 | B.14 |
| Cb-2918 | 123 | B.14 |
| Cb-2919 | 124 | B.14 |
| Cb-2920 | 125 | B.14 |
| Cb-2921 | 126 | B.14 |
| Cb-2922 | 127 | B.14 |
| Cb-2923 | 128 | B.14 |
| Cb-2924 | 129 | B.14 |
| Cb-2925 | 130 | B.14 |
| Cb-2926 | 131 | B.14 |
| Cb-2927 | 132 | B.14 |
| Cb-2928 | 133 | B.14 |
| Cb-2929 | 134 | B.14 |
| Cb-2930 | 135 | B.14 |
| Cb-2931 | 136 | B.14 |
| Cb-2932 | 137 | B.14 |
| Cb-2933 | 138 | B.14 |
| Cb-2934 | 139 | B.14 |
| Cb-2935 | 140 | B.14 |
| Cb-2936 | 141 | B.14 |
| Cb-2937 | 142 | B.14 |
| Cb-2938 | 143 | B.14 |
| Cb-2939 | 144 | B.14 |
| Cb-2940 | 145 | B.14 |
| Cb-2941 | 146 | B.14 |
| Cb-2942 | 147 | B.14 |
| Cb-2943 | 148 | B.14 |
| Cb-2944 | 149 | B.14 |
| Cb-2945 | 150 | B.14 |
| Cb-2946 | 151 | B.14 |
| Cb-2947 | 152 | B.14 |
| Cb-2948 | 153 | B.14 |
| Cb-2949 | 154 | B.14 |
| Cb-2950 | 155 | B.14 |
| Cb-2951 | 156 | B.14 |
| Cb-2952 | 157 | B.14 |
| Cb-2953 | 158 | B.14 |
| Cb-2954 | 159 | B.14 |
| Cb-2955 | 160 | B.14 |
| Cb-2956 | 161 | B.14 |
| Cb-2957 | 162 | B.14 |
| Cb-2958 | 163 | B.14 |
| Cb-2959 | 164 | B.14 |
| Cb-2960 | 165 | B.14 |
| Cb-2961 | 166 | B.14 |
| Cb-2962 | 167 | B.14 |
| Cb-2963 | 168 | B.14 |
| Cb-2964 | 169 | B.14 |
| Cb-2965 | 170 | B.14 |
| Cb-2966 | 171 | B.14 |
| Cb-2967 | 172 | B.14 |
| Cb-2968 | 173 | B.14 |
| Cb-2969 | 174 | B.14 |
| Cb-2970 | 175 | B.14 |
| Cb-2971 | 176 | B.14 |
| Cb-2972 | 177 | B.14 |
| Cb-2973 | 178 | B.14 |
| Cb-2974 | 179 | B.14 |
| Cb-2975 | 180 | B.14 |
| Cb-2976 | 181 | B.14 |
| Cb-2977 | 182 | B.14 |
| Cb-2978 | 183 | B.14 |
| Cb-2979 | 184 | B.14 |
| Cb-2980 | 185 | B.14 |
| Cb-2981 | 186 | B.14 |
| Cb-2982 | 187 | B.14 |
| Cb-2983 | 188 | B.14 |
| Cb-2984 | 189 | B.14 |
| Cb-2985 | 190 | B.14 |
| Cb-2986 | 191 | B.14 |
| Cb-2987 | 192 | B.14 |
| Cb-2988 | 193 | B.14 |
| Cb-2989 | 194 | B.14 |
| Cb-2990 | 195 | B.14 |
| Cb-2991 | 196 | B.14 |
| Cb-2992 | 197 | B.14 |
| Cb-2993 | 198 | B.14 |
| Cb-2994 | 199 | B.14 |
| Cb-2995 | 200 | B.14 |
| Cb-2996 | 201 | B.14 |
| Cb-2997 | 202 | B.14 |
| Cb-2998 | 203 | B.14 |
| Cb-2999 | 204 | B.14 |
| Cb-3000 | 205 | B.14 |
| Cb-3001 | 206 | B.14 |
| Cb-3002 | 207 | B.14 |
| Cb-3003 | 208 | B.14 |
| Cb-3004 | 209 | B.14 |
| Cb-3005 | 210 | B.14 |
| Cb-3006 | 211 | B.14 |
| Cb-3007 | 212 | B.14 |
| Cb-3008 | 213 | B.14 |
| Cb-3009 | 214 | B.14 |
| Cb-3010 | 215 | B.14 |
| Cb-3011 | 1 | B.15 |
| Cb-3012 | 2 | B.15 |
| Cb-3013 | 3 | B.15 |
| Cb-3014 | 4 | B.15 |
| Cb-3015 | 5 | B.15 |
| Cb-3016 | 6 | B.15 |
| Cb-3017 | 7 | B.15 |
| Cb-3018 | 8 | B.15 |
| Cb-3019 | 9 | B.15 |
| Cb-3020 | 10 | B.15 |
| Cb-3021 | 11 | B.15 |
| Cb-3022 | 12 | B.15 |
| Cb-3023 | 13 | B.15 |
| Cb-3024 | 14 | B.15 |
| Cb-3025 | 15 | B.15 |
| Cb-3026 | 16 | B.15 |
| Cb-3027 | 17 | B.15 |
| Cb-3028 | 18 | B.15 |
| Cb-3029 | 19 | B.15 |
| Cb-3030 | 20 | B.15 |
| Cb-3031 | 21 | B.15 |
| Cb-3032 | 22 | B.15 |
| Cb-3033 | 23 | B.15 |
| Cb-3034 | 24 | B.15 |

| Comb. | Com. A | Com. B |
|---|---|---|
| Cb-3035 | 25 | B.15 |
| Cb-3036 | 26 | B.15 |
| Cb-3037 | 27 | B.15 |
| Cb-3038 | 28 | B.15 |
| Cb-3039 | 29 | B.15 |
| Cb-3040 | 30 | B.15 |
| Cb-3041 | 31 | B.15 |
| Cb-3042 | 32 | B.15 |
| Cb-3043 | 33 | B.15 |
| Cb-3044 | 34 | B.15 |
| Cb-3045 | 35 | B.15 |
| Cb-3046 | 36 | B.15 |
| Cb-3047 | 37 | B.15 |
| Cb-3048 | 38 | B.15 |
| Cb-3049 | 39 | B.15 |
| Cb-3050 | 40 | B.15 |
| Cb-3051 | 41 | B.15 |
| Cb-3052 | 42 | B.15 |
| Cb-3053 | 43 | B.15 |
| Cb-3054 | 44 | B.15 |
| Cb-3055 | 45 | B.15 |
| Cb-3056 | 46 | B.15 |
| Cb-3057 | 47 | B.15 |
| Cb-3058 | 48 | B.15 |
| Cb-3059 | 49 | B.15 |
| Cb-3060 | 50 | B.15 |
| Cb-3061 | 51 | B.15 |
| Cb-3062 | 52 | B.15 |
| Cb-3063 | 53 | B.15 |
| Cb-3064 | 54 | B.15 |
| Cb-3065 | 55 | B.15 |
| Cb-3066 | 56 | B.15 |
| Cb-3067 | 57 | B.15 |
| Cb-3068 | 58 | B.15 |
| Cb-3069 | 59 | B.15 |
| Cb-3070 | 60 | B.15 |
| Cb-3071 | 61 | B.15 |
| Cb-3072 | 62 | B.15 |
| Cb-3073 | 63 | B.15 |
| Cb-3074 | 64 | B.15 |
| Cb-3075 | 65 | B.15 |
| Cb-3076 | 66 | B.15 |
| Cb-3077 | 67 | B.15 |
| Cb-3078 | 68 | B.15 |
| Cb-3079 | 69 | B.15 |
| Cb-3080 | 70 | B.15 |
| Cb-3081 | 71 | B.15 |
| Cb-3082 | 72 | B.15 |
| Cb-3083 | 73 | B.15 |
| Cb-3084 | 74 | B.15 |
| Cb-3085 | 75 | B.15 |
| Cb-3086 | 76 | B.15 |
| Cb-3087 | 77 | B.15 |
| Cb-3088 | 78 | B.15 |
| Cb-3089 | 79 | B.15 |
| Cb-3090 | 80 | B.15 |
| Cb-3091 | 81 | B.15 |
| Cb-3092 | 82 | B.15 |
| Cb-3093 | 83 | B.15 |
| Cb-3094 | 84 | B.15 |
| Cb-3095 | 85 | B.15 |
| Cb-3096 | 86 | B.15 |
| Cb-3097 | 87 | B.15 |
| Cb-3098 | 88 | B.15 |
| Cb-3099 | 89 | B.15 |
| Cb-3100 | 90 | B.15 |
| Cb-3101 | 91 | B.15 |
| Cb-3102 | 92 | B.15 |
| Cb-3103 | 93 | B.15 |
| Cb-3104 | 94 | B.15 |
| Cb-3105 | 95 | B.15 |
| Cb-3106 | 96 | B.15 |
| Cb-3107 | 97 | B.15 |
| Cb-3108 | 98 | B.15 |
| Cb-3109 | 99 | B.15 |
| Cb-3110 | 100 | B.15 |
| Cb-3111 | 101 | B.15 |
| Cb-3112 | 102 | B.15 |
| Cb-3113 | 103 | B.15 |
| Cb-3114 | 104 | B.15 |
| Cb-3115 | 105 | B.15 |
| Cb-3116 | 106 | B.15 |
| Cb-3117 | 107 | B.15 |
| Cb-3118 | 108 | B.15 |
| Cb-3119 | 109 | B.15 |
| Cb-3120 | 110 | B.15 |
| Cb-3121 | 111 | B.15 |
| Cb-3122 | 112 | B.15 |
| Cb-3123 | 113 | B.15 |
| Cb-3124 | 114 | B.15 |
| Cb-3125 | 115 | B.15 |
| Cb-3126 | 116 | B.15 |
| Cb-3127 | 117 | B.15 |
| Cb-3128 | 118 | B.15 |
| Cb-3129 | 119 | B.15 |
| Cb-3130 | 120 | B.15 |
| Cb-3131 | 121 | B.15 |
| Cb-3132 | 122 | B.15 |
| Cb-3133 | 123 | B.15 |
| Cb-3134 | 124 | B.15 |
| Cb-3135 | 125 | B.15 |
| Cb-3136 | 126 | B.15 |
| Cb-3137 | 127 | B.15 |
| Cb-3138 | 128 | B.15 |
| Cb-3139 | 129 | B.15 |
| Cb-3140 | 130 | B.15 |
| Cb-3141 | 131 | B.15 |
| Cb-3142 | 132 | B.15 |
| Cb-3143 | 133 | B.15 |
| Cb-3144 | 134 | B.15 |
| Cb-3145 | 135 | B.15 |
| Cb-3146 | 136 | B.15 |
| Cb-3147 | 137 | B.15 |
| Cb-3148 | 138 | B.15 |
| Cb-3149 | 139 | B.15 |
| Cb-3150 | 140 | B.15 |
| Cb-3151 | 141 | B.15 |
| Cb-3152 | 142 | B.15 |
| Cb-3153 | 143 | B.15 |
| Cb-3154 | 144 | B.15 |
| Cb-3155 | 145 | B.15 |
| Cb-3156 | 146 | B.15 |
| Cb-3157 | 147 | B.15 |
| Cb-3158 | 148 | B.15 |
| Cb-3159 | 149 | B.15 |
| Cb-3160 | 150 | B.15 |
| Cb-3161 | 151 | B.15 |
| Cb-3162 | 152 | B.15 |
| Cb-3163 | 153 | B.15 |
| Cb-3164 | 154 | B.15 |
| Cb-3165 | 155 | B.15 |
| Cb-3166 | 156 | B.15 |
| Cb-3167 | 157 | B.15 |
| Cb-3168 | 158 | B.15 |
| Cb-3169 | 159 | B.15 |
| Cb-3170 | 160 | B.15 |
| Cb-3171 | 161 | B.15 |
| Cb-3172 | 162 | B.15 |
| Cb-3173 | 163 | B.15 |
| Cb-3174 | 164 | B.15 |
| Cb-3175 | 165 | B.15 |
| Cb-3176 | 166 | B.15 |
| Cb-3177 | 167 | B.15 |
| Cb-3178 | 168 | B.15 |
| Cb-3179 | 169 | B.15 |
| Cb-3180 | 170 | B.15 |
| Cb-3181 | 171 | B.15 |
| Cb-3182 | 172 | B.15 |
| Cb-3183 | 173 | B.15 |
| Cb-3184 | 174 | B.15 |
| Cb-3185 | 175 | B.15 |
| Cb-3186 | 176 | B.15 |
| Cb-3187 | 177 | B.15 |
| Cb-3188 | 178 | B.15 |

| Comb. | Com. A | Com. B |
|---|---|---|
| Cb-3189 | 179 | B.15 |
| Cb-3190 | 180 | B.15 |
| Cb-3191 | 181 | B.15 |
| Cb-3192 | 182 | B.15 |
| Cb-3193 | 183 | B.15 |
| Cb-3194 | 184 | B.15 |
| Cb-3195 | 185 | B.15 |
| Cb-3196 | 186 | B.15 |
| Cb-3197 | 187 | B.15 |
| Cb-3198 | 188 | B.15 |
| Cb-3199 | 189 | B.15 |
| Cb-3200 | 190 | B.15 |
| Cb-3201 | 191 | B.15 |
| Cb-3202 | 192 | B.15 |
| Cb-3203 | 193 | B.15 |
| Cb-3204 | 194 | B.15 |
| Cb-3205 | 195 | B.15 |
| Cb-3206 | 196 | B.15 |
| Cb-3207 | 197 | B.15 |
| Cb-3208 | 198 | B.15 |
| Cb-3209 | 199 | B.15 |
| Cb-3210 | 200 | B.15 |
| Cb-3211 | 201 | B.15 |
| Cb-3212 | 202 | B.15 |
| Cb-3213 | 203 | B.15 |
| Cb-3214 | 204 | B.15 |
| Cb-3215 | 205 | B.15 |
| Cb-3216 | 206 | B.15 |
| Cb-3217 | 207 | B.15 |
| Cb-3218 | 208 | B.15 |
| Cb-3219 | 209 | B.15 |
| Cb-3220 | 210 | B.15 |
| Cb-3221 | 211 | B.15 |
| Cb-3222 | 212 | B.15 |
| Cb-3223 | 213 | B.15 |
| Cb-3224 | 214 | B.15 |
| Cb-3225 | 215 | B.15 |
| Cb-3226 | 1 | B.16 |
| Cb-3227 | 2 | B.16 |
| Cb-3228 | 3 | B.16 |
| Cb-3229 | 4 | B.16 |
| Cb-3230 | 5 | B.16 |
| Cb-3231 | 6 | B.16 |
| Cb-3232 | 7 | B.16 |
| Cb-3233 | 8 | B.16 |
| Cb-3234 | 9 | B.16 |
| Cb-3235 | 10 | B.16 |
| Cb-3236 | 11 | B.16 |
| Cb-3237 | 12 | B.16 |
| Cb-3238 | 13 | B.16 |
| Cb-3239 | 14 | B.16 |
| Cb-3240 | 15 | B.16 |
| Cb-3241 | 16 | B.16 |
| Cb-3242 | 17 | B.16 |
| Cb-3243 | 18 | B.16 |
| Cb-3244 | 19 | B.16 |
| Cb-3245 | 20 | B.16 |
| Cb-3246 | 21 | B.16 |
| Cb-3247 | 22 | B.16 |
| Cb-3248 | 23 | B.16 |
| Cb-3249 | 24 | B.16 |
| Cb-3250 | 25 | B.16 |
| Cb-3251 | 26 | B.16 |
| Cb-3252 | 27 | B.16 |
| Cb-3253 | 28 | B.16 |
| Cb-3254 | 29 | B.16 |
| Cb-3255 | 30 | B.16 |
| Cb-3256 | 31 | B.16 |
| Cb-3257 | 32 | B.16 |
| Cb-3258 | 33 | B.16 |
| Cb-3259 | 34 | B.16 |
| Cb-3260 | 35 | B.16 |
| Cb-3261 | 36 | B.16 |
| Cb-3262 | 37 | B.16 |
| Cb-3263 | 38 | B.16 |
| Cb-3264 | 39 | B.16 |
| Cb-3265 | 40 | B.16 |
| Cb-3266 | 41 | B.16 |
| Cb-3267 | 42 | B.16 |
| Cb-3268 | 43 | B.16 |
| Cb-3269 | 44 | B.16 |
| Cb-3270 | 45 | B.16 |
| Cb-3271 | 46 | B.16 |
| Cb-3272 | 47 | B.16 |
| Cb-3273 | 48 | B.16 |
| Cb-3274 | 49 | B.16 |
| Cb-3275 | 50 | B.16 |
| Cb-3276 | 51 | B.16 |
| Cb-3277 | 52 | B.16 |
| Cb-3278 | 53 | B.16 |
| Cb-3279 | 54 | B.16 |
| Cb-3280 | 55 | B.16 |
| Cb-3281 | 56 | B.16 |
| Cb-3282 | 57 | B.16 |
| Cb-3283 | 58 | B.16 |
| Cb-3284 | 59 | B.16 |
| Cb-3285 | 60 | B.16 |
| Cb-3286 | 61 | B.16 |
| Cb-3287 | 62 | B.16 |
| Cb-3288 | 63 | B.16 |
| Cb-3289 | 64 | B.16 |
| Cb-3290 | 65 | B.16 |
| Cb-3291 | 66 | B.16 |
| Cb-3292 | 67 | B.16 |
| Cb-3293 | 68 | B.16 |
| Cb-3294 | 69 | B.16 |
| Cb-3295 | 70 | B.16 |
| Cb-3296 | 71 | B.16 |
| Cb-3297 | 72 | B.16 |
| Cb-3298 | 73 | B.16 |
| Cb-3299 | 74 | B.16 |
| Cb-3300 | 75 | B.16 |
| Cb-3301 | 76 | B.16 |
| Cb-3302 | 77 | B.16 |
| Cb-3303 | 78 | B.16 |
| Cb-3304 | 79 | B.16 |
| Cb-3305 | 80 | B.16 |
| Cb-3306 | 81 | B.16 |
| Cb-3307 | 82 | B.16 |
| Cb-3308 | 83 | B.16 |
| Cb-3309 | 84 | B.16 |
| Cb-3310 | 85 | B.16 |
| Cb-3311 | 86 | B.16 |
| Cb-3312 | 87 | B.16 |
| Cb-3313 | 88 | B.16 |
| Cb-3314 | 89 | B.16 |
| Cb-3315 | 90 | B.16 |
| Cb-3316 | 91 | B.16 |
| Cb-3317 | 92 | B.16 |
| Cb-3318 | 93 | B.16 |
| Cb-3319 | 94 | B.16 |
| Cb-3320 | 95 | B.16 |
| Cb-3321 | 96 | B.16 |
| Cb-3322 | 97 | B.16 |
| Cb-3323 | 98 | B.16 |
| Cb-3324 | 99 | B.16 |
| Cb-3325 | 100 | B.16 |
| Cb-3326 | 101 | B.16 |
| Cb-3327 | 102 | B.16 |
| Cb-3328 | 103 | B.16 |
| Cb-3329 | 104 | B.16 |
| Cb-3330 | 105 | B.16 |
| Cb-3331 | 106 | B.16 |
| Cb-3332 | 107 | B.16 |
| Cb-3333 | 108 | B.16 |
| Cb-3334 | 109 | B.16 |
| Cb-3335 | 110 | B.16 |
| Cb-3336 | 111 | B.16 |
| Cb-3337 | 112 | B.16 |
| Cb-3338 | 113 | B.16 |
| Cb-3339 | 114 | B.16 |
| Cb-3340 | 115 | B.16 |
| Cb-3341 | 116 | B.16 |
| Cb-3342 | 117 | B.16 |

| Comb. | Com. A | Com. B |
|---|---|---|
| Cb-3343 | 118 | B.16 |
| Cb-3344 | 119 | B.16 |
| Cb-3345 | 120 | B.16 |
| Cb-3346 | 121 | B.16 |
| Cb-3347 | 122 | B.16 |
| Cb-3348 | 123 | B.16 |
| Cb-3349 | 124 | B.16 |
| Cb-3350 | 125 | B.16 |
| Cb-3351 | 126 | B.16 |
| Cb-3352 | 127 | B.16 |
| Cb-3353 | 128 | B.16 |
| Cb-3354 | 129 | B.16 |
| Cb-3355 | 130 | B.16 |
| Cb-3356 | 131 | B.16 |
| Cb-3357 | 132 | B.16 |
| Cb-3358 | 133 | B.16 |
| Cb-3359 | 134 | B.16 |
| Cb-3360 | 135 | B.16 |
| Cb-3361 | 136 | B.16 |
| Cb-3362 | 137 | B.16 |
| Cb-3363 | 138 | B.16 |
| Cb-3364 | 139 | B.16 |
| Cb-3365 | 140 | B.16 |
| Cb-3366 | 141 | B.16 |
| Cb-3367 | 142 | B.16 |
| Cb-3368 | 143 | B.16 |
| Cb-3369 | 144 | B.16 |
| Cb-3370 | 145 | B.16 |
| Cb-3371 | 146 | B.16 |
| Cb-3372 | 147 | B.16 |
| Cb-3373 | 148 | B.16 |
| Cb-3374 | 149 | B.16 |
| Cb-3375 | 150 | B.16 |
| Cb-3376 | 151 | B.16 |
| Cb-3377 | 152 | B.16 |
| Cb-3378 | 153 | B.16 |
| Cb-3379 | 154 | B.16 |
| Cb-3380 | 155 | B.16 |
| Cb-3381 | 156 | B.16 |
| Cb-3382 | 157 | B.16 |
| Cb-3383 | 158 | B.16 |
| Cb-3384 | 159 | B.16 |
| Cb-3385 | 160 | B.16 |
| Cb-3386 | 161 | B.16 |
| Cb-3387 | 162 | B.16 |
| Cb-3388 | 163 | B.16 |
| Cb-3389 | 164 | B.16 |
| Cb-3390 | 165 | B.16 |
| Cb-3391 | 166 | B.16 |
| Cb-3392 | 167 | B.16 |
| Cb-3393 | 168 | B.16 |
| Cb-3394 | 169 | B.16 |
| Cb-3395 | 170 | B.16 |
| Cb-3396 | 171 | B.16 |
| Cb-3397 | 172 | B.16 |
| Cb-3398 | 173 | B.16 |
| Cb-3399 | 174 | B.16 |
| Cb-3400 | 175 | B.16 |
| Cb-3401 | 176 | B.16 |
| Cb-3402 | 177 | B.16 |
| Cb-3403 | 178 | B.16 |
| Cb-3404 | 179 | B.16 |
| Cb-3405 | 180 | B.16 |
| Cb-3406 | 181 | B.16 |
| Cb-3407 | 182 | B.16 |
| Cb-3408 | 183 | B.16 |
| Cb-3409 | 184 | B.16 |
| Cb-3410 | 185 | B.16 |
| Cb-3411 | 186 | B.16 |
| Cb-3412 | 187 | B.16 |
| Cb-3413 | 188 | B.16 |
| Cb-3414 | 189 | B.16 |
| Cb-3415 | 190 | B.16 |
| Cb-3416 | 191 | B.16 |
| Cb-3417 | 192 | B.16 |
| Cb-3418 | 193 | B.16 |
| Cb-3419 | 194 | B.16 |
| Cb-3420 | 195 | B.16 |
| Cb-3421 | 196 | B.16 |
| Cb-3422 | 197 | B.16 |
| Cb-3423 | 198 | B.16 |
| Cb-3424 | 199 | B.16 |
| Cb-3425 | 200 | B.16 |
| Cb-3426 | 201 | B.16 |
| Cb-3427 | 202 | B.16 |
| Cb-3428 | 203 | B.16 |
| Cb-3429 | 204 | B.16 |
| Cb-3430 | 205 | B.16 |
| Cb-3431 | 206 | B.16 |
| Cb-3432 | 207 | B.16 |
| Cb-3433 | 208 | B.16 |
| Cb-3434 | 209 | B.16 |
| Cb-3435 | 210 | B.16 |
| Cb-3436 | 211 | B.16 |
| Cb-3437 | 212 | B.16 |
| Cb-3438 | 213 | B.16 |
| Cb-3439 | 214 | B.16 |
| Cb-3440 | 215 | B.16 |
| Cb-3441 | 1 | B.17 |
| Cb-3442 | 2 | B.17 |
| Cb-3443 | 3 | B.17 |
| Cb-3444 | 4 | B.17 |
| Cb-3445 | 5 | B.17 |
| Cb-3446 | 6 | B.17 |
| Cb-3447 | 7 | B.17 |
| Cb-3448 | 8 | B.17 |
| Cb-3449 | 9 | B.17 |
| Cb-3450 | 10 | B.17 |
| Cb-3451 | 11 | B.17 |
| Cb-3452 | 12 | B.17 |
| Cb-3453 | 13 | B.17 |
| Cb-3454 | 14 | B.17 |
| Cb-3455 | 15 | B.17 |
| Cb-3456 | 16 | B.17 |
| Cb-3457 | 17 | B.17 |
| Cb-3458 | 18 | B.17 |
| Cb-3459 | 19 | B.17 |
| Cb-3460 | 20 | B.17 |
| Cb-3461 | 21 | B.17 |
| Cb-3462 | 22 | B.17 |
| Cb-3463 | 23 | B.17 |
| Cb-3464 | 24 | B.17 |
| Cb-3465 | 25 | B.17 |
| Cb-3466 | 26 | B.17 |
| Cb-3467 | 27 | B.17 |
| Cb-3468 | 28 | B.17 |
| Cb-3469 | 29 | B.17 |
| Cb-3470 | 30 | B.17 |
| Cb-3471 | 31 | B.17 |
| Cb-3472 | 32 | B.17 |
| Cb-3473 | 33 | B.17 |
| Cb-3474 | 34 | B.17 |
| Cb-3475 | 35 | B.17 |
| Cb-3476 | 36 | B.17 |
| Cb-3477 | 37 | B.17 |
| Cb-3478 | 38 | B.17 |
| Cb-3479 | 39 | B.17 |
| Cb-3480 | 40 | B.17 |
| Cb-3481 | 41 | B.17 |
| Cb-3482 | 42 | B.17 |
| Cb-3483 | 43 | B.17 |
| Cb-3484 | 44 | B.17 |
| Cb-3485 | 45 | B.17 |
| Cb-3486 | 46 | B.17 |
| Cb-3487 | 47 | B.17 |
| Cb-3488 | 48 | B.17 |
| Cb-3489 | 49 | B.17 |
| Cb-3490 | 50 | B.17 |
| Cb-3491 | 51 | B.17 |
| Cb-3492 | 52 | B.17 |
| Cb-3493 | 53 | B.17 |
| Cb-3494 | 54 | B.17 |
| Cb-3495 | 55 | B.17 |
| Cb-3496 | 56 | B.17 |

| Comb. | Com. A | Com. B |
|---|---|---|
| Cb-3497 | 57 | B.17 |
| Cb-3498 | 58 | B.17 |
| Cb-3499 | 59 | B.17 |
| Cb-3500 | 60 | B.17 |
| Cb-3501 | 61 | B.17 |
| Cb-3502 | 62 | B.17 |
| Cb-3503 | 63 | B.17 |
| Cb-3504 | 64 | B.17 |
| Cb-3505 | 65 | B.17 |
| Cb-3506 | 66 | B.17 |
| Cb-3507 | 67 | B.17 |
| Cb-3508 | 68 | B.17 |
| Cb-3509 | 69 | B.17 |
| Cb-3510 | 70 | B.17 |
| Cb-3511 | 71 | B.17 |
| Cb-3512 | 72 | B.17 |
| Cb-3513 | 73 | B.17 |
| Cb-3514 | 74 | B.17 |
| Cb-3515 | 75 | B.17 |
| Cb-3516 | 76 | B.17 |
| Cb-3517 | 77 | B.17 |
| Cb-3518 | 78 | B.17 |
| Cb-3519 | 79 | B.17 |
| Cb-3520 | 80 | B.17 |
| Cb-3521 | 81 | B.17 |
| Cb-3522 | 82 | B.17 |
| Cb-3523 | 83 | B.17 |
| Cb-3524 | 84 | B.17 |
| Cb-3525 | 85 | B.17 |
| Cb-3526 | 86 | B.17 |
| Cb-3527 | 87 | B.17 |
| Cb-3528 | 88 | B.17 |
| Cb-3529 | 89 | B.17 |
| Cb-3530 | 90 | B.17 |
| Cb-3531 | 91 | B.17 |
| Cb-3532 | 92 | B.17 |
| Cb-3533 | 93 | B.17 |
| Cb-3534 | 94 | B.17 |
| Cb-3535 | 95 | B.17 |
| Cb-3536 | 96 | B.17 |
| Cb-3537 | 97 | B.17 |
| Cb-3538 | 98 | B.17 |
| Cb-3539 | 99 | B.17 |
| Cb-3540 | 100 | B.17 |
| Cb-3541 | 101 | B.17 |
| Cb-3542 | 102 | B.17 |
| Cb-3543 | 103 | B.17 |
| Cb-3544 | 104 | B.17 |
| Cb-3545 | 105 | B.17 |
| Cb-3546 | 106 | B.17 |
| Cb-3547 | 107 | B.17 |
| Cb-3548 | 108 | B.17 |
| Cb-3549 | 109 | B.17 |
| Cb-3550 | 110 | B.17 |
| Cb-3551 | 111 | B.17 |
| Cb-3552 | 112 | B.17 |
| Cb-3553 | 113 | B.17 |
| Cb-3554 | 114 | B.17 |
| Cb-3555 | 115 | B.17 |
| Cb-3556 | 116 | B.17 |
| Cb-3557 | 117 | B.17 |
| Cb-3558 | 118 | B.17 |
| Cb-3559 | 119 | B.17 |
| Cb-3560 | 120 | B.17 |
| Cb-3561 | 121 | B.17 |
| Cb-3562 | 122 | B.17 |
| Cb-3563 | 123 | B.17 |
| Cb-3564 | 124 | B.17 |
| Cb-3565 | 125 | B.17 |
| Cb-3566 | 126 | B.17 |
| Cb-3567 | 127 | B.17 |
| Cb-3568 | 128 | B.17 |
| Cb-3569 | 129 | B.17 |
| Cb-3570 | 130 | B.17 |
| Cb-3571 | 131 | B.17 |
| Cb-3572 | 132 | B.17 |
| Cb-3573 | 133 | B.17 |
| Cb-3574 | 134 | B.17 |
| Cb-3575 | 135 | B.17 |
| Cb-3576 | 136 | B.17 |
| Cb-3577 | 137 | B.17 |
| Cb-3578 | 138 | B.17 |
| Cb-3579 | 139 | B.17 |
| Cb-3580 | 140 | B.17 |
| Cb-3581 | 141 | B.17 |
| Cb-3582 | 142 | B.17 |
| Cb-3583 | 143 | B.17 |
| Cb-3584 | 144 | B.17 |
| Cb-3585 | 145 | B.17 |
| Cb-3586 | 146 | B.17 |
| Cb-3587 | 147 | B.17 |
| Cb-3588 | 148 | B.17 |
| Cb-3589 | 149 | B.17 |
| Cb-3590 | 150 | B.17 |
| Cb-3591 | 151 | B.17 |
| Cb-3592 | 152 | B.17 |
| Cb-3593 | 153 | B.17 |
| Cb-3594 | 154 | B.17 |
| Cb-3595 | 155 | B.17 |
| Cb-3596 | 156 | B.17 |
| Cb-3597 | 157 | B.17 |
| Cb-3598 | 158 | B.17 |
| Cb-3599 | 159 | B.17 |
| Cb-3600 | 160 | B.17 |
| Cb-3601 | 161 | B.17 |
| Cb-3602 | 162 | B.17 |
| Cb-3603 | 163 | B.17 |
| Cb-3604 | 164 | B.17 |
| Cb-3605 | 165 | B.17 |
| Cb-3606 | 166 | B.17 |
| Cb-3607 | 167 | B.17 |
| Cb-3608 | 168 | B.17 |
| Cb-3609 | 169 | B.17 |
| Cb-3610 | 170 | B.17 |
| Cb-3611 | 171 | B.17 |
| Cb-3612 | 172 | B.17 |
| Cb-3613 | 173 | B.17 |
| Cb-3614 | 174 | B.17 |
| Cb-3615 | 175 | B.17 |
| Cb-3616 | 176 | B.17 |
| Cb-3617 | 177 | B.17 |
| Cb-3618 | 178 | B.17 |
| Cb-3619 | 179 | B.17 |
| Cb-3620 | 180 | B.17 |
| Cb-3621 | 181 | B.17 |
| Cb-3622 | 182 | B.17 |
| Cb-3623 | 183 | B.17 |
| Cb-3624 | 184 | B.17 |
| Cb-3625 | 185 | B.17 |
| Cb-3626 | 186 | B.17 |
| Cb-3627 | 187 | B.17 |
| Cb-3628 | 188 | B.17 |
| Cb-3629 | 189 | B.17 |
| Cb-3630 | 190 | B.17 |
| Cb-3631 | 191 | B.17 |
| Cb-3632 | 192 | B.17 |
| Cb-3633 | 193 | B.17 |
| Cb-3634 | 194 | B.17 |
| Cb-3635 | 195 | B.17 |
| Cb-3636 | 196 | B.17 |
| Cb-3637 | 197 | B.17 |
| Cb-3638 | 198 | B.17 |
| Cb-3639 | 199 | B.17 |
| Cb-3640 | 200 | B.17 |
| Cb-3641 | 201 | B.17 |
| Cb-3642 | 202 | B.17 |
| Cb-3643 | 203 | B.17 |
| Cb-3644 | 204 | B.17 |
| Cb-3645 | 205 | B.17 |
| Cb-3646 | 206 | B.17 |
| Cb-3647 | 207 | B.17 |
| Cb-3648 | 208 | B.17 |
| Cb-3649 | 209 | B.17 |
| Cb-3650 | 210 | B.17 |

| Comb. | Com. A | Com. B |
|---|---|---|
| Cb-3651 | 211 | B.17 |
| Cb-3652 | 212 | B.17 |
| Cb-3653 | 213 | B.17 |
| Cb-3654 | 214 | B.17 |
| Cb-3655 | 215 | B.17 |
| Cb-3656 | 1 | B.18 |
| Cb-3657 | 2 | B.18 |
| Cb-3658 | 3 | B.18 |
| Cb-3659 | 4 | B.18 |
| Cb-3660 | 5 | B.18 |
| Cb-3661 | 6 | B.18 |
| Cb-3662 | 7 | B.18 |
| Cb-3663 | 8 | B.18 |
| Cb-3664 | 9 | B.18 |
| Cb-3665 | 10 | B.18 |
| Cb-3666 | 11 | B.18 |
| Cb-3667 | 12 | B.18 |
| Cb-3668 | 13 | B.18 |
| Cb-3669 | 14 | B.18 |
| Cb-3670 | 15 | B.18 |
| Cb-3671 | 16 | B.18 |
| Cb-3672 | 17 | B.18 |
| Cb-3673 | 18 | B.18 |
| Cb-3674 | 19 | B.18 |
| Cb-3675 | 20 | B.18 |
| Cb-3676 | 21 | B.18 |
| Cb-3677 | 22 | B.18 |
| Cb-3678 | 23 | B.18 |
| Cb-3679 | 24 | B.18 |
| Cb-3680 | 25 | B.18 |
| Cb-3681 | 26 | B.18 |
| Cb-3682 | 27 | B.18 |
| Cb-3683 | 28 | B.18 |
| Cb-3684 | 29 | B.18 |
| Cb-3685 | 30 | B.18 |
| Cb-3686 | 31 | B.18 |
| Cb-3687 | 32 | B.18 |
| Cb-3688 | 33 | B.18 |
| Cb-3689 | 34 | B.18 |
| Cb-3690 | 35 | B.18 |
| Cb-3691 | 36 | B.18 |
| Cb-3692 | 37 | B.18 |
| Cb-3693 | 38 | B.18 |
| Cb-3694 | 39 | B.18 |
| Cb-3695 | 40 | B.18 |
| Cb-3696 | 41 | B.18 |
| Cb-3697 | 42 | B.18 |
| Cb-3698 | 43 | B.18 |
| Cb-3699 | 44 | B.18 |
| Cb-3700 | 45 | B.18 |
| Cb-3701 | 46 | B.18 |
| Cb-3702 | 47 | B.18 |
| Cb-3703 | 48 | B.18 |
| Cb-3704 | 49 | B.18 |
| Cb-3705 | 50 | B.18 |
| Cb-3706 | 51 | B.18 |
| Cb-3707 | 52 | B.18 |
| Cb-3708 | 53 | B.18 |
| Cb-3709 | 54 | B.18 |
| Cb-3710 | 55 | B.18 |
| Cb-3711 | 56 | B.18 |
| Cb-3712 | 57 | B.18 |
| Cb-3713 | 58 | B.18 |
| Cb-3714 | 59 | B.18 |
| Cb-3715 | 60 | B.18 |
| Cb-3716 | 61 | B.18 |
| Cb-3717 | 62 | B.18 |
| Cb-3718 | 63 | B.18 |
| Cb-3719 | 64 | B.18 |
| Cb-3720 | 65 | B.18 |
| Cb-3721 | 66 | B.18 |
| Cb-3722 | 67 | B.18 |
| Cb-3723 | 68 | B.18 |
| Cb-3724 | 69 | B.18 |
| Cb-3725 | 70 | B.18 |
| Cb-3726 | 71 | B.18 |
| Cb-3727 | 72 | B.18 |
| Cb-3728 | 73 | B.18 |
| Cb-3729 | 74 | B.18 |
| Cb-3730 | 75 | B.18 |
| Cb-3731 | 76 | B.18 |
| Cb-3732 | 77 | B.18 |
| Cb-3733 | 78 | B.18 |
| Cb-3734 | 79 | B.18 |
| Cb-3735 | 80 | B.18 |
| Cb-3736 | 81 | B.18 |
| Cb-3737 | 82 | B.18 |
| Cb-3738 | 83 | B.18 |
| Cb-3739 | 84 | B.18 |
| Cb-3740 | 85 | B.18 |
| Cb-3741 | 86 | B.18 |
| Cb-3742 | 87 | B.18 |
| Cb-3743 | 88 | B.18 |
| Cb-3744 | 89 | B.18 |
| Cb-3745 | 90 | B.18 |
| Cb-3746 | 91 | B.18 |
| Cb-3747 | 92 | B.18 |
| Cb-3748 | 93 | B.18 |
| Cb-3749 | 94 | B.18 |
| Cb-3750 | 95 | B.18 |
| Cb-3751 | 96 | B.18 |
| Cb-3752 | 97 | B.18 |
| Cb-3753 | 98 | B.18 |
| Cb-3754 | 99 | B.18 |
| Cb-3755 | 100 | B.18 |
| Cb-3756 | 101 | B.18 |
| Cb-3757 | 102 | B.18 |
| Cb-3758 | 103 | B.18 |
| Cb-3759 | 104 | B.18 |
| Cb-3760 | 105 | B.18 |
| Cb-3761 | 106 | B.18 |
| Cb-3762 | 107 | B.18 |
| Cb-3763 | 108 | B.18 |
| Cb-3764 | 109 | B.18 |
| Cb-3765 | 110 | B.18 |
| Cb-3766 | 111 | B.18 |
| Cb-3767 | 112 | B.18 |
| Cb-3768 | 113 | B.18 |
| Cb-3769 | 114 | B.18 |
| Cb-3770 | 115 | B.18 |
| Cb-3771 | 116 | B.18 |
| Cb-3772 | 117 | B.18 |
| Cb-3773 | 118 | B.18 |
| Cb-3774 | 119 | B.18 |
| Cb-3775 | 120 | B.18 |
| Cb-3776 | 121 | B.18 |
| Cb-3777 | 122 | B.18 |
| Cb-3778 | 123 | B.18 |
| Cb-3779 | 124 | B.18 |
| Cb-3780 | 125 | B.18 |
| Cb-3781 | 126 | B.18 |
| Cb-3782 | 127 | B.18 |
| Cb-3783 | 128 | B.18 |
| Cb-3784 | 129 | B.18 |
| Cb-3785 | 130 | B.18 |
| Cb-3786 | 131 | B.18 |
| Cb-3787 | 132 | B.18 |
| Cb-3788 | 133 | B.18 |
| Cb-3789 | 134 | B.18 |
| Cb-3790 | 135 | B.18 |
| Cb-3791 | 136 | B.18 |
| Cb-3792 | 137 | B.18 |
| Cb-3793 | 138 | B.18 |
| Cb-3794 | 139 | B.18 |
| Cb-3795 | 140 | B.18 |
| Cb-3796 | 141 | B.18 |
| Cb-3797 | 142 | B.18 |
| Cb-3798 | 143 | B.18 |
| Cb-3799 | 144 | B.18 |
| Cb-3800 | 145 | B.18 |
| Cb-3801 | 146 | B.18 |
| Cb-3802 | 147 | B.18 |
| Cb-3803 | 148 | B.18 |
| Cb-3804 | 149 | B.18 |

| Comb. | Com. A | Com. B |
|---|---|---|
| Cb-3805 | 150 | B.18 |
| Cb-3806 | 151 | B.18 |
| Cb-3807 | 152 | B.18 |
| Cb-3808 | 153 | B.18 |
| Cb-3809 | 154 | B.18 |
| Cb-3810 | 155 | B.18 |
| Cb-3811 | 156 | B.18 |
| Cb-3812 | 157 | B.18 |
| Cb-3813 | 158 | B.18 |
| Cb-3814 | 159 | B.18 |
| Cb-3815 | 160 | B.18 |
| Cb-3816 | 161 | B.18 |
| Cb-3817 | 162 | B.18 |
| Cb-3818 | 163 | B.18 |
| Cb-3819 | 164 | B.18 |
| Cb-3820 | 165 | B.18 |
| Cb-3821 | 166 | B.18 |
| Cb-3822 | 167 | B.18 |
| Cb-3823 | 168 | B.18 |
| Cb-3824 | 169 | B.18 |
| Cb-3825 | 170 | B.18 |
| Cb-3826 | 171 | B.18 |
| Cb-3827 | 172 | B.18 |
| Cb-3828 | 173 | B.18 |
| Cb-3829 | 174 | B.18 |
| Cb-3830 | 175 | B.18 |
| Cb-3831 | 176 | B.18 |
| Cb-3832 | 177 | B.18 |
| Cb-3833 | 178 | B.18 |
| Cb-3834 | 179 | B.18 |
| Cb-3835 | 180 | B.18 |
| Cb-3836 | 181 | B.18 |
| Cb-3837 | 182 | B.18 |
| Cb-3838 | 183 | B.18 |
| Cb-3839 | 184 | B.18 |
| Cb-3840 | 185 | B.18 |
| Cb-3841 | 186 | B.18 |
| Cb-3842 | 187 | B.18 |
| Cb-3843 | 188 | B.18 |
| Cb-3844 | 189 | B.18 |
| Cb-3845 | 190 | B.18 |
| Cb-3846 | 191 | B.18 |
| Cb-3847 | 192 | B.18 |
| Cb-3848 | 193 | B.18 |
| Cb-3849 | 194 | B.18 |
| Cb-3850 | 195 | B.18 |
| Cb-3851 | 196 | B.18 |
| Cb-3852 | 197 | B.18 |
| Cb-3853 | 198 | B.18 |
| Cb-3854 | 199 | B.18 |
| Cb-3855 | 200 | B.18 |
| Cb-3856 | 201 | B.18 |
| Cb-3857 | 202 | B.18 |
| Cb-3858 | 203 | B.18 |
| Cb-3859 | 204 | B.18 |
| Cb-3860 | 205 | B.18 |
| Cb-3861 | 206 | B.18 |
| Cb-3862 | 207 | B.18 |
| Cb-3863 | 208 | B.18 |
| Cb-3864 | 209 | B.18 |
| Cb-3865 | 210 | B.18 |
| Cb-3866 | 211 | B.18 |
| Cb-3867 | 212 | B.18 |
| Cb-3868 | 213 | B.18 |
| Cb-3869 | 214 | B.18 |
| Cb-3870 | 215 | B.18 |
| Cb-3871 | 1 | B.16 |
| Cb-3872 | 2 | B.16 |
| Cb-3873 | 3 | B.16 |
| Cb-3874 | 4 | B.16 |
| Cb-3875 | 5 | B.16 |
| Cb-3876 | 6 | B.16 |
| Cb-3877 | 7 | B.16 |
| Cb-3878 | 8 | B.16 |
| Cb-3879 | 9 | B.16 |
| Cb-3880 | 10 | B.16 |
| Cb-3881 | 11 | B.16 |
| Cb-3882 | 12 | B.16 |
| Cb-3883 | 13 | B.16 |
| Cb-3884 | 14 | B.16 |
| Cb-3885 | 15 | B.16 |
| Cb-3886 | 16 | B.16 |
| Cb-3887 | 17 | B.16 |
| Cb-3888 | 18 | B.16 |
| Cb-3889 | 19 | B.16 |
| Cb-3890 | 20 | B.16 |
| Cb-3891 | 21 | B.16 |
| Cb-3892 | 22 | B.16 |
| Cb-3893 | 23 | B.16 |
| Cb-3894 | 24 | B.16 |
| Cb-3895 | 25 | B.16 |
| Cb-3896 | 26 | B.16 |
| Cb-3897 | 27 | B.16 |
| Cb-3898 | 28 | B.16 |
| Cb-3899 | 29 | B.16 |
| Cb-3900 | 30 | B.16 |
| Cb-3901 | 31 | B.16 |
| Cb-3902 | 32 | B.16 |
| Cb-3903 | 33 | B.16 |
| Cb-3904 | 34 | B.16 |
| Cb-3905 | 35 | B.16 |
| Cb-3906 | 36 | B.16 |
| Cb-3907 | 37 | B.16 |
| Cb-3908 | 38 | B.16 |
| Cb-3909 | 39 | B.16 |
| Cb-3910 | 40 | B.16 |
| Cb-3911 | 41 | B.16 |
| Cb-3912 | 42 | B.16 |
| Cb-3913 | 43 | B.16 |
| Cb-3914 | 44 | B.16 |
| Cb-3915 | 45 | B.16 |
| Cb-3916 | 46 | B.16 |
| Cb-3917 | 47 | B.16 |
| Cb-3918 | 48 | B.16 |
| Cb-3919 | 49 | B.16 |
| Cb-3920 | 50 | B.16 |
| Cb-3921 | 51 | B.16 |
| Cb-3922 | 52 | B.16 |
| Cb-3923 | 53 | B.16 |
| Cb-3924 | 54 | B.16 |
| Cb-3925 | 55 | B.16 |
| Cb-3926 | 56 | B.16 |
| Cb-3927 | 57 | B.16 |
| Cb-3928 | 58 | B.16 |
| Cb-3929 | 59 | B.16 |
| Cb-3930 | 60 | B.16 |
| Cb-3931 | 61 | B.16 |
| Cb-3932 | 62 | B.16 |
| Cb-3933 | 63 | B.16 |
| Cb-3934 | 64 | B.16 |
| Cb-3935 | 65 | B.16 |
| Cb-3936 | 66 | B.16 |
| Cb-3937 | 67 | B.16 |
| Cb-3938 | 68 | B.16 |
| Cb-3939 | 69 | B.16 |
| Cb-3940 | 70 | B.16 |
| Cb-3941 | 71 | B.16 |
| Cb-3942 | 72 | B.16 |
| Cb-3943 | 73 | B.16 |
| Cb-3944 | 74 | B.16 |
| Cb-3945 | 75 | B.16 |
| Cb-3946 | 76 | B.16 |
| Cb-3947 | 77 | B.16 |
| Cb-3948 | 78 | B.16 |
| Cb-3949 | 79 | B.16 |
| Cb-3950 | 80 | B.16 |
| Cb-3951 | 81 | B.16 |
| Cb-3952 | 82 | B.16 |
| Cb-3953 | 83 | B.16 |
| Cb-3954 | 84 | B.16 |
| Cb-3955 | 85 | B.16 |
| Cb-3956 | 86 | B.16 |
| Cb-3957 | 87 | B.16 |
| Cb-3958 | 88 | B.16 |

-continued

| Comb. | Com. A | Com. B |
|---|---|---|
| Cb-3959 | 89 | B.16 |
| Cb-3960 | 90 | B.16 |
| Cb-3961 | 91 | B.16 |
| Cb-3962 | 92 | B.16 |
| Cb-3963 | 93 | B.16 |
| Cb-3964 | 94 | B.16 |
| Cb-3965 | 95 | B.16 |
| Cb-3966 | 96 | B.16 |
| Cb-3967 | 97 | B.16 |
| Cb-3968 | 98 | B.16 |
| Cb-3969 | 99 | B.16 |
| Cb-3970 | 100 | B.16 |
| Cb-3971 | 101 | B.16 |
| Cb-3972 | 102 | B.16 |
| Cb-3973 | 103 | B.16 |
| Cb-3974 | 104 | B.16 |
| Cb-3975 | 105 | B.16 |
| Cb-3976 | 106 | B.16 |
| Cb-3977 | 107 | B.16 |
| Cb-3978 | 108 | B.16 |
| Cb-3979 | 109 | B.16 |
| Cb-3980 | 110 | B.16 |
| Cb-3981 | 111 | B.16 |
| Cb-3982 | 112 | B.16 |
| Cb-3983 | 113 | B.16 |
| Cb-3984 | 114 | B.16 |
| Cb-3985 | 115 | B.16 |
| Cb-3986 | 116 | B.16 |
| Cb-3987 | 117 | B.16 |
| Cb-3988 | 118 | B.16 |
| Cb-3989 | 119 | B.16 |
| Cb-3990 | 120 | B.16 |
| Cb-3991 | 121 | B.16 |
| Cb-3992 | 122 | B.16 |
| Cb-3993 | 123 | B.16 |
| Cb-3994 | 124 | B.16 |
| Cb-3995 | 125 | B.16 |
| Cb-3996 | 126 | B.16 |
| Cb-3997 | 127 | B.16 |
| Cb-3998 | 128 | B.16 |
| Cb-3999 | 129 | B.16 |
| Cb-4000 | 130 | B.16 |
| Cb-4001 | 131 | B.16 |
| Cb-4002 | 132 | B.16 |
| Cb-4003 | 133 | B.16 |
| Cb-4004 | 134 | B.16 |
| Cb-4005 | 135 | B.16 |
| Cb-4006 | 136 | B.16 |
| Cb-4007 | 137 | B.16 |
| Cb-4008 | 138 | B.16 |
| Cb-4009 | 139 | B.16 |
| Cb-4010 | 140 | B.16 |
| Cb-4011 | 141 | B.16 |
| Cb-4012 | 142 | B.16 |
| Cb-4013 | 143 | B.16 |
| Cb-4014 | 144 | B.16 |
| Cb-4015 | 145 | B.16 |
| Cb-4016 | 146 | B.16 |
| Cb-4017 | 147 | B.16 |
| Cb-4018 | 148 | B.16 |
| Cb-4019 | 149 | B.16 |
| Cb-4020 | 150 | B.16 |
| Cb-4021 | 151 | B.16 |
| Cb-4022 | 152 | B.16 |
| Cb-4023 | 153 | B.16 |
| Cb-4024 | 154 | B.16 |
| Cb-4025 | 155 | B.16 |
| Cb-4026 | 156 | B.16 |
| Cb-4027 | 157 | B.16 |
| Cb-4028 | 158 | B.16 |
| Cb-4029 | 159 | B.16 |
| Cb-4030 | 160 | B.16 |
| Cb-4031 | 161 | B.16 |
| Cb-4032 | 162 | B.16 |
| Cb-4033 | 163 | B.16 |
| Cb-4034 | 164 | B.16 |
| Cb-4035 | 165 | B.16 |
| Cb-4036 | 166 | B.16 |
| Cb-4037 | 167 | B.16 |
| Cb-4038 | 168 | B.16 |
| Cb-4039 | 169 | B.16 |
| Cb-4040 | 170 | B.16 |
| Cb-4041 | 171 | B.16 |
| Cb-4042 | 172 | B.16 |
| Cb-4043 | 173 | B.16 |
| Cb-4044 | 174 | B.16 |
| Cb-4045 | 175 | B.16 |
| Cb-4046 | 176 | B.16 |
| Cb-4047 | 177 | B.16 |
| Cb-4048 | 178 | B.16 |
| Cb-4049 | 179 | B.16 |
| Cb-4050 | 180 | B.16 |
| Cb-4051 | 181 | B.16 |
| Cb-4052 | 182 | B.16 |
| Cb-4053 | 183 | B.16 |
| Cb-4054 | 184 | B.16 |
| Cb-4055 | 185 | B.16 |
| Cb-4056 | 186 | B.16 |
| Cb-4057 | 187 | B.16 |
| Cb-4058 | 188 | B.16 |
| Cb-4059 | 189 | B.16 |
| Cb-4060 | 190 | B.16 |
| Cb-4061 | 191 | B.16 |
| Cb-4062 | 192 | B.16 |
| Cb-4063 | 193 | B.16 |
| Cb-4064 | 194 | B.16 |
| Cb-4065 | 195 | B.16 |
| Cb-4066 | 196 | B.16 |
| Cb-4067 | 197 | B.16 |
| Cb-4068 | 198 | B.16 |
| Cb-4069 | 199 | B.16 |
| Cb-4070 | 200 | B.16 |
| Cb-4071 | 201 | B.16 |
| Cb-4072 | 202 | B.16 |
| Cb-4073 | 203 | B.16 |
| Cb-4074 | 204 | B.16 |
| Cb-4075 | 205 | B.16 |
| Cb-4076 | 206 | B.16 |
| Cb-4077 | 207 | B.16 |
| Cb-4078 | 208 | B.16 |
| Cb-4079 | 209 | B.16 |
| Cb-4080 | 210 | B.16 |
| Cb-4081 | 211 | B.16 |
| Cb-4082 | 212 | B.16 |
| Cb-4083 | 213 | B.16 |
| Cb-4084 | 214 | B.16 |
| Cb-4085 | 215 | B.16 |
| Cb-4086 | 1 | B.17 |
| Cb-4087 | 2 | B.17 |
| Cb-4088 | 3 | B.17 |
| Cb-4089 | 4 | B.17 |
| Cb-4090 | 5 | B.17 |
| Cb-4091 | 6 | B.17 |
| Cb-4092 | 7 | B.17 |
| Cb-4093 | 8 | B.17 |
| Cb-4094 | 9 | B.17 |
| Cb-4095 | 10 | B.17 |
| Cb-4096 | 11 | B.17 |
| Cb-4097 | 12 | B.17 |
| Cb-4098 | 13 | B.17 |
| Cb-4099 | 14 | B.17 |
| Cb-4100 | 15 | B.17 |
| Cb-4101 | 16 | B.17 |
| Cb-4102 | 17 | B.17 |
| Cb-4103 | 18 | B.17 |
| Cb-4104 | 19 | B.17 |
| Cb-4105 | 20 | B.17 |
| Cb-4106 | 21 | B.17 |
| Cb-4107 | 22 | B.17 |
| Cb-4108 | 23 | B.17 |
| Cb-4109 | 24 | B.17 |
| Cb-4110 | 25 | B.17 |
| Cb-4111 | 26 | B.17 |
| Cb-4112 | 27 | B.17 |

| Comb. | Com. A | Com. B |
|---|---|---|
| Cb-4113 | 28 | B.17 |
| Cb-4114 | 29 | B.17 |
| Cb-4115 | 30 | B.17 |
| Cb-4116 | 31 | B.17 |
| Cb-4117 | 32 | B.17 |
| Cb-4118 | 33 | B.17 |
| Cb-4119 | 34 | B.17 |
| Cb-4120 | 35 | B.17 |
| Cb-4121 | 36 | B.17 |
| Cb-4122 | 37 | B.17 |
| Cb-4123 | 38 | B.17 |
| Cb-4124 | 39 | B.17 |
| Cb-4125 | 40 | B.17 |
| Cb-4126 | 41 | B.17 |
| Cb-4127 | 42 | B.17 |
| Cb-4128 | 43 | B.17 |
| Cb-4129 | 44 | B.17 |
| Cb-4130 | 45 | B.17 |
| Cb-4131 | 46 | B.17 |
| Cb-4132 | 47 | B.17 |
| Cb-4133 | 48 | B.17 |
| Cb-4134 | 49 | B.17 |
| Cb-4135 | 50 | B.17 |
| Cb-4136 | 51 | B.17 |
| Cb-4137 | 52 | B.17 |
| Cb-4138 | 53 | B.17 |
| Cb-4139 | 54 | B.17 |
| Cb-4140 | 55 | B.17 |
| Cb-4141 | 56 | B.17 |
| Cb-4142 | 57 | B.17 |
| Cb-4143 | 58 | B.17 |
| Cb-4144 | 59 | B.17 |
| Cb-4145 | 60 | B.17 |
| Cb-4146 | 61 | B.17 |
| Cb-4147 | 62 | B.17 |
| Cb-4148 | 63 | B.17 |
| Cb-4149 | 64 | B.17 |
| Cb-4150 | 65 | B.17 |
| Cb-4151 | 66 | B.17 |
| Cb-4152 | 67 | B.17 |
| Cb-4153 | 68 | B.17 |
| Cb-4154 | 69 | B.17 |
| Cb-4155 | 70 | B.17 |
| Cb-4156 | 71 | B.17 |
| Cb-4157 | 72 | B.17 |
| Cb-4158 | 73 | B.17 |
| Cb-4159 | 74 | B.17 |
| Cb-4160 | 75 | B.17 |
| Cb-4161 | 76 | B.17 |
| Cb-4162 | 77 | B.17 |
| Cb-4163 | 78 | B.17 |
| Cb-4164 | 79 | B.17 |
| Cb-4165 | 80 | B.17 |
| Cb-4166 | 81 | B.17 |
| Cb-4167 | 82 | B.17 |
| Cb-4168 | 83 | B.17 |
| Cb-4169 | 84 | B.17 |
| Cb-4170 | 85 | B.17 |
| Cb-4171 | 86 | B.17 |
| Cb-4172 | 87 | B.17 |
| Cb-4173 | 88 | B.17 |
| Cb-4174 | 89 | B.17 |
| Cb-4175 | 90 | B.17 |
| Cb-4176 | 91 | B.17 |
| Cb-4177 | 92 | B.17 |
| Cb-4178 | 93 | B.17 |
| Cb-4179 | 94 | B.17 |
| Cb-4180 | 95 | B.17 |
| Cb-4181 | 96 | B.17 |
| Cb-4182 | 97 | B.17 |
| Cb-4183 | 98 | B.17 |
| Cb-4184 | 99 | B.17 |
| Cb-4185 | 100 | B.17 |
| Cb-4186 | 101 | B.17 |
| Cb-4187 | 102 | B.17 |
| Cb-4188 | 103 | B.17 |
| Cb-4189 | 104 | B.17 |
| Cb-4190 | 105 | B.17 |
| Cb-4191 | 106 | B.17 |
| Cb-4192 | 107 | B.17 |
| Cb-4193 | 108 | B.17 |
| Cb-4194 | 109 | B.17 |
| Cb-4195 | 110 | B.17 |
| Cb-4196 | 111 | B.17 |
| Cb-4197 | 112 | B.17 |
| Cb-4198 | 113 | B.17 |
| Cb-4199 | 114 | B.17 |
| Cb-4200 | 115 | B.17 |
| Cb-4201 | 116 | B.17 |
| Cb-4202 | 117 | B.17 |
| Cb-4203 | 118 | B.17 |
| Cb-4204 | 119 | B.17 |
| Cb-4205 | 120 | B.17 |
| Cb-4206 | 121 | B.17 |
| Cb-4207 | 122 | B.17 |
| Cb-4208 | 123 | B.17 |
| Cb-4209 | 124 | B.17 |
| Cb-4210 | 125 | B.17 |
| Cb-4211 | 126 | B.17 |
| Cb-4212 | 127 | B.17 |
| Cb-4213 | 128 | B.17 |
| Cb-4214 | 129 | B.17 |
| Cb-4215 | 130 | B.17 |
| Cb-4216 | 131 | B.17 |
| Cb-4217 | 132 | B.17 |
| Cb-4218 | 133 | B.17 |
| Cb-4219 | 134 | B.17 |
| Cb-4220 | 135 | B.17 |
| Cb-4221 | 136 | B.17 |
| Cb-4222 | 137 | B.17 |
| Cb-4223 | 138 | B.17 |
| Cb-4224 | 139 | B.17 |
| Cb-4225 | 140 | B.17 |
| Cb-4226 | 141 | B.17 |
| Cb-4227 | 142 | B.17 |
| Cb-4228 | 143 | B.17 |
| Cb-4229 | 144 | B.17 |
| Cb-4230 | 145 | B.17 |
| Cb-4231 | 146 | B.17 |
| Cb-4232 | 147 | B.17 |
| Cb-4233 | 148 | B.17 |
| Cb-4234 | 149 | B.17 |
| Cb-4235 | 150 | B.17 |
| Cb-4236 | 151 | B.17 |
| Cb-4237 | 152 | B.17 |
| Cb-4238 | 153 | B.17 |
| Cb-4239 | 154 | B.17 |
| Cb-4240 | 155 | B.17 |
| Cb-4241 | 156 | B.17 |
| Cb-4242 | 157 | B.17 |
| Cb-4243 | 158 | B.17 |
| Cb-4244 | 159 | B.17 |
| Cb-4245 | 160 | B.17 |
| Cb-4246 | 161 | B.17 |
| Cb-4247 | 162 | B.17 |
| Cb-4248 | 163 | B.17 |
| Cb-4249 | 164 | B.17 |
| Cb-4250 | 165 | B.17 |
| Cb-4251 | 166 | B.17 |
| Cb-4252 | 167 | B.17 |
| Cb-4253 | 168 | B.17 |
| Cb-4254 | 169 | B.17 |
| Cb-4255 | 170 | B.17 |
| Cb-4256 | 171 | B.17 |
| Cb-4257 | 172 | B.17 |
| Cb-4258 | 173 | B.17 |
| Cb-4259 | 174 | B.17 |
| Cb-4260 | 175 | B.17 |
| Cb-4261 | 176 | B.17 |
| Cb-4262 | 177 | B.17 |
| Cb-4263 | 178 | B.17 |
| Cb-4264 | 179 | B.17 |
| Cb-4265 | 180 | B.17 |
| Cb-4266 | 181 | B.17 |

| Comb. | Com. A | Com. B | Comb. | Com. A | Com. B |
|---|---|---|---|---|---|
| Cb-4267 | 182 | B.17 | Cb-4344 | 44 | B.18 |
| Cb-4268 | 183 | B.17 | Cb-4345 | 45 | B.18 |
| Cb-4269 | 184 | B.17 | Cb-4346 | 46 | B.18 |
| Cb-4270 | 185 | B.17 | Cb-4347 | 47 | B.18 |
| Cb-4271 | 186 | B.17 | Cb-4348 | 48 | B.18 |
| Cb-4272 | 187 | B.17 | Cb-4349 | 49 | B.18 |
| Cb-4273 | 188 | B.17 | Cb-4350 | 50 | B.18 |
| Cb-4274 | 189 | B.17 | Cb-4351 | 51 | B.18 |
| Cb-4275 | 190 | B.17 | Cb-4352 | 52 | B.18 |
| Cb-4276 | 191 | B.17 | Cb-4353 | 53 | B.18 |
| Cb-4277 | 192 | B.17 | Cb-4354 | 54 | B.18 |
| Cb-4278 | 193 | B.17 | Cb-4355 | 55 | B.18 |
| Cb-4279 | 194 | B.17 | Cb-4356 | 56 | B.18 |
| Cb-4280 | 195 | B.17 | Cb-4357 | 57 | B.18 |
| Cb-4281 | 196 | B.17 | Cb-4358 | 58 | B.18 |
| Cb-4282 | 197 | B.17 | Cb-4359 | 59 | B.18 |
| Cb-4283 | 198 | B.17 | Cb-4360 | 60 | B.18 |
| Cb-4284 | 199 | B.17 | Cb-4361 | 61 | B.18 |
| Cb-4285 | 200 | B.17 | Cb-4362 | 62 | B.18 |
| Cb-4286 | 201 | B.17 | Cb-4363 | 63 | B.18 |
| Cb-4287 | 202 | B.17 | Cb-4364 | 64 | B.18 |
| Cb-4288 | 203 | B.17 | Cb-4365 | 65 | B.18 |
| Cb-4289 | 204 | B.17 | Cb-4366 | 66 | B.18 |
| Cb-4290 | 205 | B.17 | Cb-4367 | 67 | B.18 |
| Cb-4291 | 206 | B.17 | Cb-4368 | 68 | B.18 |
| Cb-4292 | 207 | B.17 | Cb-4369 | 69 | B.18 |
| Cb-4293 | 208 | B.17 | Cb-4370 | 70 | B.18 |
| Cb-4294 | 209 | B.17 | Cb-4371 | 71 | B.18 |
| Cb-4295 | 210 | B.17 | Cb-4372 | 72 | B.18 |
| Cb-4296 | 211 | B.17 | Cb-4373 | 73 | B.18 |
| Cb-4297 | 212 | B.17 | Cb-4374 | 74 | B.18 |
| Cb-4298 | 213 | B.17 | Cb-4375 | 75 | B.18 |
| Cb-4299 | 214 | B.17 | Cb-4376 | 76 | B.18 |
| Cb-4300 | 215 | B.17 | Cb-4377 | 77 | B.18 |
| Cb-4301 | 1 | B.18 | Cb-4378 | 78 | B.18 |
| Cb-4302 | 2 | B.18 | Cb-4379 | 79 | B.18 |
| Cb-4303 | 3 | B.18 | Cb-4380 | 80 | B.18 |
| Cb-4304 | 4 | B.18 | Cb-4381 | 81 | B.18 |
| Cb-4305 | 5 | B.18 | Cb-4382 | 82 | B.18 |
| Cb-4306 | 6 | B.18 | Cb-4383 | 83 | B.18 |
| Cb-4307 | 7 | B.18 | Cb-4384 | 84 | B.18 |
| Cb-4308 | 8 | B.18 | Cb-4385 | 85 | B.18 |
| Cb-4309 | 9 | B.18 | Cb-4386 | 86 | B.18 |
| Cb-4310 | 10 | B.18 | Cb-4387 | 87 | B.18 |
| Cb-4311 | 11 | B.18 | Cb-4388 | 88 | B.18 |
| Cb-4312 | 12 | B.18 | Cb-4389 | 89 | B.18 |
| Cb-4313 | 13 | B.18 | Cb-4390 | 90 | B.18 |
| Cb-4314 | 14 | B.18 | Cb-4391 | 91 | B.18 |
| Cb-4315 | 15 | B.18 | Cb-4392 | 92 | B.18 |
| Cb-4316 | 16 | B.18 | Cb-4393 | 93 | B.18 |
| Cb-4317 | 17 | B.18 | Cb-4394 | 94 | B.18 |
| Cb-4318 | 18 | B.18 | Cb-4395 | 95 | B.18 |
| Cb-4319 | 19 | B.18 | Cb-4396 | 96 | B.18 |
| Cb-4320 | 20 | B.18 | Cb-4397 | 97 | B.18 |
| Cb-4321 | 21 | B.18 | Cb-4398 | 98 | B.18 |
| Cb-4322 | 22 | B.18 | Cb-4399 | 99 | B.18 |
| Cb-4323 | 23 | B.18 | Cb-4400 | 100 | B.18 |
| Cb-4324 | 24 | B.18 | Cb-4401 | 101 | B.18 |
| Cb-4325 | 25 | B.18 | Cb-4402 | 102 | B.18 |
| Cb-4326 | 26 | B.18 | Cb-4403 | 103 | B.18 |
| Cb-4327 | 27 | B.18 | Cb-4404 | 104 | B.18 |
| Cb-4328 | 28 | B.18 | Cb-4405 | 105 | B.18 |
| Cb-4329 | 29 | B.18 | Cb-4406 | 106 | B.18 |
| Cb-4330 | 30 | B.18 | Cb-4407 | 107 | B.18 |
| Cb-4331 | 31 | B.18 | Cb-4408 | 108 | B.18 |
| Cb-4332 | 32 | B.18 | Cb-4409 | 109 | B.18 |
| Cb-4333 | 33 | B.18 | Cb-4410 | 110 | B.18 |
| Cb-4334 | 34 | B.18 | Cb-4411 | 111 | B.18 |
| Cb-4335 | 35 | B.18 | Cb-4412 | 112 | B.18 |
| Cb-4336 | 36 | B.18 | Cb-4413 | 113 | B.18 |
| Cb-4337 | 37 | B.18 | Cb-4414 | 114 | B.18 |
| Cb-4338 | 38 | B.18 | Cb-4415 | 115 | B.18 |
| Cb-4339 | 39 | B.18 | Cb-4416 | 116 | B.18 |
| Cb-4340 | 40 | B.18 | Cb-4417 | 117 | B.18 |
| Cb-4341 | 41 | B.18 | Cb-4418 | 118 | B.18 |
| Cb-4342 | 42 | B.18 | Cb-4419 | 119 | B.18 |
| Cb-4343 | 43 | B.18 | Cb-4420 | 120 | B.18 |

| Comb. | Com. A | Com. B |
|---|---|---|
| Cb-4421 | 121 | B.18 |
| Cb-4422 | 122 | B.18 |
| Cb-4423 | 123 | B.18 |
| Cb-4424 | 124 | B.18 |
| Cb-4425 | 125 | B.18 |
| Cb-4426 | 126 | B.18 |
| Cb-4427 | 127 | B.18 |
| Cb-4428 | 128 | B.18 |
| Cb-4429 | 129 | B.18 |
| Cb-4430 | 130 | B.18 |
| Cb-4431 | 131 | B.18 |
| Cb-4432 | 132 | B.18 |
| Cb-4433 | 133 | B.18 |
| Cb-4434 | 134 | B.18 |
| Cb-4435 | 135 | B.18 |
| Cb-4436 | 136 | B.18 |
| Cb-4437 | 137 | B.18 |
| Cb-4438 | 138 | B.18 |
| Cb-4439 | 139 | B.18 |
| Cb-4440 | 140 | B.18 |
| Cb-4441 | 141 | B.18 |
| Cb-4442 | 142 | B.18 |
| Cb-4443 | 143 | B.18 |
| Cb-4444 | 144 | B.18 |
| Cb-4445 | 145 | B.18 |
| Cb-4446 | 146 | B.18 |
| Cb-4447 | 147 | B.18 |
| Cb-4448 | 148 | B.18 |
| Cb-4449 | 149 | B.18 |
| Cb-4450 | 150 | B.18 |
| Cb-4451 | 151 | B.18 |
| Cb-4452 | 152 | B.18 |
| Cb-4453 | 153 | B.18 |
| Cb-4454 | 154 | B.18 |
| Cb-4455 | 155 | B.18 |
| Cb-4456 | 156 | B.18 |
| Cb-4457 | 157 | B.18 |
| Cb-4458 | 158 | B.18 |
| Cb-4459 | 159 | B.18 |
| Cb-4460 | 160 | B.18 |
| Cb-4461 | 161 | B.18 |
| Cb-4462 | 162 | B.18 |
| Cb-4463 | 163 | B.18 |
| Cb-4464 | 164 | B.18 |
| Cb-4465 | 165 | B.18 |
| Cb-4466 | 166 | B.18 |
| Cb-4467 | 167 | B.18 |
| Cb-4468 | 168 | B.18 |
| Cb-4469 | 169 | B.18 |
| Cb-4470 | 170 | B.18 |
| Cb-4471 | 171 | B.18 |
| Cb-4472 | 172 | B.18 |
| Cb-4473 | 173 | B.18 |
| Cb-4474 | 174 | B.18 |
| Cb-4475 | 175 | B.18 |
| Cb-4476 | 176 | B.18 |
| Cb-4477 | 177 | B.18 |
| Cb-4478 | 178 | B.18 |
| Cb-4479 | 179 | B.18 |
| Cb-4480 | 180 | B.18 |
| Cb-4481 | 181 | B.18 |
| Cb-4482 | 182 | B.18 |
| Cb-4483 | 183 | B.18 |
| Cb-4484 | 184 | B.18 |
| Cb-4485 | 185 | B.18 |
| Cb-4486 | 186 | B.18 |
| Cb-4487 | 187 | B.18 |
| Cb-4488 | 188 | B.18 |
| Cb-4489 | 189 | B.18 |
| Cb-4490 | 190 | B.18 |
| Cb-4491 | 191 | B.18 |
| Cb-4492 | 192 | B.18 |
| Cb-4493 | 193 | B.18 |
| Cb-4494 | 194 | B.18 |
| Cb-4495 | 195 | B.18 |
| Cb-4496 | 196 | B.18 |
| Cb-4497 | 197 | B.18 |
| Cb-4498 | 198 | B.18 |
| Cb-4499 | 199 | B.18 |
| Cb-4500 | 200 | B.18 |
| Cb-4501 | 201 | B.18 |
| Cb-4502 | 202 | B.18 |
| Cb-4503 | 203 | B.18 |
| Cb-4504 | 204 | B.18 |
| Cb-4505 | 205 | B.18 |
| Cb-4506 | 206 | B.18 |
| Cb-4507 | 207 | B.18 |
| Cb-4508 | 208 | B.18 |
| Cb-4509 | 209 | B.18 |
| Cb-4510 | 210 | B.18 |
| Cb-4511 | 211 | B.18 |
| Cb-4512 | 212 | B.18 |
| Cb-4513 | 213 | B.18 |
| Cb-4514 | 214 | B.18 |
| Cb-4515 | 215 | B.18 |
| Cb-4516 | 1 | B.19 |
| Cb-4517 | 2 | B.19 |
| Cb-4518 | 3 | B.19 |
| Cb-4519 | 4 | B.19 |
| Cb-4520 | 5 | B.19 |
| Cb-4521 | 6 | B.19 |
| Cb-4522 | 7 | B.19 |
| Cb-4523 | 8 | B.19 |
| Cb-4524 | 9 | B.19 |
| Cb-4525 | 10 | B.19 |
| Cb-4526 | 11 | B.19 |
| Cb-4527 | 12 | B.19 |
| Cb-4528 | 13 | B.19 |
| Cb-4529 | 14 | B.19 |
| Cb-4530 | 15 | B.19 |
| Cb-4531 | 16 | B.19 |
| Cb-4532 | 17 | B.19 |
| Cb-4533 | 18 | B.19 |
| Cb-4534 | 19 | B.19 |
| Cb-4535 | 20 | B.19 |
| Cb-4536 | 21 | B.19 |
| Cb-4537 | 22 | B.19 |
| Cb-4538 | 23 | B.19 |
| Cb-4539 | 24 | B.19 |
| Cb-4540 | 25 | B.19 |
| Cb-4541 | 26 | B.19 |
| Cb-4542 | 27 | B.19 |
| Cb-4543 | 28 | B.19 |
| Cb-4544 | 29 | B.19 |
| Cb-4545 | 30 | B.19 |
| Cb-4546 | 31 | B.19 |
| Cb-4547 | 32 | B.19 |
| Cb-4548 | 33 | B.19 |
| Cb-4549 | 34 | B.19 |
| Cb-4550 | 35 | B.19 |
| Cb-4551 | 36 | B.19 |
| Cb-4552 | 37 | B.19 |
| Cb-4553 | 38 | B.19 |
| Cb-4554 | 39 | B.19 |
| Cb-4555 | 40 | B.19 |
| Cb-4556 | 41 | B.19 |
| Cb-4557 | 42 | B.19 |
| Cb-4558 | 43 | B.19 |
| Cb-4559 | 44 | B.19 |
| Cb-4560 | 45 | B.19 |
| Cb-4561 | 46 | B.19 |
| Cb-4562 | 47 | B.19 |
| Cb-4563 | 48 | B.19 |
| Cb-4564 | 49 | B.19 |
| Cb-4565 | 50 | B.19 |
| Cb-4566 | 51 | B.19 |
| Cb-4567 | 52 | B.19 |
| Cb-4568 | 53 | B.19 |
| Cb-4569 | 54 | B.19 |
| Cb-4570 | 55 | B.19 |
| Cb-4571 | 56 | B.19 |
| Cb-4572 | 57 | B.19 |
| Cb-4573 | 58 | B.19 |
| Cb-4574 | 59 | B.19 |

| Comb. | Com. A | Com. B | Comb. | Com. A | Com. B |
|---|---|---|---|---|---|
| Cb-4575 | 60 | B.19 | Cb-4652 | 137 | B.19 |
| Cb-4576 | 61 | B.19 | Cb-4653 | 138 | B.19 |
| Cb-4577 | 62 | B.19 | Cb-4654 | 139 | B.19 |
| Cb-4578 | 63 | B.19 | Cb-4655 | 140 | B.19 |
| Cb-4579 | 64 | B.19 | Cb-4656 | 141 | B.19 |
| Cb-4580 | 65 | B.19 | Cb-4657 | 142 | B.19 |
| Cb-4581 | 66 | B.19 | Cb-4658 | 143 | B.19 |
| Cb-4582 | 67 | B.19 | Cb-4659 | 144 | B.19 |
| Cb-4583 | 68 | B.19 | Cb-4660 | 145 | B.19 |
| Cb-4584 | 69 | B.19 | Cb-4661 | 146 | B.19 |
| Cb-4585 | 70 | B.19 | Cb-4662 | 147 | B.19 |
| Cb-4586 | 71 | B.19 | Cb-4663 | 148 | B.19 |
| Cb-4587 | 72 | B.19 | Cb-4664 | 149 | B.19 |
| Cb-4588 | 73 | B.19 | Cb-4665 | 150 | B.19 |
| Cb-4589 | 74 | B.19 | Cb-4666 | 151 | B.19 |
| Cb-4590 | 75 | B.19 | Cb-4667 | 152 | B.19 |
| Cb-4591 | 76 | B.19 | Cb-4668 | 153 | B.19 |
| Cb-4592 | 77 | B.19 | Cb-4669 | 154 | B.19 |
| Cb-4593 | 78 | B.19 | Cb-4670 | 155 | B.19 |
| Cb-4594 | 79 | B.19 | Cb-4671 | 156 | B.19 |
| Cb-4595 | 80 | B.19 | Cb-4672 | 157 | B.19 |
| Cb-4596 | 81 | B.19 | Cb-4673 | 158 | B.19 |
| Cb-4597 | 82 | B.19 | Cb-4674 | 159 | B.19 |
| Cb-4598 | 83 | B.19 | Cb-4675 | 160 | B.19 |
| Cb-4599 | 84 | B.19 | Cb-4676 | 161 | B.19 |
| Cb-4600 | 85 | B.19 | Cb-4677 | 162 | B.19 |
| Cb-4601 | 86 | B.19 | Cb-4678 | 163 | B.19 |
| Cb-4602 | 87 | B.19 | Cb-4679 | 164 | B.19 |
| Cb-4603 | 88 | B.19 | Cb-4680 | 165 | B.19 |
| Cb-4604 | 89 | B.19 | Cb-4681 | 166 | B.19 |
| Cb-4605 | 90 | B.19 | Cb-4682 | 167 | B.19 |
| Cb-4606 | 91 | B.19 | Cb-4683 | 168 | B.19 |
| Cb-4607 | 92 | B.19 | Cb-4684 | 169 | B.19 |
| Cb-4608 | 93 | B.19 | Cb-4685 | 170 | B.19 |
| Cb-4609 | 94 | B.19 | Cb-4686 | 171 | B.19 |
| Cb-4610 | 95 | B.19 | Cb-4687 | 172 | B.19 |
| Cb-4611 | 96 | B.19 | Cb-4688 | 173 | B.19 |
| Cb-4612 | 97 | B.19 | Cb-4689 | 174 | B.19 |
| Cb-4613 | 98 | B.19 | Cb-4690 | 175 | B.19 |
| Cb-4614 | 99 | B.19 | Cb-4691 | 176 | B.19 |
| Cb-4615 | 100 | B.19 | Cb-4692 | 177 | B.19 |
| Cb-4616 | 101 | B.19 | Cb-4693 | 178 | B.19 |
| Cb-4617 | 102 | B.19 | Cb-4694 | 179 | B.19 |
| Cb-4618 | 103 | B.19 | Cb-4695 | 180 | B.19 |
| Cb-4619 | 104 | B.19 | Cb-4696 | 181 | B.19 |
| Cb-4620 | 105 | B.19 | Cb-4697 | 182 | B.19 |
| Cb-4621 | 106 | B.19 | Cb-4698 | 183 | B.19 |
| Cb-4622 | 107 | B.19 | Cb-4699 | 184 | B.19 |
| Cb-4623 | 108 | B.19 | Cb-4700 | 185 | B.19 |
| Cb-4624 | 109 | B.19 | Cb-4701 | 186 | B.19 |
| Cb-4625 | 110 | B.19 | Cb-4702 | 187 | B.19 |
| Cb-4626 | 111 | B.19 | Cb-4703 | 188 | B.19 |
| Cb-4627 | 112 | B.19 | Cb-4704 | 189 | B.19 |
| Cb-4628 | 113 | B.19 | Cb-4705 | 190 | B.19 |
| Cb-4629 | 114 | B.19 | Cb-4706 | 191 | B.19 |
| Cb-4630 | 115 | B.19 | Cb-4707 | 192 | B.19 |
| Cb-4631 | 116 | B.19 | Cb-4708 | 193 | B.19 |
| Cb-4632 | 117 | B.19 | Cb-4709 | 194 | B.19 |
| Cb-4633 | 118 | B.19 | Cb-4710 | 195 | B.19 |
| Cb-4634 | 119 | B.19 | Cb-4711 | 196 | B.19 |
| Cb-4635 | 120 | B.19 | Cb-4712 | 197 | B.19 |
| Cb-4636 | 121 | B.19 | Cb-4713 | 198 | B.19 |
| Cb-4637 | 122 | B.19 | Cb-4714 | 199 | B.19 |
| Cb-4638 | 123 | B.19 | Cb-4715 | 200 | B.19 |
| Cb-4639 | 124 | B.19 | Cb-4716 | 201 | B.19 |
| Cb-4640 | 125 | B.19 | Cb-4717 | 202 | B.19 |
| Cb-4641 | 126 | B.19 | Cb-4718 | 203 | B.19 |
| Cb-4642 | 127 | B.19 | Cb-4719 | 204 | B.19 |
| Cb-4643 | 128 | B.19 | Cb-4720 | 205 | B.19 |
| Cb-4644 | 129 | B.19 | Cb-4721 | 206 | B.19 |
| Cb-4645 | 130 | B.19 | Cb-4722 | 207 | B.19 |
| Cb-4646 | 131 | B.19 | Cb-4723 | 208 | B.19 |
| Cb-4647 | 132 | B.19 | Cb-4724 | 209 | B.19 |
| Cb-4648 | 133 | B.19 | Cb-4725 | 210 | B.19 |
| Cb-4649 | 134 | B.19 | Cb-4726 | 211 | B.19 |
| Cb-4650 | 135 | B.19 | Cb-4727 | 212 | B.19 |
| Cb-4651 | 136 | B.19 | Cb-4728 | 213 | B.19 |

| Comb. | Com. A | Com. B |
|---|---|---|
| Cb-4729 | 214 | B.19 |
| Cb-4730 | 215 | B.19 |
| Cb-4731 | 1 | B.20 |
| Cb-4732 | 2 | B.20 |
| Cb-4733 | 3 | B.20 |
| Cb-4734 | 4 | B.20 |
| Cb-4735 | 5 | B.20 |
| Cb-4736 | 6 | B.20 |
| Cb-4737 | 7 | B.20 |
| Cb-4738 | 8 | B.20 |
| Cb-4739 | 9 | B.20 |
| Cb-4740 | 10 | B.20 |
| Cb-4741 | 11 | B.20 |
| Cb-4742 | 12 | B.20 |
| Cb-4743 | 13 | B.20 |
| Cb-4744 | 14 | B.20 |
| Cb-4745 | 15 | B.20 |
| Cb-4746 | 16 | B.20 |
| Cb-4747 | 17 | B.20 |
| Cb-4748 | 18 | B.20 |
| Cb-4749 | 19 | B.20 |
| Cb-4750 | 20 | B.20 |
| Cb-4751 | 21 | B.20 |
| Cb-4752 | 22 | B.20 |
| Cb-4753 | 23 | B.20 |
| Cb-4754 | 24 | B.20 |
| Cb-4755 | 25 | B.20 |
| Cb-4756 | 26 | B.20 |
| Cb-4757 | 27 | B.20 |
| Cb-4758 | 28 | B.20 |
| Cb-4759 | 29 | B.20 |
| Cb-4760 | 30 | B.20 |
| Cb-4761 | 31 | B.20 |
| Cb-4762 | 32 | B.20 |
| Cb-4763 | 33 | B.20 |
| Cb-4764 | 34 | B.20 |
| Cb-4765 | 35 | B.20 |
| Cb-4766 | 36 | B.20 |
| Cb-4767 | 37 | B.20 |
| Cb-4768 | 38 | B.20 |
| Cb-4769 | 39 | B.20 |
| Cb-4770 | 40 | B.20 |
| Cb-4771 | 41 | B.20 |
| Cb-4772 | 42 | B.20 |
| Cb-4773 | 43 | B.20 |
| Cb-4774 | 44 | B.20 |
| Cb-4775 | 45 | B.20 |
| Cb-4776 | 46 | B.20 |
| Cb-4777 | 47 | B.20 |
| Cb-4778 | 48 | B.20 |
| Cb-4779 | 49 | B.20 |
| Cb-4780 | 50 | B.20 |
| Cb-4781 | 51 | B.20 |
| Cb-4782 | 52 | B.20 |
| Cb-4783 | 53 | B.20 |
| Cb-4784 | 54 | B.20 |
| Cb-4785 | 55 | B.20 |
| Cb-4786 | 56 | B.20 |
| Cb-4787 | 57 | B.20 |
| Cb-4788 | 58 | B.20 |
| Cb-4789 | 59 | B.20 |
| Cb-4790 | 60 | B.20 |
| Cb-4791 | 61 | B.20 |
| Cb-4792 | 62 | B.20 |
| Cb-4793 | 63 | B.20 |
| Cb-4794 | 64 | B.20 |
| Cb-4795 | 65 | B.20 |
| Cb-4796 | 66 | B.20 |
| Cb-4797 | 67 | B.20 |
| Cb-4798 | 68 | B.20 |
| Cb-4799 | 69 | B.20 |
| Cb-4800 | 70 | B.20 |
| Cb-4801 | 71 | B.20 |
| Cb-4802 | 72 | B.20 |
| Cb-4803 | 73 | B.20 |
| Cb-4804 | 74 | B.20 |
| Cb-4805 | 75 | B.20 |
| Cb-4806 | 76 | B.20 |
| Cb-4807 | 77 | B.20 |
| Cb-4808 | 78 | B.20 |
| Cb-4809 | 79 | B.20 |
| Cb-4810 | 80 | B.20 |
| Cb-4811 | 81 | B.20 |
| Cb-4812 | 82 | B.20 |
| Cb-4813 | 83 | B.20 |
| Cb-4814 | 84 | B.20 |
| Cb-4815 | 85 | B.20 |
| Cb-4816 | 86 | B.20 |
| Cb-4817 | 87 | B.20 |
| Cb-4818 | 88 | B.20 |
| Cb-4819 | 89 | B.20 |
| Cb-4820 | 90 | B.20 |
| Cb-4821 | 91 | B.20 |
| Cb-4822 | 92 | B.20 |
| Cb-4823 | 93 | B.20 |
| Cb-4824 | 94 | B.20 |
| Cb-4825 | 95 | B.20 |
| Cb-4826 | 96 | B.20 |
| Cb-4827 | 97 | B.20 |
| Cb-4828 | 98 | B.20 |
| Cb-4829 | 99 | B.20 |
| Cb-4830 | 100 | B.20 |
| Cb-4831 | 101 | B.20 |
| Cb-4832 | 102 | B.20 |
| Cb-4833 | 103 | B.20 |
| Cb-4834 | 104 | B.20 |
| Cb-4835 | 105 | B.20 |
| Cb-4836 | 106 | B.20 |
| Cb-4837 | 107 | B.20 |
| Cb-4838 | 108 | B.20 |
| Cb-4839 | 109 | B.20 |
| Cb-4840 | 110 | B.20 |
| Cb-4841 | 111 | B.20 |
| Cb-4842 | 112 | B.20 |
| Cb-4843 | 113 | B.20 |
| Cb-4844 | 114 | B.20 |
| Cb-4845 | 115 | B.20 |
| Cb-4846 | 116 | B.20 |
| Cb-4847 | 117 | B.20 |
| Cb-4848 | 118 | B.20 |
| Cb-4849 | 119 | B.20 |
| Cb-4850 | 120 | B.20 |
| Cb-4851 | 121 | B.20 |
| Cb-4852 | 122 | B.20 |
| Cb-4853 | 123 | B.20 |
| Cb-4854 | 124 | B.20 |
| Cb-4855 | 125 | B.20 |
| Cb-4856 | 126 | B.20 |
| Cb-4857 | 127 | B.20 |
| Cb-4858 | 128 | B.20 |
| Cb-4859 | 129 | B.20 |
| Cb-4860 | 130 | B.20 |
| Cb-4861 | 131 | B.20 |
| Cb-4862 | 132 | B.20 |
| Cb-4863 | 133 | B.20 |
| Cb-4864 | 134 | B.20 |
| Cb-4865 | 135 | B.20 |
| Cb-4866 | 136 | B.20 |
| Cb-4867 | 137 | B.20 |
| Cb-4868 | 138 | B.20 |
| Cb-4869 | 139 | B.20 |
| Cb-4870 | 140 | B.20 |
| Cb-4871 | 141 | B.20 |
| Cb-4872 | 142 | B.20 |
| Cb-4873 | 143 | B.20 |
| Cb-4874 | 144 | B.20 |
| Cb-4875 | 145 | B.20 |
| Cb-4876 | 146 | B.20 |
| Cb-4877 | 147 | B.20 |
| Cb-4878 | 148 | B.20 |
| Cb-4879 | 149 | B.20 |
| Cb-4880 | 150 | B.20 |
| Cb-4881 | 151 | B.20 |
| Cb-4882 | 152 | B.20 |

| Comb. | Com. A | Com. B |
|---|---|---|
| Cb-4883 | 153 | B.20 |
| Cb-4884 | 154 | B.20 |
| Cb-4885 | 155 | B.20 |
| Cb-4886 | 156 | B.20 |
| Cb-4887 | 157 | B.20 |
| Cb-4888 | 158 | B.20 |
| Cb-4889 | 159 | B.20 |
| Cb-4890 | 160 | B.20 |
| Cb-4891 | 161 | B.20 |
| Cb-4892 | 162 | B.20 |
| Cb-4893 | 163 | B.20 |
| Cb-4894 | 164 | B.20 |
| Cb-4895 | 165 | B.20 |
| Cb-4896 | 166 | B.20 |
| Cb-4897 | 167 | B.20 |
| Cb-4898 | 168 | B.20 |
| Cb-4899 | 169 | B.20 |
| Cb-4900 | 170 | B.20 |
| Cb-4901 | 171 | B.20 |
| Cb-4902 | 172 | B.20 |
| Cb-4903 | 173 | B.20 |
| Cb-4904 | 174 | B.20 |
| Cb-4905 | 175 | B.20 |
| Cb-4906 | 176 | B.20 |
| Cb-4907 | 177 | B.20 |
| Cb-4908 | 178 | B.20 |
| Cb-4909 | 179 | B.20 |
| Cb-4910 | 180 | B.20 |
| Cb-4911 | 181 | B.20 |
| Cb-4912 | 182 | B.20 |
| Cb-4913 | 183 | B.20 |
| Cb-4914 | 184 | B.20 |
| Cb-4915 | 185 | B.20 |
| Cb-4916 | 186 | B.20 |
| Cb-4917 | 187 | B.20 |
| Cb-4918 | 188 | B.20 |
| Cb-4919 | 189 | B.20 |
| Cb-4920 | 190 | B.20 |
| Cb-4921 | 191 | B.20 |
| Cb-4922 | 192 | B.20 |
| Cb-4923 | 193 | B.20 |
| Cb-4924 | 194 | B.20 |
| Cb-4925 | 195 | B.20 |
| Cb-4926 | 196 | B.20 |
| Cb-4927 | 197 | B.20 |
| Cb-4928 | 198 | B.20 |
| Cb-4929 | 199 | B.20 |
| Cb-4930 | 200 | B.20 |
| Cb-4931 | 201 | B.20 |
| Cb-4932 | 202 | B.20 |
| Cb-4933 | 203 | B.20 |
| Cb-4934 | 204 | B.20 |
| Cb-4935 | 205 | B.20 |
| Cb-4936 | 206 | B.20 |
| Cb-4937 | 207 | B.20 |
| Cb-4938 | 208 | B.20 |
| Cb-4939 | 209 | B.20 |
| Cb-4940 | 210 | B.20 |
| Cb-4941 | 211 | B.20 |
| Cb-4942 | 212 | B.20 |
| Cb-4943 | 213 | B.20 |
| Cb-4944 | 214 | B.20 |
| Cb-4945 | 215 | B.20 |
| Cb-4946 | 1 | B.21 |
| Cb-4947 | 2 | B.21 |
| Cb-4948 | 3 | B.21 |
| Cb-4949 | 4 | B.21 |
| Cb-4950 | 5 | B.21 |
| Cb-4951 | 6 | B.21 |
| Cb-4952 | 7 | B.21 |
| Cb-4953 | 8 | B.21 |
| Cb-4954 | 9 | B.21 |
| Cb-4955 | 10 | B.21 |
| Cb-4956 | 11 | B.21 |
| Cb-4957 | 12 | B.21 |
| Cb-4958 | 13 | B.21 |
| Cb-4959 | 14 | B.21 |
| Cb-4960 | 15 | B.21 |
| Cb-4961 | 16 | B.21 |
| Cb-4962 | 17 | B.21 |
| Cb-4963 | 18 | B.21 |
| Cb-4964 | 19 | B.21 |
| Cb-4965 | 20 | B.21 |
| Cb-4966 | 21 | B.21 |
| Cb-4967 | 22 | B.21 |
| Cb-4968 | 23 | B.21 |
| Cb-4969 | 24 | B.21 |
| Cb-4970 | 25 | B.21 |
| Cb-4971 | 26 | B.21 |
| Cb-4972 | 27 | B.21 |
| Cb-4973 | 28 | B.21 |
| Cb-4974 | 29 | B.21 |
| Cb-4975 | 30 | B.21 |
| Cb-4976 | 31 | B.21 |
| Cb-4977 | 32 | B.21 |
| Cb-4978 | 33 | B.21 |
| Cb-4979 | 34 | B.21 |
| Cb-4980 | 35 | B.21 |
| Cb-4981 | 36 | B.21 |
| Cb-4982 | 37 | B.21 |
| Cb-4983 | 38 | B.21 |
| Cb-4984 | 39 | B.21 |
| Cb-4985 | 40 | B.21 |
| Cb-4986 | 41 | B.21 |
| Cb-4987 | 42 | B.21 |
| Cb-4988 | 43 | B.21 |
| Cb-4989 | 44 | B.21 |
| Cb-4990 | 45 | B.21 |
| Cb-4991 | 46 | B.21 |
| Cb-4992 | 47 | B.21 |
| Cb-4993 | 48 | B.21 |
| Cb-4994 | 49 | B.21 |
| Cb-4995 | 50 | B.21 |
| Cb-4996 | 51 | B.21 |
| Cb-4997 | 52 | B.21 |
| Cb-4998 | 53 | B.21 |
| Cb-4999 | 54 | B.21 |
| Cb-5000 | 55 | B.21 |
| Cb-5001 | 56 | B.21 |
| Cb-5002 | 57 | B.21 |
| Cb-5003 | 58 | B.21 |
| Cb-5004 | 59 | B.21 |
| Cb-5005 | 60 | B.21 |
| Cb-5006 | 61 | B.21 |
| Cb-5007 | 62 | B.21 |
| Cb-5008 | 63 | B.21 |
| Cb-5009 | 64 | B.21 |
| Cb-5010 | 65 | B.21 |
| Cb-5011 | 66 | B.21 |
| Cb-5012 | 67 | B.21 |
| Cb-5013 | 68 | B.21 |
| Cb-5014 | 69 | B.21 |
| Cb-5015 | 70 | B.21 |
| Cb-5016 | 71 | B.21 |
| Cb-5017 | 72 | B.21 |
| Cb-5018 | 73 | B.21 |
| Cb-5019 | 74 | B.21 |
| Cb-5020 | 75 | B.21 |
| Cb-5021 | 76 | B.21 |
| Cb-5022 | 77 | B.21 |
| Cb-5023 | 78 | B.21 |
| Cb-5024 | 79 | B.21 |
| Cb-5025 | 80 | B.21 |
| Cb-5026 | 81 | B.21 |
| Cb-5027 | 82 | B.21 |
| Cb-5028 | 83 | B.21 |
| Cb-5029 | 84 | B.21 |
| Cb-5030 | 85 | B.21 |
| Cb-5031 | 86 | B.21 |
| Cb-5032 | 87 | B.21 |
| Cb-5033 | 88 | B.21 |
| Cb-5034 | 89 | B.21 |
| Cb-5035 | 90 | B.21 |
| Cb-5036 | 91 | B.21 |

-continued

| Comb. | Com. A | Com. B |
|---|---|---|
| Cb-5037 | 92 | B.21 |
| Cb-5038 | 93 | B.21 |
| Cb-5039 | 94 | B.21 |
| Cb-5040 | 95 | B.21 |
| Cb-5041 | 96 | B.21 |
| Cb-5042 | 97 | B.21 |
| Cb-5043 | 98 | B.21 |
| Cb-5044 | 99 | B.21 |
| Cb-5045 | 100 | B.21 |
| Cb-5046 | 101 | B.21 |
| Cb-5047 | 102 | B.21 |
| Cb-5048 | 103 | B.21 |
| Cb-5049 | 104 | B.21 |
| Cb-5050 | 105 | B.21 |
| Cb-5051 | 106 | B.21 |
| Cb-5052 | 107 | B.21 |
| Cb-5053 | 108 | B.21 |
| Cb-5054 | 109 | B.21 |
| Cb-5055 | 110 | B.21 |
| Cb-5056 | 111 | B.21 |
| Cb-5057 | 112 | B.21 |
| Cb-5058 | 113 | B.21 |
| Cb-5059 | 114 | B.21 |
| Cb-5060 | 115 | B.21 |
| Cb-5061 | 116 | B.21 |
| Cb-5062 | 117 | B.21 |
| Cb-5063 | 118 | B.21 |
| Cb-5064 | 119 | B.21 |
| Cb-5065 | 120 | B.21 |
| Cb-5066 | 121 | B.21 |
| Cb-5067 | 122 | B.21 |
| Cb-5068 | 123 | B.21 |
| Cb-5069 | 124 | B.21 |
| Cb-5070 | 125 | B.21 |
| Cb-5071 | 126 | B.21 |
| Cb-5072 | 127 | B.21 |
| Cb-5073 | 128 | B.21 |
| Cb-5074 | 129 | B.21 |
| Cb-5075 | 130 | B.21 |
| Cb-5076 | 131 | B.21 |
| Cb-5077 | 132 | B.21 |
| Cb-5078 | 133 | B.21 |
| Cb-5079 | 134 | B.21 |
| Cb-5080 | 135 | B.21 |
| Cb-5081 | 136 | B.21 |
| Cb-5082 | 137 | B.21 |
| Cb-5083 | 138 | B.21 |
| Cb-5084 | 139 | B.21 |
| Cb-5085 | 140 | B.21 |
| Cb-5086 | 141 | B.21 |
| Cb-5087 | 142 | B.21 |
| Cb-5088 | 143 | B.21 |
| Cb-5089 | 144 | B.21 |
| Cb-5090 | 145 | B.21 |
| Cb-5091 | 146 | B.21 |
| Cb-5092 | 147 | B.21 |
| Cb-5093 | 148 | B.21 |
| Cb-5094 | 149 | B.21 |
| Cb-5095 | 150 | B.21 |
| Cb-5096 | 151 | B.21 |
| Cb-5097 | 152 | B.21 |
| Cb-5098 | 153 | B.21 |
| Cb-5099 | 154 | B.21 |
| Cb-5100 | 155 | B.21 |
| Cb-5101 | 156 | B.21 |
| Cb-5102 | 157 | B.21 |
| Cb-5103 | 158 | B.21 |
| Cb-5104 | 159 | B.21 |
| Cb-5105 | 160 | B.21 |
| Cb-5106 | 161 | B.21 |
| Cb-5107 | 162 | B.21 |
| Cb-5108 | 163 | B.21 |
| Cb-5109 | 164 | B.21 |
| Cb-5110 | 165 | B.21 |
| Cb-5111 | 166 | B.21 |
| Cb-5112 | 167 | B.21 |
| Cb-5113 | 168 | B.21 |
| Cb-5114 | 169 | B.21 |
| Cb-5115 | 170 | B.21 |
| Cb-5116 | 171 | B.21 |
| Cb-5117 | 172 | B.21 |
| Cb-5118 | 173 | B.21 |
| Cb-5119 | 174 | B.21 |
| Cb-5120 | 175 | B.21 |
| Cb-5121 | 176 | B.21 |
| Cb-5122 | 177 | B.21 |
| Cb-5123 | 178 | B.21 |
| Cb-5124 | 179 | B.21 |
| Cb-5125 | 180 | B.21 |
| Cb-5126 | 181 | B.21 |
| Cb-5127 | 182 | B.21 |
| Cb-5128 | 183 | B.21 |
| Cb-5129 | 184 | B.21 |
| Cb-5130 | 185 | B.21 |
| Cb-5131 | 186 | B.21 |
| Cb-5132 | 187 | B.21 |
| Cb-5133 | 188 | B.21 |
| Cb-5134 | 189 | B.21 |
| Cb-5135 | 190 | B.21 |
| Cb-5136 | 191 | B.21 |
| Cb-5137 | 192 | B.21 |
| Cb-5138 | 193 | B.21 |
| Cb-5139 | 194 | B.21 |
| Cb-5140 | 195 | B.21 |
| Cb-5141 | 196 | B.21 |
| Cb-5142 | 197 | B.21 |
| Cb-5143 | 198 | B.21 |
| Cb-5144 | 199 | B.21 |
| Cb-5145 | 200 | B.21 |
| Cb-5146 | 201 | B.21 |
| Cb-5147 | 202 | B.21 |
| Cb-5148 | 203 | B.21 |
| Cb-5149 | 204 | B.21 |
| Cb-5150 | 205 | B.21 |
| Cb-5151 | 206 | B.21 |
| Cb-5152 | 207 | B.21 |
| Cb-5153 | 208 | B.21 |
| Cb-5154 | 209 | B.21 |
| Cb-5155 | 210 | B.21 |
| Cb-5156 | 211 | B.21 |
| Cb-5157 | 212 | B.21 |
| Cb-5158 | 213 | B.21 |
| Cb-5159 | 214 | B.21 |
| Cb-5160 | 215 | B.21 |
| Cb-5161 | 1 | B.22 |
| Cb-5162 | 2 | B.22 |
| Cb-5163 | 3 | B.22 |
| Cb-5164 | 4 | B.22 |
| Cb-5165 | 5 | B.22 |
| Cb-5166 | 6 | B.22 |
| Cb-5167 | 7 | B.22 |
| Cb-5168 | 8 | B.22 |
| Cb-5169 | 9 | B.22 |
| Cb-5170 | 10 | B.22 |
| Cb-5171 | 11 | B.22 |
| Cb-5172 | 12 | B.22 |
| Cb-5173 | 13 | B.22 |
| Cb-5174 | 14 | B.22 |
| Cb-5175 | 15 | B.22 |
| Cb-5176 | 16 | B.22 |
| Cb-5177 | 17 | B.22 |
| Cb-5178 | 18 | B.22 |
| Cb-5179 | 19 | B.22 |
| Cb-5180 | 20 | B.22 |
| Cb-5181 | 21 | B.22 |
| Cb-5182 | 22 | B.22 |
| Cb-5183 | 23 | B.22 |
| Cb-5184 | 24 | B.22 |
| Cb-5185 | 25 | B.22 |
| Cb-5186 | 26 | B.22 |
| Cb-5187 | 27 | B.22 |
| Cb-5188 | 28 | B.22 |
| Cb-5189 | 29 | B.22 |
| Cb-5190 | 30 | B.22 |

| Comb. | Com. A | Com. B |
|---|---|---|
| Cb-5191 | 31 | B.22 |
| Cb-5192 | 32 | B.22 |
| Cb-5193 | 33 | B.22 |
| Cb-5194 | 34 | B.22 |
| Cb-5195 | 35 | B.22 |
| Cb-5196 | 36 | B.22 |
| Cb-5197 | 37 | B.22 |
| Cb-5198 | 38 | B.22 |
| Cb-5199 | 39 | B.22 |
| Cb-5200 | 40 | B.22 |
| Cb-5201 | 41 | B.22 |
| Cb-5202 | 42 | B.22 |
| Cb-5203 | 43 | B.22 |
| Cb-5204 | 44 | B.22 |
| Cb-5205 | 45 | B.22 |
| Cb-5206 | 46 | B.22 |
| Cb-5207 | 47 | B.22 |
| Cb-5208 | 48 | B.22 |
| Cb-5209 | 49 | B.22 |
| Cb-5210 | 50 | B.22 |
| Cb-5211 | 51 | B.22 |
| Cb-5212 | 52 | B.22 |
| Cb-5213 | 53 | B.22 |
| Cb-5214 | 54 | B.22 |
| Cb-5215 | 55 | B.22 |
| Cb-5216 | 56 | B.22 |
| Cb-5217 | 57 | B.22 |
| Cb-5218 | 58 | B.22 |
| Cb-5219 | 59 | B.22 |
| Cb-5220 | 60 | B.22 |
| Cb-5221 | 61 | B.22 |
| Cb-5222 | 62 | B.22 |
| Cb-5223 | 63 | B.22 |
| Cb-5224 | 64 | B.22 |
| Cb-5225 | 65 | B.22 |
| Cb-5226 | 66 | B.22 |
| Cb-5227 | 67 | B.22 |
| Cb-5228 | 68 | B.22 |
| Cb-5229 | 69 | B.22 |
| Cb-5230 | 70 | B.22 |
| Cb-5231 | 71 | B.22 |
| Cb-5232 | 72 | B.22 |
| Cb-5233 | 73 | B.22 |
| Cb-5234 | 74 | B.22 |
| Cb-5235 | 75 | B.22 |
| Cb-5236 | 76 | B.22 |
| Cb-5237 | 77 | B.22 |
| Cb-5238 | 78 | B.22 |
| Cb-5239 | 79 | B.22 |
| Cb-5240 | 80 | B.22 |
| Cb-5241 | 81 | B.22 |
| Cb-5242 | 82 | B.22 |
| Cb-5243 | 83 | B.22 |
| Cb-5244 | 84 | B.22 |
| Cb-5245 | 85 | B.22 |
| Cb-5246 | 86 | B.22 |
| Cb-5247 | 87 | B.22 |
| Cb-5248 | 88 | B.22 |
| Cb-5249 | 89 | B.22 |
| Cb-5250 | 90 | B.22 |
| Cb-5251 | 91 | B.22 |
| Cb-5252 | 92 | B.22 |
| Cb-5253 | 93 | B.22 |
| Cb-5254 | 94 | B.22 |
| Cb-5255 | 95 | B.22 |
| Cb-5256 | 96 | B.22 |
| Cb-5257 | 97 | B.22 |
| Cb-5258 | 98 | B.22 |
| Cb-5259 | 99 | B.22 |
| Cb-5260 | 100 | B.22 |
| Cb-5261 | 101 | B.22 |
| Cb-5262 | 102 | B.22 |
| Cb-5263 | 103 | B.22 |
| Cb-5264 | 104 | B.22 |
| Cb-5265 | 105 | B.22 |
| Cb-5266 | 106 | B.22 |
| Cb-5267 | 107 | B.22 |
| Cb-5268 | 108 | B.22 |
| Cb-5269 | 109 | B.22 |
| Cb-5270 | 110 | B.22 |
| Cb-5271 | 111 | B.22 |
| Cb-5272 | 112 | B.22 |
| Cb-5273 | 113 | B.22 |
| Cb-5274 | 114 | B.22 |
| Cb-5275 | 115 | B.22 |
| Cb-5276 | 116 | B.22 |
| Cb-5277 | 117 | B.22 |
| Cb-5278 | 118 | B.22 |
| Cb-5279 | 119 | B.22 |
| Cb-5280 | 120 | B.22 |
| Cb-5281 | 121 | B.22 |
| Cb-5282 | 122 | B.22 |
| Cb-5283 | 123 | B.22 |
| Cb-5284 | 124 | B.22 |
| Cb-5285 | 125 | B.22 |
| Cb-5286 | 126 | B.22 |
| Cb-5287 | 127 | B.22 |
| Cb-5288 | 128 | B.22 |
| Cb-5289 | 129 | B.22 |
| Cb-5290 | 130 | B.22 |
| Cb-5291 | 131 | B.22 |
| Cb-5292 | 132 | B.22 |
| Cb-5293 | 133 | B.22 |
| Cb-5294 | 134 | B.22 |
| Cb-5295 | 135 | B.22 |
| Cb-5296 | 136 | B.22 |
| Cb-5297 | 137 | B.22 |
| Cb-5298 | 138 | B.22 |
| Cb-5299 | 139 | B.22 |
| Cb-5300 | 140 | B.22 |
| Cb-5301 | 141 | B.22 |
| Cb-5302 | 142 | B.22 |
| Cb-5303 | 143 | B.22 |
| Cb-5304 | 144 | B.22 |
| Cb-5305 | 145 | B.22 |
| Cb-5306 | 146 | B.22 |
| Cb-5307 | 147 | B.22 |
| Cb-5308 | 148 | B.22 |
| Cb-5309 | 149 | B.22 |
| Cb-5310 | 150 | B.22 |
| Cb-5311 | 151 | B.22 |
| Cb-5312 | 152 | B.22 |
| Cb-5313 | 153 | B.22 |
| Cb-5314 | 154 | B.22 |
| Cb-5315 | 155 | B.22 |
| Cb-5316 | 156 | B.22 |
| Cb-5317 | 157 | B.22 |
| Cb-5318 | 158 | B.22 |
| Cb-5319 | 159 | B.22 |
| Cb-5320 | 160 | B.22 |
| Cb-5321 | 161 | B.22 |
| Cb-5322 | 162 | B.22 |
| Cb-5323 | 163 | B.22 |
| Cb-5324 | 164 | B.22 |
| Cb-5325 | 165 | B.22 |
| Cb-5326 | 166 | B.22 |
| Cb-5327 | 167 | B.22 |
| Cb-5328 | 168 | B.22 |
| Cb-5329 | 169 | B.22 |
| Cb-5330 | 170 | B.22 |
| Cb-5331 | 171 | B.22 |
| Cb-5332 | 172 | B.22 |
| Cb-5333 | 173 | B.22 |
| Cb-5334 | 174 | B.22 |
| Cb-5335 | 175 | B.22 |
| Cb-5336 | 176 | B.22 |
| Cb-5337 | 177 | B.22 |
| Cb-5338 | 178 | B.22 |
| Cb-5339 | 179 | B.22 |
| Cb-5340 | 180 | B.22 |
| Cb-5341 | 181 | B.22 |
| Cb-5342 | 182 | B.22 |
| Cb-5343 | 183 | B.22 |
| Cb-5344 | 184 | B.22 |

-continued

| Comb. | Com. A | Com. B |
|---|---|---|
| Cb-5345 | 185 | B.22 |
| Cb-5346 | 186 | B.22 |
| Cb-5347 | 187 | B.22 |
| Cb-5348 | 188 | B.22 |
| Cb-5349 | 189 | B.22 |
| Cb-5350 | 190 | B.22 |
| Cb-5351 | 191 | B.22 |
| Cb-5352 | 192 | B.22 |
| Cb-5353 | 193 | B.22 |
| Cb-5354 | 194 | B.22 |
| Cb-5355 | 195 | B.22 |
| Cb-5356 | 196 | B.22 |
| Cb-5357 | 197 | B.22 |
| Cb-5358 | 198 | B.22 |
| Cb-5359 | 199 | B.22 |
| Cb-5360 | 200 | B.22 |
| Cb-5361 | 201 | B.22 |
| Cb-5362 | 202 | B.22 |
| Cb-5363 | 203 | B.22 |
| Cb-5364 | 204 | B.22 |
| Cb-5365 | 205 | B.22 |
| Cb-5366 | 206 | B.22 |
| Cb-5367 | 207 | B.22 |
| Cb-5368 | 208 | B.22 |
| Cb-5369 | 209 | B.22 |
| Cb-5370 | 210 | B.22 |
| Cb-5371 | 211 | B.22 |
| Cb-5372 | 212 | B.22 |
| Cb-5373 | 213 | B.22 |
| Cb-5374 | 214 | B.22 |
| Cb-5375 | 215 | B.22 |
| Cb-5376 | 1 | B.23 |
| Cb-5377 | 2 | B.23 |
| Cb-5378 | 3 | B.23 |
| Cb-5379 | 4 | B.23 |
| Cb-5380 | 5 | B.23 |
| Cb-5381 | 6 | B.23 |
| Cb-5382 | 7 | B.23 |
| Cb-5383 | 8 | B.23 |
| Cb-5384 | 9 | B.23 |
| Cb-5385 | 10 | B.23 |
| Cb-5386 | 11 | B.23 |
| Cb-5387 | 12 | B.23 |
| Cb-5388 | 13 | B.23 |
| Cb-5389 | 14 | B.23 |
| Cb-5390 | 15 | B.23 |
| Cb-5391 | 16 | B.23 |
| Cb-5392 | 17 | B.23 |
| Cb-5393 | 18 | B.23 |
| Cb-5394 | 19 | B.23 |
| Cb-5395 | 20 | B.23 |
| Cb-5396 | 21 | B.23 |
| Cb-5397 | 22 | B.23 |
| Cb-5398 | 23 | B.23 |
| Cb-5399 | 24 | B.23 |
| Cb-5400 | 25 | B.23 |
| Cb-5401 | 26 | B.23 |
| Cb-5402 | 27 | B.23 |
| Cb-5403 | 28 | B.23 |
| Cb-5404 | 29 | B.23 |
| Cb-5405 | 30 | B.23 |
| Cb-5406 | 31 | B.23 |
| Cb-5407 | 32 | B.23 |
| Cb-5408 | 33 | B.23 |
| Cb-5409 | 34 | B.23 |
| Cb-5410 | 35 | B.23 |
| Cb-5411 | 36 | B.23 |
| Cb-5412 | 37 | B.23 |
| Cb-5413 | 38 | B.23 |
| Cb-5414 | 39 | B.23 |
| Cb-5415 | 40 | B.23 |
| Cb-5416 | 41 | B.23 |
| Cb-5417 | 42 | B.23 |
| Cb-5418 | 43 | B.23 |
| Cb-5419 | 44 | B.23 |
| Cb-5420 | 45 | B.23 |
| Cb-5421 | 46 | B.23 |
| Cb-5422 | 47 | B.23 |
| Cb-5423 | 48 | B.23 |
| Cb-5424 | 49 | B.23 |
| Cb-5425 | 50 | B.23 |
| Cb-5426 | 51 | B.23 |
| Cb-5427 | 52 | B.23 |
| Cb-5428 | 53 | B.23 |
| Cb-5429 | 54 | B.23 |
| Cb-5430 | 55 | B.23 |
| Cb-5431 | 56 | B.23 |
| Cb-5432 | 57 | B.23 |
| Cb-5433 | 58 | B.23 |
| Cb-5434 | 59 | B.23 |
| Cb-5435 | 60 | B.23 |
| Cb-5436 | 61 | B.23 |
| Cb-5437 | 62 | B.23 |
| Cb-5438 | 63 | B.23 |
| Cb-5439 | 64 | B.23 |
| Cb-5440 | 65 | B.23 |
| Cb-5441 | 66 | B.23 |
| Cb-5442 | 67 | B.23 |
| Cb-5443 | 68 | B.23 |
| Cb-5444 | 69 | B.23 |
| Cb-5445 | 70 | B.23 |
| Cb-5446 | 71 | B.23 |
| Cb-5447 | 72 | B.23 |
| Cb-5448 | 73 | B.23 |
| Cb-5449 | 74 | B.23 |
| Cb-5450 | 75 | B.23 |
| Cb-5451 | 76 | B.23 |
| Cb-5452 | 77 | B.23 |
| Cb-5453 | 78 | B.23 |
| Cb-5454 | 79 | B.23 |
| Cb-5455 | 80 | B.23 |
| Cb-5456 | 81 | B.23 |
| Cb-5457 | 82 | B.23 |
| Cb-5458 | 83 | B.23 |
| Cb-5459 | 84 | B.23 |
| Cb-5460 | 85 | B.23 |
| Cb-5461 | 86 | B.23 |
| Cb-5462 | 87 | B.23 |
| Cb-5463 | 88 | B.23 |
| Cb-5464 | 89 | B.23 |
| Cb-5465 | 90 | B.23 |
| Cb-5466 | 91 | B.23 |
| Cb-5467 | 92 | B.23 |
| Cb-5468 | 93 | B.23 |
| Cb-5469 | 94 | B.23 |
| Cb-5470 | 95 | B.23 |
| Cb-5471 | 96 | B.23 |
| Cb-5472 | 97 | B.23 |
| Cb-5473 | 98 | B.23 |
| Cb-5474 | 99 | B.23 |
| Cb-5475 | 100 | B.23 |
| Cb-5476 | 101 | B.23 |
| Cb-5477 | 102 | B.23 |
| Cb-5478 | 103 | B.23 |
| Cb-5479 | 104 | B.23 |
| Cb-5480 | 105 | B.23 |
| Cb-5481 | 106 | B.23 |
| Cb-5482 | 107 | B.23 |
| Cb-5483 | 108 | B.23 |
| Cb-5484 | 109 | B.23 |
| Cb-5485 | 110 | B.23 |
| Cb-5486 | 111 | B.23 |
| Cb-5487 | 112 | B.23 |
| Cb-5488 | 113 | B.23 |
| Cb-5489 | 114 | B.23 |
| Cb-5490 | 115 | B.23 |
| Cb-5491 | 116 | B.23 |
| Cb-5492 | 117 | B.23 |
| Cb-5493 | 118 | B.23 |
| Cb-5494 | 119 | B.23 |
| Cb-5495 | 120 | B.23 |
| Cb-5496 | 121 | B.23 |
| Cb-5497 | 122 | B.23 |
| Cb-5498 | 123 | B.23 |

-continued

| Comb. | Com. A | Com. B |
|---|---|---|
| Cb-5499 | 124 | B.23 |
| Cb-5500 | 125 | B.23 |
| Cb-5501 | 126 | B.23 |
| Cb-5502 | 127 | B.23 |
| Cb-5503 | 128 | B.23 |
| Cb-5504 | 129 | B.23 |
| Cb-5505 | 130 | B.23 |
| Cb-5506 | 131 | B.23 |
| Cb-5507 | 132 | B.23 |
| Cb-5508 | 133 | B.23 |
| Cb-5509 | 134 | B.23 |
| Cb-5510 | 135 | B.23 |
| Cb-5511 | 136 | B.23 |
| Cb-5512 | 137 | B.23 |
| Cb-5513 | 138 | B.23 |
| Cb-5514 | 139 | B.23 |
| Cb-5515 | 140 | B.23 |
| Cb-5516 | 141 | B.23 |
| Cb-5517 | 142 | B.23 |
| Cb-5518 | 143 | B.23 |
| Cb-5519 | 144 | B.23 |
| Cb-5520 | 145 | B.23 |
| Cb-5521 | 146 | B.23 |
| Cb-5522 | 147 | B.23 |
| Cb-5523 | 148 | B.23 |
| Cb-5524 | 149 | B.23 |
| Cb-5525 | 150 | B.23 |
| Cb-5526 | 151 | B.23 |
| Cb-5527 | 152 | B.23 |
| Cb-5528 | 153 | B.23 |
| Cb-5529 | 154 | B.23 |
| Cb-5530 | 155 | B.23 |
| Cb-5531 | 156 | B.23 |
| Cb-5532 | 157 | B.23 |
| Cb-5533 | 158 | B.23 |
| Cb-5534 | 159 | B.23 |
| Cb-5535 | 160 | B.23 |
| Cb-5536 | 161 | B.23 |
| Cb-5537 | 162 | B.23 |
| Cb-5538 | 163 | B.23 |
| Cb-5539 | 164 | B.23 |
| Cb-5540 | 165 | B.23 |
| Cb-5541 | 166 | B.23 |
| Cb-5542 | 167 | B.23 |
| Cb-5543 | 168 | B.23 |
| Cb-5544 | 169 | B.23 |
| Cb-5545 | 170 | B.23 |
| Cb-5546 | 171 | B.23 |
| Cb-5547 | 172 | B.23 |
| Cb-5548 | 173 | B.23 |
| Cb-5549 | 174 | B.23 |
| Cb-5550 | 175 | B.23 |
| Cb-5551 | 176 | B.23 |
| Cb-5552 | 177 | B.23 |
| Cb-5553 | 178 | B.23 |
| Cb-5554 | 179 | B.23 |
| Cb-5555 | 180 | B.23 |
| Cb-5556 | 181 | B.23 |
| Cb-5557 | 182 | B.23 |
| Cb-5558 | 183 | B.23 |
| Cb-5559 | 184 | B.23 |
| Cb-5560 | 185 | B.23 |
| Cb-5561 | 186 | B.23 |
| Cb-5562 | 187 | B.23 |
| Cb-5563 | 188 | B.23 |
| Cb-5564 | 189 | B.23 |
| Cb-5565 | 190 | B.23 |
| Cb-5566 | 191 | B.23 |
| Cb-5567 | 192 | B.23 |
| Cb-5568 | 193 | B.23 |
| Cb-5569 | 194 | B.23 |
| Cb-5570 | 195 | B.23 |
| Cb-5571 | 196 | B.23 |
| Cb-5572 | 197 | B.23 |
| Cb-5573 | 198 | B.23 |
| Cb-5574 | 199 | B.23 |
| Cb-5575 | 200 | B.23 |
| Cb-5576 | 201 | B.23 |
| Cb-5577 | 202 | B.23 |
| Cb-5578 | 203 | B.23 |
| Cb-5579 | 204 | B.23 |
| Cb-5580 | 205 | B.23 |
| Cb-5581 | 206 | B.23 |
| Cb-5582 | 207 | B.23 |
| Cb-5583 | 208 | B.23 |
| Cb-5584 | 209 | B.23 |
| Cb-5585 | 210 | B.23 |
| Cb-5586 | 211 | B.23 |
| Cb-5587 | 212 | B.23 |
| Cb-5588 | 213 | B.23 |
| Cb-5589 | 214 | B.23 |
| Cb-5590 | 215 | B.23 |
| Cb-5591 | 1 | B.24 |
| Cb-5592 | 2 | B.24 |
| Cb-5593 | 3 | B.24 |
| Cb-5594 | 4 | B.24 |
| Cb-5595 | 5 | B.24 |
| Cb-5596 | 6 | B.24 |
| Cb-5597 | 7 | B.24 |
| Cb-5598 | 8 | B.24 |
| Cb-5599 | 9 | B.24 |
| Cb-5600 | 10 | B.24 |
| Cb-5601 | 11 | B.24 |
| Cb-5602 | 12 | B.24 |
| Cb-5603 | 13 | B.24 |
| Cb-5604 | 14 | B.24 |
| Cb-5605 | 15 | B.24 |
| Cb-5606 | 16 | B.24 |
| Cb-5607 | 17 | B.24 |
| Cb-5608 | 18 | B.24 |
| Cb-5609 | 19 | B.24 |
| Cb-5610 | 20 | B.24 |
| Cb-5611 | 21 | B.24 |
| Cb-5612 | 22 | B.24 |
| Cb-5613 | 23 | B.24 |
| Cb-5614 | 24 | B.24 |
| Cb-5615 | 25 | B.24 |
| Cb-5616 | 26 | B.24 |
| Cb-5617 | 27 | B.24 |
| Cb-5618 | 28 | B.24 |
| Cb-5619 | 29 | B.24 |
| Cb-5620 | 30 | B.24 |
| Cb-5621 | 31 | B.24 |
| Cb-5622 | 32 | B.24 |
| Cb-5623 | 33 | B.24 |
| Cb-5624 | 34 | B.24 |
| Cb-5625 | 35 | B.24 |
| Cb-5626 | 36 | B.24 |
| Cb-5627 | 37 | B.24 |
| Cb-5628 | 38 | B.24 |
| Cb-5629 | 39 | B.24 |
| Cb-5630 | 40 | B.24 |
| Cb-5631 | 41 | B.24 |
| Cb-5632 | 42 | B.24 |
| Cb-5633 | 43 | B.24 |
| Cb-5634 | 44 | B.24 |
| Cb-5635 | 45 | B.24 |
| Cb-5636 | 46 | B.24 |
| Cb-5637 | 47 | B.24 |
| Cb-5638 | 48 | B.24 |
| Cb-5639 | 49 | B.24 |
| Cb-5640 | 50 | B.24 |
| Cb-5641 | 51 | B.24 |
| Cb-5642 | 52 | B.24 |
| Cb-5643 | 53 | B.24 |
| Cb-5644 | 54 | B.24 |
| Cb-5645 | 55 | B.24 |
| Cb-5646 | 56 | B.24 |
| Cb-5647 | 57 | B.24 |
| Cb-5648 | 58 | B.24 |
| Cb-5649 | 59 | B.24 |
| Cb-5650 | 60 | B.24 |
| Cb-5651 | 61 | B.24 |
| Cb-5652 | 62 | B.24 |

| Comb. | Com. A | Com. B |
|---|---|---|
| Cb-5653 | 63 | B.24 |
| Cb-5654 | 64 | B.24 |
| Cb-5655 | 65 | B.24 |
| Cb-5656 | 66 | B.24 |
| Cb-5657 | 67 | B.24 |
| Cb-5658 | 68 | B.24 |
| Cb-5659 | 69 | B.24 |
| Cb-5660 | 70 | B.24 |
| Cb-5661 | 71 | B.24 |
| Cb-5662 | 72 | B.24 |
| Cb-5663 | 73 | B.24 |
| Cb-5664 | 74 | B.24 |
| Cb-5665 | 75 | B.24 |
| Cb-5666 | 76 | B.24 |
| Cb-5667 | 77 | B.24 |
| Cb-5668 | 78 | B.24 |
| Cb-5669 | 79 | B.24 |
| Cb-5670 | 80 | B.24 |
| Cb-5671 | 81 | B.24 |
| Cb-5672 | 82 | B.24 |
| Cb-5673 | 83 | B.24 |
| Cb-5674 | 84 | B.24 |
| Cb-5675 | 85 | B.24 |
| Cb-5676 | 86 | B.24 |
| Cb-5677 | 87 | B.24 |
| Cb-5678 | 88 | B.24 |
| Cb-5679 | 89 | B.24 |
| Cb-5680 | 90 | B.24 |
| Cb-5681 | 91 | B.24 |
| Cb-5682 | 92 | B.24 |
| Cb-5683 | 93 | B.24 |
| Cb-5684 | 94 | B.24 |
| Cb-5685 | 95 | B.24 |
| Cb-5686 | 96 | B.24 |
| Cb-5687 | 97 | B.24 |
| Cb-5688 | 98 | B.24 |
| Cb-5689 | 99 | B.24 |
| Cb-5690 | 100 | B.24 |
| Cb-5691 | 101 | B.24 |
| Cb-5692 | 102 | B.24 |
| Cb-5693 | 103 | B.24 |
| Cb-5694 | 104 | B.24 |
| Cb-5695 | 105 | B.24 |
| Cb-5696 | 106 | B.24 |
| Cb-5697 | 107 | B.24 |
| Cb-5698 | 108 | B.24 |
| Cb-5699 | 109 | B.24 |
| Cb-5700 | 110 | B.24 |
| Cb-5701 | 111 | B.24 |
| Cb-5702 | 112 | B.24 |
| Cb-5703 | 113 | B.24 |
| Cb-5704 | 114 | B.24 |
| Cb-5705 | 115 | B.24 |
| Cb-5706 | 116 | B.24 |
| Cb-5707 | 117 | B.24 |
| Cb-5708 | 118 | B.24 |
| Cb-5709 | 119 | B.24 |
| Cb-5710 | 120 | B.24 |
| Cb-5711 | 121 | B.24 |
| Cb-5712 | 122 | B.24 |
| Cb-5713 | 123 | B.24 |
| Cb-5714 | 124 | B.24 |
| Cb-5715 | 125 | B.24 |
| Cb-5716 | 126 | B.24 |
| Cb-5717 | 127 | B.24 |
| Cb-5718 | 128 | B.24 |
| Cb-5719 | 129 | B.24 |
| Cb-5720 | 130 | B.24 |
| Cb-5721 | 131 | B.24 |
| Cb-5722 | 132 | B.24 |
| Cb-5723 | 133 | B.24 |
| Cb-5724 | 134 | B.24 |
| Cb-5725 | 135 | B.24 |
| Cb-5726 | 136 | B.24 |
| Cb-5727 | 137 | B.24 |
| Cb-5728 | 138 | B.24 |
| Cb-5729 | 139 | B.24 |
| Cb-5730 | 140 | B.24 |
| Cb-5731 | 141 | B.24 |
| Cb-5732 | 142 | B.24 |
| Cb-5733 | 143 | B.24 |
| Cb-5734 | 144 | B.24 |
| Cb-5735 | 145 | B.24 |
| Cb-5736 | 146 | B.24 |
| Cb-5737 | 147 | B.24 |
| Cb-5738 | 148 | B.24 |
| Cb-5739 | 149 | B.24 |
| Cb-5740 | 150 | B.24 |
| Cb-5741 | 151 | B.24 |
| Cb-5742 | 152 | B.24 |
| Cb-5743 | 153 | B.24 |
| Cb-5744 | 154 | B.24 |
| Cb-5745 | 155 | B.24 |
| Cb-5746 | 156 | B.24 |
| Cb-5747 | 157 | B.24 |
| Cb-5748 | 158 | B.24 |
| Cb-5749 | 159 | B.24 |
| Cb-5750 | 160 | B.24 |
| Cb-5751 | 161 | B.24 |
| Cb-5752 | 162 | B.24 |
| Cb-5753 | 163 | B.24 |
| Cb-5754 | 164 | B.24 |
| Cb-5755 | 165 | B.24 |
| Cb-5756 | 166 | B.24 |
| Cb-5757 | 167 | B.24 |
| Cb-5758 | 168 | B.24 |
| Cb-5759 | 169 | B.24 |
| Cb-5760 | 170 | B.24 |
| Cb-5761 | 171 | B.24 |
| Cb-5762 | 172 | B.24 |
| Cb-5763 | 173 | B.24 |
| Cb-5764 | 174 | B.24 |
| Cb-5765 | 175 | B.24 |
| Cb-5766 | 176 | B.24 |
| Cb-5767 | 177 | B.24 |
| Cb-5768 | 178 | B.24 |
| Cb-5769 | 179 | B.24 |
| Cb-5770 | 180 | B.24 |
| Cb-5771 | 181 | B.24 |
| Cb-5772 | 182 | B.24 |
| Cb-5773 | 183 | B.24 |
| Cb-5774 | 184 | B.24 |
| Cb-5775 | 185 | B.24 |
| Cb-5776 | 186 | B.24 |
| Cb-5777 | 187 | B.24 |
| Cb-5778 | 188 | B.24 |
| Cb-5779 | 189 | B.24 |
| Cb-5780 | 190 | B.24 |
| Cb-5781 | 191 | B.24 |
| Cb-5782 | 192 | B.24 |
| Cb-5783 | 193 | B.24 |
| Cb-5784 | 194 | B.24 |
| Cb-5785 | 195 | B.24 |
| Cb-5786 | 196 | B.24 |
| Cb-5787 | 197 | B.24 |
| Cb-5788 | 198 | B.24 |
| Cb-5789 | 199 | B.24 |
| Cb-5790 | 200 | B.24 |
| Cb-5791 | 201 | B.24 |
| Cb-5792 | 202 | B.24 |
| Cb-5793 | 203 | B.24 |
| Cb-5794 | 204 | B.24 |
| Cb-5795 | 205 | B.24 |
| Cb-5796 | 206 | B.24 |
| Cb-5797 | 207 | B.24 |
| Cb-5798 | 208 | B.24 |
| Cb-5799 | 209 | B.24 |
| Cb-5800 | 210 | B.24 |
| Cb-5801 | 211 | B.24 |
| Cb-5802 | 212 | B.24 |
| Cb-5803 | 213 | B.24 |
| Cb-5804 | 214 | B.24 |
| Cb-5805 | 215 | B.24 |
| Cb-5806 | 1 | B.25 |

| Comb. | Com. A | Com. B | | Comb. | Com. A | Com. B |
|---|---|---|---|---|---|---|
| Cb-5807 | 2 | B.25 | | Cb-5884 | 79 | B.25 |
| Cb-5808 | 3 | B.25 | | Cb-5885 | 80 | B.25 |
| Cb-5809 | 4 | B.25 | | Cb-5886 | 81 | B.25 |
| Cb-5810 | 5 | B.25 | | Cb-5887 | 82 | B.25 |
| Cb-5811 | 6 | B.25 | | Cb-5888 | 83 | B.25 |
| Cb-5812 | 7 | B.25 | | Cb-5889 | 84 | B.25 |
| Cb-5813 | 8 | B.25 | | Cb-5890 | 85 | B.25 |
| Cb-5814 | 9 | B.25 | | Cb-5891 | 86 | B.25 |
| Cb-5815 | 10 | B.25 | | Cb-5892 | 87 | B.25 |
| Cb-5816 | 11 | B.25 | | Cb-5893 | 88 | B.25 |
| Cb-5817 | 12 | B.25 | | Cb-5894 | 89 | B.25 |
| Cb-5818 | 13 | B.25 | | Cb-5895 | 90 | B.25 |
| Cb-5819 | 14 | B.25 | | Cb-5896 | 91 | B.25 |
| Cb-5820 | 15 | B.25 | | Cb-5897 | 92 | B.25 |
| Cb-5821 | 16 | B.25 | | Cb-5898 | 93 | B.25 |
| Cb-5822 | 17 | B.25 | | Cb-5899 | 94 | B.25 |
| Cb-5823 | 18 | B.25 | | Cb-5900 | 95 | B.25 |
| Cb-5824 | 19 | B.25 | | Cb-5901 | 96 | B.25 |
| Cb-5825 | 20 | B.25 | | Cb-5902 | 97 | B.25 |
| Cb-5826 | 21 | B.25 | | Cb-5903 | 98 | B.25 |
| Cb-5827 | 22 | B.25 | | Cb-5904 | 99 | B.25 |
| Cb-5828 | 23 | B.25 | | Cb-5905 | 100 | B.25 |
| Cb-5829 | 24 | B.25 | | Cb-5906 | 101 | B.25 |
| Cb-5830 | 25 | B.25 | | Cb-5907 | 102 | B.25 |
| Cb-5831 | 26 | B.25 | | Cb-5908 | 103 | B.25 |
| Cb-5832 | 27 | B.25 | | Cb-5909 | 104 | B.25 |
| Cb-5833 | 28 | B.25 | | Cb-5910 | 105 | B.25 |
| Cb-5834 | 29 | B.25 | | Cb-5911 | 106 | B.25 |
| Cb-5835 | 30 | B.25 | | Cb-5912 | 107 | B.25 |
| Cb-5836 | 31 | B.25 | | Cb-5913 | 108 | B.25 |
| Cb-5837 | 32 | B.25 | | Cb-5914 | 109 | B.25 |
| Cb-5838 | 33 | B.25 | | Cb-5915 | 110 | B.25 |
| Cb-5839 | 34 | B.25 | | Cb-5916 | 111 | B.25 |
| Cb-5840 | 35 | B.25 | | Cb-5917 | 112 | B.25 |
| Cb-5841 | 36 | B.25 | | Cb-5918 | 113 | B.25 |
| Cb-5842 | 37 | B.25 | | Cb-5919 | 114 | B.25 |
| Cb-5843 | 38 | B.25 | | Cb-5920 | 115 | B.25 |
| Cb-5844 | 39 | B.25 | | Cb-5921 | 116 | B.25 |
| Cb-5845 | 40 | B.25 | | Cb-5922 | 117 | B.25 |
| Cb-5846 | 41 | B.25 | | Cb-5923 | 118 | B.25 |
| Cb-5847 | 42 | B.25 | | Cb-5924 | 119 | B.25 |
| Cb-5848 | 43 | B.25 | | Cb-5925 | 120 | B.25 |
| Cb-5849 | 44 | B.25 | | Cb-5926 | 121 | B.25 |
| Cb-5850 | 45 | B.25 | | Cb-5927 | 122 | B.25 |
| Cb-5851 | 46 | B.25 | | Cb-5928 | 123 | B.25 |
| Cb-5852 | 47 | B.25 | | Cb-5929 | 124 | B.25 |
| Cb-5853 | 48 | B.25 | | Cb-5930 | 125 | B.25 |
| Cb-5854 | 49 | B.25 | | Cb-5931 | 126 | B.25 |
| Cb-5855 | 50 | B.25 | | Cb-5932 | 127 | B.25 |
| Cb-5856 | 51 | B.25 | | Cb-5933 | 128 | B.25 |
| Cb-5857 | 52 | B.25 | | Cb-5934 | 129 | B.25 |
| Cb-5858 | 53 | B.25 | | Cb-5935 | 130 | B.25 |
| Cb-5859 | 54 | B.25 | | Cb-5936 | 131 | B.25 |
| Cb-5860 | 55 | B.25 | | Cb-5937 | 132 | B.25 |
| Cb-5861 | 56 | B.25 | | Cb-5938 | 133 | B.25 |
| Cb-5862 | 57 | B.25 | | Cb-5939 | 134 | B.25 |
| Cb-5863 | 58 | B.25 | | Cb-5940 | 135 | B.25 |
| Cb-5864 | 59 | B.25 | | Cb-5941 | 136 | B.25 |
| Cb-5865 | 60 | B.25 | | Cb-5942 | 137 | B.25 |
| Cb-5866 | 61 | B.25 | | Cb-5943 | 138 | B.25 |
| Cb-5867 | 62 | B.25 | | Cb-5944 | 139 | B.25 |
| Cb-5868 | 63 | B.25 | | Cb-5945 | 140 | B.25 |
| Cb-5869 | 64 | B.25 | | Cb-5946 | 141 | B.25 |
| Cb-5870 | 65 | B.25 | | Cb-5947 | 142 | B.25 |
| Cb-5871 | 66 | B.25 | | Cb-5948 | 143 | B.25 |
| Cb-5872 | 67 | B.25 | | Cb-5949 | 144 | B.25 |
| Cb-5873 | 68 | B.25 | | Cb-5950 | 145 | B.25 |
| Cb-5874 | 69 | B.25 | | Cb-5951 | 146 | B.25 |
| Cb-5875 | 70 | B.25 | | Cb-5952 | 147 | B.25 |
| Cb-5876 | 71 | B.25 | | Cb-5953 | 148 | B.25 |
| Cb-5877 | 72 | B.25 | | Cb-5954 | 149 | B.25 |
| Cb-5878 | 73 | B.25 | | Cb-5955 | 150 | B.25 |
| Cb-5879 | 74 | B.25 | | Cb-5956 | 151 | B.25 |
| Cb-5880 | 75 | B.25 | | Cb-5957 | 152 | B.25 |
| Cb-5881 | 76 | B.25 | | Cb-5958 | 153 | B.25 |
| Cb-5882 | 77 | B.25 | | Cb-5959 | 154 | B.25 |
| Cb-5883 | 78 | B.25 | | Cb-5960 | 155 | B.25 |

| Comb. | Com. A | Com. B |
|---|---|---|
| Cb-5961 | 156 | B.25 |
| Cb-5962 | 157 | B.25 |
| Cb-5963 | 158 | B.25 |
| Cb-5964 | 159 | B.25 |
| Cb-5965 | 160 | B.25 |
| Cb-5966 | 161 | B.25 |
| Cb-5967 | 162 | B.25 |
| Cb-5968 | 163 | B.25 |
| Cb-5969 | 164 | B.25 |
| Cb-5970 | 165 | B.25 |
| Cb-5971 | 166 | B.25 |
| Cb-5972 | 167 | B.25 |
| Cb-5973 | 168 | B.25 |
| Cb-5974 | 169 | B.25 |
| Cb-5975 | 170 | B.25 |
| Cb-5976 | 171 | B.25 |
| Cb-5977 | 172 | B.25 |
| Cb-5978 | 173 | B.25 |
| Cb-5979 | 174 | B.25 |
| Cb-5980 | 175 | B.25 |
| Cb-5981 | 176 | B.25 |
| Cb-5982 | 177 | B.25 |
| Cb-5983 | 178 | B.25 |
| Cb-5984 | 179 | B.25 |
| Cb-5985 | 180 | B.25 |
| Cb-5986 | 181 | B.25 |
| Cb-5987 | 182 | B.25 |
| Cb-5988 | 183 | B.25 |
| Cb-5989 | 184 | B.25 |
| Cb-5990 | 185 | B.25 |
| Cb-5991 | 186 | B.25 |
| Cb-5992 | 187 | B.25 |
| Cb-5993 | 188 | B.25 |
| Cb-5994 | 189 | B.25 |
| Cb-5995 | 190 | B.25 |
| Cb-5996 | 191 | B.25 |
| Cb-5997 | 192 | B.25 |
| Cb-5998 | 193 | B.25 |
| Cb-5999 | 194 | B.25 |
| Cb-6000 | 195 | B.25 |
| Cb-6001 | 196 | B.25 |
| Cb-6002 | 197 | B.25 |
| Cb-6003 | 198 | B.25 |
| Cb-6004 | 199 | B.25 |
| Cb-6005 | 200 | B.25 |
| Cb-6006 | 201 | B.25 |
| Cb-6007 | 202 | B.25 |
| Cb-6008 | 203 | B.25 |
| Cb-6009 | 204 | B.25 |
| Cb-6010 | 205 | B.25 |
| Cb-6011 | 206 | B.25 |
| Cb-6012 | 207 | B.25 |
| Cb-6013 | 208 | B.25 |
| Cb-6014 | 209 | B.25 |
| Cb-6015 | 210 | B.25 |
| Cb-6016 | 211 | B.25 |
| Cb-6017 | 212 | B.25 |
| Cb-6018 | 213 | B.25 |
| Cb-6019 | 214 | B.25 |
| Cb-6020 | 215 | B.25 |
| Cb-6021 | 1 | B.26 |
| Cb-6022 | 2 | B.26 |
| Cb-6023 | 3 | B.26 |
| Cb-6024 | 4 | B.26 |
| Cb-6025 | 5 | B.26 |
| Cb-6026 | 6 | B.26 |
| Cb-6027 | 7 | B.26 |
| Cb-6028 | 8 | B.26 |
| Cb-6029 | 9 | B.26 |
| Cb-6030 | 10 | B.26 |
| Cb-6031 | 11 | B.26 |
| Cb-6032 | 12 | B.26 |
| Cb-6033 | 13 | B.26 |
| Cb-6034 | 14 | B.26 |
| Cb-6035 | 15 | B.26 |
| Cb-6036 | 16 | B.26 |
| Cb-6037 | 17 | B.26 |
| Cb-6038 | 18 | B.26 |
| Cb-6039 | 19 | B.26 |
| Cb-6040 | 20 | B.26 |
| Cb-6041 | 21 | B.26 |
| Cb-6042 | 22 | B.26 |
| Cb-6043 | 23 | B.26 |
| Cb-6044 | 24 | B.26 |
| Cb-6045 | 25 | B.26 |
| Cb-6046 | 26 | B.26 |
| Cb-6047 | 27 | B.26 |
| Cb-6048 | 28 | B.26 |
| Cb-6049 | 29 | B.26 |
| Cb-6050 | 30 | B.26 |
| Cb-6051 | 31 | B.26 |
| Cb-6052 | 32 | B.26 |
| Cb-6053 | 33 | B.26 |
| Cb-6054 | 34 | B.26 |
| Cb-6055 | 35 | B.26 |
| Cb-6056 | 36 | B.26 |
| Cb-6057 | 37 | B.26 |
| Cb-6058 | 38 | B.26 |
| Cb-6059 | 39 | B.26 |
| Cb-6060 | 40 | B.26 |
| Cb-6061 | 41 | B.26 |
| Cb-6062 | 42 | B.26 |
| Cb-6063 | 43 | B.26 |
| Cb-6064 | 44 | B.26 |
| Cb-6065 | 45 | B.26 |
| Cb-6066 | 46 | B.26 |
| Cb-6067 | 47 | B.26 |
| Cb-6068 | 48 | B.26 |
| Cb-6069 | 49 | B.26 |
| Cb-6070 | 50 | B.26 |
| Cb-6071 | 51 | B.26 |
| Cb-6072 | 52 | B.26 |
| Cb-6073 | 53 | B.26 |
| Cb-6074 | 54 | B.26 |
| Cb-6075 | 55 | B.26 |
| Cb-6076 | 56 | B.26 |
| Cb-6077 | 57 | B.26 |
| Cb-6078 | 58 | B.26 |
| Cb-6079 | 59 | B.26 |
| Cb-6080 | 60 | B.26 |
| Cb-6081 | 61 | B.26 |
| Cb-6082 | 62 | B.26 |
| Cb-6083 | 63 | B.26 |
| Cb-6084 | 64 | B.26 |
| Cb-6085 | 65 | B.26 |
| Cb-6086 | 66 | B.26 |
| Cb-6087 | 67 | B.26 |
| Cb-6088 | 68 | B.26 |
| Cb-6089 | 69 | B.26 |
| Cb-6090 | 70 | B.26 |
| Cb-6091 | 71 | B.26 |
| Cb-6092 | 72 | B.26 |
| Cb-6093 | 73 | B.26 |
| Cb-6094 | 74 | B.26 |
| Cb-6095 | 75 | B.26 |
| Cb-6096 | 76 | B.26 |
| Cb-6097 | 77 | B.26 |
| Cb-6098 | 78 | B.26 |
| Cb-6099 | 79 | B.26 |
| Cb-6100 | 80 | B.26 |
| Cb-6101 | 81 | B.26 |
| Cb-6102 | 82 | B.26 |
| Cb-6103 | 83 | B.26 |
| Cb-6104 | 84 | B.26 |
| Cb-6105 | 85 | B.26 |
| Cb-6106 | 86 | B.26 |
| Cb-6107 | 87 | B.26 |
| Cb-6108 | 88 | B.26 |
| Cb-6109 | 89 | B.26 |
| Cb-6110 | 90 | B.26 |
| Cb-6111 | 91 | B.26 |
| Cb-6112 | 92 | B.26 |
| Cb-6113 | 93 | B.26 |
| Cb-6114 | 94 | B.26 |

| Comb. | Com. A | Com. B |
| --- | --- | --- |
| Cb-6115 | 95 | B.26 |
| Cb-6116 | 96 | B.26 |
| Cb-6117 | 97 | B.26 |
| Cb-6118 | 98 | B.26 |
| Cb-6119 | 99 | B.26 |
| Cb-6120 | 100 | B.26 |
| Cb-6121 | 101 | B.26 |
| Cb-6122 | 102 | B.26 |
| Cb-6123 | 103 | B.26 |
| Cb-6124 | 104 | B.26 |
| Cb-6125 | 105 | B.26 |
| Cb-6126 | 106 | B.26 |
| Cb-6127 | 107 | B.26 |
| Cb-6128 | 108 | B.26 |
| Cb-6129 | 109 | B.26 |
| Cb-6130 | 110 | B.26 |
| Cb-6131 | 111 | B.26 |
| Cb-6132 | 112 | B.26 |
| Cb-6133 | 113 | B.26 |
| Cb-6134 | 114 | B.26 |
| Cb-6135 | 115 | B.26 |
| Cb-6136 | 116 | B.26 |
| Cb-6137 | 117 | B.26 |
| Cb-6138 | 118 | B.26 |
| Cb-6139 | 119 | B.26 |
| Cb-6140 | 120 | B.26 |
| Cb-6141 | 121 | B.26 |
| Cb-6142 | 122 | B.26 |
| Cb-6143 | 123 | B.26 |
| Cb-6144 | 124 | B.26 |
| Cb-6145 | 125 | B.26 |
| Cb-6146 | 126 | B.26 |
| Cb-6147 | 127 | B.26 |
| Cb-6148 | 128 | B.26 |
| Cb-6149 | 129 | B.26 |
| Cb-6150 | 130 | B.26 |
| Cb-6151 | 131 | B.26 |
| Cb-6152 | 132 | B.26 |
| Cb-6153 | 133 | B.26 |
| Cb-6154 | 134 | B.26 |
| Cb-6155 | 135 | B.26 |
| Cb-6156 | 136 | B.26 |
| Cb-6157 | 137 | B.26 |
| Cb-6158 | 138 | B.26 |
| Cb-6159 | 139 | B.26 |
| Cb-6160 | 140 | B.26 |
| Cb-6161 | 141 | B.26 |
| Cb-6162 | 142 | B.26 |
| Cb-6163 | 143 | B.26 |
| Cb-6164 | 144 | B.26 |
| Cb-6165 | 145 | B.26 |
| Cb-6166 | 146 | B.26 |
| Cb-6167 | 147 | B.26 |
| Cb-6168 | 148 | B.26 |
| Cb-6169 | 149 | B.26 |
| Cb-6170 | 150 | B.26 |
| Cb-6171 | 151 | B.26 |
| Cb-6172 | 152 | B.26 |
| Cb-6173 | 153 | B.26 |
| Cb-6174 | 154 | B.26 |
| Cb-6175 | 155 | B.26 |
| Cb-6176 | 156 | B.26 |
| Cb-6177 | 157 | B.26 |
| Cb-6178 | 158 | B.26 |
| Cb-6179 | 159 | B.26 |
| Cb-6180 | 160 | B.26 |
| Cb-6181 | 161 | B.26 |
| Cb-6182 | 162 | B.26 |
| Cb-6183 | 163 | B.26 |
| Cb-6184 | 164 | B.26 |
| Cb-6185 | 165 | B.26 |
| Cb-6186 | 166 | B.26 |
| Cb-6187 | 167 | B.26 |
| Cb-6188 | 168 | B.26 |
| Cb-6189 | 169 | B.26 |
| Cb-6190 | 170 | B.26 |
| Cb-6191 | 171 | B.26 |
| Cb-6192 | 172 | B.26 |
| Cb-6193 | 173 | B.26 |
| Cb-6194 | 174 | B.26 |
| Cb-6195 | 175 | B.26 |
| Cb-6196 | 176 | B.26 |
| Cb-6197 | 177 | B.26 |
| Cb-6198 | 178 | B.26 |
| Cb-6199 | 179 | B.26 |
| Cb-6200 | 180 | B.26 |
| Cb-6201 | 181 | B.26 |
| Cb-6202 | 182 | B.26 |
| Cb-6203 | 183 | B.26 |
| Cb-6204 | 184 | B.26 |
| Cb-6205 | 185 | B.26 |
| Cb-6206 | 186 | B.26 |
| Cb-6207 | 187 | B.26 |
| Cb-6208 | 188 | B.26 |
| Cb-6209 | 189 | B.26 |
| Cb-6210 | 190 | B.26 |
| Cb-6211 | 191 | B.26 |
| Cb-6212 | 192 | B.26 |
| Cb-6213 | 193 | B.26 |
| Cb-6214 | 194 | B.26 |
| Cb-6215 | 195 | B.26 |
| Cb-6216 | 196 | B.26 |
| Cb-6217 | 197 | B.26 |
| Cb-6218 | 198 | B.26 |
| Cb-6219 | 199 | B.26 |
| Cb-6220 | 200 | B.26 |
| Cb-6221 | 201 | B.26 |
| Cb-6222 | 202 | B.26 |
| Cb-6223 | 203 | B.26 |
| Cb-6224 | 204 | B.26 |
| Cb-6225 | 205 | B.26 |
| Cb-6226 | 206 | B.26 |
| Cb-6227 | 207 | B.26 |
| Cb-6228 | 208 | B.26 |
| Cb-6229 | 209 | B.26 |
| Cb-6230 | 210 | B.26 |
| Cb-6231 | 211 | B.26 |
| Cb-6232 | 212 | B.26 |
| Cb-6233 | 213 | B.26 |
| Cb-6234 | 214 | B.26 |
| Cb-6235 | 215 | B.26 |

In another aspect of the present invention, the biopesticide is preferably a one biopesticide (L) selected from the groups (L1), (L3), (L5), (L7) and (L8) as further defined below.

In another aspect of the present invention, the invention relates to a composition comprising
1) a (thio)phosphoric acid triamide (T) as defined above and
2) at least one biopesticide (L) selected from the groups (L1), (L3), (L5), (L7) and (L8):
(L1) Microbial pesticides with fungicidal, bactericidal, viricidal and/or plant defense activator activity selected from:
   (L11) *Ampelomyces quisqualis*,
   (L12) *Aspergillus flavus*,
   (L13) *Aureobasidium pullulans*,
   (L14) *Bacillus amyloliquefaciens*,
   (L15) *Bacillus mojavensis*,
   (L16) *Bacillus pumilus*,
   (L17) *Bacillus simplex*,
   (L18) *Bacillus solisalsi*,
   (L19) *Bacillus subtilis*,
   (L20) *Bacillus subtilis* var. *amyloliquefaciens*,
   (L21) *Candida oleophila*, or *C. saitoana*,
   (L22) *Clavibacter michiganensis* (bacteriophages),
   (L23) *Coniothyrium minitans*,
   (L24) *Cryphonectria parasitica*,
   (L25) *Cryptococcus albidus*, (L26) *Dilophosphora alopecuri,*
(L27) *Fusarium oxysporum,*
(L28) *Clonostachys rosea* f. *catenulate* (also named *Gliocladium catenulatum*),
(L29) *Gliocladium roseum,*
(L30) *Lysobacter antibioticus,* or *L. enzymogenes,*
(L31) *Metschnikowia fructicola,*
(L32) *Microdochium dimerum,*
(L33) *Microsphaeropsis ochracea,*
(L34) *Muscodor albus,*
(L35) *Paenibacillus polymyxa,*
(L36) *Pantoea vagans,*
(L37) *Phlebiopsis gigantea,*
(L38) *Pseudomonas* sp., or *Pseudomonas chloraphis,*
(L39) *Pseudozyma flocculosa,*
(L40) *Pichia anomala,*
(L41) *Pythium oligandrum,*
(L42) *Sphaerodes mycoparasitica,*
(L43) *Streptomyces griseoviridis, S. lydicus,* or *S.violaceusniger,*
(L44) *Talaromyces flavus,*
(L45) *Trichoderma asperellum, T. atroviride, T. fertile, T. gamsii, T. harmatum, T. harzianum, T. stromaticum, T. virens* (also named *Gliocladium virens*), *T. viride,* or mixture of *T. harzianum* and *T. viride,* or mixture of *T. polysporum* and *T. harzianum,*
(L46) *Typhula phacorrhiza,*
(L47) *Ulocladium oudemansii,*
(L48) *Verticillium dahlia,*
(L49) zucchini yellow mosaic virus (avirulent strain);
(L3) Microbial pesticides with insecticidal, acaricidal, molluscidal and/or nematicidal activity selected from:
(L51) *Agrobacterium radiobacter,*
(L52) *Bacillus cereus,*
(L53) *Bacillus firmus,*
(L54) *Bacillus thuringiensis, B. t.* ssp. *aizawai, B. t.* ssp. *israelensis, B. t.* ssp. *galleriae, B. t.* ssp. *kurstaki,* or *B. t.* ssp. *tenebrionis,*
(L55) *Beauveria bassiana,* or *B. brongniartii,*
(L56) *Burkholderia* sp.,
(L57) *Chromobacterium subtsugae,*
(L58) *Cydia pomonella* granulosis virus,
(L59) *Cryptophlebia leucotreta* granulovirus (CrleGV),
(L60) *Isaria fumosorosea,*
(L61) *Heterorhabditis* bacteriophora,
(L62) *Lecanicillium longisporum,* or *L. muscarium* (formerly *Verticillium lecanii*),
(L63) *Metarhizium anisopliae,* or *M. anisopliae* var. *acridum,*
(L64) *Nomuraea rileyi,*
(L65) *Paecilomyces fumosoroseus,* or *P. lilacinus,*
(L66) *Paenibacillus popilliae,*
(L67) *Pasteuria* spp., *P. nishizawae, P. penetrans, P. ramose, P. reneformis, P. thornea,* or *P. usgae,*
(L68) *Pseudomonas fluorescens,*
(L69) *Steinernema carpocapsae, S. feltiae,* or *S. kraussei*;
(L5) Microbial pesticides with plant stress reducing, plant growth regulator, plant growth promoting and/or yield enhancing activity selected from:
(L81) *Azospirillum amazonense, A. brasilense, A. lipoferum, A. irakense,* or *A. halopraeferens,*
(L82) *Bradyrhizobium* sp., *B. elkanii, B. japonicum, B. liaoningense,* or *B. lupini,*
(L83) *Delftia acidovorans,*
(L84) VA *mycorrhiza* selected from the genera *Glomus, Acaulospora, Entrophosphora, Gigaspora, Scutellospora* and *Sclerocytis,*
(L85) VA *mycorrhiza* selected from the group consisting of *Glomus fasciculatum, G. caledonium, G. mosseae, G. versiforme, G. intraradices* and *G. etunicatum,*
(L86) *Mesorhizobium* sp.,
(L87) *Paenibacillus alvei,*
(L88) *Penicillium bilaiae,*
(L89) *Rhizobium leguminosarum* by. *phaseoli,* R. I. *trifolii,* R. I. by. *viciae,* or *R. tropici,*
(L90) *Sinorhizobium meliloti,*
(L91) *Enterobacter* spp., *E. ludwigii, E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. mori, E. nimipressuralis, E. oryzae, E. pulveris, E. pyrinus, E. radicincitans, E. taylorae, E. turicensis,* or *E. sakazakii,*
(L92) *Oxalobacteraceae* spp., *Herbaspirillum seropedicae* (DSM No.: 6445) (free-living nitrogen fixing bacterium), *Janthinobacterium lividum* (DSM No.: 1522) (violacein-producing bacterium), or *Pseudoduganella violaceinigra* (DSM No.: 15887) (violacein-producing bacterium);
(L7) Metabolites produced by the microbial pesticides selected from:
(L93) siderophores, bacillibactin
(L94) antibiotiics such as zwittermicin-A, kanosamine, polyoxine, bacilysin, violacein
(L95) enzymes such as alpha-amylase, chitinases, pektinases, phosphatase (acid and alkaline) and phytase
(L96) phytohormones and precursors thereof and volatile compounds, such as auxines, gibberellin-like substances, cytokinin-like compounds, acetoin, 2,3-butanediol, ethylene, indole acetic acid,
(L97) lipopeptides such as iturins, plipastatins, surfactins, agrastatin, agrastatin A, bacillomycin, bacillomycin D, fengycin,
(L98) antibacterial polyketides such as difficidin, macrolactin and bacilaene
(L99) antifungal metabolites such as pyrones, cytosporone, 6-pentyl-2H-pyran-2-one (also termed 6-pentyl-a-pyrone), koninginins (complex pyranes), in particular those metabolites produced by *Trichoderma* species,
(L8) Biochemical pesticides with insecticidal, acaricidal, molluscidal, pheromone and/or nematicidal activity selected from:
L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone (B.27), 2-methyl 1-butanol, methyl eugenol, methyl jasmonate (B.28), (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodes,* Catnip oil, Neem oil (B.29), Quillay extract (B.30), Tagetes oil.

Preferred metabolites are the above-listed lipopeptides (L97), in particular produced by *B. subtilis* and *B. amyloliquefaciens*. Further preferred metabolites are the antifungal metabolites (L99), in particular those produced by *Trichoderma* species, for example *T. viride, T. atroviride, T. aureoviride, T. harzianum, T. koningii*.

Accordingly, the present invention furthermore relates to compositions comprising as compound I (component 1, referred to as "Co.1") a (thio)phosphoric acid triamide (T) as defined herein above and as compound II (component 2, referred to as "Co. 2") a biopesticide as defined herein, i.e. a combination of component 1 and 2. In preferred embodiments, such compositions may be selected from the component 1 of Table 3 in the column titled "Co. 1" and from component 2 of Table 3 in the column titled "Co. 2". N-n-butylthiophosphoric acid triamide (NBPT) is referred to as "(W)". N-(n-propyl) thiophosphoric acid triamide (NPPT) or any mixtures comprising NBPT and NPPT, wherein NBPT is present in amounts of from 1 to 99.99 wt. %, more preferably from 10 to 99.9 wt. %, most preferably from 20 to 99 wt. %, particularly preferably from 30 to 98 wt. %, more particularly preferably from 40 to 95 wt. %, most particularly preferably from 50 to 90 wt. %, especially from 60 to 85 wt. %, especially preferably from 72 to 80 wt. %, for example from 74 to 77 wt. %, in each case based on the total weight of the (thio)phosphoric acid triamides (T) contained in the composition (Q), is referred to as (Y). NBPT and/or NPPT but not comprising any nitrification inhibitor of the compound of formula I is referred to as (Z), thus, all compositions or mixtures X223 to X333 do not comprise any nitrification inhibitor of the compound of formula I. NBPT and/or NPPT and additionally comprising a urea-containing fertilizer is referred to as (U), wherein such urea-containing fertilizer is preferably urea, formaldehyde urea, UAN, urea sulfur, stabilized urea, urea based NPK-fertilizers, or urea ammonium sulfate and is most preferably UAN. The application of the compositions or mixtures X1 to X444 can be carried out in a way that its individual components (for example Co. 1 and Co. 2, in case of X334 to X444 NBPT/NPPT and the urea-containing fertilizer and Co. 2) are applied either simultaneously or with a time lag as further specified below. Preferred embodiments thus include the specified combinations or compositions comprising component 1 and 2 as defined in the compositions or mixtures X1 to X444 of the following Table 3:

| Mixt. | Co. 1 | Co. 2 |
|---|---|---|
| X1 | (W) | L11 |
| X2 | (W) | L12 |
| X3 | (W) | L13 |
| X4 | (W) | L14 |
| X5 | (W) | L15 |
| X6 | (W) | L16 |
| X7 | (W) | L17 |
| X8 | (W) | L18 |
| X9 | (W) | L19 |
| X10 | (W) | L20 |
| X11 | (W) | L21 |
| X12 | (W) | L22 |
| X13 | (W) | L23 |
| X14 | (W) | L24 |
| X15 | (W) | L25 |
| X16 | (W) | L26 |
| X17 | (W) | L27 |
| X18 | (W) | L28 |
| X19 | (W) | L29 |
| X20 | (W) | L30 |
| X21 | (W) | L31 |
| X22 | (W) | L32 |
| X23 | (W) | L33 |
| X24 | (W) | L34 |
| X25 | (W) | L35 |
| X26 | (W) | L36 |
| X27 | (W) | L37 |
| X28 | (W) | L38 |
| X29 | (W) | L39 |
| X30 | (W) | L40 |
| X31 | (W) | L41 |
| X32 | (W) | L42 |
| X33 | (W) | L43 |
| X34 | (W) | L44 |
| X35 | (W) | L45 |
| X36 | (W) | L46 |
| X37 | (W) | L47 |
| X38 | (W) | L48 |
| X39 | (W) | L49 |
| X40 | (W) | L51 |
| X41 | (W) | L52 |
| X42 | (W) | L53 |
| X43 | (W) | L54 |
| X44 | (W) | L55 |
| X45 | (W) | L56 |
| X46 | (W) | L57 |
| X47 | (W) | L58 |
| X48 | (W) | L59 |
| X49 | (W) | L60 |
| X50 | (W) | L61 |
| X51 | (W) | L62 |
| X52 | (W) | L63 |
| X53 | (W) | L64 |
| X54 | (W) | L65 |
| X55 | (W) | L66 |
| X56 | (W) | L67 |
| X57 | (W) | L68 |
| X58 | (W) | L69 |
| X59 | (W) | L81 |
| X60 | (W) | L82 |
| X61 | (W) | L83 |
| X62 | (W) | L84 |
| X63 | (W) | L85 |
| X64 | (W) | L86 |
| X65 | (W) | L87 |
| X66 | (W) | L88 |
| X67 | (W) | L89 |
| X68 | (W) | L90 |
| X69 | (W) | L91 |
| X70 | (W) | L92 |
| X71 | (W) | L93 |
| X72 | (W) | L94 |
| X73 | (W) | L95 |
| X74 | (W) | L96 |
| X75 | (W) | L97 |
| X76 | (W) | L98 |
| X77 | (W) | L99 |
| X78 | (W) | L1 |
| X79 | (W) | L3 |
| X80 | (W) | L5 |
| X81 | (W) | L7 |
| X82 | (W) | B.1 |
| X83 | (W) | B.2 |
| X84 | (W) | B.3 |
| X85 | (W) | B.4 |
| X86 | (W) | B.5 |
| X87 | (W) | B.6 |
| X88 | (W) | B.7 |
| X89 | (W) | B.8 |
| X90 | (W) | B.9 |
| X91 | (W) | B.10 |
| X92 | (W) | B.11 |
| X93 | (W) | B.12 |
| X94 | (W) | B.13 |
| X95 | (W) | B.14 |
| X96 | (W) | B.15 |
| X97 | (W) | B.16 |
| X98 | (W) | B.17 |
| X99 | (W) | B.18 |
| X100 | (W) | B.19 |
| X101 | (W) | B.20 |
| X102 | (W) | B.21 |
| X103 | (W) | B.22 |
| X104 | (W) | B.23 |
| X105 | (W) | B.24 |

| Mixt. | Co. 1 | Co. 2 |
|---|---|---|
| X106 | (W) | B.25 |
| X107 | (W) | B.26 |
| X108 | (W) | B.27 |
| X109 | (W) | B.28 |
| X110 | (W) | B.29 |
| X111 | (W) | L8 |
| X112 | (Y) | L11 |
| X113 | (Y) | L12 |
| X114 | (Y) | L13 |
| X115 | (Y) | L14 |
| X116 | (Y) | L15 |
| X117 | (Y) | L16 |
| X118 | (Y) | L17 |
| X119 | (Y) | L18 |
| X120 | (Y) | L19 |
| X121 | (Y) | L20 |
| X122 | (Y) | L21 |
| X123 | (Y) | L22 |
| X124 | (Y) | L23 |
| X125 | (Y) | L24 |
| X126 | (Y) | L25 |
| X127 | (Y) | L26 |
| X128 | (Y) | L27 |
| X129 | (Y) | L28 |
| X130 | (Y) | L29 |
| X131 | (Y) | L30 |
| X132 | (Y) | L31 |
| X133 | (Y) | L32 |
| X134 | (Y) | L33 |
| X135 | (Y) | L34 |
| X136 | (Y) | L35 |
| X137 | (Y) | L36 |
| X138 | (Y) | L37 |
| X139 | (Y) | L38 |
| X140 | (Y) | L39 |
| X141 | (Y) | L40 |
| X142 | (Y) | L41 |
| X143 | (Y) | L42 |
| X144 | (Y) | L43 |
| X145 | (Y) | L44 |
| X146 | (Y) | L45 |
| X147 | (Y) | L46 |
| X148 | (Y) | L47 |
| X149 | (Y) | L48 |
| X150 | (Y) | L49 |
| X151 | (Y) | L51 |
| X152 | (Y) | L52 |
| X153 | (Y) | L53 |
| X154 | (Y) | L54 |
| X155 | (Y) | L55 |
| X156 | (Y) | L56 |
| X157 | (Y) | L57 |
| X158 | (Y) | L58 |
| X159 | (Y) | L59 |
| X160 | (Y) | L60 |
| X161 | (Y) | L61 |
| X162 | (Y) | L62 |
| X163 | (Y) | L63 |
| X164 | (Y) | L64 |
| X165 | (Y) | L65 |
| X166 | (Y) | L66 |
| X167 | (Y) | L67 |
| X168 | (Y) | L68 |
| X169 | (Y) | L69 |
| X170 | (Y) | L81 |
| X171 | (Y) | L82 |
| X172 | (Y) | L83 |
| X173 | (Y) | L84 |
| X174 | (Y) | L85 |
| X175 | (Y) | L86 |
| X176 | (Y) | L87 |
| X177 | (Y) | L88 |
| X178 | (Y) | L89 |
| X179 | (Y) | L90 |
| X180 | (Y) | L91 |
| X181 | (Y) | L92 |
| X182 | (Y) | L93 |
| X183 | (Y) | L94 |
| X184 | (Y) | L95 |
| X185 | (Y) | L96 |
| X186 | (Y) | L97 |
| X187 | (Y) | L98 |
| X188 | (Y) | L99 |
| X189 | (Y) | L1 |
| X190 | (Y) | L3 |
| X191 | (Y) | L5 |
| X192 | (Y) | L7 |
| X193 | (Y) | B.1 |
| X194 | (Y) | B.2 |
| X195 | (Y) | B.3 |
| X196 | (Y) | B.4 |
| X197 | (Y) | B.5 |
| X198 | (Y) | B.6 |
| X199 | (Y) | B.7 |
| X200 | (Y) | B.8 |
| X201 | (Y) | B.9 |
| X202 | (Y) | B.10 |
| X203 | (Y) | B.11 |
| X204 | (Y) | B.12 |
| X205 | (Y) | B.13 |
| X206 | (Y) | B.14 |
| X207 | (Y) | B.15 |
| X208 | (Y) | B.16 |
| X209 | (Y) | B.17 |
| X210 | (Y) | B.18 |
| X211 | (Y) | B.19 |
| X212 | (Y) | B.20 |
| X213 | (Y) | B.21 |
| X214 | (Y) | B.22 |
| X215 | (Y) | B.23 |
| X216 | (Y) | B.24 |
| X217 | (Y) | B.25 |
| X218 | (Y) | B.26 |
| X219 | (Y) | B.27 |
| X220 | (Y) | B.28 |
| X221 | (Y) | B.29 |
| X222 | (Y) | L8 |
| X223 | (Z) | L11 |
| X224 | (Z) | L12 |
| X225 | (Z) | L13 |
| X226 | (Z) | L14 |
| X227 | (Z) | L15 |
| X228 | (Z) | L16 |
| X229 | (Z) | L17 |
| X230 | (Z) | L18 |
| X231 | (Z) | L19 |
| X232 | (Z) | L20 |
| X233 | (Z) | L21 |
| X234 | (Z) | L22 |
| X235 | (Z) | L23 |
| X236 | (Z) | L24 |
| X237 | (Z) | L25 |
| X238 | (Z) | L26 |
| X239 | (Z) | L27 |
| X240 | (Z) | L28 |
| X241 | (Z) | L29 |
| X242 | (Z) | L30 |
| X243 | (Z) | L31 |
| X244 | (Z) | L32 |
| X245 | (Z) | L33 |
| X246 | (Z) | L34 |
| X247 | (Z) | L35 |
| X248 | (Z) | L36 |
| X249 | (Z) | L37 |
| X250 | (Z) | L38 |
| X251 | (Z) | L39 |
| X252 | (Z) | L40 |
| X253 | (Z) | L41 |
| X254 | (Z) | L42 |
| X255 | (Z) | L43 |
| X256 | (Z) | L44 |
| X257 | (Z) | L45 |
| X258 | (Z) | L46 |
| X259 | (Z) | L47 |

| Mixt. | Co. 1 | Co. 2 |
|---|---|---|
| X260 | (Z) | L48 |
| X261 | (Z) | L49 |
| X262 | (Z) | L51 |
| X263 | (Z) | L52 |
| X264 | (Z) | L53 |
| X265 | (Z) | L54 |
| X266 | (Z) | L55 |
| X267 | (Z) | L56 |
| X268 | (Z) | L57 |
| X269 | (Z) | L58 |
| X270 | (Z) | L59 |
| X271 | (Z) | L60 |
| X272 | (Z) | L61 |
| X273 | (Z) | L62 |
| X274 | (Z) | L63 |
| X275 | (Z) | L64 |
| X276 | (Z) | L65 |
| X277 | (Z) | L66 |
| X278 | (Z) | L67 |
| X279 | (Z) | L68 |
| X280 | (Z) | L69 |
| X281 | (Z) | L81 |
| X282 | (Z) | L82 |
| X283 | (Z) | L83 |
| X284 | (Z) | L84 |
| X285 | (Z) | L85 |
| X286 | (Z) | L86 |
| X287 | (Z) | L87 |
| X288 | (Z) | L88 |
| X289 | (Z) | L89 |
| X290 | (Z) | L90 |
| X291 | (Z) | L91 |
| X292 | (Z) | L92 |
| X293 | (Z) | L93 |
| X294 | (Z) | L94 |
| X295 | (Z) | L95 |
| X296 | (Z) | L96 |
| X297 | (Z) | L97 |
| X298 | (Z) | L98 |
| X299 | (Z) | L99 |
| X300 | (Z) | L1 |
| X301 | (Z) | L3 |
| X302 | (Z) | L5 |
| X303 | (Z) | L7 |
| X304 | (Z) | B.1 |
| X305 | (Z) | B.2 |
| X306 | (Z) | B.3 |
| X307 | (Z) | B.4 |
| X308 | (Z) | B.5 |
| X309 | (Z) | B.6 |
| X310 | (Z) | B.7 |
| X311 | (Z) | B.8 |
| X312 | (Z) | B.9 |
| X313 | (Z) | B.10 |
| X314 | (Z) | B.11 |
| X315 | (Z) | B.12 |
| X316 | (Z) | B.13 |
| X317 | (Z) | B.14 |
| X318 | (Z) | B.15 |
| X319 | (Z) | B.16 |
| X320 | (Z) | B.17 |
| X321 | (Z) | B.18 |
| X322 | (Z) | B.19 |
| X323 | (Z) | B.20 |
| X324 | (Z) | B.21 |
| X325 | (Z) | B.22 |
| X326 | (Z) | B.23 |
| X327 | (Z) | B.24 |
| X328 | (Z) | B.25 |
| X329 | (Z) | B.26 |
| X330 | (Z) | B.27 |
| X331 | (Z) | B.28 |
| X332 | (Z) | B.29 |
| X333 | (Z) | L8 |
| X334 | (U) | L11 |
| X335 | (U) | L12 |
| X336 | (U) | L13 |
| X337 | (U) | L14 |
| X338 | (U) | L15 |
| X339 | (U) | L16 |
| X340 | (U) | L17 |
| X341 | (U) | L18 |
| X342 | (U) | L19 |
| X343 | (U) | L20 |
| X344 | (U) | L21 |
| X345 | (U) | L22 |
| X346 | (U) | L23 |
| X347 | (U) | L24 |
| X348 | (U) | L25 |
| X349 | (U) | L26 |
| X350 | (U) | L27 |
| X351 | (U) | L28 |
| X352 | (U) | L29 |
| X353 | (U) | L30 |
| X354 | (U) | L31 |
| X355 | (U) | L32 |
| X356 | (U) | L33 |
| X357 | (U) | L34 |
| X358 | (U) | L35 |
| X359 | (U) | L36 |
| X360 | (U) | L37 |
| X361 | (U) | L38 |
| X362 | (U) | L39 |
| X363 | (U) | L40 |
| X364 | (U) | L41 |
| X365 | (U) | L42 |
| X366 | (U) | L43 |
| X367 | (U) | L44 |
| X368 | (U) | L45 |
| X369 | (U) | L46 |
| X370 | (U) | L47 |
| X371 | (U) | L48 |
| X372 | (U) | L49 |
| X373 | (U) | L51 |
| X374 | (U) | L52 |
| X375 | (U) | L53 |
| X376 | (U) | L54 |
| X377 | (U) | L55 |
| X378 | (U) | L56 |
| X379 | (U) | L57 |
| X380 | (U) | L58 |
| X381 | (U) | L59 |
| X382 | (U) | L60 |
| X383 | (U) | L61 |
| X384 | (U) | L62 |
| X385 | (U) | L63 |
| X386 | (U) | L64 |
| X387 | (U) | L65 |
| X388 | (U) | L66 |
| X389 | (U) | L67 |
| X390 | (U) | L68 |
| X391 | (U) | L69 |
| X392 | (U) | L81 |
| X393 | (U) | L82 |
| X394 | (U) | L83 |
| X395 | (U) | L84 |
| X396 | (U) | L85 |
| X397 | (U) | L86 |
| X398 | (U) | L87 |
| X399 | (U) | L88 |
| X400 | (U) | L89 |
| X401 | (U) | L90 |
| X402 | (U) | L91 |
| X403 | (U) | L92 |
| X404 | (U) | L93 |
| X405 | (U) | L94 |
| X406 | (U) | L95 |
| X407 | (U) | L96 |
| X408 | (U) | L97 |
| X409 | (U) | L98 |
| X410 | (U) | L99 |
| X411 | (U) | L1 |
| X412 | (U) | L3 |
| X413 | (U) | L5 |

-continued

| Mixt. | Co. 1 | Co. 2 |
|---|---|---|
| X414 | (U) | L7 |
| X415 | (U) | B.1 |
| X416 | (U) | B.2 |
| X417 | (U) | B.3 |
| X418 | (U) | B.4 |
| X419 | (U) | B.5 |
| X420 | (U) | B.6 |
| X421 | (U) | B.7 |
| X422 | (U) | B.8 |
| X423 | (U) | B.9 |
| X424 | (U) | B.10 |
| X425 | (U) | B.11 |
| X426 | (U) | B.12 |
| X427 | (U) | B.13 |
| X428 | (U) | B.14 |
| X429 | (U) | B.15 |
| X430 | (U) | B.16 |
| X431 | (U) | B.17 |
| X432 | (U) | B.18 |
| X433 | (U) | B.19 |
| X434 | (U) | B.20 |
| X435 | (U) | B.21 |
| X436 | (U) | B.22 |
| X437 | (U) | B.23 |
| X438 | (U) | B.24 |
| X439 | (U) | B.25 |
| X440 | (U) | B.26 |
| X441 | (U) | B.27 |
| X442 | (U) | B.28 |
| X443 | (U) | B.29 |
| X444 | (U) | L8 |

In further specific embodiments, the present invention relates to the use of compositions for increasing the health of a plant, which comprise the combination of a biopesticide and a nitrification inhibitor as defined herein and additionally a fertilizer. Such compositions may be used and provided as agricultural mixtures.

In further specific embodiments, the present invention relates to the use of compositions for increasing the health of a plant, which comprise the combination of a biopesticide and (T) and additionally a fertilizer, particularly which comprise the combination of a biopesticide and (T) as specified in Table 3 and additionally a fertilizer, wherein the fertilizer is most preferably a urea-containing fertilizer. Such compositions may be used and provided as agricultural mixtures.

In further specific embodiments, the present invention relates to the use of compositions for increasing the biopesticidal activity of a biopesticide, which comprise the combination of a biopesticide and (T) and additionally a fertilizer, particularly which comprise the combination of a biopesticide and (T) as specified in Table 3 and additionally a fertilizer, wherein the fertilizer is most preferably a urea-containing fertilizer. Such compositions may be used and provided as agricultural mixtures.

The use of a combination as defined herein above, in particular of a combination of (T) or a nitrification inhibitor as defined herein above and a biopesticide as defined herein above, or of a composition as defined herein for increasing the health of a plant may be a single use, or it may be a repeated use. As single use, the combination or corresponding compositions may be provided to their target sites, e.g. soil or loci, or objects, e.g. plants, only once in a physiologically relevant time interval, e.g. once a year, or once every 2 to 5 years, or once during the lifetime of a plant.

In other embodiments, the use may be repeated at least once per time period, e.g. the combination as defined herein above, or a composition as defined herein may be used for increasing the health of a plant two times within a time interval of days, weeks or months. The term "at least once" as used in the context of a use of the combination means that the combination may be used two times, or several times, i.e. that a repetition or multiple repetitions of an application or treatment with the combinationmay be envisaged. Such a repetition may a 2 times, 3 times, 4 times, 5 times, 6 times, 7 times, 8 times, 9 times, 10 times or more frequent repetition of the use.

The combination according to the present invention or its components may be used in any suitable form. For example, it may be used as coated or uncoated granule, in liquid or semi-liquid form, as sprayable entity, or in irrigation approaches etc. In further embodiments, the components may be used in different forms. In specific embodiments, the components may be applied or used as such, i.e.without formulations, fertilizer, additional water, coatings, or any further ingredient.

The term "irrigation" as used herein refers to the watering of plants or loci or soils or soil substituents where a plant grows or is intended to grow, wherein said watering includes the provision of the combination or a corresponding composition according to the present invention together with water.

In a further aspect the invention relates to a composition for increasing the health of a plant comprising (T) or at least one nitrification inhibitor wherein said nitrification inhibitor is a compound of formula I or a derivative as defined herein above; and at least one biopesticide as defined herein above. In a preferred embodiment, the composition comprises the combination of a nitrification inhibitor or (T) and a biopesticide as defined in Table 2 or Table 3, supra.

In further specific embodiments, the agricultural composition further comprises a carrier.

The term "composition for increasing the health of a plant" as used herein refers to a composition which is suitable, e.g. comprises effective concentrations and amounts of ingredients such as (T) or nitrification inhibitors, in particular compounds of formula I or derivatives as defined herein, and biopesticides for increasing the health of a plant. This includes the reduction of nitrification in any context or environment in which nitrification may occur and the reduction of biotic stress factors due to a fungicidal effect to fungi such as phytopathogenic fungi. In one embodiment, the nitrification and biotic stress may be reduced in or on or at the locus of a plant. Typically, the nitrification may be reduced in the root zone of a plant. In specific embodiments, the composition may be an agricultural composition, i.e. a composition adapated to the use in the agricultural field. "Effective amounts" or "effective concentrations" of (T) or nitrification inhibitors and biopesticides as defined herein may be determined according to suitable in vitro and in vivo testings known to the skilled person. These amounts and concentrations may be adjusted to the locus, plant, soil, climate conditions or any other suitable parameter which may have an influence on nitrification processes, and/or on competitive plant growth.

An "carrier" as used herein is a substance or composition which facilitates the delivery and/or release of the ingredients to the place or lcous of destination. The term includes, for instance, agrochemical carriers which facilitate the delivery and/or release of agrochemicals in their field of use, in particular on or into plants.

Examples of suitable carriers include solid carriers such as phytogels, or hydrogels, or mineral earths e.g. silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., urea, urea based NPK, UAN, ammonium sulfate, ammonium phosphate, ammonium nitrate, ureas, and products of vegetable origin, such as cereal meal, tree bark meal, wood meal and nutshell meal, cellulose powders and other solid carriers. Further suitable examples of carriers include fumed silica or precipitated silica, which may, for instance, be used in solid formulations as flow aid, anti-caking aid, milling aid and as carrier for liquid active ingredients. Additional examples of suitable carriers are microparticles, for instance microparticles which stick to plant leaves and release their content over a certain period of time. In specific embodiments, agrochemical carriers such as composite gel microparticles that can be used to deliver plant-protection active principles, e.g. as described in U.S. Pat. No. 6,180,141; or compositions comprising at least one phytoactive compound and an encapsulating adjuvant, wherein the adjuvant comprises a fungal cell or a fragment thereof, e.g. as described in WO 2005/102045; or carrier granules, coated with a lipophilic tackifier on the surface, wherein the carrier granule adheres to the surface of plants, grasses and weeds, e.g. as disclosed in US 2007/0280981 may be used. In further specific embodiments, such carriers may include specific, strongly binding molecule which assure that the carrier sticks to the plant till its content is completely delivered. For instance, the carrier may be or comprise cellulose binding domains (CBDs) have been described as useful agents for attachment of molecular species to cellulose (see U.S. Pat. No. 6,124,117); or direct fusions between a CBD and an enzyme; or a multifunctional fusion protein which may be used for delivery of encapsulated agents, wherein the multifunctional fusion proteins may consist of a first binding domain which is a carbohydrate binding domain and a second binding domain, wherein either the first binding domain or the second binding domain can bind to a microparticle (see also WO 03/031477). Further suitable examples of carriers include bifunctional fusion proteins consisting of a CBD and an anti-RR6 antibody fragment binding to a microparticle, which complex may be deposited onto treads or cut grass (see also WO 03/031477). In another specific embodiment the carrier may be active ingredient carrier granules that adhere to the surface of plants, grasses and weeds etc. using a moisture-active coating, for instance including gum arabic, guar gum, gum karaya, gum tragacanth and locust bean gum. Upon application of the inventive granule onto a plant surface, water from precipitation, irrigation, dew, co-application with the granules from special application equipment, or guttation water from the plant itself may provide sufficient moisture for adherence of the granule to the plant surface (see also US 2007/0280981).

In another specific embodiment the carrier, e.g. an agrochemical carrier may be or comprise polyaminoacids. Polyaminoacids may be obtained according to any suitable process, e.g. by polymerization of single or multiple amino acids such as glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, histidine and/or ornithine. Polyaminoacids may be combined with a combination of a nitrification inhibitor or (T) and a biopesticide according to the present invention and, in certain embodiments, also with further carriers, e.g. agrochemical carriers as mentioned herein above, or other nitrification inhibitors as mentioned herein in any suitable ratio. For example, polyaminoacids may be combined with (T) or a nitrification inhibitor according to the present invention in a ratio of 1 to 10 (polyaminoacids) vs. 0.5 to 2 (combination according to the present invention, or (T) or nitrification inhibitor according to the present invention).

For compositions according to the invention comprising nitrification inhibitor as defined herein above and a biopesticide, the weight ratio of the nitrification inhibitor as defined herein above and the biopesticide generally depends from the properties of the active substances used, usually it is in the range of from 1:1000 to 1000:1, regularly in the range of from 1:500 to 500:1, preferably in the range of from 1:250 to 250:1, more preferably in the range of from 1:100 to 100:1, most preferably in the range of from 1:70 to 70:1, particularly preferably in the range of from 1:50 to 50:1, particularly more preferably in the range of from 1:30 to 30:1, particularly most preferably in the range from 1:20 to 20:1, particularly in the range of from 1:15 to 15:1, especially preferably in the range of from 1:10 to 10:1, especially more preferably in the range of from 1:8 to 8:1, especially most preferably in the range of from 1:6.5 to 6.5:1, especially in the range of from 1:5 to 5:1, in particular preferably in the range of 1:4 to 4:1, in particular more preferably in the range of from 1:3 to 3:1, in particular most preferably in the range of from 2.5:1 to 1:2.5, in particular in the range of from 1:2 to 2:1, for example in the range of from 1:1.5 to 1.5:1. For compositions according to the invention, the weight ratio of the nitrification inhibitor as defined herein above and the biopesticide generally depends from the properties of the active substances used, usually it is not more than 1000:1, regularly not more than 250:1, preferably not more than 100:1, more preferably not more than 50:1, most preferably not more than 30:1, particularly preferably not more than 15:1, particularly more preferably not more than 8:1, particularly most preferably not more than 4:1, particularly not more than 2:1, especially preferably not more than 1:1, especially more preferably not more than 1:2, especially most preferably not more than 1:4, especially not more than 1:8, in particular preferably not more than 1:15, in particular more preferably not more than 1:30, in particular most preferably not more than 1:50, in particular not more than 1:100, for example preferably not more than 1:250, for example not more than 1:1000. For compositions according to the invention, the weight ratio of the nitrification inhibitor as defined herein above and the biopesticide generally depends from the properties of the active substances used, usually it is at least 1000:1, regularly at least 250:1, preferably at least 100:1, more preferably at least 50:1, most preferably at least 30:1, particularly preferably at least 15:1, particularly more preferably at least 8:1, particularly most preferably at least 4:1, particularly at least 2:1, especially preferably at least 1:1, especially more preferably at least 1:2, especially most preferably at least 1:4, especially at least 1:8, in particular preferably at least 1:15, in particular more preferably at least 1:30, in particular most preferably at least 1:50, in particular at least 1:100, for example preferably at least 1:250, for example at least 1:1000.

For compositions according to the invention comprising (T) and a biopesticide, the weight ratio of (T) and the biopesticide generally depends from the properties of the active substances used, usually it is in the range of from 1:1000 to 1000:1, regularly in the range of from 1:500 to 500:1, preferably in the range of from 1:250 to 250:1, more preferably in the range of from 1:100 to 100:1, most preferably in the range of from 1:70 to 70:1, particularly preferably in the range of from 1:50 to 50:1, particularly more preferably in the range of from 1:30 to 30:1, particularly most preferably in the range from 1:20 to 20:1, particularly in the range of from 1:15 to 15:1, especially preferably in the range of from 1:10 to 10:1, especially more preferably in the range of from 1:8 to 8:1, especially most preferably in the range of from 1:6.5 to 6.5:1, especially in the range of from 1:5 to 5:1, in particular preferably in the range of 1:4 to 4:1, in particular more preferably in the range of from 1:3 to 3:1, in particular most preferably in the range of from 2.5:1 to 1:2.5, in particular in the range of from 1:2 to 2:1, for example in the range of from 1:1.5 to 1.5:1. For compositions according to the invention, the weight ratio of (T) and the biopesticide generally depends from the properties of the active substances used, usually it is not more than 1000:1, regularly not more than 250:1, preferably not more than 100:1, more preferably not more than 50:1, most preferably not more than 30:1, particularly preferably not more than 15:1, particularly more preferably not more than 8:1, particularly most preferably not more than 4:1, particularly not more than 2:1, especially preferably not more than 1:1, especially more preferably not more than 1:2, especially most preferably not more than 1:4, especially not more than 1:8, in particular preferably not more than 1:15, in particular more preferably not more than 1:30, in particular most preferably not more than 1:50, in particular not more than 1:100, for example preferably not more than 1:250, for example not more than 1:1000. For compositions according to the invention, the weight ratio of (T) and the biopesticide generally depends on the properties of the active substances used, usually it is at least 1000:1, regularly at least 250:1, preferably at least 100:1, more preferably at least 50:1, most preferably at least 30:1, particularly preferably at least 15:1, particularly more preferably at least 8:1, particularly most preferably at least 4:1, particularly at least 2:1, especially preferably at least 1:1, especially more preferably at least 1:2, especially most preferably at least 1:4, especially at least 1:8, in particular preferably at least 1:15, in particular more preferably at least 1:30, in particular most preferably at least 1:50, in particular at least 1:100, for example preferably at least 1:250, for example at least 1:1000.

The composition for increasing the health of a plant comprising at least one nitrification inhibitor as defined herein may further comprise additional ingredients, for example at least one pesticidal compound. For example, the composition may additionally comprise at least one herbicidal compound and/or at least one fungicidal compound and/or at least one insecticidal and/or nematicidal compound.

In further embodiments, the composition may, in addition to the above indicated ingredients, in particular in addition (T) or to the nitrification inhibitor of the compound of formula I, further comprise one or more alternative or additional nitrification inhibitors. Examples of envisaged alternative or additional nitrification inhibitors are linoleic acid, alpha-linolenic acid, methyl p-coumarate, methyl ferulate, methyl 3-(4-hydroxyphenyl) propionate (MHPP), Karanjin, neem-extract, including various compounds such as neemoil-coated fertilizers, neem-coated fertilizers, nimin-coated fertilizers and fertilizers with neem cake from the Indian neem tree (*Azadirachta indica*), brachialacton, p-benzoquinone sorgoleone, 2-chloro-6-(trichloromethyl)pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DM P), 1,2,4-triazole, thiourea (TU), N-(1H-pyrazolyl-methyl)acetamides such as N-((3(5)-methyl-1H-pyrazole-1-yl)methyl)acetamide, and N-(1H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, N-(3(5),4-dimethyl-pyrazole-1-ylmethyl)-formamide, mixtures of 3,4-dimethylpyrazole phospate succinic acid and 4,5-dimethylpyrazole phosphate succinic acid, neem, products based on ingredients of neem, cyan amide, melamine, zeolite powder, catechol, benzoquinone, sodium tetra borate, and zinc sulfate.

In a preferred embodiment, the composition according to the present invention may comprise a combination of a biopesticide as defined herein above, of (T) or the nitrification inhibitor of the compound of formula I and 2-chloro-6-(trichloromethyl)-pyridine (nitrapyrin or N-serve).

In a further preferred embodiment, the composition according to the present invention may comprise a combination of a biopesticide as defined herein above, of (T) or the nitrification inhibitor of the compound of formula I and 5-ethoxy-3-trichloromethyl-1,2,4-thiodiazole (terrazole, etridiazole).

In a further preferred embodiment, the composition according to the present invention may comprise a combination of a biopesticide as defined herein above, of (T) or the nitrification inhibitor of the compound of formula I and dicyandiamide (DCD, DIDIN).

In a further preferred embodiment, the composition according to the present invention may comprise a combination of a biopesticide as defined herein above, of (T) or the nitrification inhibitor of the compound of formula I and 3,4-dimethyl pyrazole phosphate (DMPP, ENTEC).

In a further preferred embodiment, the composition according to the present invention may comprise a combination of a biopesticide as defined herein above, of (T) or the nitrification inhibitor of the compound of formula I and 2-amino-4-chloro-6-methylpyrimidine (AM).

In a further preferred embodiment, the composition according to the present invention may comprise a combination of a biopesticide as defined herein above, of (T) or the nitrification inhibitor of the compound of formula I and 2-mercapto-benzothiazole (MBT).

In a further preferred embodiment, the composition according to the present invention may comprise a combination of a biopesticide as defined herein above, of (T) or the nitrification inhibitor of the compound of formula I and 2-sulfanilamidothiazole (ST).

In a further preferred embodiment, the composition according to the present invention may comprise a combination of a biopesticide as defined herein above, of (T) or the nitrification inhibitor of the compound of formula I and 3-methylpyrazol (3-MP).

In a further preferred embodiment, the composition according to the present invention may comprise a combination of a biopesticide as defined herein above, of (T) or the nitrification inhibitor of the compound of formula I and 3,5-dimethylpyrazole (DMP).

In a further preferred embodiment, the composition according to the present invention may comprise a combination of a biopesticide as defined herein above, of (T) or the nitrification inhibitor of the compound of formula I and 1,2,4-triazol.

In a further preferred embodiment, the composition according to the present invention may comprise a combination of a biopesticide as defined herein above, of (T) or the nitrification inhibitor of the compound of formula I and thiourea (TU).

In yet another preferred embodiment, the composition according to the present invention may comprise a combination of a biopesticide as defined herein above, of (T) or the nitrification inhibitor of the compound of formula I and linoleic acid.

In yet another preferred embodiment, the composition according to the present invention may comprise a combination of a biopesticide as defined herein above, of (T) or the nitrification inhibitor of the compound of formula I and alpha-linolenic acid.

In yet another preferred embodiment, the composition according to the present invention may comprise a combination of a biopesticide as defined herein above, of (T) or the nitrification inhibitor of the compound of formula I and methyl p-coumarate.

In yet another preferred embodiment, the composition according to the present invention may comprise a combination of a biopesticide as defined herein above, of (T) or the nitrification inhibitor of the compound of formula I and methyl 3-(4-hydroxyphenyl) propionate (MHPP).

In yet another preferred embodiment, the composition according to the present invention may comprise a combination of a biopesticide as defined herein above, of (T) or the nitrification inhibitor of the compound of formula I and methyl ferulate.

In yet another preferred embodiment, the composition according to the present invention may comprise a combination of a biopesticide as defined herein above, of (T) or the nitrification inhibitor of the compound of formula I and Karanjin.

In a further preferred embodiment, the composition according to the present invention may comprise a combination of a biopesticide as defined herein above, of (T) or the nitrification inhibitor of the compound of formula I and neem-extract.

In a further preferred embodiment, the composition according to the present invention may comprise a combination of a biopesticide as defined herein above, of (T) or the nitrification inhibitor of the compound of formula I and neemoil-coated fertilizers.

In a further preferred embodiment, the composition according to the present invention may comprise a combination of a biopesticide as defined herein above, of (T) or the nitrification inhibitor of the compound of formula I and neem-coated fertilizers.

In a further preferred embodiment, the composition according to the present invention may comprise a combination of a biopesticide as defined herein above, of (T) or the nitrification inhibitor of the compound of formula I and nimin-coated fertilizers.

In a further preferred embodiment, the composition according to the present invention may comprise a combination of a biopesticide as defined herein above, of (T) or the nitrification inhibitor of the compound of formula I and fertilizers with neem cake.

In yet another preferred embodiment, the composition according to the present invention may comprise a combination of a biopesticide as defined herein above, of (T) or the nitrification inhibitor of the compound of formula I and brachialacton.

In yet another preferred embodiment, the composition according to the present invention may comprise a combination of a biopesticide as defined herein above, of (T) or the nitrification inhibitor of the compound of formula I and p-benzoquinone sorgoleone.

In yet another preferred embodiment, the composition according to the present invention may comprise a combination of a biopesticide as defined herein above, of (T) or the nitrification inhibitor of the compound of formula I and 4-amino-1,2,4-triazole hydrochloride (ATC).

In yet another preferred embodiment, the composition according to the present invention may comprise a combination of a biopesticide as defined herein above, of (T) or the nitrification inhibitor of the compound of formula I and 1-amido-2-thiourea (ASU).

In further embodiments, the composition according to the present invention may comprise a combination of a biopesticide as defined herein above, of (T) or the nitrification inhibitor of the compound of formula I and two entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol and thiourea (TU).

In yet another group of embodiments, the composition according to the present invention may comprise a combination of a biopesticide as defined herein above, of (T) or the nitrification inhibitor of the compound of formula I and three, four or more entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol and thiourea (TU).

In further specific embodiments, the composition may comprise the combination of nitrification inhibitor and biopesticide as defined in Table 2 and at least one element selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST) ammoniumthiosulfate (ATU), 3-methylpyrazol (3-MP), 3,5-dimethylpyrazole (DMP), 1,2,4-triazole, thiourea (TU). N-(1H-pyrazolyl-methyl)acetamides such as N-((3(5)-methyl-1H-pyrazole-1-yl)methyl)acetamide, and N-(1H-pyrazolyl-methyl) formamides such as N-((3(5)-methyl-1H-pyrazole-1-yl)

methyl formamide, N-(4-chloro-3(5)-methyl-pyrazole-1-ylmethyl)-formamide, N-(3(5),4-dimethyl-pyrazole-1-ylmethyl)-formamide, mixtures of 3,4-dimethylpyrazole phospate succinic acid and 4,5-dimethylpyrazole phosphate succinic acid, neem, products based on ingredients of neem, cyan amide, melamine, zeolite powder, catechol, benzoquinone, sodium tetra borate, and zinc sulfate.

In further specific embodiments, the composition may comprise the combination of (T) and biopesticide as defined in Table 3 and at least one element selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (M BT), 5-ethoxy-3-trichloromethyl-1,2,4-thiodiazole (terrazole, etridiazole), 2-sulfanilamidothiazole (ST) ammoniumthiosulfate (ATU), 3-methylpyrazol (3-MP), 3,5-dimethylpyrazole (DMP), 1,2,4-triazole, thiourea (TU), N-(1H-pyrazolyl-methyl)acetamides such as N-((3(5)-methyl-1H-pyrazole-1-yl)methyl)acetamide, and N-(1H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, N-(3(5),4-dimethyl-pyrazole-1-ylmethyl)-formamide, mixtures of 3,4-dimethylpyrazole phospate succinic acid and 4,5-dimethylpyrazole phosphate succinic acid, neem, products based on ingredients of neem, cyan amide, melamine, zeolite powder, catechol, benzoquinone, sodium tetra borate, and zinc sulfate.

In further embodiments, the composition may, in addition to the above indicated ingredients, in particular in addition to a biopesticide as defined herein above, and to the nitrification inhibitor of the compound of formula I, further comprise one or more urease inhibitors. Examples of envisaged urease inhibitors include N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and LIMUS, i.e. a mixture of NBPT and NPPT with about NBTP at 63% and NPPT at 22%, secondary compounds at 10%, further secondary compounds such as amines below 4% and dimerease derivatives below 1%.

In a preferred embodiment, the composition according to the present invention may comprise a biopesticide as defined herein above and a combination of the nitrification inhibitor of the compound of formula I and N-(n-butyl) thiophosphoric acid triamide (NBPT, Agrotain).

In a further preferred embodiment, the composition according to the present invention may comprise a biopesticide as defined herein above and a combination of (T) or the nitrification inhibitor of the compound of formula I and phenylphosphorodiamidate (PPD/PPDA).

In a further preferred embodiment, the composition according to the present invention may comprise a biopesticide as defined herein above and a combination of the nitrification inhibitor of the compound of formula I and N-(n-propyl) thiophosphoric acid triamide (NPPT).

In a further preferred embodiment, the composition according to the present invention may comprise a biopesticide as defined herein above and a combination of the nitrification inhibitor of the compound of formula I and 2-nitrophenyl phosphoric triamide (2-NPT).

In a further preferred embodiment, the composition according to the present invention may comprise a biopesticide as defined herein above and a combination of (T) or the nitrification inhibitor of the compound of formula I and hydroquinone.

In a further preferred embodiment, the composition according to the present invention may comprise a biopesticide as defined herein above and a combination of (T) or the nitrification inhibitor of the compound of formula I and ammonium thiosulfate.

In a further preferred embodiment, the composition according to the present invention may comprise a biopesticide as defined herein above and a combination of the nitrification inhibitor of the compound of formula I and LIMUS.

In further embodiments, the composition according to the present invention may comprise a biopesticide as defined herein above and a combination of the nitrification inhibitor of the compound of formula I and two or more entities selected from the group comprising: N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and LIMUS.

In further embodiments, the composition may, in addition to one, more or all of the above indicated ingredients, in particular in addition to (T) or the nitrification inhibitor of the compound of formula I and a biopesticide, further comprise one or more plant growth regulators. Examples of envisaged plant growth regulators are antiauxins, auxins, cytokinins, defoliants, ethylene modulators, ethylene releasers, gibberellins, growth inhibitors, morphactins, growth retardants, growth stimulators, and further unclassified plant growth regulators.

In a preferred embodiment, the composition according to the present invention may comprise a combination of the nitrification inhibitor of the compound of formula I and a biopesticide and at least one compound selected from the group comprising: abscisic acid, amidochlor, ancymidol, 6-benzylaminopurine (=N-6 benzyladenine), brassinolide, butralin, chlormequat (chlormequat chloride), choline chloride, cyclanilide, daminozide, diflufenzopyr, dikegulac, dimethipin, 2,6-dimethylpyridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), 1-methylcyclopropene (1-MCP), naphthaleneacetic acid, N-6 benzyladenine, paclobutrazol, prohexadione (prohexadione calcium), prohydrojasmon, thidiazuron, triapenthenol, tributyl phosphorotrithioate, 2,3,5-tri-iodobenzoic acid, trinexapac-ethyl, and uniconazole.

In a preferred embodiment, the composition according to the present invention may comprise a combination of (T) and a biopesticide as defined herein above and at least one compound selected from the group comprising: abscisic acid, amidochlor, ancymidol, 6-benzylaminopurine (=N-6 benzyladenine), brassinolide, butralin, chlormequat (chlormequat chloride), choline chloride, cyclanilide, daminozide, diflufenzopyr, dikegulac, dimethipin, 2,6-dimethylpyridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), 1-methylcyclopropene (1-MCP), naphthaleneacetic acid, N-6 benzyladenine, paclobutrazol, prohexadione (prohexadione calcium), prohydrojasmon, thidiazuron, triapenthenol, tributyl phosphorotrithioate, 2,3,5-triiodobenzoic acid, trinexapac-ethyl, and uniconazole.

In further specific embodiments, the composition as defined herein above may additionally comprises an fertilizer. In case the combination of biopesticides and (T) or nitrification inhibitors is used together with a fertilizer, or when a composition is provided in combination with a fertilizer, such mixtures may be provided or used as agrochemical mixtures.

In the terms of the present invention "agrochemical mixture" means a combination of at three or more compounds. The term is, however, not restricted to a physical mixture comprising three or more compounds, but refers to any preparation form of said compounds, the use of which many be time- and/or locus-related.

The agrochemical mixtures may, for example, be formulated separately but applied in a temporal relationship, i.e. simultaneously or subsequently, the subsequent application having a time interval which allows a combined action of the compounds.

Furthermore, the individual compounds of the agrochemical mixtures according to the invention such as parts of a kit or parts of the mixture may be mixed by the user himself in a suitable mixing device. In specific embodiments further auxiliaries may be added, if appropriate.

The term "fertilizers" is to be understood as chemical compounds applied to promote plant and fruit growth. Fertilizers are typically applied either through the soil (for uptake by plant roots), through soil substituents (also for uptake by plant roots), or by foliar feeding (for uptake through leaves). The term also includes mixtures of one or more different types of fertilizers as mentioned below.

The term "fertilizers" can be subdivided into several categories including: a) organic fertilizers (composed of decayed plant/animal matter), b) inorganic fertilizers (composed of chemicals and minerals) and c) urea-containing fertilizers.

Organic fertilizers include manure, e.g. liquid manure, semi-liquid manure, biogas manure, stable manure or straw manure, slurry, liquid dungwater, sewage sludge, worm castings, peat, seaweed, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility.

Inorganic fertilizers are usually manufactured through chemical processes (such as the HaberBosch process), also using naturally occurring deposits, while chemically altering them (e.g. concentrated triple superphosphate). Naturally occurring inorganic fertilizers include Chilean sodium nitrate, mine rock phosphate, limestone, sulfate of potash, and muriate of potash, and raw potash fertilizers.

Typical solid fertilizers are in a crystalline, prilled or granulated form. Typical nitrogen containing inorganic fertilizers are ammonium nitrate, calcium ammonium nitrate, ammonium sulfate, ammonium sulfate nitrate, calcium nitrate, diammonium phosphate, monoammonium phosphate, ammonium thio sulfate and calcium cyanamide.

The inorganic fertilizer may be an NPK fertilizer. "NPK fertilizers" are inorganic fertilizers formulated in appropriate concentrations and combinations comprising the three main nutrients nitrogen (N), phosphorus (P) and potassium (K) as well as typically S, Mg, Ca, and trace elements. "NK fertilizers" comprise the two main nutrients nitrogen (N) and potassium (K) as well as typically S, Mg, Ca, and trace elements. "NP fertilizers" comprise the two main nutrients nitrogen (N) and phosphorus (P) as well as typically S, Mg, Ca, and trace elements.

Urea-containing fertilizer may, in specific embodiments, be formaldehyde urea, UAN, urea sulfur, stabilized urea, urea based NPK-fertilizers, or urea ammonium sulfate. Also envisaged is the use of urea as fertilizer. In case urea-containing fertilizers or urea are used or provided, it is particularly preferred that urease inhibitors as defined herein above may be added or additionally be present, or be used at the same time or in connection with the urea-containing fertilizers.

Fertilizers may be provided in any suitable form, e.g. as coated or uncoated granules, in liquid or semi-liquid form, as sprayable fertilizer, or via fertigation etc.

Coated fertilizers may be provided with a wide range of materials. Coatings may, for example, be applied to granular or prilled nitrogen (N) fertilizer or to multi-nutrient fertilizers. Typically, urea is used as base material for most coated fertilizers. The present invention, however, also relates to the use of other base materials for coated fertilizers, any one of the fertilizer materials defined herein. In certain embodiments, elemental sulfur may be used as fertilizer coating. The coating may be performed by spraying molten S over urea granules, followed by an application of sealant wax to close fissures in the coating. In a further embodiment, the S layer may be covered with a layer of organic polymers, preferably a thin layer of organic polymers. In another embodiment, the coated fertilizers are preferably physical mixtures of coated and non-coated fertilizers.

Further envisaged coated fertilizers may be provided by reacting resin-based polymers on the surface of the fertilizer granule. A further example of providing coated fertilizers includes the use of low permeability polyethylene polymers in combination with high permeability coatings.

In specific embodiments the composition and/or thickness of the fertilizer coating may be adjusted to control, for example, the nutrient release rate for specific applications. The duration of nutrient release from specific fertilizers may vary, e.g. from several weeks to many months. The presence of (T) or nitrification inhibitors and biopesticides in a mixture with coated fertilizers may accordingly be adapted. It is, in particular, envisaged that the nutrient release involves or is accompanied by the release of (T) or an nitrification inhibitor and biopesticide according to the present invention.

Coated fertilizers may be provided as controlled release fertilizers (CRFs). In specific embodiments these controlled release fertilizers are fully coated N-P-K fertilizers, which are homogeneous and which typically show a pre-defined longevity of release. In further embodiments, the CRFs may be provided as blended controlled release fertilizer products which may contain coated, uncoated and/or slow release components. In certain embodiments, these coated fertilizers may additionally comprise micronutrients. In specific embodiments these fertilizers may show a pre-defined longevity, e.g. in case of N-P-K fertilizers.

Additionally envisaged examples of CRFs include patterned release fertilizers. These fertilizers typically show a pre-defined release patterns (e.g. hi/standard/lo) and a pre-defined longevity. In exemplary embodiments fully coated N-P-K, Mg and micronutrients may be delivered in a patterned release manner.

Also envisaged are double coating approaches or coated fertilizers based on a programmed release.

In further embodiments the fertilizer mixture may be provided as, or may comprise or contain a slow release fertilizer. The fertilizer may, for example, be released over any suitable period of time, e.g. over a period of 1 to 5 months, preferably up to 3 months. Typical examples of ingredients of slow release fertilizers are IBDU (isobutylidenediurea), e.g. containing about 31-32% nitrogen, of which 90% is water insoluble; or UF, i.e. an urea-formaldehyde product which contains about 38% nitrogen of which about 70% may be provided as water insoluble nitrogen; or CDU (crotonylidene diurea) containing about 32% nitrogen; or MU (methylene urea) containing about 38 to 40% nitrogen, of which 25-60% is typically cold water insoluble nitrogen; or MDU (methylene diurea) containing about 40% nitrogen, of which less than 25% is cold water insoluble nitrogen; or MO (methylol urea) containing about 30% nitrogen, which may typically be used in solutions; or DMTU (diimethylene triurea) containing about 40% nitrogen, of which less than 25% is cold water insoluble nitrogen; or TMTU (tri methylene tetraurea), which may be provided as component of UF products; or TMPU (tri methylene pentaurea), which may also be provided as component of UF products; or UT (urea triazone solution) which typically contains about 28% nitrogen. The fertilizer mixture may also be long-term nitrogen-bearing fertiliser containing a mixture of acetylene diurea and at least one other organic nitrogen-bearing fertiliser selected from methylene urea, isobutylidene diurea, crotonylidene diurea, substituted triazones, triuret or mixtures thereof.

Any of the above mentioned fertilizers or fertilizer forms may suitably be combined. For instance, slow release fertilizers may be provided as coated fertilizers. They may also be combined with other fertilizers or fertilizer types. The same applies to the presence of (T) or a nitrification inhibitor or biopesticide according to the present invention, which may be adapted to the form and chemical nature of the fertilizer and accordingly be provided such that its release accompanies the release of the fertilizer, e.g. is released at the same time or with the same frequency. The present invention further relates to fertilizer or fertilizer forms as defined herein above in combination with (T) or nitrification inhibitors as defined herein above and biopesticides as defined herein above and further in combination with urease inhibitors as defined herein above. Such combinations may be provided as coated or uncaoted forms and/or as slow or fast release forms. Preferred are combinations with slow release fertilizers including a coating. In further embodiments, also different release schemes are envisaged, e.g. a slower or a faster release.

The term "fertigation" as used herein refers to the application of fertilizers, optionally soil amendments, and optionally other water-soluble products together with water through an irrigation system to a plant or to the locus where a plant is growing or is intended to grow, or to a soil substituent as defined herein below. For example, liquid fertilizers or dissolved fertilizers may be provided via fertigation directly to a plant or a locus where a plant is growing or is intended to grow. Likewise, (T) or nitrification inhibitors according to the present invention, or in combination with additional nitrification inhibitors, may be provided via fertigation to plants or to a locus where a plant is growing or is intended to grow. Fertilizers and (T) or nitrification inhibitors according to the present invention, or in combination with additional nitrification inhibitors, may be provided together, e.g. dissolved in the same charge or load of material (typically water) to be irrigated. In further embodiments, fertilizers and (T) or nitrification inhibitors may be provided at different points in time. For example, the fertilizer may be fertigated first, followed by the (T) or nitrification inhibitor, or preferably, (T) or the nitrification inhibitor may be fertigated first, followed by the fertilizer. The time intervals for these activities follow the herein above outlined time intervals for the application of fertilizers and (T) or nitrification inhibitors. Also envisaged is a repeated fertigation of fertilizers and (T) or nitrification inhibitors according to the present invention, either together or intermittently, e.g. every 2 hours, 6 hours, 12 hours, 24 hours, 2 days, 3 days, 4 days, 5 days, 6 days or more.

In particularly preferred embodiments, the fertilizer is an ammonium-containing fertilizer.

The agrochemical mixture according to the present invention may comprise one fertilizer as defined herein above and (T) or one nitrification inhibitor of formula I as defined herein above and one biopesticide as defined herein above. In further embodiments, the agrochemical mixture according to the present invention may comprise at least one or more than one fertilizer as defined herein above, e.g. 2, 3, 4, 5, 6, 6, 7, 8, 9, 10 or more different fertilizers (including inorganic, organic and urea-containing fertilizers) and (T) or at least one nitrification inhibitor of formula I and at least one biopesticide as defined herein above, preferably a combination as defined in Table 2 or Table 3.

In another group of embodiments the agrochemical mixture according to the present invention may comprise at least one or more than one (thio)phosphoric acid triamide (T) or at least one or more than one nitrification inhibitor of formula I as defined herein above, preferably more than one nitrification inhibitor of formula I selected from Table 1, e.g. 2, 3, 4, 5, 6, 6, 7, 8, 9, 10 or more different nitrification inhibitors as defined herein above or as provided in Table 1 and at least one fertilizer as defined herein above and at least one biopesticide as defined herein above.

The term "at least one" is to be understood as 1, 2, 3 or more of the respective compound selected from the group consisting of fertilizers as defined herein above (also designated as compound C), and (T) or nitrification inhibitors of formula I as defined herein above (also designated as compound A), and biopesticides (also designated as compound B).

In addition to at least one fertilizer and (T) or at least one nitrification inhibitor as defined herein above and at least one biopesticide, an agrochemical mixture may comprise further ingredients, compounds, active compounds or compositions or the like. For example, the agrochemical mixture may additionally comprise or composed with or on the basis of a carrier, e.g. anagrochemical carrier, preferably as defined herein. In further embodiments, the agrochemical mixture may further comprise at least one additional pesticidal compound. For example, the agrochemical mixture may additionally comprise at least one fungicidal compound and/or at least one insecticidal compound.

In further embodiments, the agrochemical mixture may, in addition to the above indicated ingredients further comprise alternative or additional nitrification inhibitors such as linoleic acid, alpha-linolenic acid, methyl p-coumarate, methyl ferulate, MHPP, Karanjin, brachialacton, p-benzoquinone sorgoleone, nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), ammoniumthiosulfate (ATU), 3-methylpyrazol (3-MP), 3,5-dimethylpyrazole (DMP), 1,2,4-triazol, thiourea (TU) and/or sulfathiazole (ST).

Furthermore, the invention relates to a method for increasing the health of a plant, comprising treating a plant growing on soil and/or the locus where the plant is growing or is intended to grow with a combination of (T) or at least one nitrification inhibitor and at least one biopesticide as defined herein above, preferabyl with a combination as defined in Table 2, or a composition comprising said combination.

The term "plant" is to be understood as a plant of economic importance and/or men-grown plant. In certain embodiments, the term may also be understood as plants which have no or no significant economic importance. The plant is preferably selected from agricultural, silvicultural and horticultural (including ornamental) plants. The term also relates to genetically modified plants.

The term "plant" as used herein further includes all parts of a plant such as germinating seeds, emerging seedlings, plant propagules, herbaceous vegetation as well as established woody plants including all belowground portions (such as the roots) and aboveground portions.

Within the context of the method for increasing the health of plant it is assumed that the plant is growing on soil. In specific embodiments, the plant may also grow differently, e.g. in synthetic laboratory environments or on soil substituents, or be supplemented with nutrients, water etc. by artificial or technical means. In such scenarios, the invention relates to a treatment of the zone or area where the nutrients, water etc. are provided to the plant. Also envisaged is that the plant grows in green houses or similar indoor facilities.

The term "locus" is to be understood as any type of environment, soil, soil substituents, area or material where the plant is growing or intended to grow. Preferably, the term relates to soil or soil substituent on which a plant is growing.

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibres (e.g. cotton, linen), combustibles (e.g. wood, bioethanol, biodiesel, biomass) or other chemical compounds. Preferred agricultural plants are for example cereals, e.g. wheat, rye, barley, triticale, oats, sorghum or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In a further embodiment, the plant to be treated according to the method of the invention is a horticultural plant. The term "horticultural plants" are to be understood as plants which are commonly used in horticulture, e.g. the cultivation of ornamentals, vegetables and/or fruits. Examples for ornamentals are turf, geranium, pelargonia, petunia, begonia and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In a further embodiment, the plant to be treated according to the method of the invention is an ornamental plants. "Ornamental plants" are plants which are commonly used in gardening, e.g. in parks, gardens and on balconies. Examples are turf, geranium, pelargonia, petunia, begonia and fuchsia.

In another embodiment of the present invention, the plant to be treated according to the method of the invention is a silvicultural plants. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular *Pinus* spec., fir and spruce, eucalyptus, tropical trees like teak, rubber tree, oil palm, willow (*Salix*), in particular *Salix* spec., poplar (cottonwood), in particular *Populus* spec., beech, in particular *Fagus* spec., birch, oil palm, and oak.

The term "plant propagation material" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as 6-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073.

The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The term "soil substituent" as used herein refers to a substrate which is able to allow the growth of a plant and does not comprise usual soil ingredients. This substrate is typically an anorganic substrate which may have the function of an inert medium. It may, in certain embodiments, also comprise organic elements or portions. Soil substituents may, for example, be used in hydroculture or hydroponic approaches, i.e. wherein plants are grown in soilless medium and/or aquatic based environments. Examples of suitable soil substituents, which may be used in the context of the present invention, are perlite, gravel, biochar, mineral wool, coconut husk, phyllosilicates, i.e. sheet silicate minerals, typically formed by parallel sheets of silicate tetrahedra with $Si_2O_5$ or a 2:5 ratio, or clay aggregates, in particular expanded clay aggregates with a diameter of about 10 to 40 mm. Particularly preferred is the employment of vermiculite, i.e. a phyllosilicate with 2 tetrahedral sheets for every one octahedral sheet present.

The use of soil substituents may, in specific embodiments, be combined with fertigation or irrigation as defined herein.

In specific embodiments, the treatment may be carried out during all suitable growth stages of a plant as defined herein. For example, the treatment may be carried out during the BBCH principle growth stages.

The term "BBCH principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

In one embodiment the invention relates to a method for increasing the health of a plant comprising treating a plant growing on soil or soil substituents and/or the locus where the plant is growing with a combination as defined herein above, or a corresponding composition or agricultural composition as defined herein above at a growth stage (GS) between GS 00 and GS 65 BBCH of the plant.

In one embodiment the invention relates to a method for increasing the health of a plant comprising treating a plant growing on soil or soil substituents and/or the locus where the plant is growing with a combination as defined herein above, or a corresponding composition or agricultural composition as defined herein above at a growth stage (GS) between GS 00 to GS 33 BBCH of the plant.

In a preferred embodiment the invention relates to a method for increasing the health of a plant comprising treating a plant growing on soil or soil substituents and/or the locus where the plant is growing with a combination as defined herein above, or a corresponding composition or agricultural composition as defined herein above at an early growth stage (GS), in particular a GS 00 to GS 05, or GS 00 to GS 10, or GS 00 to GS 15, or GS 00 to GS 20, or GS 00 to GS 25 or GS 00 to GS 33 BBCH of the plant. In particularly preferred embodiments, the method comprises treating a plant growing on soil or soil substituents and/or the locus where the plant is growing with a combination as defined herein above, or a corresponding composition or agricultural composition as defined herein above during growth stages including GS 00.

In a further, specific embodiment of the invention a combination as defined herein above, or a corresponding composition or agricultural composition as defined herein above is applied to a plant growing on soil or soil substituents and/or the locus where the plant is growing or is intended to grow at a growth stage between GS 00 and GS 55 BBCH, or of the plant.

In a further embodiment of the invention a combination as defined herein above, or a corresponding composition or agricultural composition as defined herein above is applied to a plant growing on soil or soil substituents and/or the locus where the plant is growing or is intended to grow at the growth stage between GS 00 and GS 47 BBCH of the plant.

In one embodiment of the invention a combination as defined herein above, or a corresponding composition or agricultural composition as defined herein above is applied to a plant growing on soil or soil substituents and/or the locus where the plant is growing or is intended to grow before and at sowing, before emergence, and until harvest (GS 00 to GS 89 BBCH), or at a growth stage (GS) between GS 00 and GS 65 BBCH of the plant.

In a preferred embodiment the invention relates to a method increasing the health of a plant comprising treating a plant growing on soil or soil substituents and/or the locus where the plant is growing with a combination as defined herein above, or a corresponding composition or agricultural composition as defined herein above wherein the plant and/or the locus where plant is growing or is intended to grow is additionally provided with at least one fertilizer. The fertilizer may be any suitable fertilizer, preferably a fertilizer as defined herein above. Also envisaged is the application of more than one fertilizer, e.g. 2, 3, 4, 5, 6, 7, 8, 9, 10 fertilizers, or of different fertilizer classes or categories.

In specific embodiments of the invention, a combination as defined herein above, or a corresponding composition or agricultural composition as defined herein above and at least one fertilizer is applied to a plant growing on soil or soil substituents and/or the locus where the plant is growing or is intended to grow at a growth stage between GS 00 and GS 33 BBCH of the plant.

In specific embodiments of the invention a combination as defined herein above, or a corresponding composition or agricultural composition as defined herein above r is applied to a plant growing on soil or soil substituents and/or the locus where the plant is growing or is intended to grow at a growth stage between GS 00 and GS 55 BBCH of the plant.

In further specific embodiments of the invention a combination as defined herein above, or a corresponding composition or agricultural composition as defined herein above and at least one fertilizer is applied to a plant growing on soil or soil substituents and/or the locus where the plant is growing or is intended to grow at sowing, before emergence, or at a growth stage (GS) between GS 00 and GS 65 BBCH of the plant.

According to a preferred embodiment of the present invention the application of (T) or said nitrification inhibitor as defined herein (component A) and of said biopesticide (component B) is carried out simultaneously or with a time lag. The term "time lag" as used herein means that either (T) or the nitrification inhibitor is applied before the biopesticide to the plant growing on soil or soil substituents and/or the locus where the plant is growing or is intended to grow; or the biopesticide is applied before (T) or the nitrification inhibitor to the plant growing on soil or soil substituents and/or the locus where the plant is growing or is intended to grow. Such time lag may be any suitable period of time which still allows to provide a nitrification inhibiting effect in the context of biopesticide usage, or which provides for a reduction in growth or elimination of fungi, bacteria, viruses or nematodes in the context of the usage of (T) or a nitrification inhibitor. For example, the time lag may be a time period of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods. Preferably, the time lag is an interval of 1 day, 2 days, 3 days, 1 week, 2 weeks or 3 weeks. The time lag preferably refers to situations in which (T) or the nitrification inhibitor as defined above is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods before the application of a biopesticide as defined herein above.

According to a preferred embodiment of the present invention the application of said combination of a nitrification inhibitor or (T) and a biopesticide as defined herein above, or a corresponding composition or agricultural composition as defined herein above and of said fertilizer (component C) as defined herein above is carried out simultaneously or with a time lag. The term "time lag" as used herein means that either (T) or the nitrification inhibitor and/or biopesticide is applied before the fertilizer to the plant growing on soil or soil substituents and/or the locus where the plant is growing or is intended to grow; or the fertilizer is applied before (T) or the nitrification inhibitor and/or biopesticide to the plant growing on soil or soil substituents and/or the locus where the plant is growing or is intended to grow. Such time lag may be any suitable period of time which still allows to provide a nitrification inhibiting effect in the context of fertilizer usage, or which provides for a reduction in growth of or elimination of fungi, bacteria, viruses or nematodes in the context of the usage of (T) or the nitrification inhibitor. For example, the time lag may be a time period of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods. Preferably, the time lag is an interval of 1 day, 2 days, 3 days, 1 week, 2 weeks or 3 weeks. The time lag preferably refers to situations in which (T) or the nitrification inhibitor as defined above is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods before the application of a fertilizer as defined herein above.

In another specific embodiment of the invention one component of a combination as defined herein above, or of a corresponding composition or agricultural composition as defined herein above is applied between GS 00 to GS 33 BBCH of the plant, or between GS 00 and GS 65 BBCH of the plant, provided that the application of the other component of said combination as defined herein above, or a of corresponding composition or agricultural composition as defined herein above is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, or more or any time period in between the mentioned time periods. It is preferred that one component of thecombination as defined herein above, or of a corresponding composition or agricultural composition as defined herein above, which is applied between GS 00 to GS 33 BBCH of the plant, is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, or 12 weeks before the application of the other component.

In another specific embodiment of the invention, at least one fertilizer as defined herein above is applied between GS 00 to GS 33 BBCH of the plant or between GS 00 and GS 65 BBCH of the plant, provided that the application of a combination as defined herein above, or of at least one component of said combination, or a corresponding composition or agricultural composition as defined herein above, is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks or more or any time period in between the mentioned time periods.

According to a specific embodiment of the present invention a plant growing on soil or soil substituents and/or the locus where the plant is growing or is intended to grow is treated at least once with at least one component of a combination as defined herein above or of a corresponding composition or agricultural composition as defined herein above, or with said combination.

In a further specific embodiment of the present invention a plant growing on soil or soil substituents and/or the locus where the plant is growing or is intended to grow is treated at least once with a combination as defined herein above, or one of its components, or a corresponding composition or agricultural composition as defined herein above, and at least once with a fertilizer as defined herein above.

The term "at least once" means that the application may be performed one time, or several times, i.e. that a repetition of the treatment with (T) or a nitrification inhibitor and/or a fertilizer may be envisaged. Such a repetition may a 2 times, 3 times, 4 times, 5 times, 6 times, 7 times, 8 times, 9 times, 10 times or more frequent repetition of the treatment with a combination as defined herein above, or one of its components, or a corresponding composition or agricultural composition as defined herein above and/or a fertilizer. The repetition of treatment with a combination as defined herein above, or one of its components, or a corresponding composition or agricultural composition as defined herein above and a fertilizer may further be different. For example, while the fertilizer may be applied only once, the a combination as defined herein above, or one of its components, or a corresponding composition or agricultural composition as defined herein above may be applied 2 times, 3 times, 4 times etc. Alternatively, while (T) or the nitrification inhibitor may be applied only once, the fertilizer may be applied 2 times, 3 times, 4 times etc. Further envisaged are all combinations of numerical different numbers of repetitions for the application of a combination as defined herein above, or one of its components, or a corresponding composition or agricultural composition as defined herein above and opitonally a fertilizer as defined herein above. Such a repeated treatment may further be combined with a time lag between the treatment of the combination as defined herein above, or one of its components, or a corresponding composition or agricultural composition as defined herein above and optionally a fertilizer as described above.

The time interval between a first application and second or subsequent application of a combination as defined herein above, or one of its components or a corresponding composition or agricultural composition as defined herein above and/or a fertilizer may be any suitable interval. This interval may range from a few seconds up to 3 months, e.g. from a few seconds up to 1 month, or from a few seconds up to 2 weeks. In further embodiments, the time interval may range from a few seconds up to 3 days or from 1 second up to 24 hours.

In further specific embodiments, a method for increasing the health of a plant as described above is carried out by treating a plant growing on soil or soil substituents and/or the locus where the plant is growing or is intended to grow with at least one agricultural mixture as defined herein above.

In another embodiment of the invention, an agrochemical mixture comprising an ammonium or urea-containing fertilizer and (T) or at least one nitrification inhibitor as defined herein above is applied before and at sowing, before emergence, and until shooting/shoot development (GS 00 to GS 33 BBCH) of the plant. In case the agricultural mixture is provided as kit of parts or as non-physical mixture, it may be applied with a time lag between the application of (T) or the nitrification inhibitor and the fertilizer or between the application of (T) or the nitrification inhibitor a secondary or further ingredient, e.g. a pesticidal compound as mentioned herein above.

In a further embodiment plant propagules are preferably treated simultaneously (together or separately) or subsequently.

The term "propagules" or "plant propagules" is to be understood to denote any structure with the capacity to give rise to a new plant, e.g. a seed, a spore, or a part of the vegetative body capable of independent growth if detached from the parent. In a preferred embodiment, the term "propagules" or "plant propagules" denotes for seed.

For a method as described above, or for a use according to the invention, the application rates of (T) or nitrification inhibitors, i.e. of the compound of formula I are between 0.01 g and 5 kg of active ingredient per hectare, preferably between 1 g and 1 kg of active ingredient per hectare, especially preferred between 50 g and 300 g of active ingredient per hectare depending on different parameters such as the specific active ingredient applied and the plant species treated. In the treatment of seed, amounts of from 0.001 g to 20 g per kg of seed, preferably from 0.01 g to 10 g per kg of seed, more preferably from 0.05 to 2 g per kg of seed of (T) or nitrification inhibitors may be generally required.

As a matter of course, if (T) or nitrification inhibitors and fertilizers (or other ingredients), or if mixtures thereof are employed, the compounds may be used in an effective and non-phytotoxic amount. This means that they are used in a quantity which allows to obtain the desired effect but which does not give rise to any phytotoxic symptoms on the treated plant or on the plant raised from the treated propagule or treated soil. For the use according to the invention, the application rates of fertilizers may be between 10 kg and 300 kg per hectare, preferably between 50 kg and 250 kg per hectare.

(T) or the nitrification inhibitor compounds according to the invention, e.g. compound I as defined herein above, or derivative thereof as defined herein above can be present in different structural or chemical modifications whose biological activity may differ. They are likewise subject matter of the present invention.

(T) or the nitrification inhibitor compounds according to the invention, their N-oxides and/or salts etc. may be converted into customary types of compositions, e.g. agrochemical or agricultural compositons such as solutions, emulsions, suspensions, dusts, powders, pastes and granules. The composition type depends on the particular intended purpose; in each case, it should ensure a fine and uniform distribution of the compound according to the invention. Examples for composition types are suspensions (SC, 00, FS), emulsifiable concentrates (EC), emulsions (EW, EO, ES), microemulsions (M E), pastes, pastilles, wettable powders or dusts (WP, SP, SS, WS, OP, OS) or granules (GR, FG, GG, MG), which can be watersoluble or wettable, as well as gel formulations for the treatment of plant propagation materials such as seeds (GF). Usually the composition types (e.g. SC, 00, FS, EC, WG, SG, WP, SP, SS, WS, GF) are employed diluted. Composition types such as OP, OS, GR, FG, GG and MG are usually used undiluted. The compositions are prepared in a known manner (see, for example, U.S. Pat. No. 3,060,084, EP 707 445 (for liquid concentrates), Browning: "Agglomeration", Chemical Engineering, Dec. 4, 1967, 147-48, Perry's Chemical Engineer's Handbook, 4th Ed., McGraw-Hili, New York, 1963, S. 8-57 und ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001). Agrochemical compositions or mixtgures may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as Nmethylpyrrolidone.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borrespers®) types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof. Examples of suitable thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

In specific embodiments, bactericides may be added for preservation and stabilization of the composition. Examples for suitable bactericides are those based on dichlorophene and benzyl alcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes, e.g. rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding compound of formula I and, if appropriate, further active substances, with at least one solid carrier. Granules, e.g. coated granules, impregnated granules and homogeneous granules, can be prepared by binding the active substances to solid carriers. Examples of such suitable solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g. ammonium sulfate, ammonium phosphate, ammonium nitrate, ureas, and products of vegetable origin, such as cereal meal, tree bark meal, wood meal and nutshell meal, cellulose powders and other solid carriers.

Examples for Composition Types are:
i) Water-soluble concentrates (SL, LS) 10 parts by weight of (T) or a nitrification inhibitor such as a compound of formula I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.
ii) Dispersible concentrates (DC) 20 parts by weight of (T) or a nitrification inhibitor such as a compound of formula I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.
iii) Emulsifiable concentrates (EC) 15 parts by weight of (T) or a nitrification inhibitor such as a compound of formula I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
iv) Emulsions (EW, EO, ES) 25 parts by weight of (T) or a nitrification inhibitor such as a compound of formula I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.
v) Suspensions (SC, 00, FS) In an agitated ball mill, 20 parts by weight of (T) or a nitrification inhibitor such as a compound of formula I according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.
vi) Water-dispersible granules and water-soluble granules (WG, SG) 50 parts by weight of (T) or a nitrification inhibitor such as a compound of formula I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.
vii) Water-dispersible powders and water-soluble powders (WP, SP, SS, WS) 75 parts by weight of (T) or a nitrification inhibitor such as a compound of formula I according to the invention are ground in a rotor-stator mill with addition of 25 parts by weight of dispersants, wetting agents and silica gel. Dilution with water gives a stable dispersion or solution of the active substance. The active substance content of the composition is 75% by weight.
viii) Gel (GF) In an agitated ball mill, 20 parts by weight of (T) or a nitrification inhibitor such as a compound of formula I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained. 2. Composition types to be applied undiluted
ix) Oustable powders (OP, OS) 5 parts by weight of (T) or a nitrification inhibitor such as a compound of formula I according to the invention are ground finely and mixed intimately with 95 parts by weight of finely divided kaolin. This gives a dustable composition having an active substance content of 5% by weight.
x) Granules (GR, FG, GG, MG) 0.5 parts by weight of (T) or a nitrification inhibitor such as a compound of formula I according to the invention is ground finely and associated with 99.5 parts by weight of carriers. Current methods are extrusion, spray-drying or the fluidized bed. This gives granules to be applied undiluted having an active substance content of 0.5% by weight.
xi) ULV solutions (UL) 10 parts by weight of (T) or a nitrification inhibitor such as a compound of formula I according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (OS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds.

These compositions can be applied to plant propagation materials, particularly seeds, diluted or undiluted.

The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying or treating agrochemical or agricultural compounds or mixtures, or compositions as defined herein, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition may be used. Typically, a FS composition may comprise 1-800 g/l of active substance, 1 200 g/l surfactant, o to 200 g/l anti-freezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring.

The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water.

To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance. The active substances may also be used successfully in the ultralow-volume process (ULV), it being possible to apply compositions comprising over 95% by weight of active substance, or even to apply the active substance without additives.

Various types of oils, wetters, adjuvants, herbicides, bactericides, biopesticideand/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

In a further specific embodiment, the present invention relates to a method for treating seed or plant propagation material. The term "seed treatment" as used herein refers to or involves steps towards the control of biotic or abiotic stresses on or in seed and the improvement of shooting and development of plants from seeds. For seed treatment it is evident that a plant suffering from biotic stresses such as different life forms including microorganisms, viruses, insects, fungi etc. or which has difficulties obtaining sufficient suitable nitrogen-sources shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. Abiotic stress includes drought, cold, increased UV, increased heat, or other changes in the environment of the plant, that leads to sub-optimal growth conditions. Methods for treating seed or plant progation material according to the invention thus lead, among other advantages, to an enhanced plant health, a better protection against biotic stresses and an increased plant yield.

Seed treatment methods for applying or treating inventive mixtures and compositions thereof, e.g. compositons or agrochemical composisitions as defined herein above, and in particular combinations of nitirificaiton inhibitors as defined herein above and biopesticides as defined herein above to plant propagation material, especially seeds, are known in the art, and include dressing, coating, filmcoating, pelleting and soaking application methods of the propagation material. Such methods are also applicable to the combinations or compositions according to the invention.

In preferred embodiments, the seed treatment may be performed with combinations of (T) or nitrification inhibitors and biopesticides as defined herein above, or with composition comprising said combinations, e.g. the combinations mentioned in Table 2 or Table 3. In specific embodiments these compositions as mentioned in Table 2 or Table 3 may additionally comprise further pesticides, e.g. fungicides and/or insecticides and/or nematicides, wherein in case of fungicides, inhibitors of complex III at Qo site (e.g. strobilurines) selected from strobilurines, azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A1.14), pyrametostrobin (A.1.15), pyraoxystrobin (A.1.16), trifloxystrobin (A.1.17) and 2 (2-(3-(2,6-di¬chlorophenyl)-1-methyl-allylideneaminooxymethyl)-phenyl)-2-methoxyimino-N methyl-acetamide (A.1.18), pyribencarb (A.1.19), triclopyricarb/chlorodincarb (A.1.20), famoxadone (A.1.21), fenamidone (A.1.21)azoxystrobin (B.1.1), coumethoxystrobin, coumoxystrobin, dimoxystrobin, enestroburin, fenaminstrobin, fenoxy¬strobin/flufenoxystrobin, fluoxastrobin, kresoxim-methyl, mandestrobine, metominostrobin, orysastrobin, picoxystrobin, pyraclostrobin (B.1.2), pyrametostrobin, pyraoxystrobin, trifloxystrobin (B. 1.3) and 2 (2-(3-(2,6-dichlorophenyl)-1-methyl-allylidene¬aminooxy¬methyl)-phenyl)-2-methoxyimino-N methyl-acetamide, pyribencarb, triclopyricarb/chlorodin¬carb, famoxadone, fenamidone are preferred, and pyraclostrobin is most preferred.

In a preferred embodiment, the compositon or combination comprising (T) or a nitrification inhibitor according to the present invention and a biopesticide, e.g. as defined herein above, is applied or treated on to the plant propagation material by a method such that the germination is not negatively impacted. Accordingly, examples of suitable methods for applying (or treating) a plant propagation material, such as a seed, is seed dressing, seed coating or seed pelleting and alike. It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in compositions or mixtures as defined herein and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

An aspect of the present invention includes application of the composition, e.g. agricultural composition or combination comprising (T) or a nitrification inhibitor according to the present invention and a biopesticide, e.g. as defined herein above, onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06/112700.

The composition, e.g. agricultural composition or combination comprising (T) or a nitrification inhibitor according to the present invention and a biopesticide, e.g. as defined herein above, can also be used in form of a "pill" or "pellet" or a suitable substrate and placing, or sowing, the treated pill, or substrate, next to a plant propagation material. Such techniques are known in the art, particularly in EP1124414, WO07/67042, and WO07/67044. Application of the composition, e.g. agricultural composition or combination comprising (T) or a nitrification inhibitor according to the present invention and a biopesticide, e.g. as defined herein above, onto plant propagation material also includes protecting the plant propagation material treated with the combination of the present invention by placing one or more biopesticide- and (T)- and nitrification inhibitor (NI)-containing particles next to a biopesticide- and NI-treated seed, wherein the amount of biopesticides is such that the pesticide-treated seed and the pesticide-containing particles together contain an Effective Dose of the biopesticide and the biopesticide dose contained in the biopesticide-treated seed is less than or equal to the Maximal Non-Phytotoxic Dose of the pesticide. Such techniques are known in the art, particularly in WO2005/120226.

Application of the combinations onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compound s present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil or soil substituents but would include any application practice that would target the seed during the planting process.

Preferably, the treatment occurs before sowing of the seed so that the sown seed has been pretreated with the combination. In particular, seed coating or seed pelleting are preferred in the treatment of the combinations according to the invention. As a result of the treatment, the ingredients in each combination are adhered on to the seed and therefore available for pest control. The treated seeds can be stored, handled, sowed and tilled in the same manner as any other active ingredient treated seed.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. Preferred examples of seed treatment formulation types or soil application for pre-mix compositions are of WS, LS, ES, FS, WG or CS-type.

The compositions in question give, after two-to-tenfold dilution, active components concentrations of from 0.01 to 60% by weight, preferably from 0.1 to 40%, in the ready-to-use preparations. Application can be carried out before or during sowing. Methods for applying or treating compositions or combinations comprising (T) or a nitrification inhibitor according to the present invention, e.g. as defined herein above on to plant propagation material, especially seeds include dressing, coating, pelleting, dusting, soaking and in-furrow application methods of the propagation material. Preferably, compositions or combinations comprising (T) or a nitrification inhibitor according to the present invention, e.g. as defined herein above are applied on to the plant propagation material by a method such that germination is not induced, e. g. by seed dressing, pelleting, coating and dusting.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation)), the end user will normally employ dilute formulations (e.g., tank mix composition).

When employed in plant protection, the total amounts of active components applied are, depending on the kind of effect desired, from 0.001 to 10 kg per ha, preferably from 0.005 to 2 kg per ha, more preferably from 0.05 to 0.9 kg per ha, in particular from 0.1 to 0.75 kg per ha. The application rates may range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e.g. Steinernema feltiae), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e.g. in the form of eggs, juvenile or any other live stages, preferably in an infetive juvenile stage) per ha.

When employed in plant protection by seed treatment, the amount of compositions or combinations comprising (T) or a nitrification inhibitor according to the present invention and a biopesticide, e.g. as defined herein above (based on total weight of active components) is in the range from 0.01-10 kg, preferably from 0.1-1000 g, more preferably from 1-100 g per 100 kilogram of plant propagation material (preferably seeds). The application rates with respect to plant propagation material preferably may range from about $1 \times 10^6$ to $1 \times 10^{12}$ (or more) CFU/seed. Preferably, the concentration is about $1 \times 10^6$ to about $1 \times 10^{11}$ CFU/seed. Alternatively, the application rates with respect to plant propagation material may range from about $1 \times 10^7$ to $1 \times 10^{14}$ (or more) CFU per 100 kg of seed, preferably from $1 \times 10^9$ to about $1 \times 10^{11}$ CFU per 100 kg of seed.

The following example is provided for illustrative purposes. It is thus understood that the example is not to be construed as limiting. The skilled person in the art will clearly be able to envisage further modifications of the principles laid out herein.

EXAMPLE 1

Soil was sampled fresh from a field (e.g. Limburgerhof), dried and sieved through a 500 µm sieve. Approximately 200 mg of soil were placed into each well of a 48 well plate. Compounds, or DMSO alone, were added at a concentration of 10 ppm, dissolved in 1% DMSO. 6 µmol ammonium sulfate was added per well as well as 4.8 mg $NaClO_3$.

Subsequently, the samples were incubated at room temperature for up to 72 hrs. After the incubation period 64 mg KCl were added and mixed. 25 µl of the supernatant were placed into a fresh plate and 260 µl of a color reaction solution (from Merck Nr 1.11799.0100) were added.

Measurements were taken with a Tecan plate Reader at 540 nm wavelength.

The results of the measurements (with a dose of 10 ppm) were that all compounds #1 to #215 as shown in Table 1, supra demonstrated an inhibition of ≥10% compared to a control (DMSO only).

EXAMPLE 2

The experimental setup below is particularly appropriate for determining the synergistic action of (T) and a biopesticide having fungicidal activity which is enhanced in the composition comprising (T) and biopesticide.

Microtest

The active compounds were formulated separately as a stock solution having a concentration of for example 10000 ppm in dimethyl sulfoxide.

1. Activity against the late blight pathogen Phytophthora infestans in the microtiter test (Phytin)

The stock solutions were mixed according to the ratio, pipetted onto a micro titer plate (MTP) and diluted with water to the stated concentrations. A spore suspension of Phytophtora infestans containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

2. Activity against leaf blotch on wheat caused by Septoria tritici (Septtr)

The stock solutions were mixed according to the ratio, pipetted onto a micro titer plate (MTP) and diluted with water to the stated concentrations. A spore suspension of Septoria tritici in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

3. Activity against wheat leaf spots caused by Leptosphaeria nodorum (Leptno)

The stock solutions were mixed according to the ratio, pipetted onto a micro titer plate (MTP) and diluted with water to the stated concentrations. A spore suspension of Leptosphaeria nodorum in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

The invention claimed is:

1. A composition comprising:
a) at least one (thio)phosphoric acid triamide (T) according to the general formula (Ia)

Ra1Ra2N—P(X)(NH2)2    (Ia)

wherein

X is oxygen or sulfur;

Ra1 is a C1 to C20 alkyl, C3 to C20 cycloalkyl, C6 to C20 aryl, or dialkylaminocarbonyl group;

Ra2 is H, or

Ra1 and Ra2 together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and b) at least one biopesticide.

2. The composition according to claim 1, wherein the biopesticide (L) is selected from the group consisting of (L1), (L3), (L5), (L7) and (L8), wherein:

(L1) comprises microbial pesticides having at least one of fungicidal, bactericidal, viricidal and plant defense activator activity selected from the group consisting of:
(L11) *Ampelomyces quisqualis*,
(L12) *Aspergillus flavus*,
(L13) *Aureobasidium pullulans*,
(L14) *Bacillus amyloliquefaciens*,
(L15) *Bacillus mojavensis*,
(L16) *Bacillus pumilus*,
(L17) *Bacillus simplex*,
(L18) *Bacillus solisalsi*,
(L19) *Bacillus subtilis*,
(L20) *Bacillus subtilis* var. *amyloliquefaciens*,
(L21) *Candida oleophila*, or *C. saitoana*,
(L22) *Clavibacter michiganensis* (bacteriophages),
(L23) *Coniothyrium minitans*,
(L24) *Cryphonectria parasitica*,
(L25) *Cryptococcus albidus*,
(L26) *Dilophosphora alopecuri*,
(L27) *Fusarium oxysporum*,
(L28) *Clonostachys rosea* f. catenulate (also named *Gliocladium catenulatum*),
(L29) *Gliocladium roseum*,
(L30) *Lysobacter antibioticus*,or *L. enzymogenes*,
(L31) *Metschnikowia fructicola*,
(L33) *Microsphaeropsis ochracea*,
(L34) *Muscodor albus*,
(L35) *Paenibacillus polymyxa*,
(L36) *Pantoea vagans*,
(L37) *Phlebiopsis gigantea*,
(L38) *Pseudomonas sp.*, or *Pseudomonas chloraphis*,
(L39) *Pseudozyma flocculosa*,
(L40) *Pichia anomala*,
(L41) *Pythium oligandrum*,
(L42) *Sphaerodes mycoparasitica*,
(L43) *Streptomyces griseoviridis, S. lydicus*, or *S.violaceusniger*,
(L44) *Talaromyces flavus*,
(L45) *Trichoderma asperellum, T. atroviride, T. fertile, T. gamsii, T. harmatum, T. harzianum, T. stromaticum, T. virens* (also named *Gliocladium virens* ), *T. viride*, or mixture of *T. harzianum* and *T. viride*, or mixture of *T. polysporum* and *T. harzianum*,
(L46) *Typhula phacorrhiza*,
(L47) *Ulocladium oudemansii*,
(L48) *Verticillium dahlia*, and
(L49) zucchini yellow mosaic virus (avirulent strain);
(L3) comprises microbial pesticides with at least one of insecticidal, acaricidal, molluscidal and nematicidal activity selected from the group consisting of:
(L51) *Agrobacterium radiobacter*,
(L52) *Bacillus cereus*,
(L53) *Bacillus firmus*,
(L54) *Bacillus thuringiensis, B. t.* ssp. *aizawai, B. t.* ssp. *israelensis, B. t.* ssp. *galleriae, B. t.* ssp. *kurstaki*, or *B. t.*ssp. *tenebrionis*,
(L55) *Beauveria bassiana*, or *B. brongniartii*,
(L56) *Burkholderia* sp.,
(L57) *Chromobacterium subtsugae*,
(L59) *Cryptophlebia leucotreta* granulovirus (CrleGV),
(L60) *Isaria fumosorosea*,
(L61) *Heterorhabditis bacteriophora*,
(L62) *Lecanicillium longisporum*, or *L. muscarium* (formerly *Verticillium lecanii*),
(L63) *Metarhizium anisopliae*, or *M. anisopliae* var. *acridum*,
(L64) *Nomuraea rileyi*,
(L65) *Paecilomyces fumosoroseus*, or *P. lilacinus*,
(L66) *Paenibacillus popilliae*,
(L67) *Pasteuria* spp., *P. nishizawae, P. penetrans, P. ramose, P. reneformis, P. thornea*, or *P. usgae*,
(L68) *Pseudomonas fluorescens*, and
(L69) *Steinernema carpocapsae, S. feltiae*, or *S. kraussei*;
(L5) comprises microbial pesticides with at least one of plant stress reducing, plant growth regulator, plant growth promoting and yield enhancing activity selected from the group consisting of:
(L81) *Azospirillum amazonense, A. brasilense, A. lipoferum, A. irakense*, or *A. halopraeferens*,
(L82) *Bradyrhizobium* sp., *B. elkanii, B. japonicum, B. liaoningense*, or *B. lupini*,
(L83) *Delftia acidovorans*,
(L84) VA mycorrhiza selected from the genera *Glomus, Acaulospora, Entrophosphora, Gigaspora, Scutellospora* and *Sclerocytis*,
(L85) VA mycorrhiza selected from the group consisting of *Glomus fasciculatum, G. caledonium, G. mosseae, G. versiforme, G. intraradices* and *G. etunicatum*,
(L86) *Mesorhizobium* sp.,
(L87) *Paenibacillus alvei*,
(L88) *Penicillium bilaiae*,
(L89) *Rhizobium leguminosarum* bv. *phaseoli, R. l. trifolii, R. l.* bv. *viciae*, or *R. tropici*,
(L90) *Sinorhizobium meliloti*,
(L91) *Enterobacter* spp., *E. ludwigii, E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. mori, E. nimipressuralis, E. oryzae, E. pulveris, E. pyrinus, E. radicincitans, E. taylorae, E. turicensis*, or *E. sakazakii*, and
(L92) *Oxalobacteraceae* spp., *Herbaspirillum seropedicae* (DSM No.: 6445) (free-living nitrogen fixing bacterium), *Janthinobacterium lividum* (DSM No.: 1522) (violacein-producing bacterium), or *Pseudoduganella violaceinigra* (DSM No.: 15887) (violacein-producing bacterium);
(L7) comprises metabolites produced by the microbial pesticides selected from the group consisting of:
(L93) siderophores, bacillibactin
(L94) antibiotics selected from the group consisting of zwittermicin-A, kanosamine, polyoxine, bacilysin, violacein
(L95) enzymes selected from the group consisting of alpha-amylase, chitinases, pektinases, phosphatase (acid and alkaline) and phytase
(L96) phytohormones and precursors thereof and volatile compounds, selected from the group consisting of auxines, gibberellin-like substances, cytokinin-like compounds, acetoin, 2,3-butanediol, ethylene, indole acetic acid,
(L97) lipopeptides selected from the group consisting of iturins, plipastatins, surfactins, agrastatin, agrastatin A, bacillomycin, bacillomycin D, fengycin,
(L98) antibacterial polyketides selected from the group consisting of difficidin, macrolactin and bacilaene, and
(L99) antifungal metabolites selected from the group consisting of pyrones, cytosporone, 6-pentyl-2H- pyran-2-one (also termed 6-pentyl-a-pyrone), koninginins (complex pyranes), and (L8) comprises biochemical pesticides with at least one of insecticidal, acaricidal, molluscidal, pheromone and nematicidal activity selected from the group consisting of:

L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone (B.27), 2-methyl 1-butanol, methyl eugenol, methyl jasmonate (B.28), (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium ambrosiodes*, Catnip oil, Neem oil (B.29), Quillay extract (B.30), and *Tagetes* oil.

3. The composition according to claim 1, wherein in the general formula (Ia) of (T) X is sulfur and/or wherein in the general formula (Ia) of (T) $R^{a1}$ is $C_1$-$C_{20}$ alkyl and $R^{a2}$ is H.

4. The composition according to claim 1, wherein the (thio)phosphoric acid triamide (T) is one of N-n-butylthiophosphoric acid triamide (NBPT) and N-n-propylthiophosphoric acid triamide (NPPT).

5. The composition according to claim 1, wherein the biopesticide is selected from the group consisting of

*Azospirillum brasilense* XOH (B.1), *A. brasilense* BR 11002 (B.2), *A. brasilense* BR 11005 (B.3), *A. brasilense* strains Ab-V5 and Ab-V6 (B.4), *Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MBI600 (B.9), *B. cereus* CNCM I-1562 (B.10), *B. firmus* CNCM I-1582 (B.11), *Bacillus pumilus* KFP9F (B.12), *B. pumilus* QST 2808 (B.13), *Bradyrhizobium japonicum* (B.14), *Coniothyrium minitans* CON/M/91-08 (B.15), *Pasteuria nishizawae* Pn1 (B.16), *Penicillium bilaiae* (B.17), *P. fluorescens* CL 145A (B.18), *Rhizobium leguminosarum* bv. *Phaseoli* (B.19), *R. l.* bv. *trifolii* RP113-7 (B.20), *R. l.* bv. *viciae* P1NP3Cst (B.21), *R. l..* bv. *viciae* SU303 (B.22), *R. l.* bv. *viciae* WSM1455 (B.23), *R. tropici* SEMIA 4080 (B.24), *Sinorhizobium meliloti* MSDJ0848 (B.25), *Trichoderma fertile* JM41R (B.26), cis-jasmone (B.27), methyl jasmonate (B.28), and Neem oil (B.29).

6. The composition according to claim 1, wherein the biopesticide is selected from the group consisting of:
(L14) *Bacillus amyloliquefaciens*,
(L16) *Bacillus pumilus*,
(L17) *Bacillus simplex*,
(L19) *Bacillus subtilis*, and
(L20) *Bacillus subtilis* var. *amyloliquefaciens*.

7. A method for increasing the health of a plant, comprising treating at least one of (a) a plant growing on at least one of soil and soil substituents and (b) at least one of the locus, soil, and soil substituents where the plant is at least one of growing or intended to grow, with a) at least one (thio)phosphoric acid triamide (T) according to the general formula (Ia)

$$R^{a1}R^{a2}N\text{---}P(X)(NH_2)_2 \qquad (Ia)$$

wherein
X is oxygen or sulfur;
$R^{a1}$ is a $C_1$ to $C_{20}$ alkyl, $C_3$ to $C_{20}$ cycloalkyl, $C_6$ to $C_{20}$ aryl, or dialkylaminocarbonyl group;
$R^{a2}$ is H, or
$R^{a1}$ and $R^{a2}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and b) at least one biopesticide.

8. The method according to claim 7, wherein the biopesticide is selected from the group consisting of:

*Azospirillum brasilense* XOH (B.1), *A. brasilense* BR 11002 (B.2), *A. brasilense* BR 11005 (B.3), *A. brasilense* strains Ab-V5 and Ab-V6 (B.4), *Bacillus amyloliquefaciens* FZB42 (B.5), *B. amyloliquefaciens* IN937a (B.6), *B. amyloliquefaciens* IT-45 (B.7), *B. amyloliquefaciens* TJ1000 (B.8), *B. amyloliquefaciens* ssp. *plantarum* MBI600 (B.9), *B. cereus* CNCM I-1562 (B.10), *B. firmus* CNCM I-1582 (B.11), *Bacillus pumilus* KFP9F (B.12), *B. pumilus* QST 2808 (B.13), *Bradyrhizobium japonicum* (B.14), *Coniothyrium minitans* CON/M/91-08 (B.15), *Pasteuria nishizawae* Pn1 (B.16), *Penicillium bilaiae* (B.17), *P. fluorescens* CL 145A (B.18), *Rhizobium leguminosarum* bv. *Phaseoli* (B.19), *R. l.* bv. *trifolii* RP113-7 (B.20), *R. l.* bv. *viciae* P1NP3Cst (B.21), *R. l.* bv. *viciae* SU303 (B.22), *R. l.* bv. *viciae* WSM1455 (B.23), *R. tropici* SEMIA 4080 (B.24), *Sinorhizobium meliloti* MSDJ0848 (B.25), *Trichoderma fertile* JM41R (B.26), cis-jasmone (B.27), methyl jasmonate (B.28), and Neem oil (B.29).

9. The method according to claim 7, wherein the application of the (thio)phosphoric acid triamide (T) and of the biopesticide is carried out simultaneously or with a time lag.

10. A method for at least one of increasing the health of a plant and increasing the biopesticidal activity of the biopesticide, the method comprising treating at least one of (a) a plant growing on at least one of soil and soil substituents and (b) at least one of the locus, soil and soil substituents where the plant is at least one of growing or intended to grow, with the composition of claim 1.

11. The composition according to claim 1, wherein in the general formula (Ia) of (T) X is sulfur.

12. The composition according to claim 1, wherein in the general formula (Ia) of (T) $R^{a1}$ is $C_1$-$C_{20}$ alkyl and $R^{a2}$ is H.

13. The method according to claim 7 further comprising providing the plant with a urea-containing fertilizer.

14. The method according to claim 13, wherein the application of the (thio)phosphoric acid triamide (T), of the biopesticide, and of the urea-containing fertilizer is carried out simultaneously or with a time lag.

15. The method according to claim 14, wherein the time lag is an interval selected from the group consisting of 1 day, 2 days, 3 days, 1 week, 2 weeks or 3 weeks.

16. The method according to claim 9, wherein the time lag is an interval selected from the group consisting of 1 day, 2 days, 3 days, 1 week, 2 weeks or 3 weeks.

* * * * *